US009435743B2

(12) United States Patent
Zdanovsky

(10) Patent No.: US 9,435,743 B2
(45) Date of Patent: Sep. 6, 2016

(54) METHODS USING A MODIFIED BACTERIOPHAGE FOR THE DETECTION OF TARGET MOLECULES

(71) Applicant: Alexey Gennadievich Zdanovsky, Madison, WI (US)

(72) Inventor: Alexey Gennadievich Zdanovsky, Madison, WI (US)

( * ) Notice: Subject to any disclaimer, the term of this patent is extended or adjusted under 35 U.S.C. 154(b) by 0 days.

(21) Appl. No.: 13/887,611

(22) Filed: May 6, 2013

(65) Prior Publication Data

US 2013/0295554 A1 Nov. 7, 2013

Related U.S. Application Data

(60) Provisional application No. 61/643,534, filed on May 7, 2012.

(51) Int. Cl.

| | |
|---|---|
| ***G01N 21/76*** | (2006.01) |
| ***C12N 15/10*** | (2006.01) |
| ***C12Q 1/66*** | (2006.01) |
| ***G01N 21/64*** | (2006.01) |

(52) U.S. Cl.

CPC ......... *G01N 21/763* (2013.01); *C12N 15/1037* (2013.01); *C12Q 1/66* (2013.01); *G01N 21/64* (2013.01)

(58) Field of Classification Search

None

See application file for complete search history.

(56) References Cited

U.S. PATENT DOCUMENTS

| | | | | |
|---|---|---|---|---|
| 2005/0255527 A1* | 11/2005 | Yang et al. | | 435/7.1 |
| 2008/0227086 A1* | 9/2008 | Vitzthum | | 435/6 |

FOREIGN PATENT DOCUMENTS

WO WO 2007/055737 * 5/2007

OTHER PUBLICATIONS

Gao et al., Proc. Natl. Acad. Sci. USA, May 1999, 96:6025-6030.*

Loset et al., PLoS ONE, Feb. 2011, 6(2): e17433.*

Burbulis, Ian et al., "Using protein-DNA chimeras to detect and count small numbers of molecules," Nature Methods, (Jan. 2005), vol. 2, No. 1, pp. 31-37.

Chen, Bi-Xing et al., "A Strategy for Immunohistochemical Signal Enhancement by End-product Amplification," Jnl of Histochemistry and Cytochemistry, (1996), vol. 44, No. 8, pp. 819-824.

Chiu, Norman H.L. et al., "Two-Site Expression Immunoassay Using a Firefly Luciferase-coding DNA Label," Clin Chem, (1999), vol. 45, No. 10, pp. 1954-1959.

Christopoulos, Theodore K. et al., "Expression Immunoassay. Antigen Quantitation Using Antibodies Labeled with Enzyme-Coding DNA Fragments," Anal. Chem., (1995), vol. 67, No. 23, pp. 4290-4294.

Guo, Yong-Chao et al., "Phage display mediated immuno-PCR," Nucleic Acids Research, (2006), vol. 34, No. 8, pp. e62: 1-6.

Hill, Philip J. et al., "Review: The application of lux genes," Biotechnol. Appl. Biochem., (1993), vol. 17, pp. 3-14.

Hill, Philip J. et al., "Use of lux genes in applied biochemistry," Jrnl of Bioluminescence and Chemiluminescence, (1994), vol. 9, Issue 3, pp. 211-215.

Johannsson, Axel et al., "A fast highly sensitive coloimetric enzyme immunoassay system demonstrating benefits of enzyme amplification in clinical chemistry," Clinica Chimica Acta, (May 30, 1985), vol. 148, Issue 2, pp. 119-124.

Kazane, Stephanie A. et al., "Site-specific DNA-antibody conjugates for specific and sensitive immuno-PCR," PNAS, (Mar. 6, 2012), vol. 109, No. 10, pp. 3731-3736.

Lansdorp, Peter M. et al., "Stepwise Amplified Immunoperoxidase (PAP) Staining. I. Cellular Morphology in Relation to Membrane Markers," J Histochemistry and Cytochemistry, (1984), vol. 32, No. 2, pp. 172-178.

Lind, Kristina et al., "Development and evaluation of three real-time immuno-PCR assemblages for quantification of PSA," J Immunol Methods, (Sep. 2005), vol. 304, Issues 1-2, pp. 107-116.

Meighen, Edward A., "Molecular Biology of Bacterial Bioluminescence," Microbiol Rev, (Mar. 1991), vol. 55, No. 1, pp. 123-142.

Niemeyer, Christof M. et al., "Detecting antigens by quantitative immuno-PCR," Nature Protocols, (2007), vol. 2, No. 8, pp. 1918-1930.

Sano, T. et al., "Immuno-PCR: very sensitive antigen detection by means of specific antibody-DNA conjugates," Science, (Oct. 1992), vol. 258, pp. 120-122.

Scholle, Michael D. et al., "Efficient construction of a large collection of phage-displayed combinatorial peptide libraries," Comb Chem High Throughput Screen, (Sep. 2005), vol. 8, Issue 6, pp. 545-551.

Schweitzer, Barry et al., "Immunoassays with rolling circle DNA amplification: A versatile platform for ultrasensitive antigen detection," PNAS, (Aug. 29, 2000), vol. 97, No. 18, pp. 10113-10119.

Smith, George P., "Filamentous fusion phage: novel expression vectors that display cloned antigens on the virion surface," Science, (Jun. 14, 1985), vol. 228, pp. 1315-1317.

Sternberger, Ludwig A. et al., "The unlabeled Antibody Enzyme Method of Immunohistochemistry: Preparation and Properties of Soluble Antigen-Antibody Complex (Horseradish Peroxidase-Antihorseradish Peroxidase) and Its Use in Identification of Spirochetes," J Histochemistry and Cytochemistry, (1970), vol. 18, No. 5, pp. 315-333.

Stewart, Gordon S.A.B. et al., "Iux genes and the applications of bacterial bioluminescence," J General Microbiology, (Jul. 1992), vol. 138, No. 7, pp. 1289-1300.

Szittner, Rose et al., "Nucleotide Sequence, Expression, and Properties of Luciferase Coded by Iux Genes from a Terrestrial Bacterium," J Biological Chemistry, (Sep. 1990), vol. 265, No. 27, pp. 16581-16587.

(Continued)

*Primary Examiner* — Nicole Kinsey White
(74) *Attorney, Agent, or Firm* — Foley & Lardner LLP

(57) ABSTRACT

The present disclosure provides methods and compositions for the detection of target molecules, comprising modified bacteriophages engineered to express a luciferase.

10 Claims, 6 Drawing Sheets

(56) References Cited

OTHER PUBLICATIONS

Takeda, Shuji et al., "Site-specific conjugation of oligonucleotides to the C-terminus of recombinant protein by expressed protein ligation," Bioorg Med Chem Lett, (May 17, 2004), vol. 14, Issue 10, pp. 2407-2410.

Tummuru, Murali K.R. et al., "Characterization of the Campylobacter fetus sapA Promoter: Evidence that the sapA Promoter is Deleted in Spontaneous Mutant Strains," J Bacteriol, (Sep. 1992), vol. 174, No. 18, pp. 5916-5922.

Manukhov, I.V. et al., "Cloning and expression of the Iux-operon of Photorhabdus luminescens, strain Zm1: nucleotide sequence of IuxAB genes and basic properties of luciferase," Genetika, (2000), vol. 36, No. 3, pp. 322-330—with English translation of abstract.

* cited by examiner

SEQUENCE LISTING

```
<160> NUMBER OF SEQ ID NOS: 34

<210> SEQ ID NO 1
<211> LENGTH: 10990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

aatgctacta ctattagtag aattgatgcc accttttcag ctcgcgcccc aaatgaaaat     60

atagctaaac aggttattga ccatttgcga aatgtatcta atggtcaaac taaatctact    120

cgttcgcaga attgggaatc aactgttaca tggaatgaaa cttccagaca ccgtacttta    180
```

-continued

```
gttgcatatt taaaacatgt tgagctacag caccagattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tctttttgat gcaatccgct ttgcttctga ctataatagt    420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttcttttg caaaagcctc tcgctatttt    600
ggtttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattctttcg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
tttttggaga ttttcaacgt gaaaaaatta ttattcgcaa ttcctttagt tgttcctttc   1620
tattctcact ccgctgaaac tgttgaaagt tgtttagcaa aaccccatac agaaaattca   1680
tttactaacg tctggaaaga cgacaaaact ttagatcgtt acgctaacta tgagggttgt   1740
ctgtggaatg ctacaggcgt tgtagtttgt actggtgacg aaactcagtg ttacggtaca   1800
tgggttccta ttgggcttgc tatccctgaa aatgagggtg gtggctctga gggtggcggt   1860
tctgagggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactgttact   2100
caaggcactg accccgttaa aacttattac cagtacactc ctgtatcatc aaaagccatg   2160
tatgacgctt actggaacgg taaattcaga gactgcgctt tccattctgg ctttaatgaa   2220
gatccattcg tttgtgaata tcaaggccaa tcgtctgacc tgcctcaacc tcctgtcaat   2280
gctggcggcg gctctggtgg tggttctggt ggcggctctg agggtggtgg ctctgagggt   2340
ggcggttctg agggtggcgg ctctgaggga ggcggttccg gtggtggctc tggttccggt   2400
gattttgatt atgaaaagat ggcaaacgct aataaggggg ctatgaccga aaatgccgat   2460
gaaaacgcgc tacagtctga cgctaaaggc aaacttgatt ctgtcgctac tgattacggt   2520
gctgctatcg atggtttcat tggtgacgtt tccggccttg ctaatggtaa tggtgctact   2580
```

-continued

```
ggtgattttg ctggctctaa ttcccaaatg gctcaagtcg gtgacggtga taattcacct   2640
ttaatgaata atttccgtca atatttacct tccctccctc aatcggttga atgtcgccct   2700
tttgtcttta gcgctggtaa accatatgaa ttttctattg attgtgacaa aataaactta   2760
ttccgtggtg tctttgcgtt tcttttatat gttgccacct ttatgtatgt attttctacg   2820
tttgctaaca tactgcgtaa taaggagtct taatcatgcc agttcttttg ggtattccgt   2880
tattattgcg tttcctcggt ttccttctgg taactttgtt cggctatctg cttacttttc   2940
ttaaaaaggg cttcggtaag atagctattg ctatttcatt gtttcttgct cttattattg   3000
ggcttaactc aattcttgtg ggttatctct ctgatattag cgctcaatta ccctctgact   3060
ttgttcaggg tgttcagtta attctcccgt ctaatgcgct tccctgtttt tatgttattc   3120
tctctgtaaa ggctgctatt ttcatttttg acgttaaaca aaaaatcgtt tcttatttgg   3180
attgggataa ataatatggc tgtttatttt gtaactggca aattaggctc tggaaagacg   3240
ctcgttagcg ttggtaagat tcaggataaa attgtagctg ggtgcaaaat agcaactaat   3300
cttgatttaa ggcttcaaaa cctcccgcaa gtcgggaggt tcgctaaaac gcctcgcgtt   3360
cttagaatac cggataagcc ttctatatct gatttgcttg ctattgggcg cggtaatgat   3420
tcctacgatg aaaataaaaa cggcttgctt gttctcgatg agtgcggtac ttggtttaat   3480
acccgttctt ggaatgataa ggaaagacag ccgattattg attggtttct acatgctcgt   3540
aaattaggat gggatattat ttttcttgtt caggacttat ctattgttga taaacaggcg   3600
cgttctgcat tagctgaaca tgttgtttat tgtcgtcgtc tggacagaat tactttacct   3660
tttgtcggta ctttatattc tcttattact ggctcgaaaa tgcctctgcc taaattacat   3720
gttggcgttg ttaaatatgg cgattctcaa ttaagcccta ctgttgagcg ttggctttat   3780
actggtaaga atttgtataa cgcatatgat actaaacagg ctttttctag taattatgat   3840
tccggtgttt attcttattt aacgccttat ttatcacacg gtcggtattt caaaccatta   3900
aatttaggtc agaagatgaa attaactaaa atatatttga aaaagttttc tcgcgttctt   3960
tgtcttgcga ttggatttgc atcagcattt acatatagtt atataaccca acctaagccg   4020
gaggttaaaa aggtagtctc tcagacctat gattttgata aattcactat tgactcttct   4080
cagcgtctta atctaagcta tcgctatgtt ttcaaggatt ctaagggaaa attaattaat   4140
agcgacgatt tacagaagca aggttattca ctcacatata ttgatttatg tactgtttcc   4200
attaaaaaag gtaattcaaa tgaaattgtt aaatgtaatt aattttgttt tcttgatgtt   4260
tgtttcatca tcttcttttg ctcaggtaat tgaaatgaat aattcgcctc tgcgcgattt   4320
tgtaacttgg tattcaaagc aatcaggcga atccgttatt gtttctcccg atgtaaaagg   4380
tactgttact gtatattcat ctgacgttaa acctgaaaat ctacgcaatt tctttatttc   4440
tgttttacgt gctaataatt ttgatatggt tggttcaatt ccttccataa ttcagaagta   4500
taatccaaac aatcaggatt atattgatga attgccatca tctgataatc aggaatatga   4560
tgataattcc gctccttctg gtggtttctt tgttccgcaa aatgataatg ttactcaaac   4620
ttttaaaatt aataacgttc gggcaaagga tttaatacga gttgtcgaat tgtttgtaaa   4680
gtctaatact tctaaatcct caaatgtatt atctattgac ggctctaatc tattagttgt   4740
tagtgcacct aaagatattt tagataacct tcctcaattc ctttctactg ttgatttgcc   4800
aactgaccag atattgattg agggtttgat atttgaggtt cagcaaggtg atgctttaga   4860
tttttcattt gctgctggct ctcagcgtgg cactgttgca ggcggtgtta atactgaccg   4920
```

-continued

```
cctcacctct gttttatctt ctgctggtgg ttcgttcggt atttttaatg gcgatgtttt   4980
agggctatca gttcgcgcat taaagactaa tagccattca aaaatattgt ctgtgccacg   5040
tattcttacg ctttcaggtc agaagggttc tatctctgtt ggccagaatg tcccttttat   5100
tactggtcgt gtgactggtg aatctgccaa tgtaaataat ccatttcaga cgattgagcg   5160
tcaaaatgta ggtatttcca tgagcgtttt tcctgttgca atggctggcg gtaatattgt   5220
tctggatatt accagcaagg ccgatagttt gagttcttct actcaggcaa gtgatgttat   5280
tactaatcaa agaagtattg ctacaacggt taatttgcgt gatggacaga ctcttttact   5340
cggtggcctc actgattata aaaacacttc tcaagattct ggcgtaccgt tcctgtctaa   5400
aatcccttta atcggcctcc tgtttagctc ccgctctgat tccaacgagg aaagcacgtt   5460
atacgtgctc gtcaaagcaa ccatagtacg cgccctgtag cggcgcatta agcgcggcgg   5520
gtgtggtggt tacgcgcagc gtgaccgcta cacttgccag cgccctagcg cccgctcctt   5580
tcgctttctt cccttccttt ctcgccacgt tcgccggctt tccccgtcaa gctctaaatc   5640
gggggctccc tttagggttc cgatttagtg ctttacggca cctcgacccc aaaaaacttg   5700
atttgggtga tggttcacgt agtgggccat cgccctgata gacggttttt cgccctttga   5760
cgttggagtc cacgttcttt aatagtggac tcttgttcca aactggaaca acactcaacc   5820
ctatctcggg ctattctttt gatttataag ggattttgcc gatttcggaa ccaccatcaa   5880
acaggatttt cgcctgctgg ggcaaaccag cgtggaccgc ttgctgcaac tctctcaggg   5940
ccaggcggtg aagggcaatc agctgttgcc cgtctcgctg gtgaaaagaa aaaccaccct   6000
ggcgcccaat acgcaaaccg cctctccccg cgcgttggcc gattcattaa tgcagctggc   6060
acgacaggtt tcccgactgg aaagcgggca gtgagcgcaa cgcaattaat gtgagttagc   6120
tcactcatta ggcaccccag gctttacact ttatgcttcc ggctcgtatg ttgtgtggaa   6180
ttgtgagcgg ataacaattt cacacaggaa acagctatga ccatgattac gaattcacta   6240
gtgattatgg taaagcaaga tgaagttatc acattgttat caaatattcg tagtaatcga   6300
tgcaagatat attctttgtt aggaagttcg catgacttga gtgaaaattt agtggtcctg   6360
cgcaattttt atcaatcggt tacgaaagcc gctatcgcga tggataatga tcatctggat   6420
attgatgttg atattactga accgtcattt gaacatttaa ctattgcgac agtcaatgaa   6480
cgccgaatga gaattgagat tgaaaatcaa gcaatttctc tgtcttaaaa tctattgaga   6540
tattctatca ctcaaatagc aatataagga ctctctatga aatttggaaa ctttttgctt   6600
acataccaac ctccccaatt ttctcaaaca gaggtaatga aacgtttggt taaattaggt   6660
cgcatctctg aggagtgtgg ttttgatacc gtatggttac tggagcatca tttcacggag   6720
tttggtttgc ttggtaaccc ttatgtcgct gctgcatatt tacttggcgc gactaaaaaa   6780
ttgaatgtag gaactgccgc tattgttctt cccacagccc atccagtacg ccaacttgaa   6840
gatgtgaatt tattggatca aatgtcaaaa ggacgatttc ggtttggtat ttgccgaggg   6900
ctttacaaca aggactttcg cgtattcggc acagatatga ataacagtcg cgccttagcg   6960
gaatgctggt acgggctgat aaagaatggc atgacagagg gatatatgga agctgataat   7020
gaacatatca agttccataa ggtaaaagta aaccccgcgg cgtatagcag aggtggcgca   7080
ccggtttatg tggtggctga atcagcttcg acgactgagt gggctgctca atttggccta   7140
ccgatgatat taagttggat tataaatact aacgaaaaga aagcacaact tgagctttat   7200
aatgaagtgg ctcaagaata tgggcacgat attcataata tcgaccattg cttatcatat   7260
ataacatctg tagatcatga ctcaattaaa gcgaaagaga tttgccggaa atttctgggg   7320
```

-continued cattggtatg attcttatgt gaatgctacg actatttttg atgattcaga ccaaacaaga 7380
ggttatgatt tcaataaagg gcagtggcgt gactttgtat taaaaggaca taaagatact 7440
aatcgccgta ttgattacag ttacgaaatc aatcccgtgg gaacgccgca ggaatgtatt 7500
gacataattc aaaaagacat tgatgctaca ggaatatcaa atatttgttg tggatttgaa 7560
gctaatggaa cagtagacga aattattgct tccatgaagc tcttccagtc tgatgtcatg 7620
ccatttctta aagaaaaaca acgttcgcta ttatattagc taaggagaaa gaaatgaaat 7680
ttggattgtt cttccttaac ttcatcaatt caacaactgt tcaagaacaa agtatagttc 7740
gcatgcagga aataacggag tatgttgata agttgaattt tgaacagatt ttagtgtatg 7800
aaaatcattt ttcagataat ggtgttgtcg gcgctcctct gactgtttct ggttttctgc 7860
tcggtttaac agagaaaatt aaaattggtt cattaaatca catcattaca actcatcatc 7920
ctgtcgccat agcggaggaa gcttgcttat tggatcagtt aagtgaaggg agatttattt 7980
tagggtttag tgattgcgaa aaaaaagatg aaatgcattt ttttaatcgc ccggttgaat 8040
atcaacagca actatttgaa gagtgttatg aaatcattaa cgatgcttta acaacaggct 8100
attgtaatcc agataacgat ttttatagct tccctaaaat atctgtaaat ccccatgctt 8160
atacgccagg cggacctcgg aaatatgtaa cagcaaccag tcatcatatt gttgagtggg 8220
cggccaaaaa aggtattcct ctcatcttta agtgggatga ttctaatgat gttagatatg 8280
aatatgctga aagatataaa gccgttgcgg ataaatatga cgttgaccta tcagagatag 8340
accatcagtt aatgatatta gttaactata acgaagatag taataaagct aaacaagaga 8400
cgcgtgcatt tattagtgat tatgttcttg aaatgcaccc taatgaaaat ttcgaaaata 8460
aacttgaaga aataattgca gaaaacgctg tcggaaatta tacggagtgt ataactgcgg 8520
ctaagttggc aattgaaaag tgtggtgcga aaagtgtatt gctgtccttt gaaccaatga 8580
atgatttgat gagccaaaaa aatgtaatca atattgttga tgataatatt aagaagtacc 8640
acatggaata tacctaatag atttcgagtt gcagcgaggc ggcaagtgaa cgaatcccca 8700
ggagcataga taactatgtg actggggtga gtgaaagcag ccaacaaagc agcagcttga 8760
aagatgaagg gtataaaaga gtatgacagc agtgctgcca tactttctaa tattatcttg 8820
aggagtaaaa caggtatgac ttcatatgtt gataaacaag aaattacagc aagctcagaa 8880
attgatgatt tgatttttc gagcgatcca ttagtgtggt cttacgacga gcaggaaaaa 8940
atcagaaaga aacttgtgct tgatgcattt cgtaatcatt ataaacattg tcgagaatat 9000
cgtcactact gtcaggcaca caaagtagat gacaatatta cggaaattga tgacatacct 9060
gtattcccaa catcggtttt taagtttact cgcttattaa cttctcagga aaacgagatt 9120
gaaagttggt ttaccagtag cggcacgaat ggtttaaaaa gtcaggtggc gcgtgacaga 9180
ttaagtattg agagactctt aggctctgtg agttatggca tgaaatatgt tggtagttgg 9240
tttgatcatc aaatagaatt agtcaatttg ggaccagata gatttaatgc tcataatatt 9300
tggtttaaat atgttatgag tttggtggaa ttgttatatc ctacgacatt taccgtaaca 9360
gaagaacgaa tagattttgt taaaacattg aatagtcttg aacgaataaa aaatcaaggg 9420
aaagatcttt gtcttattgg ttcgccatac tttatttatt tactctgcca ttatatgaaa 9480
gataaaaaaa tctcattttc tggagataaa agcctttata tcataaccgg aggcggctgg 9540
aaaagttacg aaaaagaatc tctgaaacgt gatgatttca atcatctttt atttgatact 9600
ttcaatctca gtgatattag tcagatccga gatatattta atcaagttga actcaacact 9660

-continued

```
tgtttctttg aggatgaaat gcagcgtaaa catgttccgc cgtgggtata tgcgcgagcg   9720

cttgatcctg aaacgttgaa acctgtacct gatggaacgc cggggttgat gagttatatg   9780

gatgcgtcag caaccagtta tccagcattt attgttaccg atgatgtcgg gataattagc   9840

agagaatatg gtaagtatcc cggcgtgctc gttgaaattt tacgtcgcgt caatacgagg   9900

acgcagaaag ggtgtgcttt aagcttaaac caagcattta atagttgaca taatcgaatt   9960

cccgggagag ctcgatatcg catgcggtac ctctagaaga agcttgggat ccgtcgacct  10020

gcagcaattc actggccgtc gttttacaac gtcgtgactg ggaaaaccct ggcgttaccc  10080

aacttaatcg ccttgcagca catccccctt tcgccagctg gcgtaatagc gaagaggccc  10140

gcaccgatcg cccttcccaa cagttgcgca gcctgaatgg cgaatggcgc tttgcctggt  10200

ttccggcacc agaagcggtg ccggaaagct ggctggagtg cgatcttcct gaggccgata  10260

cggtcgtcgt cccctcaaac tggcagatgc acggttacga tgcgcccatc tacaccaacg  10320

taacctatcc cattacggtc aatccgccgt ttgttcccac ggagaatccg acgggttgtt  10380

actcgctcac atttaatgtt gatgaaagct ggctacagga aggccagacg cgaattattt  10440

ttgatggcgt tcctattggt taaaaaatga gctgatttaa caaaaattta acgcgaattt  10500

taacaaaata ttaacgttta caatttaaat atttgcttat acaatcttcc tgtttttggg  10560

gcttttctga ttatcaaccg gggtacatat gattgacatg ctagttttac gattaccgtt  10620

catcgattct cttgtttgct ccagactctc aggcaatgac ctgatagcct ttgtagatct  10680

ctcaaaaata gctaccctct ccggcattaa tttatcagct agaacggttg aatatcatat  10740

tgatggtgat ttgactgtct ccggcctttc tcaccctttt gaatctttac ctacacatta  10800

ctcaggcatt gcatttaaaa tatatgaggg ttctaaaaat ttttatcctt gcgttgaaat  10860

aaaggcttct cccgcaaaag tattacaggg tcataatgtt tttggtacaa ccgatttagc  10920

tttatgctct gaggctttat tgcttaattt tgctaattct ttgccttgcc tgtatgattt  10980

attggatgtt                                                         10990


<210> SEQ ID NO 2
<211> LENGTH: 38773
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

tctcacagtg tacggaccta aagttccccc atagggggta cctaaagccc agccaatcac     60

ctaaagtcaa ccttcggttg accttgaggg ttccctaagg gttggggatg acccttgggt    120

ttgtctttgg gtgttacctt gagtgtctct ctgtgtccct atctgttaca gtctcctaaa    180

gtatcctcct aaagtcacct cctaacgtcc atcctaaagc caacacctaa agcctacacc    240

taaagaccca tcaagtcaac gcctatctta aagtttaaac ataaagacca gacctaaaga    300

ccagacctaa agacactaca taaagaccag acctaaagac gccttgttgt tagccataaa    360

gtgataacct ttaatcattg tctttattaa tacaactcac tataaggaga gacaacttaa    420

agagacttaa aagattaatt taaaatttat caaaaagagt attgacttaa agtctaacct    480

ataggatact tacagccatc gagagggaca cggcgaatag ccatcccaat cgacaccggg    540

gtcaaccgga taagtagaca gcctgataag tcgcacgaca gaaagaaatt gaccgcgcta    600

aggcccgtaa agaacgtcac gaggggcgct tagaggcacg cagattcaaa cgtcgcaacc    660
```

-continued

```
gcaaggcacg taaagcacac aaagctaagc gcgaaagaat gcttgctgcg tggcgatggg    720
ctgaacgtca agaacggcgt aaccatgagg tagctgtaga tgtactagga agaaccaata    780
acgctatgct ctgggtcaac atgttctctg ggactttaa ggcgcttgag gaacgaatcg     840
cgctgcactg gcgtaatgct gaccggatgg ctatcgctaa tggtcttacg ctcaacattg    900
ataagcaact tgacgcaatg ttaatgggct gatagtctta tcttacaggt catctgcggg    960
tggcctgaat aggtacgatt tactaactgg aagaggcact aaatgaacac gattaacatc   1020
gctaagaacg acttctctga catcgaactg gctgctatcc cgttcaacac tctggctgac   1080
cattacggtg agcgtttagc tcgcgaacag ttggcccttg agcatgagtc ttacgagatg   1140
ggtgaagcac gcttccgcaa gatgtttgag cgtcaactta aagctggtga ggttgcggat   1200
aacgctgccg ccaagcctct catcactacc ctactcccta agatgattgc acgcatcaac   1260
gactggtttg aggaagtgaa agctaagcgc ggcaagcgcc cgacagcctt ccagttcctg   1320
caagaaatca agccggaagc cgtagcgtac atcaccatta agaccactct ggcttgccta   1380
accagtgctg acaatacaac cgttcaggct gtagcaagcg caatcggtcg ggccattgag   1440
gacgaggctc gcttcggtcg tatccgtgac cttgaagcta agcacttcaa gaaaaacgtt   1500
gaggaacaac tcaacaagcg cgtagggcac gtctacaaga aagcatttat gcaagttgtc   1560
gaggctgaca tgctctctaa gggtctactc ggtggcgagg cgtggtcttc gtggcataag   1620
gaagactcta ttcatgtagg agtacgctgc atcgagatgc tcattgagtc aaccggaatg   1680
gttagcttac accgccaaaa tgctggcgta gtaggtcaag actctgagac tatcgaactc   1740
gcacctgaat acgctgaggc tatcgcaacc cgtgcaggtg cgctggctgg catctctccg   1800
atgttccaac cttgcgtagt tcctcctaag ccgtggactg gcattactgg tggtggctat   1860
tgggctaacg gtcgtcgtcc tctggcgctg gtgcgtactc acagtaagaa agcactgatg   1920
cgctacgaag acgtttacat gcctgaggtg tacaaagcga ttaacattgc gcaaaacacc   1980
gcatggaaaa tcaacaagaa agtcctagcg gtcgccaacg taatcaccaa gtggaagcat   2040
tgtccggtcg aggacatccc tgcgattgag cgtgaagaac tcccgatgaa accggaagac   2100
atcgacatga atcctgaggc tctcaccgcg tggaaacgtg ctgccgctgc tgtgtaccgc   2160
aaggacaagg ctcgcaagtc tcgccgtatc agccttgagt tcatgcttga gcaagccaat   2220
aagtttgcta accataaggc catctggttc ccttacaaca tggactggcg cggtcgtgtt   2280
tacgctgtgt caatgttcaa cccgcaaggt aacgatatga ccaaaggact gcttacgctg   2340
gcgaaaggta aaccaatcgg taaggaaggt tactactggc tgaaaatcca cggtgcaaac   2400
tgtgcgggtg tcgataaggt tccgttccct gagcgcatca agttcattga ggaaaaccac   2460
gagaacatca tggcttgcgc taagtctcca ctggagaaca cttggtgggc tgagcaagat   2520
tctccgttct gcttccttgc gttctgcttt gagtacgctg gggtacagca ccacggcctg   2580
agctataact gctcccttcc gctggcgttt gacgggtctt gctctggcat ccagcacttc   2640
tccgcgatgc tccgagatga ggtaggtggt cgcgcggtta acttgcttcc tagtgaaacc   2700
gttcaggaca tctacgggat tgttgctaag aaagtcaacg agattctaca agcagacgca   2760
atcaatggga ccgataacga agtagttacc gtgaccgatg agaacactgg tgaaatctct   2820
gagaaagtca agctgggcac taaggcactg gctggtcaat ggctggctta cggtgttact   2880
cgcagtgtga ctaagcgttc agtcatgacg ctggcttacg ggtccaaaga gttcggcttc   2940
cgtcaacaag tgctggaaga taccattcag ccagctattg attccggcaa gggtctgatg   3000
ttcactcagc cgaatcaggc tgctggatac atggctaagc tgatttggga atctgtgagc   3060
```

gtgacggtgg tagctgcggt tgaagcaatg aactggctta agtctgctgc taagctgctg 3120
gctgctgagg tcaaagataa gaagactgga gagattcttc gcaagcgttg cgctgtgcat 3180
tgggtaactc ctgatggttt ccctgtgtgg caggaataca agaagcctat tcagacgcgc 3240
ttgaacctga tgttcctcgg tcagttccgc ttacagccta ccattaacac caacaaagat 3300
agcgagattg atgcacacaa acaggagtct ggtatcgctc ctaactttgt acacagccaa 3360
gacggtagcc accttcgtaa gactgtagtg tgggcacacg agaagtacgg aatcgaatct 3420
tttgcactga ttcacgactc cttcggtacc attccggctg acgctgcgaa cctgttcaaa 3480
gcagtgcgcg aaactatggt tgacacatat gagtcttgtg atgtactggc tgatttctac 3540
gaccagttcg ctgaccagtt gcacgagtct caattggaca aaatgccagc acttccggct 3600
aaaggtaact tgaacctccg tgacatctta gagtcggact tcgcgttcgc gtaacgccaa 3660
atcaatacga ctcactatag agggacaaac tcaaggtcat tcgcaagagt ggcctttatg 3720
attgaccttc ttccggttaa tacgactcac tataggagaa ccttaaggtt taactttaag 3780
acccttaagt gttaattaga gatttaaatt aaagaattac taagagagga ctttaagtat 3840
gcgtaacttc gaaaagatga ccaaacgttc taaccgtaat gctcgtgact tcgaggcaac 3900
caaaggtcgc aagttgaata agactaagcg tgaccgctct cacaagcgta gctgggaggg 3960
tcagtaagat gggacgttta tatagtggta atctggcagc attcaaggca gcaacaaaca 4020
agctgttcca gttagactta gcggtcattt atgatgactg gtatgatgcc tatacaagaa 4080
aagattgcat acggttacgt attgaggaca ggagtggaaa cctgattgat actagcacct 4140
tctaccacca cgacgaggac gttctgttca atatgtgtac tgattggttg aaccatatgt 4200
atgaccagtt gaaggactgg aagtaatacg actcagtata gggacaatgc ttaaggtcgc 4260
tctctaggag tggccttagt catttaacca ataggagata aacattatga tgaacattaa 4320
gactaacccg tttaaagccg tgtctttcgt agagtctgcc attaagaagg ctctggataa 4380
cgctgggtat cttatcgctg aaatcaagta cgatggtgta cgcgggaaca tctgcgtaga 4440
caatactgct aacagttact ggctctctcg tgtatctaaa acgattccgg cactggagca 4500
cttaaacggg tttgatgttc gctggaagcg tctactgaac gatgaccgtt gcttctacaa 4560
agatggcttt atgcttgatg gggaactcat ggtcaagggc gtagacttta acacagggtc 4620
cggcctactg cgtaccaaat ggactgacac gaagaaccaa gagttccatg aagagttatt 4680
cgttgaacca atccgtaaga aagataaagt tccctttaag ctgcacactg gacaccttca 4740
cataaaactg tacgctatcc tcccgctgca catcgtggag tctggagaag actgtgatgt 4800
catgacgttg ctcatgcagg aacacgttaa gaacatgctg cctctgctac aggaatactt 4860
ccctgaaatc gaatggcaag cggctgaatc ttacgaggtc tacgatatgg tagaactaca 4920
gcaactgtac gagcagaagc gagcagaagg ccatgagggt ctcattgtga aagacccgat 4980
gtgtatctat aagcgcggta agaaatctgg ctggtggaaa atgaaacctg agaacgaagc 5040
tgacggtatc attcagggtc tggtatgggg tacaaaaggt ctggctaatg aaggtaaagt 5100
gattggtttt gaggtgcttc ttgagagtgg tcgtttagtt aacgccacga atatctctcg 5160
cgccttaatg gatgagttca ctgagacagt aaaagaggcc accctaagtc aatggggatt 5220
ctttagccca tacggtattg gcgacaacga tgcttgtact attaaccctt acgatggctg 5280
ggcgtgtcaa attagctaca tggaggaaac acctgatggc tctttgcggc acccatcgtt 5340
cgtaatgttc cgtggcaccg aggacaaccc tcaagagaaa atgtaatcac actggctcac 5400

-continued

```
cttcgggtgg gcctttctgc gtttataagg agacacttta tgtttaagaa ggttggtaaa   5460
ttccttgcgg ctttggcagc tatcctgacg cttgcgtata ttcttgcggt ataccctcaa   5520
gtagcactag tagtagttgg cgcttgttac ttagcggcag tgtgtgcttg cgtgtggagt   5580
atagttaact ggtaatacga ctcactaaag gaggtacaca ccatgatgta cttaatgcca   5640
ttactcatcg tcattgtagg atgccttgcg ctccactgta gcgatgatga tatgccagat   5700
ggtcacgctt aatacgactc actaaaggag acactatatg tttcgacttc attacaacaa   5760
aagcgttaag aatttcacgg ttcgccgtgc tgaccgttca atcgtatgtg cgagcgagcg   5820
ccgagctaag atacctctta ttggtaacac agttcctttg gcaccgagcg tccacatcat   5880
tatcacccgt ggtgactttg agaaagcaat agacaagaaa cgtccggttc ttagtgtggc   5940
agtgacccgc ttcccgttcg tccgtctgtt actcaaacga atcaaggagg tgttctgatg   6000
ggactgttag atggtgaagc ctgggaaaaa gaaaacccgc cagtacaagc aactgggtgt   6060
atagcttgct tagagaaaga tgaccgttat ccacacacct gtaacaaagg agctaacgat   6120
atgaccgaac gtgaacaaga gatgatcatt aagttgatag acaataatga aggtcgccca   6180
gatgatttga atggctgcgg tattctctgc tccaatgtcc cttgccacct ctgccccgca   6240
aataacgatc aaaagataac cttaggtgaa atccgagcga tggacccacg taaaccacat   6300
ctgaataaac ctgaggtaac tcctacagat gaccagcctt ccgctgagac aatcgaaggt   6360
gtcactaagc cttcccacta catgctgttt gacgacattg aggctatcga agtgattgct   6420
cgttcaatga ccgttgagca gttcaaggga tactgcttcg gtaacatctt aaagtacaga   6480
ctacgtgctg gtaagaagtc agagttagcg tacttagaga aagacctagc gaaagcagac   6540
ttctataaag aactctttga gaaacataag gataaatgtt atgcataact tcaagtcaac   6600
cccacctgcc gacagcctat ctgatgactt cacatcttgc tcagagtggt gccgaaagat   6660
gtgggaagag acattcgacg atgcgtacat caagctgtat gaactttgga aatcgagagg   6720
tcaatgacta tgtcaaacgt aaatacaggt tcacttagtg tggacaataa gaagttttgg   6780
gctaccgtag agtcctcgga gcattccttc gaggttccaa tctacgctga gaccctagac   6840
gaagctctgg agttagccga atggcaatac gttccggctg gctttgaggt tactcgtgtg   6900
cgtccttgtg tagcaccgaa gtaatacgac tcactattag ggaagactcc ctctgagaaa   6960
ccaaacgaaa cctaaaggag attaacatta tggctaagaa gattttcacc tctgcgctgg   7020
gtaccgctga accttacgct tacatcgcca agccggacta cggcaacgaa gagcgtggct   7080
ttgggaaccc tcgtggtgtc tataaagttg acctgactat tcccaacaaa gacccgcgct   7140
gccagcgtat ggtcgatgaa atcgtgaagt gtcacgaaga ggcttatgct gctgccgttg   7200
aggaatacga agctaatcca cctgctgtag ctcgtggtaa gaaaccgctg aaaccgtatg   7260
agggtgacat gccgttcttc gataacggtg acggtacgac tacctttaag ttcaaatgct   7320
acgcgtcttt ccaagacaag aagaccaaag agaccaagca catcaatctg gttgtggttg   7380
actcaaaagg taagaagatg gaagacgttc cgattatcgg tggtggctct aagctgaaag   7440
ttaaatattc tctggttcca tacaagtgga acactgctgt aggtgcgagc gttaagctgc   7500
aactggaatc cgtgatgctg gtcgaactgg ctacctttgg tggcggtgaa gacgattggg   7560
ctgacgaagt tgaagagaac ggctatgttg cctctggttc tgccaaagcg agcaaaccac   7620
gcgacgaaga aagctgggac gaagacgacg aagagtccga ggaagcagac gaagacggag   7680
acttctaagt ggaactgcgg gagaaaatcc ttgagcgaat caaggtgact tcctctgggt   7740
gttgggagtg gcagggcgct acgaacaata aagggtacgg gcaggtgtgg tgcagcaata   7800
```

-continued

```
ccggaaaggt tgtctactgt catcgcgtaa tgtctaatgc tccgaaaggt tctaccgtcc   7860
tgcactcctg tgataatcca ttatgttgta accctgaaca cctatccata ggaactccaa   7920
aagagaactc cactgacatg gtaaataagg gtcgctcaca caaggggtat aaactttcag   7980
acgaagacgt aatggcaatc atggagtcca gcgagtccaa tgtatcctta gctcgcacct   8040
atggtgtctc ccaacagact atttgtgata tacgcaaagg gaggcgacat ggcaggttac   8100
ggcgctaaag gaatccgaaa ggttggagcg tttcgctctg gcctagagga caaggtttca   8160
aagcagttgg aatcaaaagg tattaaattc gagtatgaag agtggaaagt gccttatgta   8220
attccggcga gcaatcacac ttacactcca gacttcttac ttccaaacgg tatattcgtt   8280
gagacaaagg gtctgtggga aagcgatgat agaaagaagc acttattaat tagggagcag   8340
caccccgagc tagacatccg tattgtcttc tcaagctcac gtactaagtt atacaaaggt   8400
tctccaacgt cttatggaga gttctgcgaa aagcatggta ttaagttcgc tgataaactg   8460
atacctgctg agtggataaa ggaacccaag aaggaggtcc cctttgatag attaaaaagg   8520
aaaggaggaa agaaataatg gctcgtgtac agtttaaaca acgtgaatct actgacgcaa   8580
tctttgttca ctgctcggct accaagccaa gtcagaatgt tggtgtccgt gagattcgcc   8640
agtggcacaa agagcagggt tggctcgatg tgggatacca ctttatcatc aagcgagacg   8700
gtactgtgga ggcaggacga gatgagatgg ctgtaggctc tcacgctaag ggttacaacc   8760
acaactctat cggcgtctgc cttgttggtg gtatcgacga taaaggtaag ttcgacgcta   8820
actttacgcc agcccaaatg caatcccttc gctcactgct tgtcacactg ctggctaagt   8880
acgaaggcgc tggtcttcgc gcccatcatg aggtggcgcc gaaggcttgc ccttcgttcg   8940
accttaagcg ttggtgggag aagaacgaac tggtcacttc tgaccgtgga taatgatcta   9000
ttggaagtcg ttgcgtggat ttatagaact aggagggaat tgcatggaca attcgcacga   9060
ttccgatagt gtatttcttt accacattcc ttgtgacaac tgtgggagta gtgatgggaa   9120
ctcgctgttc tctgacggac acacgttctg ctacgtatgc gagaagtgga ctgctggtaa   9180
tgaagacact aaagagaggg cttcaaaacg gaaaccctca ggaggtaaac caatgactta   9240
caacgtgtgg aacttcgggg aatccaatgg acgctactcc gcgttaactg cgagaggaat   9300
ctccaaggaa acctgtcaga aggctggcta ctggattgcc aaagtagacg gtgtgatgta   9360
ccaagtggct gactatcggg accagaacgg caacattgtg agtcagaagg ttcgagataa   9420
agataagaac tttaagacca ctggtagtca caagagtgac gctctgttcg ggaagcactt   9480
gtggaatggt ggtaagaaga ttgtcgttac agaaggtgaa atcgacatgc ttaccgtgat   9540
ggaacttcaa gactgtaagt atcctgtagt gtcgttgggt cacggtgcct ctgccgctaa   9600
gaagacatgc gctgccaact acgaatactt tgaccagttc gaacagatta tcttaatgtt   9660
cgatatggac gaagcagggc gcaaagcagt cgaagaggct gcacaggttc tacctgctgg   9720
taaggtacga gtggcagttc ttccgtgtaa ggatgcaaac gagtgtcacc taaatggtca   9780
cgaccgtgaa atcatggagc aagtgtggaa tgctggtcct tggattcctg atggtgtggt   9840
atcggctctt tcgttacgtg aacgaatccg tgagcaccta tcgtccgagg aatcagtagg   9900
tttacttttc agtggctgca ctggtatcaa cgataagacc ttaggtgccc gtggtggtga   9960
agtcattatg gtcacttccg gttccggtat gggtaagtca acgttcgtcc gtcaacaagc  10020
tctacaatgg ggcacagcga tgggcaagaa ggtaggctta gcgatgcttg aggagtccgt  10080
tgaggagacc gctgaggacc ttataggtct acacaaccgt gtccgactga gacaatccga  10140
```

-continued

```
ctcactaaag agagagatta ttgagaacgg taagttcgac caatggttcg atgaactgtt  10200
cggcaacgat acgttccatc tatatgactc attcgccgag gctgagacgg atagactgct  10260
cgctaagctg gcctacatgc gctcaggctt gggctgtgac gtaatcattc tagaccacat  10320
ctcaatcgtc gtatccgctt ctggtgaatc cgatgagcgt aagatgattg acaacctgat  10380
gaccaagctc aaagggttcg ctaagtcaac tggggtggtg ctggtcgtaa tttgtcacct  10440
taagaaccca gacaaaggta aagcacatga ggaaggtcgc cccgtttcta ttactgacct  10500
acgtggttct ggcgcactac gccaactatc tgatactatt attgcccttg agcgtaatca  10560
gcaaggcgat atgcctaacc ttgtcctcgt tcgtattctc aagtgccgct ttactggtga  10620
tactggtatc gctggctaca tggaatacaa caaggaaacc ggatggcttg aaccatcaag  10680
ttactcaggg gaagaagagt cacactcaga gtcaacagac tggtccaacg acactgactt  10740
ctgacaggat tcttgacagt tgtttcatat gaagagattg ttaagtcacg ataatcaata  10800
ggagaaatca atatgatcgt ttctgacatc gaagctaacg ccctcttaga gagcgtcact  10860
aagttccact gcggggttat ctacgactac tccaccgctg agtacgtaag ctaccgtccg  10920
agtgacttcg gtgcgtatct ggatgcgctg gaagccgagg ttgcacgagg cggtcttatt  10980
gtgttccaca acggtcacaa gtatgacgtt cctgcattga ccaaactggc aaagttgcaa  11040
ttgaaccgag agttccacct tcctcgtgag aactgtattg acacccttgt gttgtcacgt  11100
ttgattcatt ccaacctcaa ggacaccgat atgggtcttc tgcgttccgg caagttgccc  11160
ggaaaacgct ttgggtctca cgctttggag gcgtggggtt atcgcttagg cgagatgaag  11220
ggtgaataca aagacgactt taagcgtatg cttgaagagc agggtgaaga atacgttgac  11280
ggaatggagt ggtggaactt caacgaagag atgatggact ataacgttca ggacgttgtg  11340
gtaactaaag ctctccttga gaagctactc tctgacaaac attacttccc tcctgagatt  11400
gactttacgg acgtaggata cactacgttc tggtcagaat cccttgaggc cgttgacatt  11460
gaacatcgtg ctgcatggct gctcgctaaa caagagcgca acgggttccc gtttgacaca  11520
aaagcaatcg aagagttgta cgtagagtta gctgctcgcc gctctgagtt gctccgtaaa  11580
ttgaccgaaa cgttcggctc gtggtatcag cctaaaggtg gcactgagat gttctgccat  11640
ccgcgaacag gtaagccact acctaaatac cctcgcatta agacacctaa agttggtggt  11700
atctttaaga agcctaagaa caaggcacag cgagaaggcc gtgagccttg cgaacttgat  11760
acccgcgagt acgttgctgg tgctccttac accccagttg aacatgttgt gtttaaccct  11820
tcgtctcgtg accacattca gaagaaactc caagaggctg ggtgggtccc gaccaagtac  11880
accgataagg gtgctcctgt ggtggacgat gaggtactcg aaggagtacg tgtagatgac  11940
cctgagaagc aagccgctat cgacctcatt aaagagtact tgatgattca gaagcgaatc  12000
ggacagtctg ctgagggaga caaagcatgg cttcgttatg ttgctgagga tggtaagatt  12060
catggttctg ttaaccctaa tggagcagtt acgggtcgtg cgacccatgc gttcccaaac  12120
cttgcgcaaa ttccgggtgt acgttctcct tatggagagc agtgtcgcgc tgcttttggc  12180
gctgagcacc atttggatgg gataactggt aagccttggg ttcaggctgg catcgacgca  12240
tccggtcttg agctacgctg cttggctcac ttcatggctc gctttgataa cggcgagtac  12300
gctcacgaga ttcttaacgg cgacatccac actaagaacc agatagctgc tgaactacct  12360
acccgagata acgctaagac gttcatctat gggttcctct atggtgctgg tgatgagaag  12420
attggacaga ttgttggtgc tggtaaagag cgcggtaagg aactcaagaa gaaattcctt  12480
gagaacaccc ccgcgattgc agcactccgc gagtctatcc aacagacact tgtcgagtcc  12540
```

-continued

```
tctcaatggg tagctggtga gcaacaagtc aagtggaaac gccgctggat taaaggtctg  12600
gatggtcgta aggtacacgt tcgtagtcct cacgctgcct tgaataccct actgcaatct  12660
gctggtgctc tcatctgcaa actgtggatt atcaagaccg aagagatgct cgtagagaaa  12720
ggcttgaagc atggctggga tggggacttt gcgtacatgg catgggtaca tgatgaaatc  12780
caagtaggct gccgtaccga agagattgct caggtggtca ttgagaccgc acaagaagcg  12840
atgcgctggg ttggagacca ctggaacttc cggtgtcttc tggataccga aggtaagatg  12900
ggtcctaatt gggcgatttg ccactgatac aggaggctac tcatgaacga aagacactta  12960
acaggtgctg cttctgaaat gctagtagcc tacaaattta ccaaagctgg gtacactgtc  13020
tattacccta tgctgactca gagtaaagag gacttggttg tatgtaagga tggtaaattt  13080
agtaaggttc aggttaaaac agccacaacg gttcaaacca acacaggaga tgccaagcag  13140
gttaggctag gtggatgcgg taggtccgaa tataaggatg gagactttga cattcttgcg  13200
gttgtggttg acgaagatgt gcttattttc acatgggacg aagtaaaagg taagacatcc  13260
atgtgtgtcg gcaagagaaa caaaggcata aaactatagg agaaattatt atggctatga  13320
caaagaaatt taaagtgtcc ttcgacgtta ccgcaaagat gtcgtctgac gttcaggcaa  13380
tcttagagaa agatatgctg catctatgta agcaggtcgg ctcaggtgcg attgtcccca  13440
atggtaaaca gaaggaaatg attgtccagt tcctgacaca cggtatggaa ggattgatga  13500
cattcgtagt acgtacatca tttcgtgagg ccattaagga catgcacgaa gagtatgcag  13560
ataaggactc tttcaaacaa tctcctgcaa cagtacggga ggtgttctga tgtctgacta  13620
cctgaaagtg ctgcaagcaa tcaaaagttg ccctaagact ttccagtcca actatgtacg  13680
gaacaatgcg agcctcgtag cggaggccgc ttcccgtggt cacatctcgt gcctgactac  13740
tagtggacgt aacggtggcg cttgggaaat cactgcttcc ggtactcgct ttctgaaacg  13800
aatgggagga tgtgtctaat gtctcgtgac cttgtgacta ttccacgcga tgtgtggaac  13860
gatatacagg gctacatcga ctctctggaa cgtgagaacg atagccttaa gaatcaacta  13920
atggaagctg acgaatacgt agcggaacta gaggagaaac ttaatggcac ttcttgacct  13980
taaacaattc tatgagttac gtgaaggctg cgacgacaag ggtatccttg tgatggacgg  14040
cgactggctg gtcttccaag ctatgagtgc tgctgagttt gatgcctctt gggaggaaga  14100
gatttggcac cgatgctgtg accacgctaa ggcccgtcag attcttgagg attccattaa  14160
gtcctacgag acccgtaaga aggcttgggc aggtgctcca attgtccttg cgttcaccga  14220
tagtgttaac tggcgtaaag aactggttga cccgaactat aaggctaacc gtaaggccgt  14280
gaagaaacct gtagggtact ttgagttcct tgatgctctc tttgagcgcg aagagttcta  14340
ttgcatccgt gagcctatgc ttgagggtga tgacgttatg ggagttattg cttccaatcc  14400
gtctgccttc ggtgctcgta aggctgtaat catctcttgc gataaggact ttaagaccat  14460
ccctaactgt gacttcctgt ggtgtaccac tggtaacatc ctgactcaga ccgaagagtc  14520
cgctgactgg tggcacctct tccagaccat caagggtgac atcactgatg gttactcagg  14580
gattgctgga tggggtgata ccgccgagga cttcttgaat aacccgttca taaccgagcc  14640
taaaacgtct gtgcttaagt ccggtaagaa caaaggccaa gaggttacta aatgggttaa  14700
acgcgaccct gagcctcatg agacgctttg ggactgcatt aagtccattg gcgcgaaggc  14760
tggtatgacc gaagaggata ttatcaagca gggccaaatg gctcgaatcc tacggttcaa  14820
cgagtacaac tttattgaca aggagattta cctgtggaga ccgtagcgta tattggtctg  14880
```

-continued

```
ggtctttgtg ttctcggagt gtgcctcatt tcgtggggcc tttgggactt agccagaata 14940
atcaagtcgt tacacgacac taagtgataa actcaaggtc cctaaattaa tacgactcac 15000
tatagggaga taggggcctt tacgattatt actttaagat ttaactctaa gaggaatctt 15060
tattatgtta acacctatta accaattact taagaaccct aacgatattc cagatgtacc 15120
tcgtgcaacc gctgagtatc tacaggttcg attcaactat gcgtacctcg aagcgtctgg 15180
tcatatagga cttatgcgtg ctaatggttg tagtgaggcc cacatcttgg gtttcattca 15240
gggcctacag tatgcctcta acgtcattga cgagattgag ttacgcaagg aacaactaag 15300
agatgatggg gaggattgac actatgtgtt tctcaccgaa aattaaaact ccgaagatgg 15360
ataccaatca gattcgagcc gttgagccag cgcctctgac ccaagaagtg tcaagcgtgg 15420
agttcggtgg gtcttctgat gagacggata ccgagggcac cgaagtgtct ggacgcaaag 15480
gcctcaaggt cgaacgtgat gattccgtag cgaagtctaa agccagcggc aatggctccg 15540
ctcgtatgaa atcttccatc cgtaagtccg catttggagg taagaagtga tgtctgagtt 15600
cacatgtgtg gaggctaaga gtcgcttccg tgcaatccgg tggactgtgg aacaccttgg 15660
gttgcctaaa ggattcgaag gacactttgt gggctacagc ctctacgtag acgaagtgat 15720
ggacatgtct ggttgccgtg aagagtacat tctggactct accggaaaac atgtagcgta 15780
cttcgcgtgg tgcgtaagct gtgacattca ccacaaagga gacattctgg atgtaacgtc 15840
cgttgtcatt aatcctgagg cagactctaa gggcttacag cgattcctag cgaaacgctt 15900
taagtacctt gcggaactcc acgattgcga ttgggtgtct cgttgtaagc atgaaggcga 15960
gacaatgcgt gtatacttta aggaggtata agttatgggt aagaaagtta agaaggccgt 16020
gaagaaagtc accaagtccg ttaagaaagt cgttaaggaa ggggctcgtc cggttaaaca 16080
ggttgctggc ggtctagctg gtctggctgg tggtactggt gaagcacaga tggtggaagt 16140
accacaagct gccgcacaga ttgttgacgt acctgagaaa gaggtttcca ctgaggacga 16200
agcacagaca gaaagcggac gcaagaaagc tcgtgctggc ggtaagaaat ccttgagtgt 16260
agcccgtagc tccggtggcg gtatcaacat ttaatcagga ggttatcgtg gaagactgca 16320
ttgaatggac cggaggtgtc aactctaagg gttatggtcg taagtgggtt aatggtaaac 16380
ttgtgactcc acataggcac atctatgagg agacatatgg tccagttcca acaggaattg 16440
tggtgatgca tatctgcgat aaccctaggt gctataacat aaagcacctt acgcttggaa 16500
ctccaaagga taattccgag gacatggtta ccaaaggtag acaggctaaa ggagaggaac 16560
taagcaagaa acttacagag tcagacgttc tcgctatacg ctcttcaacc ttaagccacc 16620
gctccttagg agaactgtat ggagtcagtc aatcaaccat aacgcgaata ctacagcgta 16680
agacatggag acacatttaa tggctgagaa acgaacagga cttgcggagg atggcgcaaa 16740
gtctgtctat gagcgtttaa agaacgaccg tgctccctat gagacacgcg ctcagaattg 16800
cgctcaatat accatcccat cattgttccc taaggactcc gataacgcct ctacagatta 16860
tcaaactccg tggcaagccg tgggcgctcg tggtctgaac aatctagcct ctaagctcat 16920
gctggctcta ttccctatgc agacttggat gcgacttact atatctgaat atgaagcaaa 16980
gcagttactg agcgaccccg atggactcgc taaggtcgat gagggcctct cgatggtaga 17040
gcgtatcatc atgaactaca ttgagtctaa cagttaccgc gtgactctct ttgaggctct 17100
caaacagtta gtcgtagctg gtaacgtcct gctgtaccta ccggaaccgg aagggtcaaa 17160
ctataatccc atgaagctgt accgattgtc ttcttatgtg gtccaacgag acgcattcgg 17220
caacgttctg caaatggtga ctcgtgacca gatagctttt ggtgctctcc ctgaggacat 17280
```

ccgtaaggct gtagaaggtc aaggtggtga gaagaaagct gatgagacaa tcgacgtgta 17340
cactcacatc tatctggatg aggactcagg tgaatacctc cgatacgaag aggtcgaggg 17400
tatggaagtc caaggctccg atgggactta tcctaaagag gcttgcccat acatcccgat 17460
tcggatggtc agactagatg gtgaatccta cggtcgttcg tacattgagg aatacttagg 17520
tgacttacgg tcccttgaaa atctccaaga ggctatcgtc aagatgtcca tgattagctc 17580
taaggttatc ggcttagtga atcctgctgg tatcacccag ccacgccgac tgaccaaagc 17640
tcagactggt gacttcgtta ctggtcgtcc agaagacatc tcgttcctcc aactggagaa 17700
gcaagcagac tttactgtag ctaaagccgt aagtgacgct atcgaggctc gcctttcgtt 17760
tgcctttatg ttgaactctg cggttcagcg tacaggtgaa cgtgtgaccg ccgaagagat 17820
tcggtatgta gcttctgaac ttgaagatac tttaggtggt gtctactcta tcctttctca 17880
agaattacaa ttgcctctgg tacgagtgct cttgaagcaa ctacaagcca cgcaacagat 17940
tcctgagtta cctaaggaag ccgtagagcc aaccattagt acaggtctgg aagcaattgg 18000
tcgaggacaa gaccttgata agctggagcg gtgtgtcact gcgtgggctg cactggcacc 18060
tatgcgggac gaccctgata ttaaccttgc gatgattaag ttacgtattg ccaacgctat 18120
cggtattgac acttctggta ttctactcac cgaagaacag aagcaacaga agatggccca 18180
acagtctatg caaatgggta tggataatgg tgctgctgcg ctggctcaag gtatggctgc 18240
acaagctaca gcttcacctg aggctatggc tgctgccgct gattccgtag gtttacagcc 18300
gggaatttaa tacgactcac tatagggaga cctcatcttt gaaatgagcg atgacaagag 18360
gttggagtcc tcggtcttcc tgtagttcaa ctttaaggag acaataataa tggctgaatc 18420
taatgcagac gtatatgcat cttttggcgt gaactccgct gtgatgtctg gtggttccgt 18480
tgaggaacat gagcagaaca tgctggctct tgatgttgct gcccgtgatg gcgatgatgc 18540
aatcgagtta gcgtcagacg aagtggaaac agaacgtgac ctgtatgaca actctgaccc 18600
gttcggtcaa gaggatgacg aaggccgcat tcaggttcgt atcggtgatg gctctgagcc 18660
gaccgatgtg gacactggag aagaaggcgt tgagggcacc gaaggttccg aagagtttac 18720
cccactgggc gagactccag aagaactggt agctgcctct gagcaacttg gtgagcacga 18780
agagggcttc caagagatga ttaacattgc tgctgagcgt ggcatgagtg tcgagaccat 18840
tgaggctatc cagcgtgagt acgaggagaa cgaagagttg tccgccgagt cctacgctaa 18900
gctggctgaa attggctaca cgaaggcttt cattgactcg tatatccgtg gtcaagaagc 18960
tctggtggag cagtacgtaa acagtgtcat tgagtacgct ggtggtcgtg aacgttttga 19020
tgcactgtat aaccaccttg agacgcacaa ccctgaggct gcacagtcgc tggataatgc 19080
gttgaccaat cgtgacttag cgaccgttaa ggctatcatc aacttggctg gtgagtctcg 19140
cgctaaggcg ttcggtcgta agccaactcg tagtgtgact aatcgtgcta ttccggctaa 19200
acctcaggct accaagcgtg aaggctttgc ggaccgtagc gagatgatta aagctatgag 19260
tgaccctcgg tatcgcacag atgccaacta tcgtcgtcaa gtcgaacaga aagtaatcga 19320
ttcgaacttc taactagatc tcattatcat atggctagca tgactggtgg acagcaaatg 19380
ggtactaacc aaggtaaagg tgtagttgct gctggagata aactggcgtt gttcttgaag 19440
gtatttggcg gtgaagtcct gactgcgttc gctcgtacct ccgtgaccac ttctcgccac 19500
atggtacgtt ccatctccag cggtaaatcc gctcagttcc ctgttctggg tcgcactcag 19560
gcagcgtatc tggctccggg cgagaacctc gacgataaac gtaaggacat caaacacacc 19620
gagaaggtaa tcaccattga cggtctcctg acggctgacg ttctgattta tgatattgag 19680
gacgcgatga accactacga cgttcgctct gagtatacct ctcagttggg tgaatctctg 19740
gcgatggctg cggatggtgc ggttctggct gagattgccg gtctgtgtaa cgtggaaagc 19800
aaatataatg agaacatcga gggcttaggt actgctaccg taattgagac cactcagaac 19860
aaggccgcac ttaccgacca agttgcgctg ggtaaggaga ttattgcggc tctgactaag 19920
gctcgtgcgg ctctgaccaa gaactatgtt ccggctgctg accgtgtgtt ctactgtgac 19980
ccagatagct actctgcgat tctggcagca ctgatgccga acgcagcaaa ctacgctgct 20040
ctgattgacc ctgagaaggg ttctatccgc aacgttatgg gctttgaggt tgtagaagtt 20100
ccgcacctca ccgctggtgg tgctggtacc gctcgtgagg gcactactgg tcagaagcac 20160
gtcttccctg ccaataaagg tgagggtaat gtcaaggttg ctaaggacaa cgttatcggc 20220
ctgttcatgc accgctctgc ggtaggtact gttaagctgc gtgacttggc tctggagcgc 20280
gctcgccgtg ctaacttcca agcggaccag attatcgcta agtacgcaat gggccacggt 20340
ggtcttcgcc cagaagctgc aggagctgtc gtattccagt caggtgtgat gctcggggat 20400
ctcgaggggg cccaggcggc cgcactcgac tcggtacccc gatggataat gatcatctgg 20460
atattgatgt tgatattact gaaccgtcat ttgaacattt aactattgcg acagtcaatg 20520
aacgccgaat gagaattgag attgaaaatc aagcaatttc tctgtcttaa aatctattga 20580
gatattctat cactcaaata gcaatataag gactctctat gaaatttgga aactttttgc 20640
ttacatacca acctccccaa ttttctcaaa cagaggtaat gaaacgtttg gttaaattag 20700
gtcgcatctc tgaggagtgt ggttttgata ccgtatggtt actggagcat catttcacgg 20760
agtttggttt gcttggtaac ccttatgtcg ctgctgcata tttacttggc gcgactaaaa 20820
aattgaatgt aggaactgcc gctattgttc ttcccacagc ccatccagta cgccaacttg 20880
aagatgtgaa tttattggat caaatgtcaa aaggacgatt tcggtttggt atttgccgag 20940
ggctttacaa caaggacttt cgcgtattcg gcacagatat gaataacagt cgcgccttag 21000
cggaatgctg gtacgggctg ataaagaatg gcatgacaga gggatatatg gaagctgata 21060
atgaacatat caagttccat aaggtaaaag taaacccccgc ggcgtatagc agaggtggcg 21120
caccggttta tgtggtggct gaatcagctt cgacgactga gtgggctgct caatttggcc 21180
taccgatgat attaagttgg attataaata ctaacgaaaa gaaagcacaa cttgagcttt 21240
ataatgaagt ggctcaagaa tatgggcacg atattcataa tatcgaccat tgcttatcat 21300
atataacatc tgtagatcat gactcaatta aagcgaaaga gatttgccgg aaatttctgg 21360
ggcattggta tgattcttat gtgaatgcta cgactatttt tgatgattca gaccaaacaa 21420
gaggttatga tttcaataaa gggcagtggc gtgactttgt attaaaagga cataaagata 21480
ctaatcgccg tattgattac agttacgaaa tcaatcccgt gggaacgccg caggaatgta 21540
ttgacataat tcaaaaagac attgatgcta caggaatatc aaatatttgt tgtggatttg 21600
aagctaatgg aacagtagac gaaattattg cttccatgaa gctcttccag tctgatgtca 21660
tgccatttct taaagaaaaa caacgttcgc tattatatta gctaaggaga aagaaatgaa 21720
atttggattg ttcttcctta acttcatcaa ttcaacaact gttcaagaac aaagtatagt 21780
tcgcatgcag gaaataacgg agtatgttga taagttgaat tttgaacaga ttttagtgta 21840
tgaaaatcat ttttcagata atggtgttgt cggcgctcct ctgactgttt ctggttttct 21900
gctcggttta acagagaaaa ttaaaattgg ttcattaaat cacatcatta caactcatca 21960
tcctgtcgcc atagcggagg aagcttgctt attggatcag ttaagtgaag ggagatttat 22020

```
tttagggttt agtgattgcg aaaaaaaaga tgaaatgcat ttttttaatc gcccggttga  22080
atatcaacag caactatttg aagagtgtta tgaaatcatt aacgatgctt taacaacagg  22140
ctattgtaat ccagataacg atttttatag cttccctaaa atatctgtaa atccccatgc  22200
ttatacgcca ggcggacctc ggaaatatgt aacagcaacc agtcatcata ttgttgagtg  22260
ggcggccaaa aaaggtattc ctctcatctt taagtgggat gattctaatg atgttagata  22320
tgaatatgct gaaagatata aagccgttgc ggataaatat gacgttgacc tatcagagat  22380
agaccatcag ttaatgatat tagttaacta taacgaagat agtaataaag ctaaacaaga  22440
gacgcgtgca tttattagtg attatgttct tgaaatgcac cctaatgaaa atttcgaaaa  22500
taaacttgaa gaaataattg cagaaaacgc tgtcggaaat tatacggagt gtataactgc  22560
ggctaagttg gcaattgaaa agtgtggtgc gaaaagtgta ttgctgtcct ttgaaccaat  22620
gaatgatttg atgagccaaa aaaatgtaat caatattgtt gatgataata ttaagaagta  22680
ccacatggaa tatacctaat agatttcgag ttgcagcgag gcggcaagtg aacgaatccc  22740
caggagcata gataactatg tgactggggt gagtgaaagc agccaacaaa gcagcagctt  22800
gaaagatgaa gggtataaaa gagtatgaca gcagtgctgc catactttct aatattatct  22860
tgaggagtaa aacaggtatg acttcatatg ttgataaaca agaaattaca gcaagctcag  22920
aaattgatga tttgattttt tcgagcgatc catctcgaat tcgagctccg tcgacaagct  22980
tgcggccgca ctcgagtaac tagttaaccc cttggggcct ctaaacgggt cttgaggggt  23040
tttttgctga aaggaggaac tatatgcgct catacgatat gaacgttgag actgccgctg  23100
agttatcagc tgtgaacgac attctggcgt ctatcggtga acctccggta tcaacgctgg  23160
aaggtgacgc taacgcagat gcagcgaacg ctcggcgtat tctcaacaag attaaccgac  23220
agattcaatc tcgtggatgg acgttcaaca ttgaggaagg cataacgcta ctacctgatg  23280
tttactccaa cctgattgta tacagtgacg actatttatc cctaatgtct acttccggtc  23340
aatccatcta cgttaaccga ggtggctatg tgtatgaccg aacgagtcaa tcagaccgct  23400
ttgactctgg tattactgtg aacattattc gtctccgcga ctacgatgag atgcctgagt  23460
gcttccgtta ctggattgtc accaaggctt cccgtcagtt caacaaccga ttctttgggg  23520
caccggaagt agagggtgta ctccaagaag aggaagatga ggctagacgt ctctgcatgg  23580
agtatgagat ggactacggt gggtacaata tgctggatgg agatgcgttc acttctggtc  23640
tactgactcg ctaacattaa taaataagga ggctctaatg gcactcatta gccaatcaat  23700
caagaacttg aagggtggta tcagccaaca gcctgacatc cttcgttatc cagaccaagg  23760
gtcacgccaa gttaacggtt ggtcttcgga gaccgagggc ctccaaaagc gtccacctct  23820
tgttttctta aatacacttg gagacaacgg tgcgttaggt caagctccgt acatccacct  23880
gattaaccga gatgagcacg aacagtatta cgctgtgttc actggtagcg gaatccgagt  23940
gttcgacctt tctggtaacg agaagcaagt taggtatcct aacggttcca actacatcaa  24000
gaccgctaat ccacgtaacg acctgcgaat ggttactgta gcagactata cgttcatcgt  24060
taaccgtaac gttgttgcac agaagaacac aaagtctgtc aacttaccga attacaaccc  24120
taatcaagac ggattgatta acgttcgtgg tggtcagtat ggtagggaac taattgtaca  24180
cattaacggt aaagacgttg cgaagtataa gataccagat ggtagtcaac ctgaacacgt  24240
aaacaatacg gatgcccaat ggttagctga agagttagcc aagcagatgc gcactaactt  24300
gtctgattgg actgtaaatg tagggcaagg gttcatccat gtgaccgcac ctagtggtca  24360
```

-continued

```
acagattgac tccttcacga ctaaagatgg ctacgcagac cagttgatta accctgtgac  24420
ccactacgct cagtcgttct ctaagctgcc acctaatgct cctaacggct acatggtgaa  24480
aatcgtaggg gacgcctcta agtctgccga ccagtattac gttcggtatg acgctgagcg  24540
gaaagtttgg actgagactt taggttggaa cactgaggac caagttctat gggaaaccat  24600
gccacacgct cttgtgcgag ccgctgacgg taatttcgac ttcaagtggc ttgagtggtc  24660
tcctaagtct tgtggtgacg ttgacaccaa cccttggcct tcttttgttg gttcaagtat  24720
taacgatgtg ttcttcttcc gtaaccgctt aggattcctt agtggggaga acatcatatt  24780
gagtcgtaca gccaaatact tcaacttcta ccctgcgtcc attgcgaacc ttagtgatga  24840
cgaccctata gacgtagctg tgagtaccaa ccgaatagca atccttaagt acgccgttcc  24900
gttctcagaa gagttactca tctggtccga tgaagcacaa ttcgtcctga ctgcctcggg  24960
tactctcaca tctaagtcgg ttgagttgaa cctaacgacc cagtttgacg tacaggaccg  25020
agcgagacct tttgggattg ggcgtaatgt ctactttgct agtccgaggt ccagcttcac  25080
gtccatccac aggtactacg ctgtgcagga tgtcagttcc gttaagaatg ctgaggacat  25140
tacatcacac gttcctaact acatccctaa tggtgtgttc agtatttgcg gaagtggtac  25200
ggaaaacttc tgttcggtac tatctcacgg ggaccctagt aaaatcttca tgtacaaatt  25260
cctgtacctg aacgaagagt taaggcaaca gtcgtggtct cattgggact ttggggaaaa  25320
cgtacaggtt ctagcttgtc agagtatcag ctcagatatg tatgtgattc ttcgcaatga  25380
gttcaatacg ttcctagcta gaatctcttt cactaagaac gccattgact tacagggaga  25440
accctatcgt gcctttatgg acatgaagat tcgatacacg attcctagtg gaacatacaa  25500
cgatgacaca ttcactacct ctattcatat tccaacaatt tatggtgcaa acttcgggag  25560
gggcaaaatc actgtattgg agcctgatgg taagataacc gtgtttgagc aacctacggc  25620
tgggtggaat agcgaccctt ggctgagact cagcggtaac ttggagggac gcatggtgta  25680
cattgggttc aacattaact tcgtatatga gttctctaag ttcctcatca agcagactgc  25740
cgacgacggg tctacctcca cggaagacat tgggcgctta cagttacgcc gagcgtgggt  25800
taactacgag aactctggta cgtttgacat ttatgttgag aaccaatcgt ctaactggaa  25860
gtacacaatg gctggtgccc gattaggctc taacactctg agggctggga gactgaactt  25920
agggaccgga caatatcgat tccctgtggt tggtaacgcc aagttcaaca ctgtatacat  25980
cttgtcagat gagactaccc ctctgaacat cattgggtgt ggctgggaag gtaactactt  26040
acggagaagt tccggtattt aattaaatat tctccctgtg gtggctcgaa attaatacga  26100
ctcactatag ggagaacaat acgactacgg gagggttttc ttatgatgac tataagacct  26160
actaaaagta cagactttga ggtattcact ccggctcacc atgacattct tgaagctaag  26220
gctgctggta ttgagccgag tttccctgat gcttccgagt gtgtcacgtt gagcctctat  26280
gggttccctc tagctatcgg tggtaactgc ggggaccagt gctggttcgt tacgagcgac  26340
caagtgtggc gacttagtgg aaaggctaag cgaaagttcc gtaagttaat catggagtat  26400
cgcgataaga tgcttgagaa gtatgatact ctttggaatt acgtatgggt aggcaatacg  26460
tcccacattc gtttcctcaa gactatcggt gcggtattcc atgaagagta cacacgagat  26520
ggtcaatttc agttatttac aatcacgaaa ggaggataac catatgtgtt gggcagccgc  26580
aatacctatc gctatatctg gcgctcaggc tatcagtggt cagaacgctc aggccaaaat  26640
gattgccgct cagaccgctg ctggtcgtcg tcaagctatg gaaatcatga ggcagacgaa  26700
catccagaat gctgacctat cgttgcaagc tcgaagtaaa cttgaggaag cgtccgccga  26760
```

-continued gttgacctca cagaacatgc agaaggtcca agctattggg tctatccgag cggctatcgg 26820
agagagtatg cttgaaggtt cctcaatgga ccgcattaag cgagtcacag aaggacagtt 26880
cattcgggaa gccaatatgg taactgagaa ctatcgccgt gactaccaag caatcttcgc 26940
acagcaactt ggtggtactc aaagtgctgc aagtcagatt gacgaaatct ataagagcga 27000
acagaaacag aagagtaagc tacagatggt tctggaccca ctggctatca tggggtcttc 27060
cgctgcgagt gcttacgcat ccggtgcgtt cgactctaag tccacaacta aggcacctat 27120
tgttgccgct aaaggaacca agacggggag gtaatgagct atgagtaaaa ttgaatctgc 27180
ccttcaagcg gcacaaccgg gactctctcg gttacgtggt ggtgctggag gtatgggcta 27240
tcgtgcagca accactcagg ccgaacagcc aaggtcaagc ctattggaca ccattggtcg 27300
gttcgctaag gctggtgccg atatgtatac cgctaaggaa caacgagcac gagacctagc 27360
tgatgaacgc tctaacgaga ttatccgtaa gctgacccct gagcaacgtc gagaagctct 27420
caacaacggg acccttctgt atcaggatga cccatacgct atggaagcac tccgagtcaa 27480
gactggtcgt aacgctgcgt atcttgtgga cgatgacgtt atgcagaaga taaaagaggg 27540
tgtcttccgt actcgcgaag agatggaaga gtatcgccat agtcgccttc aagagggcgc 27600
taaggtatac gctgagcagt tcggcatcga ccctgaggac gttgattatc agcgtggttt 27660
caacggggac attaccgagc gtaacatctc gctgtatggt gcgcatgata acttcttgag 27720
ccagcaagct cagaagggcg ctatcatgaa cagccgagtg gaactcaacg gtgtccttca 27780
agaccctgat atgctgcgtc gtccagactc tgctgacttc tttgagaagt atatcgacaa 27840
cggtctggtt actggcgcaa tcccatctga tgctcaagcc acacagctta taagccaagc 27900
gttcagtgac gcttctagcc gtgctggtgg tgctgacttc ctgatgcgag tcggtgacaa 27960
gaaggtaaca cttaacggag ccactacgac ttaccgagag ttgattggtg aggaacagtg 28020
gaacgctctc atggtcacag cacaacgttc tcagtttgag actgacgcga agctgaacga 28080
gcagtatcgc ttgaagatta actctgcgct gaaccaagag gacccaagga cagcttggga 28140
gatgcttcaa ggtatcaagg ctgaactaga taaggtccaa cctgatgagc agatgacacc 28200
acaacgtgag tggctaatct ccgcacagga acaagttcag aatcagatga acgcatggac 28260
gaaagctcag gccaaggctc tggacgattc catgaagtca atgaacaaac ttgacgtaat 28320
cgacaagcaa ttccagaagc gaatcaacgg tgagtgggtc tcaacggatt ttaaggatat 28380
gccagtcaac gagaacactg gtgagttcaa gcatagcgat atggttaact acgccaataa 28440
gaagctcgct gagattgaca gtatggacat tccagacggt gccaaggatg ctatgaagtt 28500
gaagtacctt caagcggact ctaaggacgg agcattccgt acagccatcg gaaccatggt 28560
cactgacgct ggtcaagagt ggtctgccgc tgtgattaac ggtaagttac cagaacgaac 28620
cccagctatg gatgctctgc gcagaatccg caatgctgac cctcagttga ttgctgcgct 28680
atacccagac caagctgagc tattcctgac gatggacatg atggacaagc agggtattga 28740
ccctcaggtt attcttgatg ccgaccgact gactgttaag cggtccaaag agcaacgctt 28800
tgaggatgat aaagcattcg agtctgcact gaatgcatct aaggctcctg agattgcccg 28860
tatgccagcg tcactgcgcg aatctgcacg taagatttat gactccgtta agtatcgctc 28920
ggggaacgaa agcatggcta tggagcagat gaccaagttc cttaaggaat ctacctacac 28980
gttcactggt gatgatgttg acggtgatac cgttggtgtg attcctaaga atatgatgca 29040
ggttaactct gacccgaaat catgggagca aggtcgggat attctggagg aagcacgtaa 29100

-continued

```
gggaatcatt gcgagcaacc cttggataac caataagcaa ctgaccatgt attctcaagg  29160
tgactccatt taccttatgg acaccacagg tcaagtcaga gtccgatacg acaaagagtt  29220
actctcgaag gtctggagtg agaaccagaa gaaactcgaa gagaaagctc gtgagaaggc  29280
tctggctgat gtgaacaagc gagcacctat agttgccgct acgaaggccc gtgaagctgc  29340
tgctaaacga gtccgagaga aacgtaaaca gactcctaag ttcatctacg gacgtaagga  29400
gtaactaaag gctacataag gaggccctaa atggataagt acgataagaa cgtaccaagt  29460
gattatgatg gtctgttcca aaaggctgct gatgccaacg gggtctctta tgacctttta  29520
cgtaaagtcg cttggacaga atcacgattt gtgcctacag caaaatctaa gactggacca  29580
ttaggcatga tgcaatttac caaggcaacc gctaaggccc tcggtctgcg agttaccgat  29640
ggtccagacg acgaccgact gaaccctgag ttagctatta atgctgccgc taagcaactt  29700
gcaggtctgg tagggaagtt tgatggcgat gaactcaaag ctgcccttgc gtacaaccaa  29760
ggcgagggac gcttgggtaa tccacaactt gaggcgtact ctaagggaga cttcgcatca  29820
atctctgagg agggacgtaa ctacatgcgt aaccttctgg atgttgctaa gtcacctatg  29880
gctggacagt tggaaacttt tggtggcata accccaaagg gtaaaggcat tccggctgag  29940
gtaggattgg ctggaattgg tcacaagcag aaagtaacac aggaacttcc tgagtccaca  30000
agttttgacg ttaagggtat cgaacaggag gctacggcga aaccattcgc caaggacttt  30060
tgggagaccc acggagaaac acttgacgag tacaacagtc gttcaacctt cttcggattc  30120
aaaaatgctg ccgaagctga actctccaac tcagtcgctg ggatggcttt ccgtgctggt  30180
cgtctcgata atggttttga tgtgtttaaa gacaccatta cgccgactcg ctggaactct  30240
cacatctgga ctccagagga gttagagaag attcgaacag aggttaagaa ccctgcgtac  30300
atcaacgttg taactggtgg ttcccctgag aacctcgatg acctcattaa attggctaac  30360
gagaactttg agaatgactc ccgcgctgcc gaggctggcc taggtgccaa actgagtgct  30420
ggtattattg gtgctggtgt ggacccgctt agctatgttc ctatggtcgg tgtcactggt  30480
aagggcttta agttaatcaa taaggctctt gtagttggtg ccgaaagtgc tgctctgaac  30540
gttgcatccg aaggtctccg tacctccgta gctggtggtg acgcagacta tgcgggtgct  30600
gccttaggtg gctttgtgtt tggcgcaggc atgtctgcaa tcagtgacgc tgtagctgct  30660
ggactgaaac gcagtaaacc agaagctgag ttcgacaatg agttcatcgg tcctatgatg  30720
cgattggaag cccgtgagac agcacgaaac gccaactctg cggacctctc tcggatgaac  30780
actgagaaca tgaagtttga aggtgaacat aatggtgtcc cttatgagga cttaccaaca  30840
gagagaggtg ccgtggtgtt acatgatggc tccgttctaa gtgcaagcaa cccaatcaac  30900
cctaagactc taaaagagtt ctccgaggtt gaccctgaga aggctgcgcg aggaatcaaa  30960
ctggctgggt tcaccgagat tggcttgaag accttggggt ctgacgatgc tgacatccgt  31020
agagtggcta tcgacctcgt tcgctctcct actggtatgc agtctggtgc ctcaggtaag  31080
ttcggtgcaa cagcttctga catccatgag agacttcatg gtactgacca gcgtacttat  31140
aatgacttgt acaaagcaat gtctgacgct atgaaagacc ctgagttctc tactggcggc  31200
gctaagatgt cccgtgaaga aactcgatac actatctacc gtagagcggc actagctatt  31260
gagcgtccag aactacagaa ggcactcact ccgtctgaga gaatcgttat ggacatcatt  31320
aagcgtcact ttgacaccaa gcgtgaactt atggaaaacc cagcaatatt cggtaacaca  31380
aaggctgtga gtatcttccc tgagagtcgc cacaaaggta cttacgttcc tcacgtatat  31440
gaccgtcatg ccaaggcgct gatgattcaa cgctacggtg ccgaaggttt gcaggaaggg  31500
```

-continued

```
attgcccgct catggatgaa cagctacgtc tccagacctg aggtcaaggc cagagtcgat  31560
gagatgctta aggaattaca cggggtgaag gaagtaacac cagagatggt agagaagtac  31620
gctatggata aggcttatgg tatctcccac tcagaccagt tcaccaacag ttccataata  31680
gaagagaaca ttgagggctt agtaggtatc gagaataact cattccttga ggcacgtaac  31740
ttgtttgatt cggacctatc catcactatg ccagacggac agcaattctc agtgaatgac  31800
ctaagggact tcgatatgtt ccgcatcatg ccagcgtatg accgccgtgt caatggtgac  31860
atcgccatca tggggtctac tggtaaaacc actaaggaac ttaaggatga gattttggct  31920
ctcaaagcga aagctgaggg agacggtaag aagactggcg aggtacatgc tttaatggat  31980
accgttaaga ttcttactgg tcgtgctaga cgcaatcagg acactgtgtg ggaaacctca  32040
ctgcgtgcca tcaatgacct agggttcttc gctaagaacg cctacatggg tgctcagaac  32100
attacggaga ttgctgggat gattgtcact ggtaacgttc gtgctctagg gcatggtatc  32160
ccaattctgc gtgatacact ctacaagtct aaaccagttt cagctaagga actcaaggaa  32220
ctccatgcgt ctctgttcgg gaaggaggtg gaccagttga ttcggcctaa acgtgctgac  32280
attgtgcagc gcctaaggga agcaactgat accggacctg ccgtggcgaa catcgtaggg  32340
accttgaagt attcaacaca ggaactggct gctcgctctc cgtggactaa gctactgaac  32400
ggaaccacta actaccttct ggatgctgcg cgtcaaggta tgcttgggga tgttattagt  32460
gccaccctaa caggtaagac tacccgctgg gagaaagaag gcttccttcg tggtgcctcc  32520
gtaactcctg agcagatggc tggcatcaag tctctcatca aggaacatat ggtacgcggt  32580
gaggacggga agtttaccgt taaggacaag caagcgttct ctatggaccc acgggctatg  32640
gacttatgga gactggctga caaggtagct gatgaggcaa tgctgcgtcc acataaggtg  32700
tccttacagg attcccatgc gttcggagca ctaggtaaga tggttatgca gtttaagtct  32760
ttcactatca agtcccttaa ctctaagttc ctgcgaacct tctatgatgg atacaagaac  32820
aaccgagcga ttgacgctgc gctgagcatc atcacctcta tgggtctcgc tggtggtttc  32880
tatgctatgg ctgcacacgt caaagcatac gctctgccta aggagaaacg taaggagtac  32940
ttggagcgtg cactggaccc aaccatgatt gcccacgctg cgttatctcg tagttctcaa  33000
ttgggtgctc ctttggctat ggttgaccta gttggtggtg ttttagggtt cgagtcctcc  33060
aagatggctc gctctacgat tctacctaag gacaccgtga aggaacgtga cccaaacaaa  33120
ccgtacacct ctagagaggt aatgggcgct atgggttcaa accttctgga acagatgcct  33180
tcggctggct ttgtggctaa cgtaggggct accttaatga atgctgctgg cgtggtcaac  33240
tcacctaata aagcaaccga gcaggacttc atgactggtc ttatgaactc cacaaaagag  33300
ttagtaccga acgacccatt gactcaacag cttgtgttga agatttatga ggcgaacggt  33360
gttaacttga gggagcgtag gaaataatac gactcactat agggagaggc gaaataatct  33420
tctccctgta gtctcttaga tttactttaa ggaggtcaaa tggctaacgt aattaaaacc  33480
gttttgactt accagttaga tggctccaat cgtgatttta atatcccgtt tgagtatcta  33540
gcccgtaagt tcgtagtggt aactcttatt ggtgtagacc gaaaggtcct tacgattaat  33600
acagactatc gctttgctac acgtactact atctctctga caaaggcttg ggtccagcc   33660
gatggctaca cgaccatcga gttacgtcga gtaacctcca ctaccgaccg attggttgac  33720
tttacggatg gttcaatcct ccgcgcgtat gaccttaacg tcgctcagat tcaaacgatg  33780
cacgtagcgg aagaggcccg tgacctcact acggatacta tcggtgtcaa taacgatggt  33840
```

-continued

```
cacttggatg ctcgtggtcg tcgaattgtg aacctagcga acgccgtgga tgaccgcgat  33900
gctgttccgt ttggtcaact aaagaccatg aaccagaact catggcaagc acgtaatgaa  33960
gccttacagt tccgtaatga ggctgagact ttcagaaacc aagcggaggg ctttaagaac  34020
gagtccagta ccaacgctac gaacacaaag cagtggcgcg atgagaccaa gggtttccga  34080
gacgaagcca agcggttcaa gaatacggct ggtcaatacg ctacatctgc tgggaactct  34140
gcttccgctg cgcatcaatc tgaggtaaac gctgagaact ctgccacagc atccgctaac  34200
tctgctcatt tggcagaaca gcaagcagac cgtgcggaac gtgaggcaga caagctggaa  34260
aattacaatg gattggctgg tgcaattgat aaggtagatg gaaccaatgt gtactggaaa  34320
ggaaatattc acgctaacgg gcgcctttac atgaccacaa acggttttga ctgtggccag  34380
tatcaacagt tctttggtgg tgtcactaat cgttactctg tcatggagtg gggagatgag  34440
aacggatggc tgatgtatgt tcaacgtaga gagtggacaa cagcgatagg cggtaacatc  34500
cagttagtag taaacggaca gatcatcacc caaggtggag ccatgaccgg tcagctaaaa  34560
ttgcagaatg ggcatgttct tcaattagag tccgcatccg acaaggcgca ctatattcta  34620
tctaaagatg gtaacaggaa taactggtac attggtagag ggtcagataa caacaatgac  34680
tgtaccttcc actcctatgt acatggtacg accttaacac tcaagcagga ctatgcagta  34740
gttaacaaac acttccacgt aggtcaggcc gttgtggcca ctgatggtaa tattcaaggt  34800
actaagtggg gaggtaaatg gctggatgct tacctacgtg acagcttcgt tgcgaagtcc  34860
aaggcgtgga ctcaggtgtg gtctggtagt gctggcggtg gggtaagtgt gactgtttca  34920
caggatctcc gcttccgcaa tatctggatt aagtgtgcca acaactcttg gaacttcttc  34980
cgtactggcc ccgatggaat ctacttcata gcctctgatg gtggatggtt acgattccaa  35040
atacactcca acggtctcgg attcaagaat attgcagaca gtcgttcagt acctaatgca  35100
atcatggtgg agaacgagta attggtaaat cacaaggaaa gacgtgtagt ccacggatgg  35160
actctcaagg aggtacaagg tgctatcatt agactttaac aacgaattga ttaaggctgc  35220
tccaattgtt gggacgggtg tagcagatgt tagtgctcga ctgttctttg ggttaagcct  35280
taacgaatgg ttctacgttg ctgctatcgc ctacacagtg gttcagattg gtgccaaggt  35340
agtcgataag atgattgact ggaagaaagc caataaggag tgatatgtat ggaaaaggat  35400
aagagcctta ttacattctt agagatgttg gacactgcga tggctcagcg tatgcttgcg  35460
gacctttcgg accatgagcg tcgctctccg caactctata atgctattaa caaactgtta  35520
gaccgccaca agttccagat tggtaagttg cagccggatg ttcacatctt aggtggcctt  35580
gctggtgctc ttgaagagta caaagagaaa gtcggtgata acggtcttac ggatgatgat  35640
atttacacat tacagtgata tactcaaggc cactacagat agtggtcttt atggatgtca  35700
ttgtctatac gagatgctcc tacgtgaaat ctgaaagtta acgggaggca ttatgctaga  35760
atttttacgt aagctaatcc cttgggttct cgctgggatg ctattcgggt taggatggca  35820
tctagggtca gactcaatgg acgctaaatg gaaacaggag gtacacaatg agtacgttaa  35880
gagagttgag gctgcgaaga gcactcaaag agcaatcgat gcggtatctg ctaagtatca  35940
agaagacctt gccgcgctgg aagggagcac tgataggatt atttctgatt tgcgtagcga  36000
caataagcgg ttgcgcgtca gagtcaaaac taccggaacc tccgatggtc agtgtggatt  36060
cgagcctgat ggtcgagccg aacttgacga ccgagatgct aaacgtattc tcgcagtgac  36120
ccagaagggt gacgcatgga ttcgtgcgtt acaggatact attcgtgaac tgcaacgtaa  36180
gtaggaaatc aagtaaggag gcaatgtgtc tactcaatcc aatcgtaatg cgctcgtagt  36240
```

ggcgcaactg aaaggagact tcgtggcgtt cctattcgtc ttatggaagg cgctaaacct 36300
accggtgccc actaagtgtc agattgacat ggctaaggtg ctggcgaatg gagacaacaa 36360
gaagttcatc ttacaggctt tccgtggtat cggtaagtcg ttcatcacat gtgcgttcgt 36420
tgtgtggtcc ttatggagag accctcagtt gaagatactt atcgtatcag cctctaagga 36480
gcgtgcagac gctaactcca tctttattaa gaacatcatt gacctgctgc cattcctatc 36540
tgagttaaag ccaagacccg gacagcgtga ctcggtaatc agctttgatg taggcccagc 36600
caatcctgac cactctccta gtgtgaaatc agtaggtatc actggtcagt taactggtag 36660
ccgtgctgac attatcattg cggatgacgt tgagattccg tctaacagcg caactatggg 36720
tgcccgtgag aagctatgga ctctggttca ggagttcgct gcgttactta aaccgctgcc 36780
ttcctctcgc gttatctacc ttggtacacc tcagacagag atgactctct ataaggaact 36840
tgaggataac cgtgggtaca caaccattat ctggcctgct ctgtacccaa ggacacgtga 36900
agagaacctc tattactcac agcgtcttgc tcctatgtta cgcgctgagt acgatgagaa 36960
ccctgaggca cttgctggga ctccaacaga cccagtgcgc tttgaccgtg atgacctgcg 37020
cgagcgtgag ttggaatacg gtaaggctgg ctttacgcta cagttcatgc ttaaccctaa 37080
ccttagtgat gccgagaagt acccgctgag gcttcgtgac gctatcgtag cggccttaga 37140
cttagagaag gccccaatgc attaccagtg gcttccgaac cgtcagaaca tcattgagga 37200
ccttcctaac gttggcctta agggtgatga cctgcatacg taccacgatt gttccaacaa 37260
ctcaggtcag taccaacaga agattctggt cattgaccct agtggtcgcg gtaaggacga 37320
aacaggttac gctgtgctgt acacactgaa cggttacatc taccttatgg aagctggagg 37380
tttccgtgat ggctactccg ataagaccct tgagttactc gctaagaagg caaagcaatg 37440
gggagtccag acggttgtct acgagagtaa cttcggtgac ggtatgttcg gtaaggtatt 37500
cagtcctatc cttcttaaac accacaactg tgcgatggaa gagattcgtg cccgtggtat 37560
gaaagagatg cgtatttgcg atacccttga gccagtcatg cagactcacc gccttgtaat 37620
tcgtgatgag gtcattaggg ccgactacca gtccgctcgt gacgtagacg gtaagcatga 37680
cgttaagtac tcgttgttct accagatgac ccgtatcact cgtgagaaag gcgctctggc 37740
tcatgatgac cgattggatg cccttgcgtt aggcattgag tatctccgtg agtccatgca 37800
gttggattcc gttaaggtcg agggtgaagt acttgctgac ttccttgagg aacacatgat 37860
gcgtcctacg gttgctgcta cgcatatcat tgagatgtct gtgggaggag ttgatgtgta 37920
ctctgaggac gatgagggtt acggtacgtc tttcattgag tggtgattta tgcattagga 37980
ctgcataggg atgcactata gaccacggat ggtcagttct ttaagttact gaaaagacac 38040
gataaattaa tacgactcac tatagggaga ggagggacga aaggttacta tatagatact 38100
gaatgaatac ttatagagtg cataaagtat gcataatggt gtacctagag tgacctctaa 38160
gaatggtgat tatattgtat tagtatcacc ttaacttaag gaccaacata aagggaggag 38220
actcatgttc cgcttattgt tgaacctact gcggcataga gtcacctacc gatttcttgt 38280
ggtactttgt gctgcccttg ggtacgcatc tcttactgga gacctcagtt cactggagtc 38340
tgtcgtttgc tctatactca cttgtagcga ttagggtctt cctgaccgac tgatggctca 38400
ccgagggatt cagcggtatg attgcatcac accacttcat ccctatagag tcaagtccta 38460
aggtataccc ataaagagcc tctaatggtc tatcctaagg tctataccta aagataggcc 38520
atcctatcag tgtcacctaa agagggtctt agagagggcc tatggagttc ctatagggtc 38580

-continued ctttaaaata taccataaaa atctgagtga ctatctcaca gtgtacggac ctaaagttcc 38640
cccatagggg gtacctaaag cccagccaat cacctaaagt caaccttcgg ttgaccttga 38700
gggttcccta agggttgggg atgacccttg ggtttgtctt tgggtgttac cttgagtgtc 38760
tctctgtgtc cct 38773

<210> SEQ ID NO 3
<211> LENGTH: 44507
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (37987)..(37992)
<223> OTHER INFORMATION: a, c, t, g, unknown or other
<220> FEATURE:
<221> NAME/KEY: modified_base
<222> LOCATION: (40977)..(40982)
<223> OTHER INFORMATION: a, c, t, g, unknown or other

<400> SEQUENCE: 3
gggcggcgac ctcgcgggtt ttcgctattt atgaaaattt tccggtttaa ggcgtttccg 60
ttcttcttcg tcataactta atgtttttat ttaaaatacc ctctgaaaag aaaggaaacg 120
acaggtgctg aaagcgaggc tttttggcct ctgtcgtttc ctttctctgt ttttgtccgt 180
ggaatgaaca atggaagtca acaaaaagca gctggctgac attttcggtg cgagtatccg 240
taccattcag aactggcagg aacagggaat gcccgttctg cgaggcggtg gcaagggtaa 300
tgaggtgctt tatgactctg ccgccgtcat aaaatggtat gccgaaaggg atgctgaaat 360
tgagaacgaa aagctgcgcc gggaggttga agaactgcgg caggccagcg aggcagatct 420
ccagccagga actattgagt acgaacgcca tcgacttacg cgtgcgcagg ccgacgcaca 480
ggaactgaag aatgccagag actccgctga agtggtggaa accgcattct gtactttcgt 540
gctgtcgcgg atcgcaggtg aaattgccag tattctcgac gggctccccc tgtcggtgca 600
gcggcgtttt ccggaactgg aaaaccgaca tgttgatttc ctgaaacggg atatcatcaa 660
agccatgaac aaagcagccg cgctggatga actgataccg gggttgctga gtgaatatat 720
cgaacagtca ggttaacagg ctgcggcatt ttgtccgcgc cgggcttcgc tcactgttca 780
ggccggagcc acagaccgcc gttgaatggg cggatgctaa ttactatctc ccgaaagaat 840
ccgcatacca ggaagggcgc tgggaaacac tgccctttca gcgggccatc atgaatgcga 900
tgggcagcga ctacatccgt gaggtgaatg tggtgaagtc tgcccgtgtc ggttattcca 960
aaatgctgct gggtgtttat gcctacttta tagagcataa gcagcgcaac acccttatct 1020
ggttgccgac ggatggtgat gccgagaact ttatgaaaac ccacgttgag ccgactattc 1080
gtgatattcc gtcgctgctg gcgctggccc cgtggtatgg caaaaagcac cgggataaca 1140
cgctcaccat gaagcgtttc actaatgggc gtggcttctg gtgcctgggc ggtaaagcgg 1200
caaaaaacta ccgtgaaaag tcggtggatg tggcgggtta tgatgaactt gctgcttttg 1260
atgatgatat tgaacaggaa ggctctccga cgttcctggg tgacaagcgt attgaaggct 1320
cggtctggcc aaagtccatc cgtggctcca cgccaaaagt gagaggcacc tgtcagattg 1380
agcgtgcagc cagtgaatcc ccgcatttta tgcgttttca tgttgcctgc ccgcattgcg 1440
gggaggagca gtatcttaaa tttggcgaca aagagacgcc gtttggcctc aaatggacgc 1500
cggatgaccc ctccagcgtg ttttatctct gcgagcataa tgcctgcgtc atccgccagc 1560

-continued

```
aggagctgga ctttactgat gcccgttata tctgcgaaaa gaccgggatc tggacccgtg   1620
atggcattct ctggttttcg tcatccggtg aagagattga gccacctgac agtgtgacct   1680
ttcacatctg gacagcgtac agcccgttca ccacctgggt gcagattgtc aaagactgga   1740
tgaaaacgaa aggggatacg ggaaaacgta aaaccttcgt aaacaccacg ctcggtgaga   1800
cgtgggaggc gaaaattggc gaacgtccgg atgctgaagt gatggcagag cggaaagagc   1860
attattcagc gcccgttcct gaccgtgtgg cttacctgac cgccggtatc gactcccagc   1920
tggaccgcta cgaaatgcgc gtatggggat gggggccggg tgaggaaagc tggctgattg   1980
accggcagat tattatgggc cgccacgacg atgaacagac gctgctgcgt gtggatgagg   2040
ccatcaataa aacctatacc cgccggaatg gtgcagaaat gtcgatatcc cgtatctgct   2100
gggatactgg cgggattgac ccgaccattg tgtatgaacg ctcgaaaaaa catgggctgt   2160
tccgggtgat ccccattaaa ggggcatccg tctacggaaa gccggtggcc agcatgccac   2220
gtaagcgaaa caaaaacggg gtttacctta ccgaaatcgg tacggatacc gcgaaagagc   2280
agatttataa ccgcttcaca ctgacgccgg aaggggatga accgcttccc ggtgccgttc   2340
acttcccgaa taacccggat atttttgatc tgaccgaagc gcagcagctg actgctgaag   2400
agcaggtcga aaaatgggtg gatggcagga aaaaaatact gtgggacagc aaaaagcgac   2460
gcaatgaggc actcgactgc ttcgtttatg cgctggcggc gctgcgcatc agtatttccc   2520
gctggcagct ggatctcagt gcgctgctgg cgagcctgca ggaagaggat ggtgcagcaa   2580
ccaacaagaa aacactggca gattacgccc gtgccttatc cggagaggat gaatgacgcg   2640
acaggaagaa cttgccgctg cccgtgcggc actgcatgac ctgatgacag gtaaacgggt   2700
ggcaacagta cagaaagacg gacgaagggt ggagtttacg gccacttccg tgtctgacct   2760
gaaaaaatat attgcagagc tggaagtgca gaccggcatg acacagcgac gcaggggacc   2820
tgcaggattt tatgtatgaa aacgcccacc attcccaccc ttctggggcc ggacggcatg   2880
acatcgctgc gcgaatatgc cggttatcac ggcggtggca gcggatttgg agggcagttg   2940
cggtcgtgga acccaccgag tgaaagtgtg gatgcagccc tgttgcccaa ctttacccgt   3000
ggcaatgccc gcgcagacga tctggtacgc aataacggct atgccgccaa cgccatccag   3060
ctgcatcagg atcatatcgt cgggtctttt ttccggctca gtcatcgccc aagctggcgc   3120
tatctgggca tcggggagga agaagcccgt gccttttccc gcgaggttga agcggcatgg   3180
aaagagtttg ccgaggatga ctgctgctgc attgacgttg agcgaaaacg cacgtttacc   3240
atgatgattc gggaaggtgt ggccatgcac gcctttaacg gtgaactgtt cgttcaggcc   3300
acctgggata ccagttcgtc gcggcttttc cggacacagt tccggatggt cagcccgaag   3360
cgcatcagca acccgaacaa taccggcgac agccggaact gccgtgccgg tgtgcagatt   3420
aatgacagcg gtgcggcgct gggatattac gtcagcgagg acgggtatcc tggctggatg   3480
ccgcagaaat ggacatggat accccgtgag ttacccggcg ggcgcgcctc gttcattcac   3540
gtttttgaac ccgtggagga cgggcagact cgcggtgcaa atgtgtttta cagcgtgatg   3600
gagcagatga agatgctcga cacgctgcag aacacgcagc tgcagagcgc cattgtgaag   3660
gcgatgtatg ccgccaccat tgagagtgag ctggatacgc agtcagcgat ggattttatt   3720
ctgggcgcga acagtcagga gcagcgggaa aggctgaccg gctggattgg tgaaattgcc   3780
gcgtattacg ccgcagcgcc ggtccggctg ggaggcgcaa aagtaccgca cctgatgccg   3840
ggtgactcac tgaacctgca gacggctcag gatacggata acggctactc cgtgtttgag   3900
cagtcactgc tgcggtatat cgctgccggg ctgggtgtct cgtatgagca gctttcccgg   3960
```

```
aattacgccc agatgagcta ctccacggca cgggccagtg cgaacgagtc gtgggcgtac   4020
tttatggggc ggcgaaaatt cgtcgcatcc cgtcaggcga gccagatgtt tctgtgctgg   4080
ctggaagagg ccatcgttcg ccgcgtggtg acgttacctt caaaagcgcg cttcagtttt   4140
caggaagccc gcagtgcctg gggaactgc gactggatag gctccggtcg tatggccatc   4200
gatggtctga aagaagttca ggaagcggtg atgctgatag aagccggact gagtacctac   4260
gagaaagagt gcgcaaaacg cggtgacgac tatcaggaaa tttttgccca gcaggtccgt   4320
gaaacgatgg agcgccgtgc agccggtctt aaaccgcccg cctgggcggc tgcagcattt   4380
gaatccgggc tgcgacaatc aacagaggag gagaagagtg acagcagagc tgcgtaatct   4440
cccgcatatt gccagcatgg cctttaatga gccgctgatg cttgaacccg cctatgcgcg   4500
ggttttcttt tgtgcgcttg caggccagct tgggatcagc agcctgacgg atgcggtgtc   4560
cggcgacagc ctgactgccc aggaggcact cgcgacgctg gcattatccg gtgatgatga   4620
cggaccacga caggcccgca gttatcaggt catgaacggc atcgccgtgc tgccggtgtc   4680
cggcacgctg gtcagccgga cgcgggcgct gcagccgtac tcggggatga ccggttacaa   4740
cggcattatc gcccgtctgc aacaggctgc cagcgatccg atggtggacg gcattctgct   4800
cgatatggac acgcccggcg ggatggtggc gggggcattt gactgcgctg acatcatcgc   4860
ccgtgtgcgt gacataaaac cggtatgggc gcttgccaac gacatgaact gcagtgcagg   4920
tcagttgctt gccagtgccg cctcccggcg tctggtcacg cagaccgccc ggacaggctc   4980
catcggcgtc atgatggctc acagtaatta cggtgctgcg ctggagaaac agggtgtgga   5040
aatcacgctg atttacagcg gcagccataa ggtggatggc aacccctaca gccatcttcc   5100
ggatgacgtc cgggagacac tgcagtcccg gatggacgca acccgccaga tgtttgcgca   5160
gaaggtgtcg gcatataccg gcctgtccgt gcaggttgtg ctggataccg aggctgcagt   5220
gtacagcggt caggaggcca ttgatgccgg actggctgat gaacttgtta acagcaccga   5280
tgcgatcacc gtcatgcgtg atgcactgga tgcacgtaaa tcccgtctct caggagggcg   5340
aatgaccaaa gagactcaat caacaactgt ttcagccact gcttcgcagg ctgacgttac   5400
tgacgtggtg ccagcgacgg agggcgagaa cgccagcgcg gcgcagccgg acgtgaacgc   5460
gcagatcacc gcagcggttg cggcagaaaa cagccgcatt atggggatcc tcaactgtga   5520
ggaggctcac ggacgcgaag aacaggcacg cgtgctggca gaaacccccg gtatgaccgt   5580
gaaaacggcc cgccgcattc tggccgcagc accacagagt gcacaggcgc gcagtgacac   5640
tgcgctggat cgtctgatgc agggggcacc ggcaccgctg gctgcaggta acccggcatc   5700
tgatgccgtt aacgatttgc tgaacacacc agtgtaaggg atgtttatga cgagcaaaga   5760
aacctttacc cattaccagc cgcagggcaa cagtgacccg gctcataccg caaccgcgcc   5820
cctagacctt catcactaaa ggccgcctgt gcggcttttt ttacgggatt tttttatgtc   5880
gatgtacaca accgcccaac tgctggcggc aaatgagcag aaatttaagt ttgatccgct   5940
gtttctgcgt ctctttttcc gtgagagcta tcccttcacc acggagaaag tctatctctc   6000
acaaattccg ggactggtaa acatggcgct gtacgtttcg ccgattgttt ccggtgaggt   6060
tatccgttcc cgtggcggct ccacctctga atttacgccg ggatatgtca agccgaagca   6120
tgaagtgaat ccgcagatga ccctgcgtcg cctgccggat gaagatccgc agaatctggc   6180
ggacccggct taccgccgcc gtcgcatcat catgcagaac atgcgtgacg aagagctggc   6240
cattgctcag gtcgaagaga tgcaggcagt ttctgccgtg cttaagggca aatacaccat   6300
```

-continued

```
gaccggtgaa gccttcgatc cggttgaggt ggatatgggc cgcagtgagg agaataacat   6360
cacgcagtcc ggcggcacgg agtggagcaa gcgtgacaag tccacgtatg acccgaccga   6420
cgatatcgaa gcctacgcgc tgaacgccag cggtgtggtg aatatcatcg tgttcgatcc   6480
gaaaggctgg gcgctgttcc gttccttcaa agccgtcaag gagaagctgg atacccgtcg   6540
tggctctaat tccgagctgg agacagcggt gaaagacctg ggcaaagcgg tgtcctataa   6600
ggggatgtat ggcgatgtgg ccatcgtcgt gtattccgga cagtacgtgg aaaacggcgt   6660
caaaaagaac ttcctgccgg acaacacgat ggtgctgggg aacactcagg cacgcggtct   6720
gcgcacctat ggctgcattc aggatgcgga cgcacagcgc gaaggcatta acgcctctgc   6780
ccgttacccg aaaaactggg tgaccaccgg cgatccggcg cgtgagttca ccatgattca   6840
gtcagcaccg ctgatgctgc tggctgaccc tgatgagttc gtgtccgtac aactggcgta   6900
atcatggccc ttcggggcca ttgtttctct gtggaggagt ccatgacgaa agatgaactg   6960
attgcccgtc tccgctcgct gggtgaacaa ctgaaccgtg atgtcagcct gacggggacg   7020
aaagaagaac tggcgctccg tgtggcagag ctgaaagagg agcttgatga cacggatgaa   7080
actgccggtc aggacacccc tctcagccgg gaaaatgtgc tgaccggaca tgaaaatgag   7140
gtgggatcag cgcagccgga taccgtgatt ctggatacgt ctgaactggt cacggtcgtg   7200
gcactggtga agctgcatac tgatgcactt cacgccacgc gggatgaacc tgtggcattt   7260
gtgctgccgg gaacggcgtt tcgtgtctct gccggtgtgg cagccgaaat gacagagcgc   7320
ggcctggcca gaatgcaata acgggaggcg ctgtggctga tttcgataac ctgttcgatg   7380
ctgccattgc ccgcgccgat gaaacgatac gcgggtacat gggaacgtca gccaccatta   7440
catccggtga gcagtcaggt gcggtgatac gtggtgtttt tgatgaccct gaaaatatca   7500
gctatgccgg acagggcgtg cgcgttgaag gctccagccc gtccctgttt gtccggactg   7560
atgaggtgcg gcagctgcgg cgtggagaca cgctgaccat cggtgaggaa aatttctggg   7620
tagatcgggt ttcgccggat gatggcggaa gttgtcatct ctggcttgga cggggcgtac   7680
cgcctgccgt taaccgtcgc cgctgaaagg gggatgtatg gccataaaag gtcttgagca   7740
ggccgttgaa aacctcagcc gtatcagcaa aacggcggtg cctggtgccg ccgcaatggc   7800
cattaaccgc gttgcttcat ccgcgatatc gcagtcggcg tcacaggttg cccgtgagac   7860
aaaggtacgc cggaaactgg taaaggaaag ggccaggctg aaaagggcca cggtcaaaaa   7920
tccgcaggcc agaatcaaag ttaaccgggg ggatttgccc gtaatcaagc tgggtaatgc   7980
gcgggttgtc ctttcgcgcc gcaggcgtcg taaaaagggg cagcgttcat ccctgaaagg   8040
tggcggcagc gtgcttgtgg tgggtaaccg tcgtattccc ggcgcgttta ttcagcaact   8100
gaaaaatggc cggtggcatg tcatgcagcg tgtggctggg aaaaaccgtt accccattga   8160
tgtggtgaaa atcccgatgg cggtgccgct gaccacggcg tttaaacaaa atattgagcg   8220
gatacggcgt gaacgtcttc cgaaagagct gggctatgcg ctgcagcatc aactgaggat   8280
ggtaataaag cgatgaaaca tactgaactc cgtgcagccg tactggatgc actggagaag   8340
catgacaccg gggcgacgtt ttttgatggt cgccccgctg tttttgatga ggcggatttt   8400
ccggcagttg ccgtttatct caccggcgct gaatacacgg gcgaagagct ggacagcgat   8460
acctggcagg cggagctgca tatcgaagtt ttcctgcctg ctcaggtgcc ggattcagag   8520
ctggatgcgt ggatggagtc ccggatttat ccggtgatga gcgatatccc ggcactgtca   8580
gatttgatca ccagtatggt ggccagcggc tatgactacc ggcgcgacga tgatgcgggc   8640
ttgtggagtt cagccgatct gacttatgtc attacctatg aaatgtgagg acgctatgcc   8700
```

-continued tgtaccaaat cctacaatgc cggtgaaagg tgccgggacc accctgtggg tttataaggg 8760
gagcggtgac ccttacgcga atccgctttc agacgttgac tggtcgcgtc tggcaaaagt 8820
taaagacctg acgcccggcg aactgaccgc tgagtcctat gacgacagct atctcgatga 8880
tgaagatgca gactggactg cgaccgggca ggggcagaaa tctgccggag ataccagctt 8940
cacgctggcg tggatgcccg gagagcaggg gcagcaggcg ctgctggcgt ggtttaatga 9000
aggcgatacc cgtgcctata aaatccgctt cccgaacggc acggtcgatg tgttccgtgg 9060
ctgggtcagc agtatcggta aggcggtgac ggcgaaggaa gtgatcaccc gcacggtgaa 9120
agtcaccaat gtgggacgtc cgtcgatggc agaagatcgc agcacggtaa cagcggcaac 9180
cggcatgacc gtgacgcctg ccagcacctc ggtggtgaaa gggcagagca ccacgctgac 9240
cgtggccttc cagccggagg gcgtaaccga caagagcttt cgtgcggtgt ctgcggataa 9300
aacaaaagcc accgtgtcgg tcagtggtat gaccatcacc gtgaacggcg ttgctgcagg 9360
caaggtcaac attccggttg tatccggtaa tggtgagttt gctgcggttg cagaaattac 9420
cgtcaccgcc agttaatccg gagagtcagc gatgttcctg aaaaccgaat catttgaaca 9480
taacggtgtg accgtcacgc tttctgaact gtcagccctg cagcgcattg agcatctcgc 9540
cctgatgaaa cggcaggcag aacaggcgga gtcagacagc aaccggaagt ttactgtgga 9600
agacgccatc agaaccggcg cgtttctggt ggcgatgtcc ctgtggcata accatccgca 9660
gaagacgcag atgccgtcca tgaatgaagc cgttaaacag attgagcagg aagtgcttac 9720
cacctggccc acggaggcaa tttctcatgc tgaaaacgtg gtgtaccggc tgtctggtat 9780
gtatgagttt gtggtgaata atgcccctga acagacagag gacgccgggc ccgcagagcc 9840
tgtttctgcg ggaaagtgtt cgacggtgag ctgagttttg ccctgaaact ggcgcgtgag 9900
atggggcgac ccgactggcg tgccatgctt gccgggatgt catccacgga gtatgccgac 9960
tggcaccgct tttacagtac ccattatttt catgatgttc tgctggatat gcacttttcc 10020
gggctgacgt acaccgtgct cagcctgttt ttcagcgatc cggatatgca tccgctggat 10080
ttcagtctgc tgaaccggcg cgaggctgac gaagagcctg aagatgatgt gctgatgcag 10140
aaagcggcag ggcttgccgg aggtgtccgc tttggcccgg acgggaatga agttatcccc 10200
gcttccccgg atgtggcgga catgacggag gatgacgtaa tgctgatgac agtatcagaa 10260
gggatcgcag gaggagtccg gtatggctga accggtaggc gatctggtcg ttgatttgag 10320
tctggatgcg gccagatttg acgagcagat ggccagagtc aggcgtcatt tttctggtac 10380
ggaaagtgat gcgaaaaaaa cagcggcagt cgttgaacag tcgctgagcc gacaggcgct 10440
ggctgcacag aaagcgggga tttccgtcgg gcagtataaa gccgccatgc gtatgctgcc 10500
tgcacagttc accgacgtgg ccacgcagct tgcaggcggg caaagtccgt ggctgatcct 10560
gctgcaacag gggggggcagg tgaaggactc cttcggcggg atgatcccca tgttcagggg 10620
gcttgccggt gcgatcaccc tgccgatggt gggggccacc tcgctggcgg tggcgaccgg 10680
tgcgctggcg tatgcctggt atcagggcaa ctcaaccctg tccgatttca acaaaacgct 10740
ggtcctttcc ggcaatcagg cgggactgac ggcagatcgt atgctggtcc tgtccagagc 10800
cgggcaggcg gcagggctga cgtttaacca gaccagcgag tcactcagcg cactggttaa 10860
ggcgggggta agcggtgagg ctcagattgc gtccatcagc cagagtgtgg cgcgtttctc 10920
ctctgcatcc ggcgtggagg tggacaaggt cgctgaagcc ttcgggaagc tgaccacaga 10980
cccgacgtcg gggctgacgg cgatggctcg ccagttccat aacgtgtcgg cggagcagat 11040

-continued

```
tgcgtatgtt gctcagttgc agcgttccgg cgatgaagcc ggggcattgc aggcggcgaa  11100
cgaggccgca acgaaagggt ttgatgacca gacccgccgc ctgaaagaga acatgggcac  11160
gctggagacc tgggcagaca ggactgcgcg ggcattcaaa tccatgtggg atgcggtgct  11220
ggatattggt cgtcctgata ccgcgcagga gatgctgatt aaggcagagg ctgcgtataa  11280
gaaagcagac gacatctgga atctgcgcaa ggatgattat tttgttaacg atgaagcgcg  11340
ggcgcgttac tgggatgatc gtgaaaaggc ccgtcttgcg cttgaagccg cccgaaagaa  11400
ggctgagcag cagactcaac aggacaaaaa tgcgcagcag cagagcgata ccgaagcgtc  11460
acggctgaaa tataccgaag aggcgcagaa ggcttacgaa cggctgcaga cgccgctgga  11520
gaaatatacc gcccgtcagg aagaactgaa caaggcactg aaagacggga aaatcctgca  11580
ggcggattac aacacgctga tggcggcggc gaaaaaggat tatgaagcga cgctgaaaaa  11640
gccgaaacag tccagcgtga aggtgtctgc gggcgatcgt caggaagaca gtgctcatgc  11700
tgccctgctg acgcttcagg cagaactccg gacgctggag aagcatgccg gagcaaatga  11760
gaaaatcagc cagcagcgcc gggatttgtg gaaggcggag agtcagttcg cggtactgga  11820
ggaggcggcg caacgtcgcc agctgtctgc acaggagaaa tccctgctgg cgcataaaga  11880
tgagacgctg gagtacaaac gccagctggc tgcacttggc gacaaggtta cgtatcagga  11940
gcgcctgaac gcgctggcgc agcaggcgga taaattcgca cagcagcaac gggcaaaacg  12000
ggccgccatt gatgcgaaaa gccgggggct gactgaccgg caggcagaac gggaagccac  12060
ggaacagcgc ctgaaggaac agtatggcga taatccgctg gcgctgaata acgtcatgtc  12120
agagcagaaa aagacctggg cggctgaaga ccagcttcgc gggaactgga tggcaggcct  12180
gaagtccggc tggagtgagt gggaagagag cgccacggac agtatgtcgc aggtaaaaag  12240
tgcagccacg cagacctttg atggtattgc acagaatatg gcggcgatgc tgaccggcag  12300
tgagcagaac tggcgcagct tcacccgttc cgtgctgtcc atgatgacag aaattctgct  12360
taagcaggca atggtgggga ttgtcgggag tatcggcagc gccattggcg gggctgttgg  12420
tggcggcgca tccgcgtcag gcggtacagc cattcaggcc gctgcggcga aattccattt  12480
tgcaaccgga ggatttacgg gaaccggcgg caaatatgag ccagcgggga ttgttcaccg  12540
tggtgagttt gtcttcacga aggaggcaac cagccggatt ggcgtgggga atctttaccg  12600
gctgatgcgc ggctatgcca ccggcggtta tgtcggtaca ccgggcagca tggcagacag  12660
ccggtcgcag gcgtccggga cgtttgagca gaataaccat gtggtgatta acaacgacgg  12720
cacgaacggg cagataggtc cggctgctct gaaggcggtg tatgacatgg cccgcaaggg  12780
tgcccgtgat gaaattcaga cacagatgcg tgatggtggc ctgttctccg gaggtggacg  12840
atgaagacct tccgctggaa agtgaaaccc ggtatggatg tggcttcggt cccttctgta  12900
agaaaggtgc gctttggtga tggctattct cagcgagcgc ctgccgggct gaatgccaac  12960
ctgaaaacgt acagcgtgac gctttctgtc ccccgtgagg aggccacggt actggagtcg  13020
tttctggaag agcacggggg ctggaaatcc tttctgtgga cgccgcctta tgagtggcgg  13080
cagataaagg tgacctgcgc aaaatggtcg tcgcgggtca gtatgctgcg tgttgagttc  13140
agcgcagagt ttgaacaggt ggtgaactga tgcaggatat ccggcaggaa acactgaatg  13200
aatgcacccg tgcggagcag tcggccagcg tggtgctctg ggaaatcgac ctgacagagg  13260
tcggtggaga acgttatttt ttctgtaatg agcagaacga aaaaggtgag ccggtcacct  13320
ggcaggggcg acagtatcag ccgtatccca ttcaggggag cggttttgaa ctgaatggca  13380
aaggcaccag tacgcgcccc acgctgacgg tttctaacct gtacggtatg gtcaccggga  13440
```

-continued tggcggaaga tatgcagagt ctggtcggcg gaacggtggt ccggcgtaag gtttacgccc 13500
gttttctgga tgcggtgaac ttcgtcaacg gaaacagtta cgccgatccg gagcaggagg 13560
tgatcagccg ctggcgcatt gagcagtgca gcgaactgag cgcggtgagt gcctcctttg 13620
tactgtccac gccgacggaa acggatggcg ctgtttttcc gggacgtatc atgctggcca 13680
acacctgcac ctggacctat cgcggtgacg agtgcggtta tagcggtccg gctgtcgcgg 13740
atgaatatga ccagccaacg tccgatatca cgaaggataa atgcagcaaa tgcctgagcg 13800
gttgtaagtt ccgcaataac gtcggcaact ttggcggctt cctttccatt aacaaacttt 13860
cgcagtaaat cccatgacac agacagaatc agcgattctg gcgcacgccc ggcgatgtgc 13920
gccagcggag tcgtgcggct tcgtggtaag cacgccggag gggaaagat atttcccctg 13980
cgtgaatatc tccggtgagc cggaggctat ttccgtatgt cgccggaaga ctggctgcag 14040
gcagaaatgc agggtgagat tgtggcgctg gtccacagcc accccggtgg tctgccctgg 14100
ctgagtgagg ccgaccggcg gctgcaggtg cagagtgatt tgccgtggtg gctggtctgc 14160
cgggggacga ttcataagtt ccgctgtgtg ccgcatctca ccgggcggcg ctttgagcac 14220
ggtgtgacgg actgttacac actgttccgg gatgcttatc atctggcggg gattgagatg 14280
ccggactttc atcgtgagga tgactggtgg cgtaacggcc agaatctcta tctggataat 14340
ctggaggcga cggggctgta tcaggtgccg ttgtcagcgg cacagccggg cgatgtgctg 14400
ctgtgctgtt ttggttcatc agtgccgaat cacgccgcaa tttactgcgg cgacggcgag 14460
ctgctgcacc atattcctga acaactgagc aaacgagaga ggtacaccga caaatggcag 14520
cgacgcacac actccctctg gcgtcaccgg gcatggcgcg catctgcctt tacggggatt 14580
tacaacgatt tggtcgccgc atcgaccttc gtgtgaaaac gggggctgaa gccatccggg 14640
cactggccac acagctcccg gcgtttcgtc agaaactgag cgacggctgg tatcaggtac 14700
ggattgccgg gcgggacgtc agcacgtccg ggttaacggc gcagttacat gagactctgc 14760
ctgatggcgc tgtaattcat attgttccca gagtcgccgg ggccaagtca ggtggcgtat 14820
tccagattgt cctgggggct gccgccattg ccggatcatt ctttaccgcc ggagccaccc 14880
ttgcagcatg gggggcagcc attggggccg gtggtatgac cggcatcctg ttttctctcg 14940
gtgccagtat ggtgctcggt ggtgtggcgc agatgctggc accgaaagcc agaactcccc 15000
gtatacagac aacggataac ggtaagcaga acacctattt ctcctcactg gataacatgg 15060
ttgcccaggg caatgttctg cctgttctgt acggggaaat gcgcgtgggg tcacgcgtgg 15120
tttctcagga gatcagcacg gcagacgaag gggacggtgg tcaggttgtg gtgattggtc 15180
gctgatgcaa aatgttttat gtgaaaccgc ctgcgggcgg ttttgtcatt tatggagcgt 15240
gaggaatggg taaaggaagc agtaaggggc ataccccgcg cgaagcgaag gacaacctga 15300
agtccacgca gttgctgagt gtgatcgatg ccatcagcga agggccgatt gaaggtccgg 15360
tggatggctt aaaaagcgtg ctgctgaaca gtacgccggt gctggacact gaggggaata 15420
ccaacatatc cggtgtcacg gtggtgttcc gggctggtga gcaggagcag actccgccgg 15480
agggatttga atcctccggc tccgagacgg tgctgggtac ggaagtgaaa tatgacacgc 15540
cgatcacccg caccattacg tctgcaaaca tcgaccgtct gcgctttacc ttcggtgtac 15600
aggcactggt ggaaaccacc tcaaagggtg acaggaatcc gtcggaagtc cgcctgctgg 15660
ttcagataca acgtaacggt ggctgggtga cggaaaaaga catcaccatt aagggcaaaa 15720
ccacctcgca gtatctggcc tcggtggtga tgggtaacct gccgccgcgc ccgtttaata 15780

-continued tccggatgcg caggatgacg ccggacagca ccacagacca gctgcagaac aaaacgctct 15840
ggtcgtcata cactgaaatc atcgatgtga aacagtgcta cccgaacacg gcactggtcg 15900
gcgtgcaggt ggactcggag cagttcggca gccagcaggt gagccgtaat tatcatctgc 15960
gcgggcgtat tctgcaggtg ccgtcgaact ataacccgca gacgcggcaa tacagcggta 16020
tctgggacgg aacgtttaaa ccggcataca gcaacaacat ggcctggtgt ctgtgggata 16080
tgctgaccca tccgcgctac ggcatgggga aacgtcttgg tgcggcggat gtggataaat 16140
gggcgctgta tgtcatcggc cagtactgcg accagtcagt gccggacggc tttggcggca 16200
cggagccgcg catcacctgt aatgcgtacc tgaccacaca gcgtaaggcg tgggatgtgc 16260
tcagcgattt ctgctcggcg atgcgctgta tgccggtatg gaacgggcag acgctgacgt 16320
tcgtgcagga ccgaccgtcg gataagacgt ggacctataa ccgcagtaat gtggtgatgc 16380
cggatgatgg cgcgccgttc cgctacagct tcagcgccct gaaggaccgc cataatgccg 16440
ttgaggtgaa ctggattgac ccgaacaacg gctgggagac ggcgacagag cttgttgaag 16500
atacgcaggc cattgcccgt tacggtcgta atgttacgaa gatggatgcc tttggctgta 16560
ccagccgggg gcaggcacac cgcgccgggc tgtggctgat taaaacagaa ctgctggaaa 16620
cgcagaccgt ggatttcagc gtcggcgcag aagggcttcg ccatgtaccg ggcgatgtta 16680
ttgaaatctg cgatgatgac tatgccggta tcagcaccgg tggtcgtgtg ctggcggtga 16740
acagccagac ccggacgctg acgctcgacc gtgaaatcac gctgccatcc tccggtaccg 16800
cgctgataag cctggttgac ggaagtggca atccggtcag cgtggaggtt cagtccgtca 16860
ccgacggcgt gaaggtaaaa gtgagccgtg ttcctgacgg tgttgctgaa tacagcgtat 16920
gggagctgaa gctgccgacg ctgcgccagc gactgttccg ctgcgtgagt atccgtgaga 16980
acgacgacgg cacgtatgcc atcaccgccg tgcagcatgt gccggaaaaa gaggccatcg 17040
tggataacgg ggcgcacttt gacggcgaac agagtggcac ggtgaatggt gtcacgccgc 17100
cagcggtgca gcacctgacc gcagaagtca ctgcagacag cggggaatat caggtgctgg 17160
cgcgatggga cacaccgaag gtggtgaagg gcgtgagttt cctgctccgt ctgaccgtaa 17220
cagcggacga cggcagtgag cggctggtca gcacggcccg gacgacggaa accacatacc 17280
gcttcacgca actggcgctg ggaactaca ggctgacagt ccgggcggta aatgcgtggg 17340
ggcagcaggg cgatccggcg tcggtatcgt tccggattgc cgcaccggca gcaccgtcga 17400
ggattgagct gacgccgggc tattttcaga taaccgccac gccgcatctt gccgtttatg 17460
acccgacggt acagtttgag ttctggttct cggaaaagca gattgcggat atcagacagg 17520
ttgaaaccag cacgcgttat cttggtacgg cgctgtactg gatagccgcc agtatcaata 17580
tcaaaccggg ccatgattat tacttttata tccgcagtgt gaacaccgtt ggcaaatcgg 17640
cattcgtgga ggccgtcggt cgggcgagcg atgatgcgga aggttacctg gatttttca 17700 aaggcaagat aaccgaatcc catctcggca aggagctgct ggaaaaagtc gagctgacgg 17760
aggataacgc cagcagactg gaggagtttt cgaaagagtg gaaggatgcc agtgataagt 17820
ggaatgccat gtgggctgtc aaaattgagc agaccaaaga cggcaaacat tatgtcgcgg 17880
gtattggcct cagcatggag gacacggagg aaggcaaact gagccagttt ctggttgccg 17940
ccaatcgtat cgcatttatt gacccggcaa acgggaatga aacgccgatg tttgtggcgc 18000
agggcaacca gatattcatg aacgacgtgt tcctgaagcg cctgacggcc cccaccatta 18060
ccagcggcgg caatcctccg gccttttccc tgacaccgga cggaaagctg accgctaaaa 18120
atgcggatat cagtggcagt gtgaatgcga actccgggac gctcagtaat gtgacgatag 18180
ctgaaaactg tacgataaac ggtacgctga gggcggaaaa aatcgtcggg gacattgtaa 18240
aggcggcgag cgcggctttt ccgcgccagc gtgaaagcag tgtggactgg ccgtcaggta 18300
cccgtactgt caccgtgacc gatgaccatc cttttgatcg ccagatagtg gtgcttccgc 18360
tgacgtttcg cggaagtaag cgtactgtca gcggcaggac aacgtattcg atgtgttatc 18420
tgaaagtact gatgaacggt gcggtgattt atgatggcgc ggcgaacgag gcggtacagg 18480
tgttctcccg tattgttgac atgccagcgg gtcggggaaa cgtgatcctg acgttcacgc 18540
ttacgtccac acggcattcg gcagatattc cgccgtatac gtttgccagc gatgtgcagg 18600
ttatggtgat taagaaacag gcgctgggca tcagcgtggt ctgagtgtgt tacagaggtt 18660
cgtccgggaa cgggcgtttt attataaaac agtgagaggt gaacgatgcg taatgtgtgt 18720
attgccgttg ctgtctttgc cgcacttgcg gtgacagtca ctccggcccg tgcggaaggt 18780
ggacatggta cgtttacggt gggctatttt caagtgaaac cgggtacatt gccgtcgttg 18840
tcgggcgggg ataccggtgt gagtcatctg aaagggatta acgtgaagta ccgttatgag 18900
ctgacggaca gtgtgggggt gatggcttcc ctggggttcg ccgcgtcgaa aaagagcagc 18960
acagtgatga ccggggagga tacgtttcac tatgagagcc tgcgtggacg ttatgtgagc 19020
gtgatggccg gaccggtttt acaaatcagt aagcaggtca gtgcgtacct ggcacgacag 19080
gtttcccgac tggaaagcgg gcagtgagcg caacgcaatt aatgtgagtt agctcactca 19140
ttaggcaccc caggctttac actttatgct tccggctcgt atgttgtgtg gaattgtgag 19200
cggataacaa tttcacacag gaaacagcta tgaccatgat tacgccaagc tatttaggtg 19260
acactataga atactcaagc tatgcatcca acgcgttggg agctctccca tatggtcgac 19320
ctgcaggcgg ccgcgaattc actagtgatt atggtaaagc aagatgaagt tatcacattg 19380
ttatcaaata ttcgtagtaa tcgatgcaag atatattctt tgttaggaag ttcgcatgac 19440
ttgagtgaaa atttagtggt cctgcgcaat ttttatcaat cggttacgaa agccgctatc 19500
gcgatggata atgatcatct ggatattgat gttgatatta ctgaaccgtc atttgaacat 19560
ttaactattg cgacagtcaa tgaacgccga atgagaattg agattgaaaa tcaagcaatt 19620
tctctgtctt aaaatctatt gagatattct atcactcaaa tagcaatata aggactctct 19680
atgaaatttg gaaacttttt gcttacatac caacctcccc aattttctca aacagaggta 19740
atgaaacgtt tggttaaatt aggtcgcatc tctgaggagt gtggttttga taccgtatgg 19800
ttactggagc atcatttcac ggagtttggt ttgcttggta acccttatgt cgctgctgca 19860
tatttacttg gcgcgactaa aaaattgaat gtaggaactg ccgctattgt tcttcccaca 19920
gcccatccag tacgccaact tgaagatgtg aatttattgg atcaaatgtc aaaaggacga 19980
tttcggtttg gtatttgccg agggctttac aacaaggact ttcgcgtatt cggcacagat 20040
atgaataaca gtcgcgcctt agcggaatgc tggtacgggc tgataaagaa tggcatgaca 20100
gagggatata tggaagctga taatgaacat atcaagttcc ataaggtaaa agtaaacccc 20160
gcggcgtata gcagaggtgg cgcaccggtt tatgtggtgg ctgaatcagc ttcgacgact 20220
gagtgggctg ctcaatttgg cctaccgatg atattaagtt ggattataaa tactaacgaa 20280
aagaaagcac aacttgagct ttataatgaa gtggctcaag aatatgggca cgatattcat 20340
aatatcgacc attgcttatc atatataaca tctgtagatc atgactcaat taaagcgaaa 20400
gagatttgcc ggaaatttct ggggcattgg tatgattctt atgtgaatgc tacgactatt 20460
tttgatgatt cagaccaaac aagaggttat gatttcaata aagggcagtg gcgtgacttt 20520

-continued gtattaaaag gacataaaga tactaatcgc cgtattgatt acagttacga aatcaatccc 20580
gtgggaacgc cgcaggaatg tattgacata attcaaaaag acattgatgc tacaggaata 20640
tcaaatattt gttgtggatt tgaagctaat ggaacagtag acgaaattat tgcttccatg 20700
aagctcttcc agtctgatgt catgccattt cttaaagaaa aacaacgttc gctattatat 20760
tagctaagga gaaagaaatg aaatttggat tgttcttcct taacttcatc aattcaacaa 20820
ctgttcaaga acaaagtata gttcgcatgc aggaaataac ggagtatgtt gataagttga 20880
attttgaaca gattttagtg tatgaaaatc atttttcaga taatggtgtt gtcggcgctc 20940
ctctgactgt ttctggtttt ctgctcggtt taacagagaa aattaaaatt ggttcattaa 21000
atcacatcat tacaactcat catcctgtcg ccatagcgga ggaagcttgc ttattggatc 21060
agttaagtga agggagattt attttagggt ttagtgattg cgaaaaaaaa gatgaaatgc 21120 attttttaa tcgcccggtt gaatatcaac agcaactatt tgaagagtgt tatgaaatca 21180
ttaacgatgc tttaacaaca ggctattgta atccagataa cgatttttat agcttcccta 21240
aaatatctgt aaatccccat gcttatacgc caggcggacc tcggaaatat gtaacagcaa 21300
ccagtcatca tattgttgag tgggcggcca aaaaaggtat tcctctcatc tttaagtggg 21360
atgattctaa tgatgttaga tatgaatatg ctgaaagata taaagccgtt gcggataaat 21420
atgacgttga cctatcagag atagaccatc agttaatgat attagttaac tataacgaag 21480
atagtaataa agctaaacaa gagacgcgtg catttattag tgattatgtt cttgaaatgc 21540
accctaatga aaatttcgaa aataaacttg aagaaataat tgcagaaaac gctgtcggaa 21600
attatacgga gtgtataact gcggctaagt tggcaattga aaagtgtggt gcgaaaagtg 21660
tattgctgtc ctttgaacca atgaatgatt tgatgagcca aaaaaatgta atcaatattg 21720
ttgatgataa tattaagaag taccacatgg aatataccta atagatttcg agttgcagcg 21780
aggcggcaag tgaacgaatc cccaggagca tagataacta tgtgactggg gtgagtgaaa 21840
gcagccaaca aagcagcagc ttgaaagatg aagggtataa aagagtatga cagcagtgct 21900
gccatacttt ctaatattat cttgaggagt aaaacaggta tgacttcata tgttgataaa 21960
caagaaatta cagcaagctc agaaattgat gatttgattt tttcgagcga tccattagtg 22020
tggtcttacg acgagcagga aaaaatcaga aagaaacttg tgcttgatgc atttcgtaat 22080
cattataaac attgtcgaga atatcgtcac tactgtcagg cacacaaagt agatgacaat 22140
attacggaaa ttgatgacat acctgtattc ccaacatcgg tttttaagtt tactcgctta 22200
ttaacttctc aggaaaacga gattgaaagt tggtttacca gtagcggcac gaatggttta 22260
aaaagtcagg tggcgcgtga cagattaagt attgagagac tcttaggctc tgtgagttat 22320
ggcatgaaat atgttggtag ttggtttgat catcaaatag aattagtcaa tttgggacca 22380
gatagattta atgctcataa tatttggttt aaatatgtta tgagtttggt ggaattgtta 22440
tatcctacga catttaccgt aacagaagaa cgaatagatt ttgttaaaac attgaatagt 22500
cttgaacgaa taaaaaatca agggaaagat ctttgtctta ttggttcgcc atactttatt 22560
tatttactct gccattatat gaaagataaa aaaatctcat tttctggaga taaaagcctt 22620
tatatcataa ccggaggcgg ctggaaaagt tacgaaaaag aatctctgaa acgtgatgat 22680
ttcaatcatc ttttatttga tactttcaat ctcagtgata ttagtcagat ccgagatata 22740
tttaatcaag ttgaactcaa cacttgtttc tttgaggatg aaatgcagcg taaacatgtt 22800
ccgccgtggg tatatgcgcg agcgcttgat cctgaaacgt tgaaacctgt acctgatgga 22860
acgccggggt tgatgagtta tatggatgcg tcagcaacca gttatccagc atttattgtt 22920

-continued accgatgatg tcgggataat tagcagagaa tatggtaagt atcccggcgt gctcgttgaa 22980
attttacgtc gcgtcaatac gaggacgcag aaagggtgtg ctttaagctt aaaccaagca 23040
tttaatagtt gacataatcg aattcccgcg gccgccatgg cggccgggag catgcgacgt 23100
cgggcccaat tcgccctata gtgagtcgta ttacaattca ctggccgtcg ttttacaacg 23160
tcgtgactgg gaaaaccctg gcgttaccca acttaatcgc cttgcagcac atcccccttt 23220
cgccaggtac gccatggccg gagtggctca cagtcggtgg tccggcagta caatggatta 23280
ccgtaagacg gaaatcactc ccgggatcct ctagagtcga cctgcaggca tgcaagcttg 23340
gcgtaatcat ggtcatagct gtttcctgtg tgaaattgtt atccgctcac aattccacac 23400
aacatacgag ccggaagcat aaagtgtaaa gcctggggtg cctaatgagt gagctaactc 23460
acattaattg cgttgcgctc actgcccgct ttccagtcgg gaaacctgtc gtgccagctg 23520
cattaatgaa tcggccaacg cgcggggaga ggcggtttgc gtattgggcg ctcttccgct 23580
tcctcgctca ctgactcgct gcgctcggtc gttcggctgc ggcgagcggt atcagctcac 23640
tcaaaggcgg taatacggtt atccacagaa tcaggggata acgcaggaaa gaacatgtga 23700
gcaaaaggcc agcaaaaggc caggaaccgt aaaaaggccg cgttgctggc gtttttccat 23760
aggctccgcc cccctgacga gcatcacaaa aatcgacgct caagtcagag gtggcgaaac 23820
ccgacaggac tataaagata ccaggcgttt ccccctggaa gctccctcgt gcgctctcct 23880
gttccgaccc tgccgcttac cggatacctg tccgcctttc tcccttcggg aagcgtggcg 23940
ctttctcata gctcacgctg taggtatctc agttcggtgt aggtcgttcg ctccaagctg 24000
ggctgtgtgc acgaaccccc cgttcagccc gaccgctgcg ccttatccgg taactatcgt 24060
cttgagtcca acccggtaag acacgactta tcgccactgg cagcagccac tggtaacagg 24120
attagcagag cgaggtatgt aggcggtgct acagagttct tgaagtggtg gcctaactac 24180
ggctacacta gaaggacagt atttggtatc tgcgctctgc tgaagccagt taccttcgga 24240
aaaagagttg gtagctcttg atccggcaaa caaaccaccg ctggtagcgg tggttttttt 24300
gtttgcaagc agcagattac gcgcagaaaa aaaggatctc aagaagatcc tttgatcttt 24360
tctacggggt ctgacgctca gtggaacgaa aactcacgtt aagggatttt ggtcatgaga 24420
ttatcaaaaa ggatcttcac ctagatcctt ttaaattaaa aatgaagttt taaatcaatc 24480
taaagtatat atgagtaaac ttggtctgac agttaccaat gcttaatcag tgaggcacct 24540
atctcagcga tctgtctatt tcgttcatcc atagttgcct gactccccgt cgtgtagata 24600
actacgatac gggagggctt accatctggc cccagtgctg caatgatacc gcgagaccca 24660
cgctcaccgg ctccagattt atcagcaata aaccagccag ccggaagggc cgagcgcaga 24720
agtggtcctg caactttatc cgcctccatc cagtctatta attgttgccg ggaagctaga 24780
gtaagtagtt cgccagttaa tagtttgcgc aacgttgttg ccattgctac aggcatcgtg 24840
gtgtcacgct cgtcgtttgg tatggcttca ttcagctccg gttcccaacg atcaaggcga 24900
gttacatgat cccccatgtt gtgcaaaaaa gcggttagct ccttcggtcc tccgatcgtt 24960
gtcagaagta agttggccgc agtgttatca ctcatggtta tggcagcact gcataattct 25020
cttactgtca tgccatccgt aagatgcttt tctgtgactg gtgagtactc aaccaagtca 25080
ttctgagaat agtgtatgcg gcgaccgagt tgctcttgcc cggcgtcaat acgggataat 25140
accgcgccac atagcagaac tttaaaagtg ctcatcattg gaaaacgttc ttcggggcga 25200
aaactctcaa ggatcttacc gctgttgaga tccagttcga tgtaacccac tcgtgcaccc 25260

-continued

```
aactgatctt cagcatcttt tactttcacc agcgtttctg ggtgagcaaa aacaggaagg  25320
caaaatgccg caaaaaaggg aataagggcg acacggaaat gttgaatact catactcttc  25380
ctttttcaat attattgaag catttatcag ggttattgtc tcatgagcgg atacatattt  25440
gaatgtattt agaaaaataa acaaataggg gttccgcgca catttccccg aaaagtgcca  25500
cctgacgtct aagaaaccat tattatcatg acattaacct ataaaaatag gcgtatcacg  25560
aggccctttc gtctcgcgcg tttcggtgat gacggtgaaa acctctgaca catgcagctc  25620
ccggagacgg tcacagcttg tctgtaagcg gatgccggga gcagacaagc ccgtcagggc  25680
gcgtcagcgg gtgttggcgg gtgtcggggc tggcttaact atgcggcatc agagcagatt  25740
gtactgagag tgcaccatat gcggtgtgaa ataccgcaca gatgcgtaag gagaaaatac  25800
cgcatcaggc gccattcgcc attcaggctg cgcaactgtt gggaagggcg atcggtgcgg  25860
gcctcttcgc tattacgcca gctggcgaaa gggggatgtg ctgcaaggcg attaagttgg  25920
gtaacgccag ggttttccca gtcacgacgt tgtaaaacga cggccagtga attcgatttt  25980
aagatacatt gatgagtttg gacaaaccac aactagaatg cagtgaaaaa aatgctttat  26040
ttgtgaaatt tgtgatgcta ttgctttatt tgtaaccatt ataagctgca ataaacaagt  26100
taacaacaac aattgcattc attttatgtt tcaggttcag ggggaggtgt gggaggtttt  26160
ttaaagcaag taaaacctct acaaatgtgg tatggctgat tatgatcagt tatctagagt  26220
cgcggccgct ttacttgtac agctcgtcca tgccgagagt gatcccggcg gcggtcacga  26280
actccagcag gaccatgtga tcgcgcttct cgttggggtc tttgctcagg gcggactggg  26340
tgctcaggta gtggttgtcg ggcagcagca cggggccgtc gccgatgggg gtgttctgct  26400
ggtagtggtc ggcgagctgc acgctgccgt cctcgatgtt gtggcggatc ttgaagttca  26460
ccttgatgcc gttcttctgc ttgtcggcca tgatatagac gttgtggctg ttgtagttgt  26520
actccagctt gtgccccagg atgttgccgt cctccttgaa gtcgatgccc ttcagctcga  26580
tgcggttcac cagggtgtcg ccctcgaact tcacctcggc gcgggtcttg tagttgccgt  26640
cgtccttgaa gaagatggtg cgctcctgga cgtagccttc gggcatggcg gacttgaaga  26700
agtcgtgctg cttcatgtgg tcggggtagc ggctgaagca ctgcacgccg taggtcaggg  26760
tggtcacgag ggtgggccag ggcacgggca gcttgccggt ggtgcagatg aacttcaggg  26820
tcagcttgcc gtaggtggca tcgccctcgc cctcgccgga cacgctgaac ttgtggccgt  26880
ttacgtcgcc gtccagctcg accaggatgg gcaccacccc ggtgaacagc tcctcgccct  26940
tgctcaccat ggtggcgacc ggtggatcga tcctagcgga tctgacggtt cactaaacca  27000
gctctgctta tatagacctc ccaccgtaca cgcctaccgc ccatttgcgt caatggggcg  27060
gagttgttac gacattttgg aaagtcccgt tgattttggt gccaaaacaa actcccattg  27120
acgtcaatgg ggtggagact tggaaatccc cgtgagtcaa accgctatcc acgcccattg  27180
atgtactgcc aaaaccgcat caccatggta atagcgatga ctaatacgta gatgtactgc  27240
caagtaggaa agtcccataa ggtcatgtac tgggcataat gccaggcggg ccatttaccg  27300
tcattgacgt caataggggg cgtacttggc atatgataca cttgatgtac tgccaagtgg  27360
gcagtttacc gtaaatactc cacccattga cgtcaatgga aagtccctat tggcgttact  27420
atgggaacat acgtcattat tgacgtcaat gggcgggggt cgttgggcgg tcagccaggc  27480
gggccattta ccgtaagtta tgtaacgcgg aactccatat atgggctatg aactaatgac  27540
cccgtaattg attactatta aatcactagt gaattcgatt aaagcgacgg cacagctcgc  27600
ggaaaatatc aaagtcgttg cgcgcctcga actgcggcgg caccacctgt ttcatggcga  27660
```

-continued taatgccacg gttggagtgg ttgccgtact ggtcgagatc gttacgctca aactgcgtgg 27720
tcgcaggcag cacgatatcg gcaaagcggc aggttgaggt ccactggtta tctatggcga 27780
taaccgtttc cagcttgcgc cagccttcaa taatgcggtt gatctgctga tggcgatgga 27840
atgggttagt tccggcaaaa atacacattt tcagcggcgg cagttttacc gatttaccgt 27900
tccagttgat cactttcccc ggttcgagga tcgcatcgat aaaacgggca atcggaatgg 27960
tgctgctgta gcctttgtaa tcactgttgt cgtgaacagg cggaatcgac gtagagccgg 28020
agaaaccact cagaataacg cctttacgcc ccggcgtgcc tgcgccgtta tagtgccagc 28080
caaaaccaaa gccaccacct ggcaggccaa tttgccccag catcgccgcc agaaccacaa 28140
tcatccacgc ccactgttca ccgtgctgca tacgctgcac gcaccagcca gcaataattt 28200
gcgttctgtt cgccgccatc tgccgcgcca gcccacgaat ggtttcggca tcaatgccgg 28260
tcagtttttc agcccatgcg gcatctttcg gctgaccgtc tttctcaccc agcaggtacg 28320
gcaggaactg ctcaaaaccc acacagtagt tagcgaggaa gtttttgtcg tacaggtttt 28380
cactgtacag cgtatacgcc agcgccagtt gcagcggcac atcagtttgc gggttaaccg 28440
caatgtgctt cacatgctcg cgccccagat actcatgggt ggatgtgaca accggatcga 28500
tgctgatgac ctcaatttca ccggcggtga ctttcgcttt tagctgcgcg taatattcat 28560
aaacatcgtg atccgggcac caccagttcg cttgctggtt tttcagcaaa tcagagcccc 28620
acagcacaat ggttttgctg ttctgcaata ccagcggcca ggaggtttgc tgttcataca 28680
cttccattga gccaaccacg cgcggcagga tcacctgcgc agcaccggta gagtaatctc 28740
cgcccgtacc aacgctatta ccatgcaagg caatagcttt cgccagcatc cccgaagcgt 28800
tatggaacat ccccgtcgat tgccaaccac tggcggtcag caaggcactc ggcccgtgag 28860
ttttctgcac gcgttccagt tcttcataga acatgtcgag ggcttcatcc cagctcacgc 28920
gcacaaaacg gttatcaccg cgctgggagg tatcgctgag atggcgctta cgcagccagt 28980
ccacgcgtac catcggataa cgaatacgcg ccgcgttgtg tacgtgatcc ggcaatccgg 29040
caatcatttt cgacggatat ttatccagtt cgaacggttt tgccgccaca aagcgaccat 29100
ccttcaccgt cgcgcggata gccccccagt gcgacccggt aagaatgccc tctttcgaga 29160
tgacagcctc agtcgccgct tgcgccgcag tcgcacggcg cggcgttaac aatgacggcc 29220
ccagcatccc ggcgacggtt aagccgccga gttgtgccag aaaacgccga cgtgatgcct 29280
gaaagagatc gttattgttc attatttttc ttccttctta tcgccgtgag ccttacctgc 29340
ggtgtcagac gcattcattt gcagatattt caacaaagtg cgttcttcac gtttatcgag 29400
actggtaaag ccaatcatgc cgttgagcgt gccgatccaa ccgttagcgt caaagtgggc 29460
gatttccggt gcgccgtggc actggttaca ggtgccgttg tacaacgaat ccgcataagc 29520
ccagatcggt ttgatatcgt tcaccatgtc gcctttcttc atccacgcag tggcctgcaa 29580
cttgctccac tcggtattgg tgtcggcaac ggtggttttc tccagcgttt ttacctgctg 29640
ctgcacatca ccacgaatcg aggcaacaaa gatgcgttta cctgggaatt gggtgagtac 29700
acgctgacgt ccggcgcttt ccgtccagcc ggtaatttca atttgcagcc agtcgccgtc 29760
acgtttaagg actttcactt ccgaagcagg cagcagagaa ccagaggctt ctttatcgcc 29820
tttcgccgca taaattggct taatatcaat agagtacagc gtgtcaccac tgtcattagc 29880
actggcgcgc agctcatcga actgcttacg gaagccgcta ctcatatccg gtaactggtg 29940
ggcaatacct ttatgacagt cgatgcagga ttgattatct ttcgctgcca ccttcatctg 30000

-continued

```
acgtgccgct tcaggatgct gcttcgcatg atccatcgca tcgtagttat ggcaggagcg  30060
gcaggttgcc gagttgtttt ctttcattcg cgcccattca cgctcggcaa gttccgcgcg  30120
tttggcttcg aatttttcag gtgtatcaat ggagtgagca ataaaggtct ggtagatatc  30180
attgctcgct tccagtttgc gcttcaccat gcctggaata tccggcggga tatgacagtc  30240
atggcattca gctcgcacgc cggaggcgtt ctggaaatgc accgactgtt tatattcttc  30300
atacaccggt tgcatactgt ggcaactgac acaaaattcg gttgtgctgg tgactttgat  30360
cccaacgtgt ggcaatacaa tcagcgcaat gccaatcaca atcccaattg cgaccagcgc  30420
cagtaccgac caacgagcac tgggtcggcg tagcgcgttc cagagtttcc gcataatagc  30480
ccctgtaaaa ttatggttta gtgaagcgat cttaatgagc aaatatgaac agcggcactg  30540
gtcaggatga acggcttacg gcagaatatg aacagatatg aacagaatga gtaaaaccct  30600
ctgatgccac atcacattgt tattgttgaa gatgagccgg ttacccaggc gcgattacaa  30660
tcttacttca ctcaggaggg gtataccgtt tccgttacag cgagcggtgc cgggctgcgg  30720
gaaattatgc agaatcagcc ggtagattta attctgctgg atatcaactt acccgatgaa  30780
aatggcctga tgttaacccg cgccctgcga gaacgctcaa cggtggggat tattctggtt  30840
accggacgca gcgatcggat tgaccgtatt gttgggctgg aaatgggcgc agacgattac  30900
gtcaccaaac cgctggaact gcgcgaactg gtagtacggg tgaaaaatct gctctggcga  30960
atcgacctcg cgcgacaagc tcaaccgcac actcaggaca actgctatcg ctttgccggt  31020
tattgcctga atgtgtcgcg ccatacgctg gagcgggatg gcgagccgat taaactgacc  31080
cgcgcagagt atgaaatgtt ggtggcattt gtgacgaatc cgggcgaaat tctcagccgt  31140
gaacgtctgc tacgtatgct ttctgcgcgt cgggtggaaa accctgacct gcgcaccgtc  31200
gatgtgttaa ttcgtcgttt acgtcataaa ctcagcgcgg atttactggt gacgcaacat  31260
ggtgaaggtt atttcttagc cgctgatgtg tgctgataaa aatagaccgg acgaaatccc  31320
cctggtgaca gcgagcggcg gatatgttct cggtcggcat ttttcggcgt cagaactaaa  31380
atcggtgggc tgacattatc agacaccgat tgcccctgta attgcctgat ggcctgctca  31440
actgccagtt ccccctgcca gaccatttga tcgctggcag ccataatcac tcttccccgc  31500
ttcagcccgc gatacacctg atgtgaaaga taaaacgaca ccacggtaag cggcgttttc  31560
aggttacgcc cttcacccat tgccgcctct gccgcaatgg ccgttccggc aacgacgtca  31620
atttctgggt ggcgttccag catctcctgc aacaggttac gctggatttc aatatcgtta  31680
tcaccaagcg caatatcaac aatacgcacc gggcttccgg caatggctgc gcgaaaaccc  31740
tcgaccatct ctttactgcc cccggcatta tcgggtccgg gcatcaacag cacgttcagt  31800
ggtttaccgt gcgcccattg caccaaatat cgcccaggtt gatagcccat ctgaaaccag  31860
ggtacaccaa cgcggctttt cacctgggga gcatcaatag catttaccag ttcgatcacc  31920
ggcagacttg ctacctgctt ttgcagatcg ggaaatgagg tcgtgctact accgagtaaa  31980
atggcctctg cgcccccactg tttacactgg tcgatttgtg cttgctgggt agccaactgg  32040
ctgtagccgc ctgcctccag cacttttaaa tccacaccat agcggcgagc tgcctcctgc  32100
ataccatagt tcaacgataa ccagtatgaa tctttcaggc tgggataaag cgcgcacagt  32160
ttccatgcgc gtttggcttt aagcggcata gaggcttgca ccgtgaaatg ctgcgcatca  32220
tgccagcgca acaggttatc agccgaaaat gccggcaaca tgaaaaggga aagaagtaaa  32280
aatagcagta cgcgcatgat agcctcatca ataataaggc tttatgctag atgcattccg  32340
ctttgcgact caaccttttt caccttaagt gcaccgaccg tgaatttaac cctgacccga  32400
```

-continued agactctgga tgggctttgc cctgatggcg ctgttaaccc tgaccagtac cctggtggga 32460
tggtacaacc tgcgctttat cagccaggtg gaaaaagaca acactcaggc attgattcct 32520
accatgaata tggcgcgcca gttgagcgaa gccagcgcct gggaactttt cgccgcgcag 32580
aacctgacca gtgccgataa cgaaaagatg tggcaggcgc aggggcgaat gctcaccgca 32640
caaagcctga agattaatgc gttgctgcaa gcgttacggg aacaaggttt tgataccacc 32700
gctattgaac aacaggagca ggagatctcc cgttcattac gtcagcaagg ggaactggtg 32760
gggcggcgtc tgcaactacg ccagcaacaa cggcaactca gtcagcagat agtcgctgcc 32820
gccgatgaga tcgcacgcct ggcgcaaggt caggcgaata atgcgacaac ttccgctgga 32880
gcgacccagg ccgggattta cgatttgatc gaacaagatc agcgtcaggc tgctgaaagt 32940
gcactcgatc ggctgattga tatcgatctt gagtatgtta accagatgaa tgaactgcgc 33000
cttagcgctc tgcgggtgca gcaaatggtg atgaatctgg ggctggagca gatccagaaa 33060
aatgcaccaa cgctggaaaa gcagctcaat aatgcggtga aaattctgca acgtcggcaa 33120
atacgcattg aagatccggg tgttcgtgcg caggtcgcaa caacgttaac taccgttagc 33180
caatatagcg atttgctggc gctgtatcag caggacagtg aaatcagcaa tcacctacaa 33240
actctcgcac aaaataacat cgcccagttc gcgcagttta gtagcgaagt cagtcagctg 33300
gtcgactcgg tacccgggga tccactcgtt attctcggac gagtgttcag taatgaacct 33360
ctggagagaa ccatgtatat gatcgttatc tgggttggac ttctgctttt aagcccagat 33420
aactggcctg aatatgttaa tgagagaatc ggtattcctc atgtgtggca tgttttcgtc 33480
tttgctcttg cattttcgct agcaattaat gtgcatcgat tatcagctat tgccagcgcc 33540
agatataagc gatttaagct aagaaaacgc attaagatgc aaaacgataa agtgcgatca 33600
gtaattcaaa accttacaga agagcaatct atggttttgt gcgcagccct taatgaaggc 33660
aggaagtatg tggttacatc aaaacaattc ccatacatta gtgagttgat tgagcttggt 33720
gtgttgaaca aaactttttc ccgatggaat ggaaagcata tattattccc tattgaggat 33780
atttactgga ctgaattagt tgccagctat gatccatata atattgagat aaagccaagg 33840
ccaatatcta agtaactaga taagaggaat cgattttccc ttaattttct ggcgtccact 33900
gcatgttatg ccgcgttcgc caggcttgct gtaccatgtg cgctgattct tgcgctcaat 33960
acgttgcagg ttgctttcaa tctgtttgtg gtattcagcc agcactgtaa ggtctatcgg 34020
atttagtgcg ctttctactc gtgatttcgg tttgcgattc agcgagagaa tagggcggtt 34080
aactggtttt gcgcttaccc caaccaacag gggatttgct gctttccatt gagcctgttt 34140
ctctgcgcga cgttcgcggc ggcgtgtttg tgcatccatc tggattctcc tgtcagttag 34200
ctttggtggt gtgtggcagt tgtagtcctg aacgaaaacc ccccgcgatt ggcacattgg 34260
cagctaatcc ggaatcgcac ttacggccaa tgcttcgttt cgtatcacac accccaaagc 34320
cttctgcttt gaatgctgcc cttcttcagg gcttaatttt taagagcgtc accttcatgg 34380
tggtcagtgc gtcctgctga tgtgctcagt atcaccgcca gtggtattta tgtcaacacc 34440
gccagagata atttatcacc gcagatggtt atctgtatgt tttttatatg aatttatttt 34500
ttgcaggggg gcattgtttg gtaggtgaga gatctgaatt gctatgttta gtgagttgta 34560
tctatttatt tttcaataaa tacaattggt tatgtgtttt gggggcgatc gtgaggcaaa 34620
gaaaacccgg cgctgaggcc gggttattct tgttctctgg tcaaattata tagttggaaa 34680
acaaggatgc atatatgaat gaacgatgca gaggcaatgc cgatggcgat agtgggtatc 34740

```
atgtagccgc ttatgctgga aagaagcaat aacccgcaga aaaacaaagc tccaagctca  34800
acaaaactaa gggcatagac aataactacc gatgtcatat acccatactc tctaatcttg  34860
gccagtcggc gcgttctgct tccgattaga aacgtcaagg cagcaatcag gattgcaatc  34920
atggttcctg catatgatga caatgtcgcc ccaagaccat ctctatgagc tgaaaaagaa  34980
acaccaggaa tgtagtggcg gaaaaggaga tagcaaatgc ttacgataac gtaaggaatt  35040
attactatgt aaacaccagg catgattctg ttccgcataa ttactcctga taattaatcc  35100
ttaactttgc ccacctgcct tttaaaacat tccagtatat cacttttcat tcttgcgtag  35160
caatatgcca tctcttcagc tatctcagca ttggtgacct tgttcagagg cgctgagaga  35220
tggccttttt ctgatagata atgttctgtt aaaatatctc cggcctcatc ttttgcccgc  35280
aggctaatgt ctgaaaattg aggtgacggg ttaaaaataa tatccttggc aacctttttt  35340
atatcccttt taaattttgg cttaatgact atatccaatg agtcaaaaag ctccccttca  35400
atatctgttg cccctaagac ctttaatata tcgccaaata caggtagctt ggcttctacc  35460
ttcaccgttg ttcggccgat gaaatgcata tgcataacat cgtctttggt ggttcccctc  35520
atcagtggct ctatctgaac gcgctctcca ctgcttaatg acattccttt cccgattaaa  35580
aaatctgtca gatcggatgt ggtcggcccg aaaacagttc tggcaaaacc aatggtgtcg  35640
ccttcaacaa acaaaaaaga tgggaatccc aatgattcgt catctgcgag gctgttctta  35700
atatcttcaa ctgaagcttt agagcgattt atcttctgaa ccagactctt gtcatttgtt  35760
ttggtaaaga gaaaagtttt tccatcgatt ttatgaatat acaaataatt ggagccaacc  35820
tgcaggtgat gattatcagc cagcagagaa ttaaggaaaa cagacaggtt tattgagcgc  35880
ttatctttcc ctttattttt gctgcggtaa gtcgcataaa aaccattctt cataattcaa  35940
tccatttact atgttatgtt ctgaggggag tgaaaattcc cctaattcga tgaagattct  36000
tgctcaattg ttatcagcta tgcgccgacc agaacacctt gccgatcagc caaacgtctc  36060
ttcaggccac tgactagcga taactttccc cacaacggaa caactctcat tgcatgggat  36120
cattgggtac tgtgggttta gtggttgtaa aaacacctga ccgctatccc tgatcagttt  36180
cttgaaggta aactcatcac ccccaagtct ggctatgcag aaatcacctg gctcaacagc  36240
ctgctcaggg tcaacgagaa ttaacattcc gtcaggaaag cttggcttgg agcctgttgg  36300
tgcggtcatg gaattacctt caacctcaag ccagaatgca gaatcactgg ctttttttggt  36360
tgtgcttacc catctctccg catcaccttt ggtaaaggtt ctaagctcag gtgagaacat  36420
ccctgcctga acatgagaaa aaacagggta ctcatactca cttctaagtg acggctgcat  36480
actaaccgct tcatacatct cgtagatttc tctggcgatt gaagggctaa attcttcaac  36540
gctaactttg agaatttttg caagcaatgc ggcgttataa gcatttaatg cattgatgcc  36600
attaaataaa gcaccaacgc ctgactgccc catccccatc ttgtctgcga cagattcctg  36660
ggataagcca agttcatttt tctttttttc ataaattgct ttaaggcgac gtgcgtcctc  36720
aagctgctct tgtgttaatg gtttcttttt tgtgctcata cgttaaatct atcaccgcaa  36780
gggataaata tctaacaccg tgcgtgttga ctattttacc tctggcggtg ataatggttg  36840
catgtactaa ggaggttgta tggaacaacg cataaccctg aaagattatg caatgcgctt  36900
tgggcaaacc aagacagcta aagatctcgg cgtatatcaa agcgcgatca acaaggccat  36960
tcatgcaggc cgaaagattt ttttaactat aaacgctgat ggaagcgttt atgcggaaga  37020
ggtaaagccc ttcccgagta acaaaaaaac aacagcataa ataaccccgc tcttacacat  37080
tccagccctg aaaaagggca tcaaattaaa ccacacctat ggtgtatgca tttatttgca  37140
```

tacattcaat caattgttat ctaaggaaat acttacatat ggttcgtgca aacaaacgca 37200
acgaggctct acgaatcgag agtgcgttgc ttaacaaaat cgcaatgctt ggaactgaga 37260
agacagcgga agctgtgggc gttgataagt cgcagatcag caggtggaag agggactgga 37320
ttccaaagtt ctcaatgctg cttgctgttc ttgaatgggg ggtcgttgac gacgacatgg 37380
ctcgattggc gcgacaagtt gctgcgattc tcaccaataa aaaacgcccg gcggcaaccg 37440
agcgttctga acaaatccag atggagttct gaggtcatta ctggatctat caacaggagt 37500
cattatgaca aatacagcaa aaatactcaa cttcggcaga ggtaactttg ccggacagga 37560
gcgtaatgtg gcagatctcg atgatggtta cgccagacta tcaaatatgc tgcttgaggc 37620
ttattcgggc gcagatctga ccaagcgaca gtttaaagtg ctgcttgcca ttctgcgtaa 37680
aacctatggg tggaataaac caatggacag aatcaccgat tctcaactta gcgagattac 37740
aaagttacct gtcaaacggt gcaatgaagc caagttagaa ctcgtcagaa tgaatattat 37800
caagcagcaa ggcggcatgt ttggaccaaa taaaaacatc tcagaatggt gcatccctca 37860
aaacgaggga aaatccccta aaacgaggga taaaacatcc ctcaaattgg gggattgcta 37920
tccctcaaaa caggggggaca caaaagacac tattacaaaa gaaaaaagaa aagattattc 37980
gtcagannnn nntggcgaat cctctgacca gccagaaaac gacctttctg tggtgaaacc 38040
ggatgctgca attcagagcg gcagcaagtg ggggacagca gaagacctga ccgccgcaga 38100
gtggatgttt gacatggtga agactatcgc accatcagcc agaaaaccga attttgctgg 38160
gtgggctaac gatatccgcc tgatgcgtga acgtgacgga cgtaaccacc gcgacatgtg 38220
tgtgctgttc cgctgggcat gccaggacaa cttctggtcc ggtaacgtgc tgagcccggc 38280
caaactccgc gataagtgga cccaactcga aatcaaccgt aacaagcaac aggcaggcgt 38340
gacagccagc aaaccaaaac tcgacctgac aaacacagac tggatttacg gggtggatct 38400
atgaaaaaca tcgccgcaca gatggttaac tttgaccgtg agcagatgcg tcggatcgcc 38460
aacaacatgc cggaacagta cgacgaaaag ccgcaggtac agcaggtagc gcagatcatc 38520
aacggtgtgt tcagccagtt actggcaact ttcccggcga gcctggctaa ccgtgaccag 38580
aacgaagtga acgaaatccg tcgccagtgg gttctggctt ttcgggaaaa cgggatcacc 38640
acgatggaac aggttaacgc aggaatgcgc gtagcccgtc ggcagaatcg accatttctg 38700
ccatcacccg ggcagtttgt tgcatggtgc cgggaagaag catccgttac cgccggactg 38760
ccaaacgtca gcgagctggt tgatatggtt tacgagtatt gccggaagcg aggcctgtat 38820
ccggatgcgg agtcttatcc gtggaaatca aacgcgcact actggctggt taccaacctg 38880
tatcagaaca tgcgggccaa tgcgcttact gatgcggaat tacgccgtaa ggccgcagat 38940
gagcttgtcc atatgactgc gagaattaac cgtggtgagg cgatccctga accagtaaaa 39000
caacttcctg tcatgggcgg tagacctcta aatcgtgcac aggctctggc gaagatcgca 39060
gaaatcaaag ctaagttcgg actgaaagga gcaagtgtat gacgggcaaa gaggcaatta 39120
ttcattacct ggggacgcat aatagcttct gtgcgccgga cgttgccgcg ctaacaggcg 39180
caacagtaac cagcataaat caggccgcgg ctaaaatggc acgggcaggt cttctggtta 39240
tcgaaggtaa ggtctggcga acggtgtatt accggtttgc taccagggaa gaacgggaag 39300
gaaagatgag cgatgaacaa actggatacg attggattcg acaacaaaaa agacctgctt 39360
atctcggtgg gcgatttggt tgatcgtggt gcagagaacg ttgaatgcct ggaattaatc 39420
acattcccct ggttcagagc tgtacgtgga aaccatgagc aaatgatgat tgatggctta 39480

-continued tcagagcgtg gaaacgttaa tcactggctg cttaatggcg gtggctggtt ctttaatctc 39540
gattacgaca aagaaattct ggctaaagct cttgcccata aagcagatga acttccgtta 39600
atcatcgaac tggtgagcaa agataaaaaa tatgttatct gccacgccga ttatcccttt 39660
gacgaatacg agtttggaaa gccagttgat catcagcagg taatctggaa ccgcgaacga 39720
atcagcaact cacaaaacgg gatcgtgaaa gaaatcaaag gcgcggacac gttcatcttt 39780
ggtcatacgc cagcagtgaa accactcaag tttgccaacc aaatgtatat cgataccggc 39840
gcagtgttct gcggaaacct aacattgatt caggtacagg gagaaggcgc atgagactcg 39900
aaagcgtagc taaatttcat tcgccaaaaa gcccgatgat gagcgactca ccacgggcca 39960
cggcttctga ctctctttcc ggtactgatg tgatggctgc tatggggatg gcgcaatcac 40020
aagccggatt cggtatggct gcattctgcg gtaagcacga actcagccag aacgacaaac 40080
aaaaggctat caactatctg atgcaatttg cacacaaggt atcggggaaa taccgtggtg 40140
tggcaaagct tgaaggaaat actaaggcaa aggtactgca agtgctcgca acattcgctt 40200
atgcggatta ttgccgtagt gccgcgacgc cgggggcaag atgcagagat tgccatggta 40260
caggccgtgc ggttgatatt gccaaaacag agctgtgggg gagagttgtc gagaaagagt 40320
gcggaagatg caaaggcgtc ggctattcaa ggatgccagc aagcgcagca tatcgcgctg 40380
tgacgatgct aatcccaaac cttacccaac ccacctggtc acgcactgtt aagccgctgt 40440
atgacgctct ggtggtgcaa tgccacaaag aagagtcaat cgcagacaac attttgaatg 40500
cggtcacacg ttagcagcat gattgccacg gatggcaaca tattaacggc atgatattga 40560
cttattgaat aaaattgggt aaatttgact caacgatggg ttaattcgct cgttgtggta 40620
gtgagatgaa aagaggcggc gcttactacc gattccgcct agttggtcac ttcgacgtat 40680
cgtctggaac tccaaccatc gcaggcagag aggtctgcaa aatgcaatcc cgaaacagtt 40740
cgcaggtaat agttagagcc tgcataacgg tttcgggatt ttttatatct gcacaacagg 40800
taagagcatt gagtcgataa tcgtgaagag tcggcgagcc tggttagcca gtgctctttc 40860
cgttgtgctg aattaagcga ataccggaag cagaaccgga tcaccaaatg cgtacaggcg 40920
tcatcgccgc ccagcaacag cacaacccaa actgagccgt agccactgtc tgtcctnnnn 40980
nnattagtaa tagttacgct gcggcctttt acacatgacc ttcgtgaaag cgggtggcag 41040
gaggtcgcgc taacaacctc ctgccgtttt gcccgtgcat atcggtcacg aacaaatctg 41100
attactaaac acagtagcct ggatttgttc tatcagtaat cgaccttatt cctaattaaa 41160
tagagcaaat ccccttattg ggggtaagac atgaagatgc cagaaaaaca tgacctgttg 41220
gccgccattc tcgcggcaaa ggaacaaggc atcggggcaa tccttgcgtt tgcaatggcg 41280
taccttcgcg gcagatataa tggcggtgcg tttacaaaaa cagtaatcga cgcaacgatg 41340
tgcgccatta tcgcctggtt cattcgtgac cttctcgact tcgccggact aagtagcaat 41400
ctcgcttata taacgagcgt gtttatcggc tacatcggta ctgactcgat tggttcgctt 41460
atcaaacgct tcgctgctaa aaaagccgga gtagaagatg gtagaaatca ataatcaacg 41520
taaggcgttc ctcgatatgc tggcgtggtc ggagggaact gataacggac gtcagaaaac 41580
cagaaatcat ggttatgacg tcattgtagg cggagagcta tttactgatt actccgatca 41640
ccctcgcaaa cttgtcacgc taaacccaaa actcaaatca acaggcgccg gacgctacca 41700
gcttctttcc cgttggtggg atgcctaccg caagcagctt ggcctgaaag acttctctcc 41760
gaaaagtcag gacgctgtgg cattgcagca gattaaggag cgtggcgctt tacctatgat 41820
tgatcgtggt gatatccgtc aggcaatcga ccgttgcagc aatatctggg cttcactgcc 41880
gggcgctggt tatggtcagt tcgagcataa ggctgacagc ctgattgcaa aattcaaaga 41940
agcgggcgga acggtcagag agattgatgt atgagcagag tcaccgcgat tatctccgct 42000
ctggttatct gcatcatcgt ctgcctgtca tgggctgtta atcattaccg tgataacgcc 42060
attacctaca aagcccagcg cgacaaaaat gccagagaac tgaagctggc gaacgcggca 42120
attactgaca tgcagatgcg tcagcgtgat gttgctgcgc tcgatgcaaa atacacgaag 42180
gagttagctg atgctaaagc tgaaaatgat gctctgcgtg atgatgttgc cgctggtcgt 42240
cgtcggttgc acatcaaagc agtctgtcag tcagtgcgtg aagccaccac cgcctccggc 42300
gtggataatg cagcctcccc ccgactggca gacaccgctg aacgggatta tttcaccctc 42360
agagagaggc tgatcactat gcaaaaacaa ctggaaggaa cccagaagta tattaatgag 42420
cagtgcagat agagttgccc atatcgatgg gcaactcatg caattattgt gagcaataca 42480
cacgcgcttc cagcggagta taaatgccta aagtaataaa accgagcaat ccatttacga 42540
atgtttgctg ggtttctgtt ttaacaacat tttctgcgcc gccacaaatt ttggctgcat 42600
cgacagtttt cttctgccca attccagaaa cgaagaaatg atgggtgatg gtttcctttg 42660
gtgctactgc tgccggtttg ttttgaacag taaacgtctg ttgagcacat cctgtaataa 42720
gcagggccag cgcagtagcg agtagcattt ttttcatggt gttattcccg atgctttttg 42780
aagttcgcag aatcgtatgt gtagaaaatt aaacaaaccc taaacaatga gttgaaattt 42840
catattgtta atatttatta atgtatgtca ggtgcgatga atcgtcattg tattcccgga 42900
ttaactatgt ccacagccct gacggggaac ttctctgcgg gagtgtccgg gaataattaa 42960
aacgatgcac acagggttta gcgcgtacac gtattgcatt atgccaacgc cccggtgctg 43020
acacggaaga aaccggacgt tatgatttag cgtggaaaga tttgtgtagt gttctgaatg 43080
ctctcagtaa atagtaatga attatcaaag gtatagtaat atcttttatg ttcatggata 43140
tttgtaaccc atcggaaaac tcctgcttta gcaagatttt ccctgtattg ctgaaatgtg 43200
atttctcttg atttcaacct atcataggac gtttctataa gatgcgtgtt tcttgagaat 43260
ttaacattta caaccttttt aagtcctttt attaacacgg tgttatcgtt ttctaacacg 43320
atgtgaatat tatctgtggc tagatagtaa atataatgtg agacgttgtg acgttttagt 43380
tcagaataaa acaattcaca gtctaaatct tttcgcactt gatcgaatat ttctttaaaa 43440
atggcaacct gagccattgg taaaaccttc catgtgatac gagggcgcgt agtttgcatt 43500
atcgttttta tcgtttcaat ctggtctgac ctccttgtgt tttgttgatg atttatgtca 43560
aatattagga atgttttcac ttaatagtat tggttgcgta acaaagtgcg gtcctgctgg 43620
cattctggag ggaaatacaa ccgacagatg tatgtaaggc caacgtgctc aaatcttcat 43680
acagaaagat ttgaagtaat attttaaccg ctagatgaag agcaagcgca tggagcgaca 43740
aaatgaataa agaacaatct gctgatgatc cctccgtgga tctgattcgt gtaaaaaata 43800
tgcttaatag caccatttct atgagttacc ctgatgttgt aattgcatgt atagaacata 43860
aggtgtctct ggaagcattc agagcaattg aggcagcgtt ggtgaagcac gataataata 43920
tgaaggatta ttccctggtg gttgactgat caccataact gctaatcatt caaactattt 43980
agtctgtgac agagccaaca cgcagtctgt cactgtcagg aaagtggtaa aactgcaact 44040
caattactgc aatgccctcg taattaagtg aatttacaat atcgtcctgt tcggagggaa 44100
gaacgcggga tgttcattct tcatcacttt taattgatgt atatgctctc ttttctgacg 44160
ttagtctccg acggcaggct tcaatgaccc aggctgagaa attcccggac ccttttttgct 44220 caagagcgat gttaatttgt tcaatcattt ggttaggaaa gcggatgttg cgggttgttg 44280
ttctgcgggt tctgttcttc gttgacatga ggttgccccg tattcagtgt cgctgatttg 44340
tattgtctga agttgttttt acgttaagtt gatgcagatc aattaatacg atacctgcgt 44400
cataattgat tatttgacgt ggtttgatgg cctccacgca cgttgtgata tgtagatgat 44460
aatcattatc actttacggg tcctttccgg tgatccgaca ggttacg 44507

<210> SEQ ID NO 4
<211> LENGTH: 51940
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
ctgtctctta tacacatctc aaccctgaag ctcttgttgg ctagtgcgta gtcgttggca 60
agcttgcatg cctgcagtag ggataacagg gtaatgtcga cttgcatgcc tgcataaatt 120
tgaattttat aaaaaattat gttataattc gcgcagtacg atggataatg atcatctgga 180
tattgatgtt gatattactg aaccgtcatt tgaacattta actattgcga cagtcaatga 240
acgccgaatg agaattgaga ttgaaaatca agcaatttct ctgtcttaaa atctattgag 300
atattctatc actcaaatag caatataagg actctctatg aaatttggaa actttttgct 360
tacataccaa cctccccaat tttctcaaac agaggtaatg aaacgtttgg ttaaattagg 420
tcgcatctct gaggagtgtg gttttgatac cgtatggtta ctggagcatc atttcacgga 480
gtttggtttg cttggtaacc cttatgtcgc tgctgcatat ttacttggcg cgactaaaaa 540
attgaatgta ggaactgccg ctattgttct tcccacagcc catccagtac gccaacttga 600
agatgtgaat ttattggatc aaatgtcaaa aggacgattt cggtttggta tttgccgagg 660
gctttacaac aaggactttc gcgtattcgg cacagatatg aataacagtc gcgccttagc 720
ggaatgctgg tacgggctga taaagaatgg catgacagag ggatatatgg aagctgataa 780
tgaacatatc aagttccata aggtaaaagt aaaccccgcg gcgtatagca gaggtggcgc 840
accggtttat gtggtggctg aatcagcttc gacgactgag tgggctgctc aatttggcct 900
accgatgata ttaagttgga ttataaatac taacgaaaag aaagcacaac ttgagcttta 960
taatgaagtg gctcaagaat atgggcacga tattcataat atcgaccatt gcttatcata 1020
tataacatct gtagatcatg actcaattaa agcgaaagag atttgccgga aatttctggg 1080
gcattggtat gattcttatg tgaatgctac gactattttt gatgattcag accaaacaag 1140
aggttatgat ttcaataaag ggcagtggcg tgactttgta ttaaaaggac ataaagatac 1200
taatcgccgt attgattaca gttacgaaat caatcccgtg ggaacgccgc aggaatgtat 1260
tgacataatt caaaaagaca ttgatgctac aggaatatca aatatttgtt gtggatttga 1320
agctaatgga acagtagacg aaattattgc ttccatgaag ctcttccagt ctgatgtcat 1380
gccatttctt aaagaaaaac aacgttcgct attatattag ctaaggagaa agaaatgaaa 1440
tttggattgt tcttccttaa cttcatcaat tcaacaactg ttcaagaaca aagtatagtt 1500
cgcatgcagg aaataacgga gtatgttgat aagttgaatt ttgaacagat tttagtgtat 1560
gaaaatcatt tttcagataa tggtgttgtc ggcgctcctc tgactgtttc tggttttctg 1620
ctcggtttaa cagagaaaat taaaattggt tcattaaatc acatcattac aactcatcat 1680
cctgtcgcca tagcggagga agcttgctta ttggatcagt taagtgaagg gagatttatt 1740

-continued

```
ttagggttta gtgattgcga aaaaaaagat gaaatgcatt tttttaatcg cccggttgaa   1800
tatcaacagc aactatttga agagtgttat gaaatcatta acgatgcttt aacaacaggc   1860
tattgtaatc cagataacga tttttatagc ttccctaaaa tatctgtaaa tccccatgct   1920
tatacgccag gcggacctcg gaaatatgta acagcaacca gtcatcatat tgttgagtgg   1980
gcggccaaaa aaggtattcc tctcatcttt aagtgggatg attctaatga tgttagatat   2040
gaatatgctg aaagatataa agccgttgcg gataaatatg acgttgacct atcagagata   2100
gaccatcagt taatgatatt agttaactat aacgaagata gtaataaagc taaacaagag   2160
acgcgtgcat ttattagtga ttatgttctt gaaatgcacc ctaatgaaaa tttcgaaaat   2220
aaacttgaag aaataattgc agaaaacgct gtcggaaatt atacggagtg tataactgcg   2280
gctaagttgg caattgaaaa gtgtggtgcg aaaagtgtat tgctgtcctt tgaaccaatg   2340
aatgatttga tgagccaaaa aaatgtaatc aatattgttg atgataatat taagaagtac   2400
cacatggaat atacctaata gatttcgagt tgcagcgagg cggcaagtga acgaatcccc   2460
aggagcatag ataactatgt gactggggtg agtgaaagca gccaacaaag cagcagcttg   2520
aaagatgaag ggtataaaag agtatgacag cagtgctgcc atactttcta atattatctt   2580
gaggagtaaa acaggtatga cttcatatgt tgataaacaa gaaattacag caagctcaga   2640
aattgatgat ttgatttttt cgagcgatcc atagatctgg agctaaggaa gctaaaatgg   2700
agaaaaaaat cactggatat accaccgttg atatatccca atggcatcgt aaagaacatt   2760
ttgaggcatt tcagtcagtt gctcaatgta cctataacca gaccgttcag ctggatatta   2820
cggccttttt aaagaccgta aagaaaaata agcacaagtt ttatccggcc tttattcaca   2880
ttcttgcccg cctgatgaat gctcatccgg aattccgtat ggcaatgaaa gacggtgagc   2940
tggtgatatg ggatagtgtt cacccttgtt acaccgtttt ccatgagcaa actgaaacgt   3000
tttcatcgct ctggagtgaa taccacgacg atttccggca gtttctacac atatattcgc   3060
aagatgtggc gtgttacggt gaaaacctgg cctatttccc taaagggttt attgagaata   3120
tgtttttcgt ctcagccaat ccctgggtga gtttcaccag ttttgattta aacgtggcca   3180
atatggacaa cttcttcgcc cccgttttca ccatgggcaa atattatacg caaggcgaca   3240
aggtgctgat gccgctggcg attcaggttc atcatgccgt ctgtgatggc ttccatgtcg   3300
gcagaatgct taatgaatta caacagtact gcgatgagtg gcagggcggg gcgtaatttc   3360
aattcattac cctgttatcc ctacccgaga aaattcatcg atgatggttg agatgtgtat   3420
aagagacagg ttaaatctat caccgcaagg gataaatatc taacaccgtg cgtgttgact   3480
attttacctc tggcggtgat aatggttgca tgtactaagg aggttgtatg gaacaacgca   3540
taaccctgaa agattatgca atgcgctttg ggcaaaccaa gacagctaaa gatctcggcg   3600
tatatcaaag cgcgatcaac aaggccattc atgcaggccg aaagattttt ttaactataa   3660
acgctgatgg aagcgtttat gcggaagagg taaagccctt cccgagtaac aaaaaaacaa   3720
cagcataaat aaccccgctc ttacacattc cagccctgaa aaagggcatc aaattaaacc   3780
acacctatgg tgtatgcatt tatttgcata cattcaatca attgttatct aaggaaatac   3840
ttacatatgg ttcgtgcaaa caaacgcaac gaggctctac gaatcgagag tgcgttgctt   3900
aacaaaatcg caatgcttgg aactgagaag acagcggaag ctgtgggcgt tgataagtcg   3960
cagatcagca ggtggaagag ggactggatt ccaaagttct caatgctgct tgctgttctt   4020
gaatgggggg tcgttgacga cgacatggct cgattggcgc gacaagttgc tgcgattctc   4080
accaataaaa aacgcccggc ggcaaccgag cgttctgaac aaatccagat ggagttctga   4140
```

-continued

```
ggtcattact ggatctatca acaggagtca ttatgacaaa tacagcaaaa atactcaact   4200
tcggcagagg taactttgcc ggacaggagc gtaatgtggc agatctcgat gatggttacg   4260
ccagactatc aaatatgctg cttgaggctt attcgggcgc agatctgacc aagcgacagt   4320
ttaaagtgct gcttgccatt ctgcgtaaaa cctatgggtg gaataaacca atggacagaa   4380
tcaccgattc tcaacttagc gagattacaa agttacctgt caaacggtgc aatgaagcca   4440
agttagaact cgtcagaatg aatattatca agcagcaagg cggcatgttt ggaccaaata   4500
aaaacatctc agaatggtgc atccctcaaa acgagggaaa atcccctaaa acgagggata   4560
aaacatccct caaattgggg gattgctatc cctcaaaaca gggggacaca aaagacacta   4620
ttacaaaaga aaaaagaaaa gattattcgt cagagaattc tggcgaatcc tctgaccagc   4680
cagaaaacga cctttctgtg gtgaaaccgg atgctgcaat tcagagcggc agcaagtggg   4740
ggacagcaga agacctgacc gccgcagagt ggatgtttga catggtgaag actatcgcac   4800
catcagccag aaaaccgaat tttgctgggt gggctaacga tatccgcctg atgcgtgaac   4860
gtgacggacg taaccaccgc gacatgtgtg tgctgttccg ctgggcatgc caggacaact   4920
tctggtccgg taacgtgctg agcccggcca aactccgcga taagtggacc caactcgaaa   4980
tcaaccgtaa caagcaacag gcaggcgtga cagccagcaa accaaaactc gacctgacaa   5040
acacagactg gatttacggg gtggatctat gaaaaacatc gccgcacaga tggttaactt   5100
tgaccgtgag cagatgcgtc ggatcgccaa caacatgccg gaacagtacg acgaaaagcc   5160
gcaggtacag caggtagcgc agatcatcaa cggtgtgttc agccagttac tggcaacttt   5220
cccggcgagc ctggctaacc gtgaccagaa cgaagtgaac gaaatccgtc gccagtgggt   5280
tctggctttt cgggaaaacg ggatcaccac gatggaacag gttaacgcag gaatgcgcgt   5340
agcccgtcgg cagaatcgac catttctgcc atcacccggg cagtttgttg catggtgccg   5400
ggaagaagca tccgttaccg ccggactgcc aaacgtcagc gagctggttg atatggttta   5460
cgagtattgc cggaagcgag gcctgtatcc ggatgcggag tcttatccgt ggaaatcaaa   5520
cgcgcactac tggctggtta ccaacctgta tcagaacatg cgggccaatg cgcttactga   5580
tgcggaatta cgccgtaagg ccgcagatga gcttgtccat atgactgcga gaattaaccg   5640
tggtgaggcg atccctgaac cagtaaaaca acttcctgtc atgggcggta gacctctaaa   5700
tcgtgcacag gctctggcga agatcgcaga aatcaaagct aagttcggac tgaaaggagc   5760
aagtgtatga cgggcaaaga ggcaattatt cattacctgg ggacgcataa tagcttctgt   5820
gcgccggacg ttgccgcgct aacaggcgca acagtaacca gcataaatca ggccgcggct   5880
aaaatggcac gggcaggtct tctggttatc gaaggtaagg tctggcgaac ggtgtattac   5940
cggtttgcta ccagggaaga acgggaagga aagatgagca cgaacctggt ttttaaggag   6000
tgtcgccaga gtgccgcgat gaaacgggta ttggcggtat atggagttaa aagatgacca   6060
tctacattac tgagctaata acaggcctgc tggtaatcgc aggccttttt atttggggga   6120
gagggaagtc atgaaaaaac taacctttga aattcgatct ccagcacatc agcaaaacgc   6180
tattcacgca gtacagcaaa tccttccaga cccaaccaaa ccaatcgtag taaccattca   6240
ggaacgcaac cgcagcttag accaaaacag gaagctatgg gcctgcttag gtgacgtctc   6300
tcgtcaggtt gaatggcatg gtcgctggct ggatgcagaa agctggaagt gtgtgtttac   6360
cgcagcatta aagcagcagg atgttgttcc taaccttgcc gggaatggct ttgtggtaat   6420
aggccagtca accagcagga tgcgtgtagg cgaatttgcg gagctattag agcttataca   6480
```

```
ggcattcggt acagagcgtg gcgttaagtg gtcagacgaa gcgagactgg ctctggagtg   6540
gaaagcgaga tggggagaca gggctgcatg ataaatgtcg ttagtttctc cggtggcagg   6600
acgtcagcat atttgctctg gctaatggag caaaagcgac gggcaggtaa agacgtgcat   6660
tacgttttca tggatacagg ttgtgaacat ccaatgacat atcggtttgt cagggaagtt   6720
gtgaagttct gggatatacc gctcaccgta ttgcaggttg atatcaaccc ggagcttgga   6780
cagccaaatg gttatacggt atgggaacca aaggatattc agacgcgaat gcctgttctg   6840
aagccattta tcgatatggt aaagaaatat ggcactccat acgtcggcgg cgcgttctgc   6900
actgacagat taaaactcgt tcccttcacc aaatactgtg atgaccattt cgggcgaggg   6960
aattacacca cgtggattgg catcagagct gatgaaccga agcggctaaa gccaaagcct   7020
ggaatcagat atcttgctga actgtcagac tttgagaagg aagatatcct cgcatggtgg   7080
aagcaacaac cattcgattt gcaaataccg gaacatctcg gtaactgcat attctgcatt   7140
aaaaaatcaa cgcaaaaaat cggacttgcc tgcaaagatg aggagggatt gcagcgtgtt   7200
tttaatgagg tcatcacggg atcccatgtg cgtgacggac atcgggaaac gccaaaggag   7260
attatgtacc gaggaagaat gtcgctggac ggtatcgcga aaatgtattc agaaaatgat   7320
tatcaagccc tgtatcagga catggtacga gctaaaagat tcgataccgg ctcttgttct   7380
gagtcatgcg aaatatttgg agggcagctt gatttcgact tcgggaggga agctgcatga   7440
tgcgatgtta tcggtgcggt gaatgcaaag aagataaccg cttccgacca aatcaacctt   7500
actggaatcg atggtgtctc cggtgtgaaa gaacaccaac aggggtgtta ccactaccgc   7560
aggaaaagga ggacgtgtgg cgagacagcg acgaagtatc accgacataa tctgcgaaaa   7620
ctgcaaatac cttccaacga aacgcaccag aaataaaccc aagccaatcc caaaagaatc   7680
tgacgtaaaa accttcaact acacggctca cctgtgggat atccggtggc taagacgtcg   7740
tgcgaggaaa acaaggtgat tgaccaaaat cgaagttacg aacaagaaag cgtcgagcga   7800
gctttaacgt gcgctaactg cggtcagaag ctgcatgtgc tggaagttca cgtgtgtgag   7860
cactgctgcg cagaactgat gagcgatccg aatagctcga tgcacgagga agaagatgat   7920
ggctaaacca gcgcgaagac gatgtaaaaa cgatgaatgc cgggaatggt ttcaccctgc   7980
attcgctaat cagtggtggt gctctccaga gtgtggaacc aagatagcac tcgaacgacg   8040
aagtaaagaa cgcgaaaaag cggaaaaagc agcagagaag aaacgacgac gagaggagca   8100
gaaacagaaa gataaactta agattcgaaa actcgcctta aagccccgca gttactggat   8160
taaacaagcc caacaagccg taaacgcctt catcagagaa agagaccgcg acttaccatg   8220
tatctcgtgc ggaacgctca cgtctgctca gtgggatgcc ggacattacc ggacaactgc   8280
tgcggcacct caactccgat ttaatgaacg caatattcac aagcaatgcg tggtgtgcaa   8340
ccagcacaaa agcggaaatc tcgttccgta tcgcgtcgaa ctgattagcc gcatcgggca   8400
ggaagcagta gacgaaatcg aatcaaacca taaccgccat cgctggacta tcgaagagtg   8460
caaggcgatc aaggcagagt accaacagaa actcaaagac ctgcgaaata gcagaagtga   8520
ggccgcatga cgttctcagt aaaaaccatt ccagacatgc tcgttgaagc atacggaaat   8580
cagacagaag tagcacgcag actgaaatgt agtcgcggta cggtcagaaa atacgttgat   8640
gataaagacg ggaaaatgca cgccatcgtc aacgacgttc tcatggttca tcgcggatgg   8700
agtgaaagag atgcgctatt acgaaaaaat tgatggcagc aaataccgaa atatttgggt   8760
agttggcgat ctgcacggat gctacacgaa cctgatgaac aaactggata cgattggatt   8820
cgacaacaaa aaagacctgc ttatctcggt gggcgatttg gttgatcgtg gtgcagagaa   8880
```

cgttgaatgc ctggaattaa tcacattccc ctggttcaga gctgtacgtg gaaaccatga 8940
gcaaatgatg attgatggct tatcagagcg tggaaacgtt aatcactggc tgcttaatgg 9000
cggtggctgg ttctttaatc tcgattacga caaagaaatt ctggctaaag ctcttgccca 9060
taaagcagat gaacttccgt taatcatcga actggtgagc aaagataaaa aatatgttat 9120
ctgccacgcc gattatccct ttgacgaata cgagtttgga aagccagttg atcatcagca 9180
ggtaatctgg aaccgcgaac gaatcagcaa ctcacaaaac gggatcgtga aagaaatcaa 9240
aggcgcggac acgttcatct ttggtcatac gccagcagtg aaaccactca agtttgccaa 9300
ccaaatgtat atcgataccg gcgcagtgtt ctgcggaaac ctaacattga ttcaggtaca 9360
gggagaaggc gcatgagact cgaaagcgta gctaaatttc attcgccaaa aagcccgatg 9420
atgagcgact caccacgggc cacggcttct gactctcttt ccggtactga tgtgatggct 9480
gctatgggga tggcgcaatc acaagccgga ttcggtatgg ctgcattctg cggtaagcac 9540
gaactcagcc agaacgacaa acaaaaggct atcaactatc tgatgcaatt tgcacacaag 9600
gtatcgggga aataccgtgg tgtggcaaag cttgaaggaa atactaaggc aaaggtactg 9660
caagtgctcg caacattcgc ttatgcggat tattgccgta gtgccgcgac gccgggggca 9720
agatgcagag attgccatgg tacaggccgt gcggttgata ttgccaaaac agagctgtgg 9780
gggagagttg tcgagaaaga gtgcggaaga tgcaaaggcg tcggctattc aaggatgcca 9840
gcaagcgcag catatcgcgc tgtgacgatg ctaatcccaa accttaccca acccacctgg 9900
tcacgcactg ttaagccgct gtatgacgct ctggtggtgc aatgccacaa agaagagtca 9960
atcgcagaca acattttgaa tgcggtcaca cgttagcagc atgattgcca cggatggcaa 10020
catattaacg gcatgatatt gacttattga ataaaattgg gtaaatttga ctcaacgatg 10080
ggttaattcg ctcgttgtgg tagtgagatg aaaagaggcg gcgcttacta ccgattccgc 10140
ctagttggtc acttcgacgt atcgtctgga actccaacca tcgcaggcag agaggtctgc 10200
aaaatgcaat cccgaaacag ttcgcaggta atagttagag cctgcataac ggtttcggga 10260
ttttttatat ctgcacaaca ggtaagagca ttgagtcgat aatcgtgaag agtcggcgag 10320
cctggttagc cagtgctctt tccgttgtgc tgaattaagc gaataccgga agcagaaccg 10380
gatcaccaaa tgcgtacagg cgtcatcgcc gcccagcaac agcacaaccc aaactgagcc 10440
gtagccactg tctgtcctga attcattagt aatagttacg ctgcggcctt ttacacatga 10500
ccttcgtgaa agcgggtggc aggaggtcgc gctaacaacc tcctgccgtt ttgcccgtgc 10560
atatcggtca cgaacaaatc tgattactaa acacagtagc ctggatttgt tctatcagta 10620
atcgacctta ttcctaatta aatagagcaa atccccttat tgggggtaag acatgaagat 10680
gccagaaaaa catgacctgt tggccgccat tctcgcggca aaggaacaag gcatcggggc 10740
aatccttgcg tttgcaatgg cgtaccttcg cggcagatat aatggcggtg cgtttacaaa 10800
aacagtaatc gacgcaacga tgtgcgccat tatcgcctgg ttcattcgtg accttctcga 10860
cttcgccgga ctaagtagca atctcgctta tataacgagc gtgtttatcg gctacatcgg 10920
tactgactcg attggttcgc ttatcaaacg cttcgctgct aaaaaagccg gagtagaaga 10980
tggtagaaat caataatcaa cgtaaggcgt tcctcgatat gctggcgtgg tcggagggaa 11040
ctgataacgg acgtcagaaa accagaaatc atggttatga cgtcattgta ggcggagagc 11100
tatttactga ttactccgat caccctcgca aacttgtcac gctaaaccca aaactcaaat 11160
caacaggcgc cggacgctac cagcttcttt cccgttggtg ggatgcctac cgcaagcagc 11220

-continued ttggcctgaa agacttctct ccgaaaagtc aggacgctgt ggcattgcag cagattaagg 11280
agcgtggcgc tttacctatg attgatcgtg gtgatatccg tcaggcaatc gaccgttgca 11340
gcaatatctg ggcttcactg ccgggcgctg gttatggtca gttcgagcat aaggctgaca 11400
gcctgattgc aaaattcaaa gaagcgggcg gaacggtcag agagattgat gtatgagcag 11460
agtcaccgcg attatctccg ctctggttat ctgcatcatc gtctgcctgt catgggctgt 11520
taatcattac cgtgataacg ccattaccta caaagcccag cgcgacaaaa atgccagaga 11580
actgaagctg gcgaacgcgg caattactga catgcagatg cgtcagcgtg atgttgctgc 11640
gctcgatgca aaatacacga aggagttagc tgatgctaaa gctgaaaatg atgctctgcg 11700
tgatgatgtt gccgctggtc gtcgtcggtt gcacatcaaa gcagtctgtc agtcagtgcg 11760
tgaagccacc accgcctccg gcgtggataa tgcagcctcc ccccgactgg cagacaccgc 11820
tgaacgggat tatttcaccc tcagagagag gctgatcact atgcaaaaac aactggaagg 11880
aacccagaag tatattaatg agcagtgcag atagagttgc ccatatcgat gggcaactca 11940
tgcaattatt gtgagcaata cacacgcgct tccagcggag tataaatgcc taaagtaata 12000
aaaccgagca atccatttac gaatgtttgc tgggtttctg ttttaacaac attttctgcg 12060
ccgccacaaa ttttggctgc atcgacagtt ttcttctgcc caattccaga aacgaagaaa 12120
tgatgggtga tggtttcctt tggtgctact gctgccggtt tgttttgaac agtaaacgtc 12180
tgttgagcac atcctgtaat aagcagggcc agcgcagtag cgagtagcat ttttttcatg 12240
gtgttattcc cgatgctttt tgaagttcgc agaatcgtat gtgtagaaaa ttaaacaaac 12300
cctaaacaat gagttgaaat ttcatattgt taatatttat taatgtatgt caggtgcgat 12360
gaatcgtcat tgtattcccg gattaactat gtccacagcc ctgacgggga acttctctgc 12420
gggagtgtcc gggaataatt aaaacgatgc acacagggtt tagcgcgtac acgtattgca 12480
ttatgccaac gccccggtgc tgacacggaa gaaaccggac gttatgattt agcgtggaaa 12540
gatttgtgta gtgttctgaa tgctctcagt aaatagtaat gaattatcaa aggtatagta 12600
atatctttta tgttcatgga tatttgtaac ccatcggaaa actcctgctt tagcaagatt 12660
ttccctgtat tgctgaaatg tgatttctct tgatttcaac ctatcatagg acgtttctat 12720
aagatgcgtg tttcttgaga atttaacatt tacaaccttt ttaagtcctt ttattaacac 12780
ggtgttatcg ttttctaaca cgatgtgaat attatctgtg gctagatagt aaatataatg 12840
tgagacgttg tgacgtttta gttcagaata aaacaattca cagtctaaat cttttcgcac 12900
ttgatcgaat atttctttaa aaatggcaac ctgagccatt ggtaaaacct tccatgtgat 12960
acgagggcgc gtagtttgca ttatcgtttt tatcgtttca atctggtctg acctccttgt 13020
gttttgttga tgatttatgt caaatattag gaatgttttc acttaatagt attggttgcg 13080
taacaaagtg cggtcctgct ggcattctgg agggaaatac aaccgacaga tgtatgtaag 13140
gccaacgtgc tcaaatcttc atacagaaag atttgaagta atattttaac cgctagatga 13200
agagcaagcg catggagcga caaaatgaat aaagaacaat ctgctgatga tccctccgtg 13260
gatctgattc gtgtaaaaaa tatgcttaat agcaccattt ctatgagtta ccctgatgtt 13320
gtaattgcat gtatagaaca taaggtgtct ctggaagcat tcagagcaat tgaggcagcg 13380
ttggtgaagc acgataataa tatgaaggat tattccctgg tggttgactg atcaccataa 13440
ctgctaatca ttcaaactat ttagtctgtg acagagccaa cacgcagtct gtcactgtca 13500
ggaaagtggt aaaactgcaa ctcaattact gcaatgccct cgtaattaag tgaatttaca 13560
atatcgtcct gttcggaggg aagaacgcgg gatgttcatt cttcatcact tttaattgat 13620
gtatatgctc tcttttctga cgttagtctc cgacggcagg cttcaatgac ccaggctgag 13680
aaattcccgg accctttttg ctcaagagcg atgttaattt gttcaatcat ttggttagga 13740
aagcggatgt tgcgggttgt tgttctgcgg gttctgttct tcgttgacat gaggttgccc 13800
cgtattcagt gtcgctgatt tgtattgtct gaagttgttt ttacgttaag ttgatgcaga 13860
tcaattaata cgatacctgc gtcataattg attatttgac gtggtttgat ggcctccacg 13920
cacgttgtga tatgtagatg ataatcatta tcactttacg ggtcctttcc ggtgatccga 13980
caggttacgg ggcggcgacc tcgcgggttt tcgctattta tgaaaatttt ccggtttaag 14040
gcgtttccgt tcttcttcgt cataacttaa tgtttttatt taaaataccc tctgaaaaga 14100
aaggaaacga caggtgctga aagcgaggct ttttggcctc tgtcgtttcc tttctctgtt 14160
tttgtccgtg gaatgaacaa tggaagtcaa caaaaagcag ctggctgaca ttttcggtgc 14220
gagtatccgt accattcaga actggcagga acagggaatg cccgttctgc gaggcggtgg 14280
caagggtaat gaggtgcttt atgactctgc cgccgtcata aaatggtatg ccgaaaggga 14340
tgctgaaatt gagaacgaaa agctgcgccg ggaggttgaa gaactgcggc aggccagcga 14400
ggcagatctc cagccaggaa ctattgagta cgaacgccat cgacttacgc gtgcgcaggc 14460
cgacgcacag gaactgaaga atgccagaga ctccgctgaa gtggtggaaa ccgcattctg 14520
tactttcgtg ctgtcgcgga tcgcaggtga aattgccagt attctcgacg ggctccccct 14580
gtcggtgcag cggcgttttc cggaactgga aaaccgacat gttgatttcc tgaaacggga 14640
tatcatcaaa gccatgaaca aagcagccgc gctggatgaa ctgataccgg ggttgctgag 14700
tgaatatatc gaacagtcag gttaacaggc tgcggcattt tgtccgcgcc gggcttcgct 14760
cactgttcag gccggagcca cagaccgccg ttgaatgggc ggatgctaat tactatctcc 14820
cgaaagaatc cgcataccag gaagggcgct gggaaacact gccctttcag cgggccatca 14880
tgaatgcgat gggcagcgac tacatccgtg aggtgaatgt ggtgaagtct gcccgtgtcg 14940
gttattccaa aatgctgctg ggtgtttatg cctactttat agagcataag cagcgcaaca 15000
cccttatctg gttgccgacg gatggtgatg ccgagaactt tatgaaaacc cacgttgagc 15060
cgactattcg tgatattccg tcgctgctgg cgctggcccc gtggtatggc aaaaagcacc 15120
gggataacac gctcaccatg aagcgtttca ctaatgggcg tggcttctgg tgcctgggcg 15180
gtaaagcggc aaaaaactac cgtgaaaagt cggtggatgt ggcgggttat gatgaacttg 15240
ctgcttttga tgatgatatt gaacaggaag gctctccgac gttcctgggt gacaagcgta 15300
ttgaaggctc ggtctggcca aagtccatcc gtggctccac gccaaaagtg agaggcacct 15360
gtcagattga gcgtgcagcc agtgaatccc cgcattttat gcgttttcat gttgcctgcc 15420
cgcattgcgg ggaggagcag tatcttaaat ttggcgacaa agagacgccg tttggcctca 15480
aatggacgcc ggatgacccc tccagcgtgt tttatctctg cgagcataat gcctgcgtca 15540
tccgccagca ggagctggac tttactgatg cccgttatat ctgcgaaaag accgggatct 15600
ggacccgtga tggcattctc tggttttcgt catccggtga agagattgag ccacctgaca 15660
gtgtgacctt tcacatctgg acagcgtaca gcccgttcac cacctgggtg cagattgtca 15720
aagactggat gaaaacgaaa ggggatacgg gaaaacgtaa aaccttcgta aacaccacgc 15780
tcggtgagac gtgggaggcg aaaattggcg aacgtccgga tgctgaagtg atggcagagc 15840
ggaaagagca ttattcagcg cccgttcctg accgtgtggc ttacctgacc gccggtatcg 15900
actcccagct ggaccgctac gaaatgcgcg tatggggatg gggggccgggt gaggaaagct 15960

-continued

```
ggctgattga ccggcagatt attatgggcc gccacgacga tgaacagacg ctgctgcgtg  16020
tggatgaggc catcaataaa acctataccc gccggaatgg tgcagaaatg tcgatatccc  16080
gtatctgctg ggatactggc gggattgacc cgaccattgt gtatgaacgc tcgaaaaaac  16140
atgggctgtt ccgggtgatc cccattaaag gggcatccgt ctacggaaag ccggtggcca  16200
gcatgccacg taagcgaaac aaaaacgggg tttaccttac cgaaatcggt acggataccg  16260
cgaaagagca gatttataac cgcttcacac tgacgccgga aggggatgaa ccgcttcccg  16320
gtgccgttca cttcccgaat aacccggata tttttgatct gaccgaagcg cagcagctga  16380
ctgctgaaga gcaggtcgaa aaatgggtgg atggcaggaa aaaaatactg tgggacagca  16440
aaaagcgacg caatgaggca ctcgactgct tcgtttatgc gctggcggcg ctgcgcatca  16500
gtatttcccg ctggcagctg gatctcagtg cgctgctggc gagcctgcag gaagaggatg  16560
gtgcagcaac caacaagaaa acactggcag attacgcccg tgccttatcc ggagaggatg  16620
aatgacgcga caggaagaac ttgccgctgc ccgtgcggca ctgcatgacc tgatgacagg  16680
taaacgggtg gcaacagtac agaaagacgg acgaagggtg gagtttacgg ccacttccgt  16740
gtctgacctg aaaaaatata ttgcagagct ggaagtgcag accggcatga cacagcgacg  16800
caggggacct gcaggatttt atgtatgaaa acgcccacca ttcccaccct tctggggccg  16860
gacggcatga catcgctgcg cgaatatgcc ggttatcacg gcggtggcag cggatttgga  16920
gggcagttgc ggtcgtggaa cccaccgagt gaaagtgtgg atgcagccct gttgcccaac  16980
tttacccgtg gcaatgcccg cgcagacgat ctggtacgca ataacggcta tgccgccaac  17040
gccatccagc tgcatcagga tcatatcgtc gggtcttttt tccggctcag tcatcgccca  17100
agctggcgct atctgggcat cggggaggaa gaagcccgtg ccttttcccg cgaggttgaa  17160
gcggcatgga aagagtttgc cgaggatgac tgctgctgca ttgacgttga gcgaaaacgc  17220
acgtttacca tgatgattcg ggaaggtgtg gccatgcacg cctttaacgg tgaactgttc  17280
gttcaggcca cctgggatac cagttcgtcg cggcttttcc ggacacagtt ccggatggtc  17340
agcccgaagc gcatcagcaa cccgaacaat accggcgaca gccggaactg ccgtgccggt  17400
gtgcagatta atgacagcgg tgcggcgctg ggatattacg tcagcgagga cgggtatcct  17460
ggctggatgc cgcagaaatg gacatggata ccccgtgagt tacccggcgg gcgcgcctcg  17520
ttcattcacg tttttgaacc cgtggaggac gggcagactc gcggtgcaaa tgtgttttac  17580
agcgtgatgg agcagatgaa gatgctcgac acgctgcaga acacgcagct gcagagcgcc  17640
attgtgaagg cgatgtatgc cgccaccatt gagagtgagc tggatacgca gtcagcgatg  17700
gattttattc tgggcgcgaa cagtcaggag cagcgggaaa ggctgaccgg ctggattggt  17760
gaaattgccg cgtattacgc cgcagcgccg gtccggctgg gaggcgcaaa agtaccgcac  17820
ctgatgccgg gtgactcact gaacctgcag acggctcagg atacggataa cggctactcc  17880
gtgtttgagc agtcactgct gcggtatatc gctgccgggc tgggtgtctc gtatgagcag  17940
ctttcccgga attacgccca gatgagctac tccacggcac gggccagtgc gaacgagtcg  18000
tgggcgtact ttatggggcg gcgaaaattc gtcgcatccc gtcaggcgag ccagatgttt  18060
ctgtgctggc tggaagaggc catcgttcgc cgcgtggtga cgttaccttc aaaagcgcgc  18120
ttcagttttc aggaagcccg cagtgcctgg gggaactgcg actggatagg ctccggtcgt  18180
atggccatcg atggtctgaa agaagttcag gaagcggtga tgctgataga agccggactg  18240
agtacctacg agaaagagtg cgcaaaacgc ggtgacgact atcaggaaat tttgcccag  18300
caggtccgtg aaacgatgga gcgccgtgca gccggtctta aaccgcccgc ctgggcggct  18360
```

```
gcagcatttg aatccgggct gcgacaatca acagaggagg agaagagtga cagcagagct  18420
gcgtaatctc ccgcatattg ccagcatggc ctttaatgag ccgctgatgc ttgaacccgc  18480
ctatgcgcgg gttttctttt gtgcgcttgc aggccagctt gggatcagca gcctgacgga  18540
tgcggtgtcc ggcgacagcc tgactgccca ggaggcactc gcgacgctgg cattatccgg  18600
tgatgatgac ggaccacgac aggcccgcag ttatcaggtc atgaacggca tcgccgtgct  18660
gccggtgtcc ggcacgctgg tcagccggac gcgggcgctg cagccgtact cggggatgac  18720
cggttacaac ggcattatcg cccgtctgca acaggctgcc agcgatccga tggtggacgg  18780
cattctgctc gatatggaca cgcccggcgg gatggtggcg gggcatttg actgcgctga  18840
catcatcgcc cgtgtgcgtg acataaaacc ggtatgggcg cttgccaacg acatgaactg  18900
cagtgcaggt cagttgcttg ccagtgccgc ctcccggcgt ctggtcacgc agaccgcccg  18960
gacaggctcc atcggcgtca tgatggctca cagtaattac ggtgctgcgc tggagaaaca  19020
gggtgtggaa atcacgctga tttacagcgg cagccataag gtggatggca accccctacag  19080
ccatcttccg gatgacgtcc gggagacact gcagtcccgg atggacgcaa cccgccagat  19140
gtttgcgcag aaggtgtcgg catataccgg cctgtccgtg caggttgtgc tggataccga  19200
ggctgcagtg tacagcggtc aggaggccat tgatgccgga ctggctgatg aacttgttaa  19260
cagcaccgat gcgatcaccg tcatgcgtga tgcactggat gcacgtaaat cccgtctctc  19320
aggagggcga atgaccaaag agactcaatc aacaactgtt tcagccactg cttcgcaggc  19380
tgacgttact gacgtggtgc cagcgacgga gggcgagaac gccagcgcgg cgcagccgga  19440
cgtgaacgcg cagatcaccg cagcggttgc ggcagaaaac agccgcatta tggggatcct  19500
caactgtgag gaggctcacg gacgcgaaga acaggcacgc gtgctggcag aaaccccgg  19560
tatgaccgtg aaaacggccc gccgcattct ggccgcagca ccacagagtg cacaggcgcg  19620
cagtgacact gcgctggatc gtctgatgca gggggcaccg gcaccgctgg ctgcaggtaa  19680
cccggcatct gatgccgtta acgatttgct gaacacacca gtgtaaggga tgtttatgac  19740
gagcaaagaa acctttaccc attaccagcc gcagggcaac agtgacccgg ctcataccgc  19800
aaccgcgccc ggcggattga gtgcgaaagc gcctgcaatg accccgctga tgctggacac  19860
ctccagccgt aagctggttg cgtgggatgg caccaccgac ggtgctgccg ttggcattct  19920
tgcggttgct gctgaccaga ccagcaccac gctgacgttc tacaagtccg gcacgttccg  19980
ttatgaggat gtgctctggc cggaggctgc cagcgacgag acgaaaaaac ggaccgcgtt  20040
tgccggaacg gcaatcagca tcgtttaact ttacccttca tcactaaagg ccgcctgtgc  20100
ggcttttttt acgggatttt tttatgtcga tgtacacaac cgcccaactg ctggcggcaa  20160
atgagcagaa atttaagttt gatccgctgt ttctgcgtct ctttttccgt gagagctatc  20220
ccttcaccac ggagaaagtc tatctctcac aaattccggg actggtaaac atggcgctgt  20280
acgtttcgcc gattgtttcc ggtgaggtta tccgttcccg tggcggctcc acctctgaat  20340
ttacgccggg atatgtcaag ccgaagcatg aagtgaatcc gcagatgacc ctgcgtcgcc  20400
tgccggatga agatccgcag aatctggcgg acccggctta ccgccgccgt cgcatcatca  20460
tgcagaacat gcgtgacgaa gagctggcca ttgctcaggt cgaagagatg caggcagttt  20520
ctgccgtgct taagggcaaa tacaccatga ccggtgaagc cttcgatccg gttgaggtgg  20580
atatgggccg cagtgaggag aataacatca cgcagtccgg cggcacggag tggagcaagc  20640
gtgacaagtc cacgtatgac ccgaccgacg atatcgaagc ctacgcgctg aacgccagcg  20700
```

-continued gtgtggtgaa tatcatcgtg ttcgatccga aaggctgggc gctgttccgt tccttcaaag 20760
ccgtcaagga gaagctggat acccgtcgtg gctctaattc cgagctggag acagcggtga 20820
aagacctggg caaagcggtg tcctataagg ggatgtatgg cgatgtggcc atcgtcgtgt 20880
attccggaca gtacgtggaa aacggcgtca aaaagaactt cctgccggac aacacgatgg 20940
tgctggggaa cactcaggca cgcggtctgc gcacctatgg ctgcattcag gatgcggacg 21000
cacagcgcga aggcattaac gcctctgccc gttacccgaa aaactgggtg accaccggcg 21060
atccggcgcg tgagttcacc atgattcagt cagcaccgct gatgctgctg gctgaccctg 21120
atgagttcgt gtccgtacaa ctggcgtaat catggccctt cggggccatt gtttctctgt 21180
ggaggagtcc atgacgaaag atgaactgat tgcccgtctc cgctcgctgg gtgaacaact 21240
gaaccgtgat gtcagcctga cggggacgaa agaagaactg gcgctccgtg tggcagagct 21300
gaaagaggag cttgatgaca cggatgaaac tgccggtcag gacacccctc tcagccggga 21360
aaatgtgctg accggacatg aaaatgaggt gggatcagcg cagccggata ccgtgattct 21420
ggatacgtct gaactggtca cggtcgtggc actggtgaag ctgcatactg atgcacttca 21480
cgccacgcgg gatgaacctg tggcatttgt gctgccggga acggcgtttc gtgtctctgc 21540
cggtgtggca gccgaaatga cagagcgcgg cctggccaga atgcaataac gggaggcgct 21600
gtggctgatt tcgataacct gttcgatgct gccattgccc gcgccgatga aacgatacgc 21660
gggtacatgg gaacgtcagc caccattaca tccggtgagc agtcaggtgc ggtgatacgt 21720
ggtgtttttg atgaccctga aaatatcagc tatgccggac agggcgtgcg cgttgaaggc 21780
tccagcccgt ccctgtttgt ccggactgat gaggtgcggc agctgcggcg tggagacacg 21840
ctgaccatcg gtgaggaaaa tttctgggta gatcgggttt cgccggatga tggcggaagt 21900
tgtcatctct ggcttggacg gggcgtaccg cctgccgtta accgtcgccg ctgaaagggg 21960
gatgtatggc cataaaaggt cttgagcagg ccgttgaaaa cctcagccgt atcagcaaaa 22020
cggcggtgcc tggtgccgcc gcaatggcca ttaaccgcgt tgcttcatcc gcgatatcgc 22080
agtcggcgtc acaggttgcc cgtgagacaa aggtacgccg gaaactggta aaggaaaggg 22140
ccaggctgaa aagggccacg gtcaaaaatc cgcaggccag aatcaaagtt aaccgggggg 22200
atttgcccgt aatcaagctg ggtaatgcgc gggttgtcct ttcgcgccgc aggcgtcgta 22260
aaaaggggca gcgttcatcc ctgaaaggtg gcggcagcgt gcttgtggtg ggtaaccgtc 22320
gtattcccgg cgcgtttatt cagcaactga aaaatggccg gtggcatgtc atgcagcgtg 22380
tggctgggaa aaaccgttac cccattgatg tggtgaaaat cccgatggcg gtgccgctga 22440
ccacggcgtt taaacaaaat attgagcgga tacggcgtga acgtcttccg aaagagctgg 22500
gctatgcgct gcagcatcaa ctgaggatgg taataaagcg atgaaacata ctgaactccg 22560
tgcagccgta ctggatgcac tggagaagca tgacaccggg gcgacgtttt ttgatggtcg 22620
ccccgctgtt tttgatgagg cggattttcc ggcagttgcc gtttatctca ccggcgctga 22680
atacacgggc gaagagctgg acagcgatac ctggcaggcg gagctgcata tcgaagtttt 22740
cctgcctgct caggtgccgg attcagagct ggatgcgtgg atggagtccc ggatttatcc 22800
ggtgatgagc gatatcccgg cactgtcaga tttgatcacc agtatggtgg ccagcggcta 22860
tgactaccgg cgcgacgatg atgcgggctt gtggagttca gccgatctga cttatgtcat 22920
tacctatgaa atgtgaggac gctatgcctg taccaaatcc tacaatgccg gtgaaaggtg 22980
ccgggaccac cctgtgggtt tataagggga gcggtgaccc ttacgcgaat ccgctttcag 23040
acgttgactg gtcgcgtctg gcaaaagtta aagacctgac gcccggcgaa ctgaccgctg 23100

-continued agtcctatga cgacagctat ctcgatgatg aagatgcaga ctggactgcg accgggcagg 23160
ggcagaaatc tgccggagat accagcttca cgctggcgtg gatgcccgga gagcaggggc 23220
agcaggcgct gctggcgtgg tttaatgaag gcgataccog tgcctataaa atccgcttcc 23280
cgaacggcac ggtcgatgtg ttccgtggct gggtcagcag tatcggtaag gcggtgacgg 23340
cgaaggaagt gatcacccgc acggtgaaag tcaccaatgt gggacgtccg tcgatggcag 23400
aagatcgcag cacggtaaca gcggcaaccg gcatgaccgt gacgcctgcc agcacctcgg 23460
tggtgaaagg gcagagcacc acgctgaccg tggccttcca gccggagggc gtaaccgaca 23520
agagctttcg tgcggtgtct gcggataaaa caaaagccac cgtgtcggtc agtggtatga 23580
ccatcaccgt gaacggcgtt gctgcaggca aggtcaacat tccggttgta tccggtaatg 23640
gtgagtttgc tgcggttgca gaaattaccg tcaccgccag ttaatccgga gagtcagcga 23700
tgttcctgaa aaccgaatca tttgaacata acggtgtgac cgtcacgctt tctgaactgt 23760
cagccctgca gcgcattgag catctcgccc tgatgaaacg gcaggcagaa caggcggagt 23820
cagacagcaa ccggaagttt actgtggaag acgccatcag aaccggcgcg tttctggtgg 23880
cgatgtccct gtggcataac catccgcaga agacgcagat gccgtccatg aatgaagccg 23940
ttaaacagat tgagcaggaa gtgcttacca cctggcccac ggaggcaatt tctcatgctg 24000
aaaacgtggt gtaccggctg tctggtatgt atgagtttgt ggtgaataat gcccctgaac 24060
agacagagga cgccgggccc gcagagcctg tttctgcggg aaagtgttcg acggtgagct 24120
gagttttgcc ctgaaactgg cgcgtgagat ggggcgaccc gactggcgtg ccatgcttgc 24180
cgggatgtca tccacggagt atgccgactg gcaccgcttt tacagtaccc attattttca 24240
tgatgttctg ctggatatgc acttttccgg gctgacgtac accgtgctca gcctgttttt 24300
cagcgatccg gatatgcatc cgctggattt cagtctgctg aaccggcgcg aggctgacga 24360
agagcctgaa gatgatgtgc tgatgcagaa agcggcaggg cttgccggag gtgtccgctt 24420
tggcccggac gggaatgaag ttatccccgc ttccccggat gtggcggaca tgacggagga 24480
tgacgtaatg ctgatgacag tatcagaagg gatcgcagga ggagtccggt atggctgaac 24540
cggtaggcga tctggtcgtt gatttgagtc tggatgcggc cagatttgac gagcagatgg 24600
ccagagtcag gcgtcatttt tctggtacgg aaagtgatgc gaaaaaaaca gcggcagtcg 24660
ttgaacagtc gctgagccga caggcgctgg ctgcacagaa agcggggatt tccgtcgggc 24720
agtataaagc cgccatgcgt atgctgcctg cacagttcac cgacgtggcc acgcagcttg 24780
caggcgggca aagtccgtgg ctgatcctgc tgcaacaggg ggggcaggtg aaggactcct 24840
tcggcgggat gatccccatg ttcagggggc ttgccggtgc gatcaccctg ccgatggtgg 24900
gggccacctc gctggcggtg gcgaccggtg cgctggcgta tgcctggtat cagggcaact 24960
caaccctgtc cgatttcaac aaaacgctgg tcctttccgg caatcaggcg ggactgacgg 25020
cagatcgtat gctggtcctg tccagagccg ggcaggcggc agggctgacg tttaaccaga 25080
ccagcgagtc actcagcgca ctggttaagg cgggggtaag cggtgaggct cagattgcgt 25140
ccatcagcca gagtgtggcg cgtttctcct ctgcatccgg cgtggaggtg gacaaggtcg 25200
ctgaagcctt cgggaagctg accacagacc cgacgtcggg gctgacggcg atggctcgcc 25260
agttccataa cgtgtcggcg gagcagattg cgtatgttgc tcagttgcag cgttccggcg 25320
atgaagccgg ggcattgcag gcggcgaacg aggccgcaac gaaagggttt gatgaccaga 25380
cccgccgcct gaaagagaac atgggcacgc tggagacctg ggcagacagg actgcgcggg 25440

-continued

```
cattcaaatc catgtgggat gcggtgctgg atattggtcg tcctgatacc gcgcaggaga  25500
tgctgattaa ggcagaggct gcgtataaga aagcagacga catctggaat ctgcgcaagg  25560
atgattattt tgttaacgat gaagcgcggg cgcgttactg ggatgatcgt gaaaaggccc  25620
gtcttgcgct tgaagccgcc cgaaagaagg ctgagcagca gactcaacag gacaaaaatg  25680
cgcagcagca gagcgatacc gaagcgtcac ggctgaaata taccgaagag gcgcagaagg  25740
cttacgaacg gctgcagacg ccgctggaga aatataccgc ccgtcaggaa gaactgaaca  25800
aggcactgaa agacgggaaa atcctgcagg cggattacaa cacgctgatg gcggcggcga  25860
aaaaggatta tgaagcgacg ctgaaaaagc cgaaacagtc cagcgtgaag gtgtctgcgg  25920
gcgatcgtca ggaagacagt gctcatgctg ccctgctgac gcttcaggca gaactccgga  25980
cgctggagaa gcatgccgga gcaaatgaga aaatcagcca gcagcgccgg gatttgtgga  26040
aggcggagag tcagttcgcg gtactggagg aggcggcgca acgtcgccag ctgtctgcac  26100
aggagaaatc cctgctggcg cataaagatg agacgctgga gtacaaacgc cagctggctg  26160
cacttggcga caaggttacg tatcaggagc gcctgaacgc gctggcgcag caggcggata  26220
aattcgcaca gcagcaacgg gcaaaacggg ccgccattga tgcgaaaagc cgggggctga  26280
ctgaccggca ggcagaacgg gaagccacgg aacagcgcct gaaggaacag tatggcgata  26340
atccgctggc gctgaataac gtcatgtcag agcagaaaaa gacctgggcg gctgaagacc  26400
agcttcgcgg gaactggatg gcaggcctga agtccggctg gagtgagtgg gaagagagcg  26460
ccacggacag tatgtcgcag gtaaaaagtg cagccacgca gacctttgat ggtattgcac  26520
agaatatggc ggcgatgctg accggcagtg agcagaactg gcgcagcttc acccgttccg  26580
tgctgtccat gatgacagaa attctgctta agcaggcaat ggtggggatt gtcgggagta  26640
tcggcagcgc cattggcggg gctgttggtg gcggcgcatc cgcgtcaggc ggtacagcca  26700
ttcaggccgc tgcggcgaaa ttccattttg caaccggagg atttacggga accggcggca  26760
aatatgagcc agcggggatt gttcaccgtg gtgagtttgt cttcacgaag gaggcaacca  26820
gccggattgg cgtggggaat ctttaccggc tgatgcgcgg ctatgccacc ggcggttatg  26880
tcggtacacc gggcagcatg gcagacagcc ggtcgcaggc gtccgggacg tttgagcaga  26940
ataaccatgt ggtgattaac aacgacggca cgaacgggca gataggtccg gctgctctga  27000
aggcggtgta tgacatggcc cgcaagggtg cccgtgatga aattcagaca cagatgcgtg  27060
atggtggcct gttctccgga ggtggacgat gaagaccttc cgctggaaag tgaaacccgg  27120
tatggatgtg gcttcggtcc cttctgtaag aaaggtgcgc tttggtgatg gctattctca  27180
gcgagcgcct gccgggctga atgccaacct gaaaacgtac agcgtgacgc tttctgtccc  27240
ccgtgaggag gccacggtac tggagtcgtt tctggaagag cacgggggct ggaaatcctt  27300
tctgtggacg ccgccttatg agtggcggca gataaaggtg acctgcgcaa aatggtcgtc  27360
gcgggtcagt atgctgcgtg ttgagttcag cgcagagttt gaacaggtgg tgaactgatg  27420
caggatatcc ggcaggaaac actgaatgaa tgcacccgtg cggagcagtc ggccagcgtg  27480
gtgctctggg aaatcgacct gacagaggtc ggtggagaac gttatttttt ctgtaatgag  27540
cagaacgaaa aaggtgagcc ggtcacctgg caggggcgac agtatcagcc gtatcccatt  27600
caggggagcg gttttgaact gaatggcaaa ggcaccagta cgcgccccac gctgacggtt  27660
tctaacctgt acggtatggt caccgggatg gcggaagata tgcagagtct ggtcggcgga  27720
acggtggtcc ggcgtaaggt ttacgcccgt tttctggatg cggtgaactt cgtcaacgga  27780
aacagttacg ccgatccgga gcaggaggtg atcagccgct ggcgcattga gcagtgcagc  27840
```

-continued gaactgagcg cggtgagtgc ctcctttgta ctgtccacgc cgacggaaac ggatggcgct 27900
gtttttccgg gacgtatcat gctggccaac acctgcacct ggacctatcg cggtgacgag 27960
tgcggttata gcggtccggc tgtcgcggat gaatatgacc agccaacgtc cgatatcacg 28020
aaggataaat gcagcaaatg cctgagcggt tgtaagttcc gcaataacgt cggcaacttt 28080
ggcggcttcc tttccattaa caaactttcg cagtaaatcc catgacacag acagaatcag 28140
cgattctggc gcacgcccgg cgatgtgcgc cagcggagtc gtgcggcttc gtggtaagca 28200
cgccggaggg ggaaagatat ttcccctgcg tgaatatctc cggtgagccg gaggctattt 28260
ccgtatgtcg ccggaagact ggctgcaggc agaaatgcag ggtgagattg tggcgctggt 28320
ccacagccac cccggtggtc tgccctggct gagtgaggcc gaccggcggc tgcaggtgca 28380
gagtgatttg ccgtggtggc tggtctgccg gggacgatt cataagttcc gctgtgtgcc 28440
gcatctcacc gggcggcgct ttgagcacgg tgtgacggac tgttacacac tgttccggga 28500
tgcttatcat ctggcgggga ttgagatgcc ggactttcat cgtgaggatg actggtggcg 28560
taacggccag aatctctatc tggataatct ggaggcgacg gggctgtatc aggtgccgtt 28620
gtcagcggca cagccgggcg atgtgctgct gtgctgtttt ggttcatcag tgccgaatca 28680
cgccgcaatt tactgcggcg acggcgagct gctgcaccat attcctgaac aactgagcaa 28740
acgagagagg tacaccgaca aatggcagcg acgcacacac tccctctggc gtcaccgggc 28800
atggcgcgca tctgccttta cggggattta caacgatttg gtcgccgcat cgaccttcgt 28860
gtgaaaacgg gggctgaagc catccgggca ctggccacac agctcccggc gtttcgtcag 28920
aaactgagcg acggctggta tcaggtacgg attgccgggc gggacgtcag cacgtccggg 28980
ttaacggcgc agttacatga gactctgcct gatggcgctg taattcatat tgttcccaga 29040
gtcgccgggg ccaagtcagg tggcgtattc cagattgtcc tgggggctgc cgccattgcc 29100
ggatcattct ttaccgccgg agccaccctt gcagcatggg gggcagccat tggggccggt 29160
ggtatgaccg gcatcctgtt ttctctcggt gccagtatgg tgctcggtgg tgtggcgcag 29220
atgctggcac cgaaagccag aactccccgt atacagacaa cggataacgg taagcagaac 29280
acctatttct cctcactgga taacatggtt gcccagggca atgttctgcc tgttctgtac 29340
ggggaaatgc gcgtggggtc acgcgtggtt tctcaggaga tcagcacggc agacgaaggg 29400
gacggtggtc aggttgtggt gattggtcgc tgatgcaaaa tgttttatgt gaaaccgcct 29460
gcgggcggtt ttgtcattta tggagcgtga ggaatgggta aaggaagcag taaggggcat 29520
accccgcgcg aagcgaagga caacctgaag tccacgcagt tgctgagtgt gatcgatgcc 29580
atcagcgaag ggccgattga aggtccggtg gatggcttaa aaagcgtgct gctgaacagt 29640
acgccggtgc tggacactga ggggaatacc aacatatccg gtgtcacggt ggtgttccgg 29700
gctggtgagc aggagcagac tccgccggag ggatttgaat cctccggctc cgagacggtg 29760
ctgggtacgg aagtgaaata tgacacgccg atcacccgca ccattacgtc tgcaaacatc 29820
gaccgtctgc gctttacctt cggtgtacag gcactggtgg aaaccacctc aaagggtgac 29880
aggaatccgt cggaagtccg cctgctggtt cagatacaac gtaacggtgg ctgggtgacg 29940
gaaaaagaca tcaccattaa gggcaaaacc acctcgcagt atctggcctc ggtggtgatg 30000
ggtaacctgc cgccgcgccc gtttaatatc cggatgcgca ggatgacgcc ggacagcacc 30060
acagaccagc tgcagaacaa aacgctctgg tcgtcataca ctgaaatcat cgatgtgaaa 30120
cagtgctacc cgaacacggc actggtcggc gtgcaggtgg actcggagca gttcggcagc 30180

-continued

```
cagcaggtga gccgtaatta tcatctgcgc gggcgtattc tgcaggtgcc gtcgaactat  30240
aacccgcaga cgcggcaata cagcggtatc tgggacggaa cgtttaaacc ggcatacagc  30300
aacaacatgg cctggtgtct gtgggatatg ctgacccatc cgcgctacgg catggggaaa  30360
cgtcttggtg cggcggatgt ggataaatgg gcgctgtatg tcatcggcca gtactgcgac  30420
cagtcagtgc cggacggctt tggcggcacg gagccgcgca tcacctgtaa tgcgtacctg  30480
accacacagc gtaaggcgtg ggatgtgctc agcgatttct gctcggcgat gcgctgtatg  30540
ccggtatgga acgggcagac gctgacgttc gtgcaggacc gaccgtcgga taagacgtgg  30600
acctataacc gcagtaatgt ggtgatgccg gatgatggcg cgccgttccg ctacagcttc  30660
agcgccctga aggaccgcca taatgccgtt gaggtgaact ggattgaccc gaacaacggc  30720
tgggagacgg cgacagagct tgttgaagat acgcaggcca ttgcccgtta cggtcgtaat  30780
gttacgaaga tggatgcctt tggctgtacc agccgggggc aggcacaccg cgccgggctg  30840
tggctgatta aaacagaact gctggaaacg cagaccgtgg atttcagcgt cggcgcagaa  30900
gggcttcgcc atgtaccggg cgatgttatt gaaatctgcg atgatgacta tgccggtatc  30960
agcaccggtg gtcgtgtgct ggcggtgaac agccagaccc ggacgctgac gctcgaccgt  31020
gaaatcacgc tgccatcctc cggtaccgcg ctgataagcc tggttgacgg aagtggcaat  31080
ccggtcagcg tggaggttca gtccgtcacc gacggcgtga aggtaaaagt gagccgtgtt  31140
cctgacggtg ttgctgaata cagcgtatgg gagctgaagc tgccgacgct gcgccagcga  31200
ctgttccgct gcgtgagtat ccgtgagaac gacgacggca cgtatgccat caccgccgtg  31260
cagcatgtgc cggaaaaaga ggccatcgtg gataacgggg cgcactttga cggcgaacag  31320
agtggcacgg tgaatggtgt cacgccgcca gcggtgcagc acctgaccgc agaagtcact  31380
gcagacagcg gggaatatca ggtgctggcg cgatgggaca caccgaaggt ggtgaagggc  31440
gtgagtttcc tgctccgtct gaccgtaaca gcggacgacg gcagtgagcg gctggtcagc  31500
acggcccgga cgacggaaac cacataccgc ttcacgcaac tggcgctggg gaactacagg  31560
ctgacagtcc gggcggtaaa tgcgtggggg cagcagggcg atccggcgtc ggtatcgttc  31620
cggattgccg caccggcagc accgtcgagg attgagctga cgccgggcta ttttcagata  31680
accgccacgc cgcatcttgc cgtttatgac ccgacggtac agtttgagtt ctggttctcg  31740
gaaaagcaga ttgcggatat cagacaggtt gaaaccagca cgcgttatct tggtacggcg  31800
ctgtactgga tagccgccag tatcaatatc aaaccgggcc atgattatta cttttatatc  31860
cgcagtgtga acaccgttgg caaatcggca ttcgtggagg ccgtcggtcg ggcgagcgat  31920
gatgcggaag gttacctgga ttttttcaaa ggcaagataa ccgaatccca tctcggcaag  31980
gagctgctgg aaaaagtcga gctgacggag gataacgcca gcagactgga ggagttttcg  32040
aaagagtgga aggatgccag tgataagtgg aatgccatgt gggctgtcaa aattgagcag  32100
accaaagacg gcaaacatta tgtcgcgggt attggcctca gcatggagga cacggaggaa  32160
ggcaaactga gccagtttct ggttgccgcc aatcgtatcg catttattga cccggcaaac  32220
gggaatgaaa cgccgatgtt tgtggcgcag ggcaaccaga tattcatgaa cgacgtgttc  32280
ctgaagcgcc tgacggcccc caccattacc agcggcggca atcctccggc cttttccctg  32340
acaccggacg gaaagctgac cgctaaaaat gcggatatca gtggcagtgt gaatgcgaac  32400
tccgggacgc tcagtaatgt gacgatagct gaaaactgta cgataaacgg tacgctgagg  32460
gcggaaaaaa tcgtcgggga cattgtaaag gcggcgagcg cggcttttcc gcgccagcgt  32520
gaaagcagtg tggactggcc gtcaggtacc cgtactgtca ccgtgaccga tgaccatcct  32580
```

-continued

```
tttgatcgcc agatagtggt gcttccgctg acgtttcgcg gaagtaagcg tactgtcagc  32640
ggcaggacaa cgtattcgat gtgttatctg aaagtactga tgaacggtgc ggtgatttat  32700
gatggcgcgg cgaacgaggc ggtacaggtg ttctcccgta ttgttgacat gccagcgggt  32760
cggggaaacg tgatcctgac gttcacgctt acgtccacac ggcattcggc agatattccg  32820
ccgtatacgt ttgccagcga tgtgcaggtt atggtgatta agaaacaggc gctgggcatc  32880
agcgtggtct gagtgtgtta cagaggttcg tccgggaacg ggcgttttat tataaaacag  32940
tgagaggtga acgatgcgta atgtgtgtat tgccgttgct gtctttgccg cacttgcggt  33000
gacagtcact ccggcccgtg cggaaggtgg acatggtacg tttacggtgg gctattttca  33060
agtgaaaccg ggtacattgc cgtcgttgtc gggcggggat accggtgtga gtcatctgaa  33120
agggattaac gtgaagtacc gttatgagct gacggacagt gtgggggtga tggcttccct  33180
ggggttcgcc gcgtcgaaaa agagcagcac agtgatgacc ggggaggata cgtttcacta  33240
tgagagcctg cgtggacgtt atgtgagcgt gatggccgga ccggttttac aaatcagtaa  33300
gcaggtcagt gcgtacgcca tggccggagt ggctcacagt cggtggtccg gcagtacaat  33360
ggattaccgt aagacggaaa tcactcccgg gtatatgaaa gagacgacca ctgccaggga  33420
cgaaagtgca atgcggcata cctcagtggc gtggagtgca ggtatacaga ttaatccggc  33480
agcgtccgtc gttgttgata ttgcttatga aggctccggc agtggcgact ggcgtactga  33540
cggattcatc gttggggtcg gttataaatt ctgattagcc aggtaacaca gtgttatgac  33600
agcccgccgg aaccggtggg ctttttttgtg gggtgaatat ggcagtaaag atttcaggag  33660
tcctgaaaga cggcacagga aaaccggtac agaactgcac cattcagctg aaagccagac  33720
gtaacagcac cacggtggtg gtgaacacgg tgggctcaga gaatccggat gaagccgggc  33780
gttacagcat ggatgtggag tacggtcagt acagtgtcat cctgcaggtt gacggttttc  33840
caccatcgca cgccgggacc atcaccgtgt atgaagattc acaaccgggg acgctgaatg  33900
attttctctg tgccatgacg gaggatgatg cccggccgga ggtgctgcgt cgtcttgaac  33960
tgatggtgga agaggtggcg cgtaacgcgt ccgtggtggc acagagtacg gcagacgcga  34020
agaaatcagc cggcgatgcc agtgcatcag ctgctcaggt cgcggccctt gtgactgatg  34080
caactgactc agcacgcgcc gccagcacgt ccgccggaca ggctgcatcg tcagctcagg  34140
aagcgtcctc cggcgcagaa gcggcatcag caaaggccac tgaagcggaa aaaagtgccg  34200
cagccgcaga gtcctcaaaa aacgcggcgg ccaccagtgc cggtgcggcg aaaacgtcag  34260
aaacgaatgc tgcagcgtca caacaatcag ccgccacgtc tgcctccacc gcggccacga  34320
aagcgtcaga ggccgccact tcagcacgag atgcggtggc ctcaaaagag gcagcaaaat  34380
catcagaaac gaacgcatca tcaagtgccg gtcgtgcagc ttcctcggca acggcggcag  34440
aaaattctgc cagggcggca aaaacgtccg agacgaatgc caggtcatct gaaacagcag  34500
cggaacggag cgcctctgcc gcggcagacg caaaaacagc ggcggcgggg agtgcgtcaa  34560
cggcatccac gaaggcgaca gaggctgcgg gaagtgcggt atcagcatcg cagagcaaaa  34620
gtgcggcaga agcggcggca atacgtgcaa aaaattcggc aaaacgtgca gaagatatag  34680
cttcagctgt cgcgcttgag gatgcggaca caacgagaaa ggggatagtg cagctcagca  34740
gtgcaaccaa cagcacgtct gaaacgcttg ctgcaacgcc aaaggcggtt aaggtggtaa  34800
tggatgaaac gaacagaaaa gcccactgga cagtccggca ctgaccggaa cgccaacagc  34860
accaaccgcg ctcaggggaa caaacaatac ccagattgcg aacaccgctt ttgtactggc  34920
```

cgcgattgca gatgttatcg acgcgtcacc tgacgcactg aatacgctga atgaactggc 34980
cgcagcgctc gggaatgatc cagattttgc taccaccatg actaacgcgc ttgcgggtaa 35040
acaaccgaag aatgcgacac tgacggcgct ggcagggctt tccacggcga aaaataaatt 35100
accgtatttt gcggaaaatg atgccgccag cctgactgaa ctgactcagg ttggcaggga 35160
tattctggca aaaaattccg ttgcagatgt tcttgaatac cttggggccg gtgagaattc 35220
ggcctttccg gcaggtgcgc cgatcccgtg gccatcagat atcgttccgt ctggctacgt 35280
cctgatgcag gggcaggcgt ttgacaaatc agcctaccca aaacttgctg tcgcgtatcc 35340
atcgggtgtg cttcctgata tgcgaggctg gacaatcaag gggaaacccg ccagcggtcg 35400
tgctgtattg tctcaggaac aggatggaat taagtcgcac acccacagtg ccagtgcatc 35460
cggtacggat ttggggacga aaaccacatc gtcgtttgat tacgggacga aaacaacagg 35520
cagtttcgat tacggcacca aatcgacgaa taacacgggg gctcatgctc acagtctgag 35580
cggttcaaca ggggccgcgg gtgctcatgc ccacacaagt ggtttaagga tgaacagttc 35640
tggctggagt cagtatggaa cagcaaccat tacaggaagt ttatccacag ttaaaggaac 35700
cagcacacag ggtattgctt atttatcgaa aacggacagt cagggcagcc acagtcactc 35760
attgtccggt acagccgtga gtgccggtgc acatgcgcat acagttggta ttggtgcgca 35820
ccagcatccg gttgttatcg gtgctcatgc ccattctttc agtattggtt cacacggaca 35880
caccatcacc gttaacgctg cgggtaacgc ggaaaacacc gtcaaaaaca ttgcatttaa 35940
ctatattgtg aggcttgcat aatggcattc agaatgagtg aacaaccacg gaccataaaa 36000
atttataatc tgctggccgg aactaatgaa tttattggtg aaggtgacgc atatattccg 36060
cctcataccg gtctgcctgc aaacagtacc gatattgcac cgccagatat tccggctggc 36120
tttgtggctg ttttcaacag tgatgaggca tcgtggcatc tcgttgaaga ccatcggggt 36180
aaaaccgtct atgacgtggc ttccggcgac gcgttattta tttctgaact cggtccgtta 36240
ccggaaaatt ttacctggtt atcgccggga ggggaatatc agaagtggaa cggcacagcc 36300
tgggtgaagg atacggaagc agaaaaactg ttccggatcc gggaggcgga agaaacaaaa 36360
aaaagcctga tgcaggtagc cagtgagcat attgcgccgc ttcaggatgc tgcagatctg 36420
gaaattgcaa cgaaggaaga aacctcgttg ctggaagcct ggaagaagta tcgggtgttg 36480
ctgaaccgtg ttgatacatc aactgcacct gatattgagt ggcctgctgt ccctgttatg 36540
gagtaatcgt tttgtgatat gccgcagaaa cgttgtatga aataacgttc tgcggttagt 36600
tagtatattg taaagctgag tattggttta tttggcgatt attatcttca ggagaataat 36660
ggaagttcta tgactcaatt gttcatagtg tttacatcac cgccaattgc ttttaagact 36720
gaacgcatga aatatggttt ttcgtcatgt tttgagtctg ctgttgatat ttctaaagtc 36780 ggttttttttt cttcgtttc tctaactatt ttccatgaaa tacatttttg attattattt 36840
gaatcaattc caattacctg aagtctttca tctataattg gcattgtatg tattggttta 36900
ttggagtaga tgcttgcttt tctgagccat agctctgata tccaaatgaa gccataggca 36960
tttgttattt tggctctgtc agctgcataa cgccaaaaaa tatatttatc tgcttgatct 37020
tcaaatgttg tattgattaa atcaattgga tggaattgtt tatcataaaa aattaatgtt 37080
tgaatgtgat aaccgtcctt taaaaaagtc gtttctgcaa gcttggctgt atagtcaact 37140
aactcttctg tcgaagtgat atttttaggc ttatctacca gttttagacg ctctttaata 37200
tcttcaggaa ttattttatt gtcatattgt atcatgctaa atgacaattt gcttatggag 37260
taatctttta attttaaata agttattctc ctggcttcat caaataaaga gtcgaatgat 37320

-continued

```
gttggcgaaa tcacatcgtc acccattgga ttgtttattt gtatgccaag agagttacag  37380
cagttataca ttctgccata gattatagct aaggcatgta ataattcgta atcttttagc  37440
gtattagcga cccatcgtct ttctgattta ataatagatg attcagttaa atatgaaggt  37500
aatttctttt gtgcaagtct gactaacttt tttataccaa tgtttaacat actttcattt  37560
gtaataaact caatgtcatt ttcttcaatg taagatgaaa taagagtagc ctttgcctcg  37620
ctatacattt ctaaatcgcc ttgtttttct atcgtattgc gagaattttt agcccaagcc  37680
attaatggat catttttcca tttttcaata acattattgt tataccaaat gtcatatcct  37740
ataatctggt ttttgttttt ttgaataata aatgttactg ttcttgcggt ttggaggaat  37800
tgattcaaat tcaagcgaaa taattcaggg tcaaaatatg tatcaatgca gcatttgagc  37860
aagtgcgata aatctttaag tcttctttcc catggttttt tagtcataaa actctccatt  37920
ttgataggtt gcatgctaga tgctgatata ttttagaggt gataaaatta actgcttaac  37980
tgtcaatgta atacaagttg tttgatcttt gcaatgattc ttatcagaaa ccatatagta  38040
aattagttac acaggaaatt tttaatatta ttattatcat tcattatgta ttaaaattag  38100
agttgtggct tggctctgct aacacgttgc tcataggaga tatggtagag ccgcagacac  38160
gtcgtatgca ggaacgtgct gcggctggct ggtgaacttc cgatagtgcg ggtgttgaat  38220
gatttccagt tgctaccgat tttacatatt ttttgcatga gagaatttgt accacctccc  38280
accgaccatc tatgactgta cgccactgtc cctaggactg ctatgtgccg gagcggacat  38340
tacaaacgtc cttctcggtg catgccactg ttgccaatga cctgcctagg aattggttag  38400
caagttacta ccggattttg taaaaacagc cctcctcata taaaaagtat tcgttcactt  38460
ccgataagcg tcgtaatttt ctatctttca tcatattcta gatccctctg aaaaaatctt  38520
ccgagtttgc taggcactga tacataactc ttttccaata attggggaag tcattcaaat  38580
ctataatagg tttcagattt gcttcaataa attctgactg tagctgctga aacgttgcgg  38640
ttgaactata tttccttata acttttacga aagagtttct ttgagtaatc acttcactca  38700
agtgcttccc tgcctccaaa cgatacctgt tagcaatatt taatagcttg aaatgatgaa  38760
gagctctgtg tttgtcttcc tgcctccagt tcgccgggca ttcaacataa aaactgatag  38820
cacccggagt tccggaaacg aaatttgcat atacccattg ctcacgaaaa aaaatgtcct  38880
tgtcgatata gggatgaatc gcttggtgta cctcatctac tgcgaaaact tgacctttct  38940
ctcccatatt gcagtcgcgg cacgatggaa ctaaattaat aggcatcacc gaaaattcag  39000
gataatgtgc aataggaaga aaatgatcta tattttttgt ctgtcctata tcaccacaaa  39060
atggacattt ttcacctgat gaaacaagca tgtcatcgta atatgttcta gcgggtttgt  39120
ttttatctcg gagattattt tcataaagct tttctaattt aacctttgtc aggttaccaa  39180
ctactaaggt tgtaggctca agagggtgtg tcctgtcgta ggtaaataac tgacctgtcg  39240
agcttaatat tctatattgt tgttctttct gcaaaaaagt ggggaagtga gtaatgaaat  39300
tatttctaac atttatctgc atcatacctt ccgagcattt attaagcatt tcgctataag  39360
ttctcgctgg aagaggtagt tttttcattg tactttacct tcatctctgt tcattatcat  39420
cgcttttaaa acggttcgac cttctaatcc tatctgacca ttataatttt ttagaatggt  39480
ttcataagaa agctctgaat caacggactg cgataataag tggtggtatc cagaatttgt  39540
cacttcaagt aaaaacacct cacgagttaa aacacctaag ttctcaccga atgtctcaat  39600
atccggacgg ataatattta ttgcttctct tgaccgtagg actttccaca tgcaggattt  39660
```

-continued

```
tggaacctct tgcagtacta ctggggaatg agttgcaatt attgctacac cattgcgtgc  39720
atcgagtaag tcgcttaatg ttcgtaaaaa agcagagagc aaaggtggat gcagatgaac  39780
ctctggttca tcgaataaaa ctaatgactt ttcgccaacg acatctacta atcttgtgat  39840
agtaaataaa acaattgcat gtccagagct cattcgaagc agatatttct ggatattgtc  39900
ataaaacaat ttagtgaatt tatcatcgtc cacttgaatc tgtggttcat tacgtcttaa  39960
ctcttcatat ttagaaatga ggctgatgag ttccatattt gaaaagtttt catcactact  40020
tagtttttg atagcttcaa gccagagttg tctttttcta tctactctca tacaaccaat  40080
aaatgctgaa atgaattcta agcggagatc gcctagtgat tttaaactat tgctggcagc  40140
attcttgagt ccaatataaa agtattgtgt accttttgct gggtcaggtt gttctttagg  40200
aggagtaaaa ggatcaaatg cactaaacga aactgaaaca agcgatcgaa aatatccctt  40260
tgggattctt gactcgataa gtctattatt ttcagagaaa aaatattcat tgttttctgg  40320
gttggtgatt gcaccaatca ttccattcaa aattgttgtt ttaccacacc cattccgccc  40380
gataaaagca tgaatgttcg tgctgggcat agaattaacc gtcacctcaa aaggtatagt  40440
taaatcactg aatccgggag cactttttct attaaatgaa aagtggaaat ctgacaattc  40500
tggcaaacca tttaacacac gtgcgaactg tccatgaatt tctgaaagag ttacccctct  40560
aagtaatgag gtgttaagga cgctttcatt ttcaatgtcg gctaatcgat ttggccatac  40620
tactaaatcc tgaatagctt taagaaggtt atgtttaaaa ccatcgctta atttgctgag  40680
attaacatag tagtcaatgc tttcacctaa ggaaaaaaac atttcaggga gttgactgaa  40740
ttttttatct attaatgaat aagtgcttac ttcttctttt tgacctacaa aaccaatttt  40800
aacatttccg atatcgcatt tttcaccatg ctcatcaaag acagtaagat aaaacattgt  40860
aacaaaggaa tagtcattcc aaccatctgc tcgtaggaat gccttatttt tttctactgc  40920
aggaatatac ccgcctcttt caataacact aaactccaac atatagtaac ccttaatttt  40980
attaaaataa ccgcaattta tttggcggca acacaggatc tctcttttaa gttactctct  41040
attacatacg ttttccatct aaaaattagt agtattgaac ttaacggggc atcgtattgt  41100
agttttccat atttagcttt ctgcttcctt ttggataacc cactgttatt catgttgcat  41160
ggtgcactgt ttataccaac gatatagtct attaatgcat atatagtatc gccgaacgat  41220
tagctcttca ggcttctgaa gaagcgtttc aagtactaat aagccgatag atagccacgg  41280
acttcgtagc catttttcat aagtgttaac ttccgctcct cgctcataac agacattcac  41340
tacagttatg gcggaaaggt atgcatgctg ggtgtgggga agtcgtgaaa gaaaagaagt  41400
cagctgcgtc gtttgacatc actgctatct tcttactggt tatgcaggtc gtagtgggtg  41460
gcacacaaag ctttgcactg gattgcgagg ctttgtgctt ctctggagtg cgacaggttt  41520
gatgacaaaa aattagcgca agaagacaaa aatcaccttg cgctaatgct ctgttacagg  41580
tcactaatac catctaagta gttgattcat agtgactgca tatgttgtgt tttacagtat  41640
tatgtagtct gtttttatg caaaatctaa tttaatatat tgatatttat atcattttac  41700
gtttctcgtt cagcttttt atactaagtt ggcattataa aaaagcattg cttatcaatt  41760
tgttgcaacg aacaggtcac tatcagtcaa aataaaatca ttatttgatt tcaattttgt  41820
cccactccct gcctctgtca tcacgatact gtgatgccat ggtgtccgac ttatgcccga  41880
gaagatgttg agcaaactta tcgcttatct gcttctcata gagtcttgca gacaaactgc  41940
gcaactcgtg aaaggtaggc ggatcccctt cgaaggaaag acctgatgct tttcgtgcgc  42000
gcataaaata ccttgatact gtgccggatg aaagcggttc gcgacgagta gatgcaatta  42060
```

```
tggtttctcc gccaagaatc tctttgcatt tatcaagtgt ttccttcatt gatattccga  42120
gagcatcaat atgcaatgct gttgggatgg caatttttac gcctgttttg ctttgctcga  42180
cataaagata tccatctacg atatcagacc acttcatttc gcataaatca ccaactcgtt  42240
gcccggtaac aacagccagt tccattgcaa gtctgagcca acatggtgat gattctgctg  42300
cttgataaat tttcaggtat tcgtcagccg taagtcttga tctccttacc tctgattttg  42360
ctgcgcgagt ggcagcgaca tggtttgttg ttatatggcc ttcagctatt gcctctcgga  42420
atgcatcgct cagtgttgat ctgattaact tggctgacgc cgccttgccc tcgtctatgt  42480
atccattgag cattgccgca atttcttttg tggtgatgtc ttcaagtgga gcatcaggca  42540
gacccctcct tattgcttta attttgctca tgtaatttat gagtgtcttc tgcttgattc  42600
ctctgctggc caggattttt tcgtagcgat caagccatga atgtaacgta acggaattat  42660
cactgttgat tctcgctgtc agaggcttgt gtttgtgtcc tgaaaataac tcaatgttgg  42720
cctgtatagc ttcagtgatt gcgattcgcc tgtctctgcc taatccaaac tctttacccg  42780
tccttgggtc cctgtagcag taatatccat tgtttcttat ataaaggtta gggggtaaat  42840
cccggcgctc atgacttcgc cttcttccca tttctgatcc tcttcaaaag gccacctgtt  42900
actggtcgat ttaagtcaac ctttaccgct gattcgtgga acagatactc tcttccatcc  42960
ttaaccggag gtgggaatat cctgcattcc cgaacccatc gacgaactgt ttcaaggctt  43020
cttggacgtc gctggcgtgc gttccactcc tgaagtgtca agtacatcgc aaagtctccg  43080
caattacacg caagaaaaaa ccgccatcag gcggcttggt gttctttcag ttcttcaatt  43140
cgaatattgg ttacgtctgc atgtgctatc tgcgcccata tcatccagtg gtcgtagcag  43200
tcgttgatgt tctccgcttc gataactctg ttgaatggct ctccattcca ttctcctgtg  43260
actcggaagt gcatttatca tctccataaa acaaaacccg ccgtagcgag ttcagataaa  43320
ataaatcccc gcgagtgcga ggattgttat gtaatattgg gtttaatcat ctatatgttt  43380
tgtacagaga gggcaagtat cgtttccacc gtactcgtga taataatttt gcacggtatc  43440
agtcatttct cgcacattgc agaatgggga tttgtcttca ttagacttat aaaccttcat  43500
ggaatatttg tatgccgact ctatatctat accttcatct acataaacac cttcgtgatg  43560
tctgcatgga gacaagacac cggatctgca caacattgat aacgcccaat ctttttgctc  43620
agactctaac tcattgatac tcatttataa actccttgca atgtatgtcg tttcagctaa  43680
acggtatcag caatgtttat gtaaagaaac agtaagataa tactcaaccc gatgtttgag  43740
tacggtcatc atctgacact acagactctg gcatcgctgt gaagacgacg cgaaattcag  43800
cattttcaca agcgttatct tttacaaaac cgatctcact ctcctttgat gcgaatgcca  43860
gcgtcagaca tcatatgcag atactcacct gcatcctgaa cccattgacc tccaaccccg  43920
taatagcgat gcgtaatgat gtcgatagtt actaacgggt cttgttcgat taactgccgc  43980
agaaactctt ccaggtcacc agtgcagtgc ttgataacag gagtcttccc aggatggcga  44040
acaacaagaa actggtttcc gtcttcacgg acttcgttgc tttccagttt agcaatacgc  44100
ttactcccat ccgagataac accttcgtaa tactcacgct gctcgttgag ttttgatttt  44160
gctgtttcaa gctcaacacg cagtttccct actgttagcg caatatcctc gttctcctgg  44220
tcgcggcgtt tgatgtattg ctggtttctt tcccgttcat ccagcagttc cagcacaatc  44280
gatggtgtta ccaattcatg gaaaaggtct gcgtcaaatc cccagtcgtc atgcattgcc  44340
tgctctgccg cttcacgcag tgcctgagag ttaatttcgc tcacttcgaa cctctctgtt  44400
```

-continued

```
tactgataag ttccagatcc tcctggcaac ttgcacaagt ccgacaaccc tgaacgacca  44460
ggcgtcttcg ttcatctatc ggatcgccac actcacaaca atgagtggca gatatagcct  44520
ggtggttcag gcggcgcatt tttattgctg tgttgcgctg taattcttct atttctgatg  44580
ctgaatcaat gatgtctgcc atctttcatt aatccctgaa ctgttggtta atacgcttga  44640
gggtgaatgc gaataataaa aaaggagcct gtagctccct gatgattttg cttttcatgt  44700
tcatcgttcc ttaaagacgc cgtttaacat gccgattgcc aggcttaaat gagtcggtgt  44760
gaatcccatc agcgttaccg tttcgcggtg cttcttcagt acgctacggc aaatgtcatc  44820
gacgttttta tccggaaact gctgtctggc tttttttgat ttcagaatta gcctgacggg  44880
caatgctgcg aagggcgttt tcctgctgag gtgtcattga acaagtccca tgtcggcaag  44940
cataagcaca cagaatatga agcccgctgc cagaaaaatg cattccgtgg ttgtcatacc  45000
tggtttctct catctgcttc tgctttcgcc accatcattt ccagcttttg tgaaagggat  45060
gcggctaacg tatgaaattc ttcgtctgtt tctactggta ttggcacaaa cctgattcca  45120
atttgagcaa ggctatgtgc catctcgata ctcgttctta actcaacaga agatgctttg  45180
tgcatacagc ccctcgttta ttatttatct cctcagccag ccgctgtgct ttcagtggat  45240
ttcggataac agaaaggccg ggaaataccc agcctcgctt tgtaacggag tagacgaaag  45300
tgattgcgcc tacccggata ttatcgtgag gatgcgtcat cgccattgct ccccaaatac  45360
aaaaccaatt tcagccagtg cctcgtccat tttttcgatg aactccggca cgatctcgtc  45420
aaaactcgcc atgtactttt catcccgctc aatcacgaca taatgcaggc cttcacgctt  45480
catacgcggg tcatagttgg caaagtacca ggcatttttt cgcgtcaccc acatgctgta  45540
ctgcacctgg gccatgtaag ctgactttat ggcctcgaaa ccaccgagcc ggaacttcat  45600
gaaatcccgg gaggtaaacg ggcatttcag ttcaaggccg ttgccgtcac tgcataaacc  45660
atcgggagag caggcggtac gcatactttc gtcgcgatag atgatcgggg attcagtaac  45720
attcacgccg gaagtgaatt caaacagggt tctggcgtcg ttctcgtact gttttcccca  45780
ggccagtgct ttagcgttaa cttccggagc cacaccggtg caaacctcag caagcagggt  45840
gtggaagtag gacattttca tgtcaggcca cttctttccg gagcggggtt ttgctatcac  45900
gttgtgaact tctgaagcgg tgatgacgcc gagccgtaat ttgtgccacg catcatcccc  45960
ctgttcgaca gctctcacat cgatcccggt acgctgcagg ataatgtccg gtgtcatgct  46020
gccaccttct gctctgcggc tttctgtttc aggaatccaa gagcttttac tgcttcggcc  46080
tgtgtcagtt ctgacgatgc acgaatgtcg cggcgaaata tctgggaaca gagcggcaat  46140
aagtcgtcat cccatgtttt atccagggcg atcagcagag tgttaatctc ctgcatggtt  46200
tcatcgttaa ccggagtgat gtcgcgttcc ggctgacgtt ctgcagtgta tgcagtattt  46260
tcgacaatgc gctcggcttc atccttgtca tagataccag caaatccgaa ggccagacgg  46320
gcacactgaa tcatggcttt atgacgtaac atccgtttgg gatgcgactg ccacggcccc  46380
gtgatttctc tgccttcgcg agttttgaat ggttcgcggc ggcattcatc catccattcg  46440
gtaacgcaga tcggatgatt acggtccttg cggtaaatcc ggcatgtaca ggattcattg  46500
tcctgctcaa agtccatgcc atcaaactgc tggttttcat tgatgatgcg ggaccagcca  46560
tcaacgccca ccaccggaac gatgccattc tgcttatcag gaaaggcgta aatttctttc  46620
gtccacggat taaggccgta ctggttggca acgatcagta atgcgatgaa ctgcgcatcg  46680
ctggcatcac ctttaaatgc cgtctggcga agagtggtga tcagttcctg tgggtcgaca  46740
gaatccatgc cgacacgttc agccagcttc ccagccagcg ttgcgagtgc agtactcatt  46800
```

cgttttatac ctctgaatca atatcaacct ggtggtgagc aatggtttca accatgtacc 46860
ggatgtgttc tgccatgcgc tcctgaaact caacatcgtc atcaaacgca cgggtaatgg 46920
attttttgct ggccccgtgg cgttgcaaat gatcgatgca tagcgattca aacaggtgct 46980
ggggcaggcc tttttccatg tcgtctgcca gttctgcctc tttctcttca cgggcgagct 47040
gctggtagtg acgcgcccag ctctgagcct caagacgatc ctgaatgtaa taagcgttca 47100
tggctgaact cctgaaatag ctgtgaaaat atcgcccgcg aaatgccggg ctgattagga 47160
aaacaggaaa gggggttagt gaatgctttt gcttgatctc agtttcagta ttaatatcca 47220
ttttttataa gcgtcgacgg cttcacgaaa catcttttca tcgccaataa aagtggcgat 47280
agtgaattta gtctggatag ccataagtgt ttgatccatt ctttgggact cctggctgat 47340
taagtatgtc gataaggcgt ttccatccgt cacgtaattt acgggtgatt cgttcaagta 47400
aagattcgga agggcagcca gcaacaggcc accctgcaat ggcatattgc atggtgtgct 47460
ccttatttat acataacgaa aaacgcctcg agtgaagcgt tattggtatg cggtaaaacc 47520
gcactcaggc ggccttgata gtcatatcat ctgaatcaaa tattcctgat gtatcgatat 47580
cggtaattct tattccttcg ctaccatcca ttggaggcca tccttcctga ccatttccat 47640
cattccagtc gaactcacac acaacaccat atgcatttaa gtcgcttgaa attgctataa 47700
gcagagcatg ttgcgccagc atgattaata cagcatttaa tacagagccg tgtttattga 47760
gtcggtattc agagtctgac cagaaattat taatctggtg aagtttttcc tctgtcatta 47820
cgtcatggtc gatttcaatt tctattgatg ctttccagtc gtaatcaatg atgtattttt 47880
tgatgtttga catctgttca tatcctcaca gataaaaaat cgccctcaca ctggagggca 47940
aagaagattt ccaataatca gaacaagtcg gctcctgttt agttacgagc gacattgctc 48000
cgtgtattca ctcgttggaa tgaatacaca gtgcagtgtt tattctgtta tttatgccaa 48060
aaataaaggc cactatcagg cagctttgtt gttctgttta ccaagttctc tggcaatcat 48120
tgccgtcgtt cgtattgccc atttatcgac atatttccca tcttccatta caggaaacat 48180
ttcttcaggc ttaaccatgc attccgattg cagcttgcat ccattgcatc gcttgaattg 48240
tccacaccat tgatttttat caatagtcgt agtcatacgg atagtcctgg tattgttcca 48300
tcacatcctg aggatgctct tcgaactctt caaattcttc ttccatatat caccttaaat 48360
agtggattgc ggtagtaaag attgtgcctg tcttttaacc acatcaggct cggtggttct 48420
cgtgtacccc tacagcgaga aatcggataa actattacaa cccctacagt ttgatgagta 48480
tagaaatgga tccactcgtt attctcggac gagtgttcag taatgaacct ctggagagaa 48540
ccatgtatat gatcgttatc tgggttggac ttctgctttt aagcccagat aactggcctg 48600
aatatgttaa tgagagaatc ggtattcctc atgtgtggca tgttttcgtc tttgctcttg 48660
cattttcgct agcaattaat gtgcatcgat tatcagctat tgccagcgcc agatataagc 48720
gatttaagct aagaaaacgc attaagatgc aaaacgataa agtgcgatca gtaattcaaa 48780
accttacaga agagcaatct atggttttgt gcgcagccct taatgaaggc aggaagtatg 48840
tggttacatc aaaacaattc ccatacatta gtgagttgat tgagcttggt gtgttgaaca 48900
aaactttttc ccgatggaat ggaaagcata tattattccc tattgaggat atttactgga 48960
ctgaattagt tgccagctat gatccatata atattgagat aaagccaagg ccaatatcta 49020
agtaactaga taagaggaat cgattttccc ttaattttct ggcgtccact gcatgttatg 49080
ccgcgttcgc caggcttgct gtaccatgtg cgctgattct tgcgctcaat acgttgcagg 49140

-continued

```
ttgctttcaa tctgtttgtg gtattcagcc agcactgtaa ggtctatcgg atttagtgcg  49200
ctttctactc gtgatttcgg tttgcgattc agcgagagaa tagggcggtt aactggtttt  49260
gcgcttaccc caaccaacag gggatttgct gctttccatt gagcctgttt ctctgcgcga  49320
cgttcgcggc ggcgtgtttg tgcatccatc tggattctcc tgtcagttag ctttggtggt  49380
gtgtggcagt tgtagtcctg aacgaaaacc ccccgcgatt ggcacattgg cagctaatcc  49440
ggaatcgcac ttacggccaa tgcttcgttt cgtatcacac accccaaagc cttctgcttt  49500
gaatgctgcc cttcttcagg gcttaatttt taagagcgtc accttcatgg tggtcagtgc  49560
gtcctgctga tgtgctcagt atcaccgcca gtggtattta tgtcaacacc gccagagata  49620
atttatcacc gcagatggtt atctgtatgt tttttatatg aatttatttt ttgcaggggg  49680
gcattgtttg gtaggtgaga gatctgaatt gctatgttta gtgagttgta tctatttatt  49740
tttcaataaa tacaattggt tatgtgtttt gggggcgatc gtgaggcaaa gaaaacccgg  49800
cgctgaggcc gggttattct tgttctctgg tcaaattata tagttggaaa acaaggatgc  49860
atatatgaat gaacgatgca gaggcaatgc cgatggcgat agtgggtatc atgtagccgc  49920
ttatgctgga aagaagcaat aacccgcaga aaaacaaagc tccaagctca acaaaactaa  49980
gggcatagac aataactacc gatgtcatat acccatactc tctaatcttg gccagtcggc  50040
gcgttctgct tccgattaga aacgtcaagg cagcaatcag gattgcaatc atggttcctg  50100
catatgatga caatgtcgcc ccaagaccat ctctatgagc tgaaaaagaa acaccaggaa  50160
tgtagtggcg gaaaaggaga tagcaaatgc ttacgataac gtaaggaatt attactatgt  50220
aaacaccagg catgattctg ttccgcataa ttactcctga taattaatcc ttaactttgc  50280
ccacctgcct tttaaaacat tccagtatat cacttttcat tcttgcgtag caatatgcca  50340
tctcttcagc tatctcagca ttggtgacct tgttcagagg cgctgagaga tggccttttt  50400
ctgatagata atgttctgtt aaaatatctc cggcctcatc ttttgcccgc aggctaatgt  50460
ctgaaaattg aggtgacggg ttaaaaataa tatccttggc aacctttttt atatcccttt  50520
taaattttgg cttaatgact atatccaatg agtcaaaaag ctccccttca atatctgttg  50580
cccctaagac ctttaatata tcgccaaata caggtagctt ggcttctacc ttcaccgttg  50640
ttcggccgat gaaatgcata tgcataacat cgtctttggt ggttcccctc atcagtggct  50700
ctatctgaac gcgctctcca ctgcttaatg acattccttt cccgattaaa aaatctgtca  50760
gatcggatgt ggtcggcccg aaaacagttc tggcaaaacc aatggtgtcg ccttcaacaa  50820
acaaaaaaga tgggaatccc aatgattcgt catctgcgag gctgttctta atatcttcaa  50880
ctgaagcttt agagcgattt atcttctgaa ccagactctt gtcatttgtt ttggtaaaga  50940
gaaaagtttt tccatcgatt ttatgaatat acaaataatt ggagccaacc tgcaggtgat  51000
gattatcagc cagcagagaa ttaaggaaaa cagacaggtt tattgagcgc ttatctttcc  51060
ctttattttt gctgcggtaa gtcgcataaa aaccattctt cataattcaa tccatttact  51120
atgttatgtt ctgaggggag tgaaaattcc cctaattcga tgaagattct tgctcaattg  51180
ttatcagcta tgcgccgacc agaacacctt gccgatcagc caaacgtctc ttcaggccac  51240
tgactagcga taactttccc cacaacggaa caactctcat tgcatgggat cattgggtac  51300
tgtgggttta gtggttgtaa aaacacctga ccgctatccc tgatcagttt cttgaaggta  51360
aactcatcac ccccaagtct ggctatgcag aaatcacctg gctcaacagc ctgctcaggg  51420
tcaacgagaa ttaacattcc gtcaggaaag cttggcttgg agcctgttgg tgcggtcatg  51480
gaattacctt caacctcaag ccagaatgca gaatcactgg ctttttggt tgtgcttacc  51540
```

catctctccg catcaccttt ggtaaaggtt ctaagctcag gtgagaacat ccctgcctga 51600
acatgagaaa aaacagggta ctcatactca cttctaagtg acggctgcat actaaccgct 51660
tcatacatct cgtagatttc tctggcgatt gaagggctaa attcttcaac gctaactttg 51720
agaatttttg caagcaatgc ggcgttataa gcatttaatg cattgatgcc attaaataaa 51780
gcaccaacgc ctgactgccc catccccatc ttgtctgcga cagattcctg ggataagcca 51840
agttcatttt tcttttttc ataaattgct ttaaggcgac gtgcgtcctc aagctgctct 51900
tgtgttaatg gtttcttttt tgtgctcata cgttaaatct 51940

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
gctttcgaat ttctgccatt catcc 25

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
ttgggcgcca tctccttggg ccaacttttg gcgaaaatg 39

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
cgttccggct aagtaacatg aaaaagacag ctatcgcgat tgcagtg 47

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
tgcccgcggc ctgcg 15

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
gcgcctggtc tgtacaccgt tcatctg 27

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
catgttactt agccggaacg 20

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
cgcaggccgc gggcgcaagc agcctgagac a 31

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
tgcggccgcc tgggccccct 20

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
agggggccca ggcggccgca gagcaggtcg cggatt 36

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
aagcgcagtc tctgaattta 20

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
catggcaagc agcctgagac agattctgga ctcccagaaa atggagtgga 50

-continued

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
ggtccaacgc cgggggcagc ggtagggata acagggtaat cca 43

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
tatggattac cctgttatcc ctaccgctgc ccccggcgtt g 41

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
gacctccact ccattttctg ggagtccaga atctgtctca ggctgcttgc 50

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
ctattttgca cccagctaca attttatcct gaatcttacc aacgc 45

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
ggcttagagc ttaattgctg aatctggtgc tgtagctca 39

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
ggggagctct gggggcagcg gtagggataa cccctcaggc tagatgc 47

<210> SEQ ID NO 22
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
tcgagcatct agcctgaggg gttatcccta ccgctgcccc cagagctccc cgc 53

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
atggtaaagc aagatgaagt tatcacattg t 31

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
atgtcaacta ttaaatgctt ggtttaag 28

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
gcgcctggtc tgtacaccgt tcatctg 27

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
ctcgagtcgg ccgcccatgg caacagtttc agcggagtga 40

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
ccatgggcgg ccgactcgag gaaagttgtt tagcaaaacc cc 42

<210> SEQ ID NO 28

<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
catgttactt agccggaacg 20

<210> SEQ ID NO 29
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (23)..(58)
<223> OTHER INFORMATION: a, c, t, g, unknown or other

<400> SEQUENCE: 29
cgacctgctc tgcggccgcc gannnnnnnn nnnnnnnnnn nnnnnnnnnn nnnnnnnnac 60
cgctgccccc 70

<210> SEQ ID NO 30
<211> LENGTH: 353
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Met Gly Ser Ser His His His His His His Ser Ser Gly Leu Val Pro
1 5 10 15

Arg Gly Ser His Arg Ser Thr Leu Glu Asp Pro Ser Gln Ser Thr Asn
20 25 30

Val Leu Gly Glu Ala Lys Lys Leu Asn Glu Ser Gln Ala Pro Lys Ala
35 40 45

Asp Asn Asn Phe Asn Lys Glu Gln Gln Asn Ala Phe Tyr Glu Ile Leu
50 55 60

Asn Met Pro Asn Leu Asn Glu Glu Gln Arg Asn Gly Phe Ile Gln Ser
65 70 75 80

Leu Lys Asp Asp Pro Ser Gln Ser Ala Asn Leu Leu Ala Glu Ala Lys
85 90 95

Lys Leu Asn Glu Ser Gln Ala Pro Lys Ala Asp Asn Lys Phe Asn Lys
100 105 110

Glu Gln Gln Asn Ala Phe Tyr Glu Ile Leu His Leu Pro Asn Leu Asn
115 120 125

Glu Glu Gln Arg Asn Gly Phe Ile Gln Ser Leu Lys Asp Asp Pro Ser
130 135 140

Gln Ser Ala Asn Leu Leu Ala Glu Ala Lys Lys Leu Asn Asp Ala Gln
145 150 155 160

Ala Pro Lys Ala Asp Asn Lys Phe Asn Lys Glu Gln Gln Asn Ala Phe
165 170 175

Tyr Glu Ile Leu His Leu Pro Asn Leu Thr Glu Glu Gln Arg Asn Gly
180 185 190

Phe Ile Gln Ser Leu Lys Asp Asp Pro Arg Ser Thr Leu Ala Ala Ala
195 200 205

```
Ser Gly Ala Ser Thr Asp Thr Tyr Lys Leu Ile Leu Asn Gly Lys Thr
    210                 215                 220

Leu Lys Gly Glu Thr Thr Thr Glu Ala Val Asp Ala Ala Thr Ala Glu
225                 230                 235                 240

Lys Val Phe Lys Gln Tyr Ala Asn Asp Asn Gly Val Asp Gly Glu Trp
                245                 250                 255

Thr Tyr Asp Asp Ala Thr Lys Thr Phe Thr Val Thr Glu Lys Pro Glu
            260                 265                 270

Val Ile Asp Ala Ser Glu Leu Thr Pro Ala Val Thr Thr Tyr Lys Leu
        275                 280                 285

Val Ile Asn Gly Lys Thr Leu Lys Gly Glu Thr Thr Thr Lys Ala Val
    290                 295                 300

Asp Ala Glu Thr Ala Glu Lys Ala Phe Lys Gln Tyr Ala Asn Asp Asn
305                 310                 315                 320

Gly Val Asp Gly Val Trp Thr Tyr Asp Asp Ala Thr Lys Thr Phe Thr
                325                 330                 335

Val Thr Glu Met Val Thr Glu Val Pro Val Val Arg Gly Gly Ser Cys
            340                 345                 350

Gly


<210> SEQ ID NO 31
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Ser Ala Cys Lys Gly Met Gly Ser Ser His His His His His His
1               5                   10                  15

Ser Ser Gly Leu Val Pro Arg Gly Ser His Met Ala Arg Ile Val Asp
            20                  25                  30

Asn Gln Arg Leu Leu Ser Thr Phe Thr Glu Tyr Ile Lys Asn Ile Ile
        35                  40                  45

Asn Thr Ser Ile Leu Asn Leu Arg Tyr Glu Ser Asn His Leu Ile Asp
    50                  55                  60

Leu Ser Arg Tyr Ala Ser Lys Ile Asn Ile Gly Ser Lys Val Asn Phe
65                  70                  75                  80

Asp Pro Ile Asp Lys Asn Gln Ile Gln Leu Phe Asn Leu Glu Ser Ser
                85                  90                  95

Lys Ile Glu Val Ile Leu Lys Asn Ala Ile Val Tyr Asn Ser Met Tyr
            100                 105                 110

Glu Asn Phe Ser Thr Ser Phe Trp Ile Arg Ile Pro Lys Tyr Phe Asn
        115                 120                 125

Ser Ile Ser Leu Asn Asn Glu Tyr Thr Ile Ile Asn Cys Met Glu Asn
    130                 135                 140

Asn Ser Gly Trp Lys Val Ser Leu Asn Tyr Gly Glu Ile Ile Trp Thr
145                 150                 155                 160

Leu Gln Asp Thr Gln Glu Ile Lys Gln Arg Val Val Phe Lys Tyr Ser
                165                 170                 175

Gln Met Ile Asn Ile Ser Asp Tyr Ile Asn Arg Trp Ile Phe Val Thr
            180                 185                 190

Ile Thr Asn Asn Arg Leu Asn Asn Ser Lys Ile Tyr Ile Asn Gly Arg
        195                 200                 205
```

-continued

```
Leu Ile Asp Gln Lys Pro Ile Ser Asn Leu Gly Asn Ile His Ala Ser
    210                 215                 220

Asn Asn Ile Met Phe Lys Leu Asp Gly Cys Arg Asp Thr His Arg Tyr
225                 230                 235                 240

Ile Trp Ile Lys Tyr Phe Asn Leu Phe Asp Lys Glu Leu Asn Glu Lys
                245                 250                 255

Glu Ile Lys Asp Leu Tyr Asp Asn Gln Ser Asn Ser Gly Ile Leu Lys
            260                 265                 270

Asp Phe Trp Gly Asp Tyr Leu Gln Tyr Asp Lys Pro Tyr Tyr Met Leu
        275                 280                 285

Asn Leu Tyr Asp Pro Asn Lys Tyr Val Asp Val Asn Asn Val Gly Ile
    290                 295                 300

Arg Gly Tyr Met Tyr Leu Lys Gly Pro Arg Gly Ser Val Met Thr Thr
305                 310                 315                 320

Asn Ile Tyr Leu Asn Ser Ser Leu Tyr Arg Gly Thr Lys Phe Ile Ile
                325                 330                 335

Lys Lys Tyr Ala Ser Gly Asn Lys Asp Asn Ile Val Arg Asn Asn Asp
            340                 345                 350

Arg Val Tyr Ile Asn Val Val Val Lys Asn Lys Glu Tyr Arg Leu Ala
        355                 360                 365

Thr Asn Ala Ser Gln Ala Gly Val Glu Lys Ile Leu Ser Ala Leu Glu
    370                 375                 380

Ile Pro Asp Val Gly Asn Leu Ser Gln Val Val Val Met Lys Ser Lys
385                 390                 395                 400

Asn Asp Gln Gly Ile Thr Asn Lys Cys Lys Met Asn Leu Gln Asp Asn
                405                 410                 415

Asn Gly Asn Asp Ile Gly Phe Ile Gly Phe His Gln Phe Asn Asn Ile
            420                 425                 430

Ala Lys Leu Val Ala Ser Asn Trp Tyr Asn Arg Gln Ile Glu Arg Ser
        435                 440                 445

Ser Arg Thr Leu Gly Cys Ser Trp Glu Phe Ile Pro Val Asp Asp Gly
    450                 455                 460

Trp Gly Glu Arg Pro Leu
465                 470
```

<210> SEQ ID NO 32
<211> LENGTH: 4838
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
agatctgcaa gtcttgcata atgtgcctgt caaatggacg aagcagggat tctgcaaacc      60

ctatgctact ccgtcaagcc gtcaattgtc tgattcgtta ccaattatga caacttgacg     120

gctacatcat tcacttttc ttcacaaccg gcacggaact cgctcgggct ggccccggtg     180

cattttttaa atacccgcga gaaatagagt tgatcgtcaa aaccaacatt gcgaccgacg     240

gtggcgatag gcatccgggt ggtgctcaaa agcagcttcg cctggctgat acgttggtcc     300

tcgcgccagc ttaagacgct aatccctaac tgctggcgga aaagatgtga cagacgcgac     360

ggcgacaagc aaacatgctg tgcgacgctg gcgatatcaa aattgctgtc tgccaggtga     420

tcgctgatgt actgacaagc ctcgcgtacc cgattatcca tcggtggatg gagcgactcg     480
```

-continued

```
ttaatcgctt ccatgcgccg cagtaacaat tgctcaagca gatttatcgc cagcagctcc    540
gaatagcgcc cttccccttg cccggcgtta atgatttgcc caaacaggtc gctgaaatgc    600
ggctggtgcg cttcatccgg gcgaaagaac cccgtattgg caaatattga cggccagtta    660
agccattcat gccagtaggc gcgcggacga aagtaaaccc actggtgata ccattcgcga    720
gcctccggat gacgaccgta gtgatgaatc tctcctggcg ggaacagcaa aatatcaccc    780
ggtcggcaaa caaattctcg tccctgattt ttcaccaccc cctgaccgcg aatggtgaga    840
ttgagaatat aacctttcat tcccagcggt cggtcgataa aaaaatcgag ataaccgttg    900
gcctcaatcg gcgttaaacc cgccaccaga tgggcattaa acgagtatcc cggcagcagg    960
ggatcatttt gcgcttcagc catacttttc atactcccgc cattcagaga agaaaccaat   1020
tgtccatatt gcatcagaca ttgccgtcac tgcgtctttt actggctctt ctcgctaacc   1080
aaaccggtaa ccccgcttat taaaagcatt ctgtaacaaa gcgggaccaa agccatgaca   1140
aaaacgcgta acaaaagtgt ctataatcac ggcagaaaag tccacattga ttatttgcac   1200
ggcgtcacac tttgctatgc catagcattt ttatccataa gattagcgga tcctacctga   1260
cgctttttat cgcaactctc tactgtttct ccatacccgt ttttttggat ggagtgaaac   1320
gatggcgatt gcaatttcta gcgccattcg ccattcaggc tgcgcaactg ttgggaaggg   1380
cgatcggtgc gggcctcttc gctattacgc cagctggcga aagggggatg tgctgcaagg   1440
cgattaagtt gggtaacgcc agggttttcc cagtcacgac gttgtaaaac gacggccagt   1500
gaattcgagc tagaaataat tttgtttaac tttaagaagg agatatacca tggcaagcag   1560
cctgagacag attctggact cccagaaaat ggagtggagg tccaacgccg gggcagcgg    1620
tagggataac agggtaatcc atatgctcga gggggcccag gcggccgcac tcgactcggt   1680
acccggggat cctctagagt cgacctgcag gcatgcaagc ttggcgtaat catggtcata   1740
gctgtttcct gtgtgaaatt gttatccgct cacaattcca cacaacatac gagccggaag   1800
cataaagtgt aaagcctggg gtgcctaatg agtgagctaa ctcacattaa ttgcgttgcg   1860
ctcactgccc gctttccagt cgggaaacct gtcgtgccag cgagctcgaa ttcggctgct   1920
aacaaagccc gaaaggaagc tgagttggct gctgccaccg ctgagcaata actagcataa   1980
ccccttgggc ctctaaacgg gtcttgaggg gttttttgct gaaaggagga actatatccg   2040
gatcggagat caattctggc gtaatagcga agaggcccgc accgatcgcc cttcccaaca   2100
gttgcgtagc ctgaatggcg aatgggacgc gccctgtagc ggcgcattaa gcgcggcggg   2160
tgtggtggtt acgcgcagcg tgaccgctac acttgccagc gccctagcgc ccgctccttt   2220
cgctttcttc ccttcctttc tcgccacgtt cgccggcttt ccccgtcaag ctctaaatcg   2280
ggggctccct ttagggttcc gatttagtgc tttacggcac ctcgacccca aaaaacttga   2340
ttagggtgat ggttcacgta gtgggccatc gccctgatag acggtttttc gccctttgac   2400
gttggagtcc acgttcttta atagtggact cttgttccaa actggaacaa cactcaaccc   2460
tatctcggtc tattcttttg atttataagg gattttgccg atttcggcct attggttaaa   2520
aaatgagctg atttaacaaa aatttaacgc gaattttaac aaaatattaa cgtttacaat   2580
ttcaggtggc acttttcggg gaaatgtgcg cggaacccct atttgtttat ttttctaaat   2640
acattcaaat atgtatccgc tcatgagaca ataaccctga taaatgcttc aataatattg   2700
aaaaaggaag agtatgagta ttcaacattt ccgtgtcgcc cttattccct tttttgcggc   2760
attttgccgt cctgtttttg ctcacccaga aacgctggtg aaagtaaaag atgctgaaga   2820
tcagttgggt gcacgagtgg gttacatcga actggatctc aacagcggta agatccttga   2880
```

gagttttcgc cccgaagaac gttttccaat gatgagcact tttaaagttc tgctatgtgg 2940
cgcggtatta tcccgtattg acgccgggca agagcaactc ggtcgccgca tacactattc 3000
tcagaatgac ttggttgagt actcaccagt cacagaaaag catcttacgg atggcatgac 3060
agtaagagaa ttatgcagtg ctgccataag catgagtgat aacactgcgg ccaacttact 3120
tctgacaacg atcggaggac cgaaggagct aaccgctttt tttcacaaca tgggggatca 3180
tgtaactcgc cttgatcgtt gggaaccgga gctgaatgaa gccataccaa acgacgagcg 3240
tgacaccacg atgcctgtag caatggcaac aacgttgcgc aaactattaa ctggcgaact 3300
acttactcta gcttcccggc aacaattaat agactggatg gaggcggata aagttgcagg 3360
accacttctg cgctcggccc ttccggctgg ctggtttatt gctgataaat ctggagccgg 3420
tgagcgtggg tctcgcggta tcattgcagc actggggcca gatggtaagc cctcccgtat 3480
cgtagttatc tacacgacgg gcagtcaggc aactatggat gaacgaaata gacagatcgc 3540
tgagataggt gcctcactga ttaagcattg gtaactgtca gaccaagttt actcatatat 3600
actttagatt gatttaaaac ttcattttta atttaaaagg atctaggtga agatcctttt 3660
tgataatctc atgaccaaaa tcccttaacg tgagttttcg ttccactgag cgtcagaccc 3720
cgtagaaaag atcaaaggat cttcttgaga tccttttttt ctgcgcgtaa tctgctgctt 3780
gcaaacaaaa aaaccaccgc taccagcggt ggtttgtttg ccggatcaag agctaccaac 3840
tctttttccg aaggtaactg gcttcagcag agcgcagata ccaaatactg tccttctagt 3900
gtagccgtag ttaggccacc acttcaagaa ctctgtagca ccgcctacat acctcgctct 3960
gctaatcctg ttaccagtgg ctgctgccag tggcgataag tcgtgtctta ccgggttgga 4020
ctcaagacga tagttaccgg ataaggcgca gcggtcgggc tgaacggggg gttcgtgcac 4080
acagcccagc ttggagcgaa cgacctacac cgaactgaga tacctacagc gtgagcattg 4140
agaaagcgcc acgcttcccg aagggagaaa ggcggacagg tatccggtaa gcggcagggt 4200
cggaacagga gagcgcacga gggagcttcc agggggaaac gcctggtatc tttatagtcc 4260
tgtcgggttt cgccacctct gacttgagcg tcgatttttg tgatgctcgt caggggggcc 4320
gagcctatgg aaaaacgcca gcaacgcggc ctttttacgg ttcctggcct tttgctggcc 4380
ttttgctcac atgttctttc ctgcgttatc ccctgattct gtggataacc gtattaccgc 4440
ctttgagtga gctgataccg ctcgccgcag ccgaacgacc gagcgcagcg agtcagtgag 4500
cgaggaagcg gaagagcgcc tgatgcggta ttttctcctt acgcatctgt gcggtatttc 4560
acaccgcata tatggtgcac tctcagtaca atctgctctg atgccgcata gttaagccag 4620
tatacactcc gctatcgcta cgtgactgca aggagatggc gcccaacagt cccccggcca 4680
cggggcctgc caccataccc acgccgaaac aagcgctcat gagcccgaag tggcgagccc 4740
gatcttcccc atcggtgatg tcggcgatat aggcgccagc aaccgcacct gtggcgccgg 4800
tgatgccggc cacgatgcgt ccggcgtaga ggatcttg 4838

<210> SEQ ID NO 33
<211> LENGTH: 40345
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (33825)..(33830)
<223> OTHER INFORMATION: a, c, t, g, unknown or other
<220> FEATURE:
<221> NAME/KEY: modified_base
<222> LOCATION: (36815)..(36820)
<223> OTHER INFORMATION: a, c, t, g, unknown or other

<400> SEQUENCE: 33
gggcggcgac ctcgcgggtt ttcgctattt atgaaaattt tccggtttaa ggcgtttccg 60
ttcttcttcg tcataactta atgtttttat ttaaaatacc ctctgaaaag aaaggaaacg 120
acaggtgctg aaagcgaggc tttttggcct ctgtcgtttc ctttctctgt tttgtccgt 180 ggaatgaaca atggaagtca acaaaaagca gctggctgac attttcggtg cgagtatccg 240
taccattcag aactggcagg aacagggaat gcccgttctg cgaggcggtg gcaagggtaa 300
tgaggtgctt tatgactctg ccgccgtcat aaaatggtat gccgaaaggg atgctgaaat 360
tgagaacgaa aagctgcgcc gggaggttga agaactgcgg caggccagcg aggcagatct 420
ccagccagga actattgagt acgaacgcca tcgacttacg cgtgcgcagg ccgacgcaca 480
ggaactgaag aatgccagag actccgctga agtggtggaa accgcattct gtactttcgt 540
gctgtcgcgg atcgcaggtg aaattgccag tattctcgac gggctccccc tgtcggtgca 600
gcggcgtttt ccggaactgg aaaaccgaca tgttgatttc ctgaaacggg atatcatcaa 660
agccatgaac aaagcagccg cgctggatga actgataccg gggttgctga gtgaatatat 720
cgaacagtca ggttaacagg ctgcggcatt ttgtccgcgc cgggcttcgc tcactgttca 780
ggccggagcc acagaccgcc gttgaatggg cggatgctaa ttactatctc ccgaaagaat 840
ccgcatacca ggaagggcgc tgggaaacac tgccctttca gcgggccatc atgaatgcga 900
tgggcagcga ctacatccgt gaggtgaatg tggtgaagtc tgcccgtgtc ggttattcca 960
aaatgctgct gggtgtttat gcctacttta tagagcataa gcagcgcaac acccttatct 1020
ggttgccgac ggatggtgat gccgagaact ttatgaaaac ccacgttgag ccgactattc 1080
gtgatattcc gtcgctgctg gcgctggccc cgtggtatgg caaaaagcac cgggataaca 1140
cgctcaccat gaagcgtttc actaatgggc gtggcttctg gtgcctgggc ggtaaagcgg 1200
caaaaaacta ccgtgaaaag tcggtggatg tggcgggtta tgatgaactt gctgcttttg 1260
atgatgatat tgaacaggaa ggctctccga cgttcctggg tgacaagcgt attgaaggct 1320
cggtctggcc aaagtccatc cgtggctcca cgccaaaagt gagaggcacc tgtcagattg 1380
agcgtgcagc cagtgaatcc ccgcatttta tgcgttttca tgttgcctgc ccgcattgcg 1440
gggaggagca gtatcttaaa tttggcgaca aagagacgcc gtttggcctc aaatggacgc 1500
cggatgaccc ctccagcgtg ttttatctct gcgagcataa tgcctgcgtc atccgccagc 1560
aggagctgga ctttactgat gcccgttata tctgcgaaaa gaccgggatc tggacccgtg 1620
atggcattct ctggttttcg tcatccggtg aagagattga gccacctgac agtgtgacct 1680
ttcacatctg gacagcgtac agcccgttca ccacctgggt gcagattgtc aaagactgga 1740
tgaaaacgaa aggggatacg ggaaaacgta aaaccttcgt aaacaccacg ctcggtgaga 1800
cgtgggaggc gaaaattggc gaacgtccgg atgctgaagt gatggcagag cggaaagagc 1860
attattcagc gcccgttcct gaccgtgtgg cttacctgac cgccggtatc gactcccagc 1920
tggaccgcta cgaaatgcgc gtatggggat gggggccggg tgaggaaagc tggctgattg 1980
accggcagat tattatgggc cgccacgacg atgaacagac gctgctgcgt gtggatgagg 2040
ccatcaataa aacctatacc cgccggaatg gtgcagaaat gtcgatatcc cgtatctgct 2100
gggatactgg cgggattgac ccgaccattg tgtatgaacg ctcgaaaaaa catgggctgt 2160

-continued

```
tccgggtgat ccccattaaa ggggcatccg tctacggaaa gccggtggcc agcatgccac   2220

gtaagcgaaa caaaaacggg gtttacctta ccgaaatcgg tacggatacc gcgaaagagc   2280

agatttataa ccgcttcaca ctgacgccgg aaggggatga accgcttccc ggtgccgttc   2340

acttcccgaa taacccggat atttttgatc tgaccgaagc gcagcagctg actgctgaag   2400

agcaggtcga aaaatgggtg gatggcagga aaaaaatact gtgggacagc aaaaagcgac   2460

gcaatgaggc actcgactgc ttcgtttatg cgctggcggc gctgcgcatc agtatttccc   2520

gctggcagct ggatctcagt gcgctgctgg cgagcctgca ggaagaggat ggtgcagcaa   2580

ccaacaagaa aacactggca gattacgccc gtgccttatc cggagaggat gaatgacgcg   2640

acaggaagaa cttgccgctg cccgtgcggc actgcatgac ctgatgacag gtaaacgggt   2700

ggcaacagta cagaaagacg gacgaagggt ggagtttacg gccacttccg tgtctgacct   2760

gaaaaaatat attgcagagc tggaagtgca gaccggcatg acacagcgac gcaggggacc   2820

tgcaggattt tatgtatgaa aacgcccacc attcccaccc ttctggggcc ggacggcatg   2880

acatcgctgc gcgaatatgc cggttatcac ggcggtggca gcggatttgg agggcagttg   2940

cggtcgtgga acccaccgag tgaaagtgtg gatgcagccc tgttgcccaa ctttacccgt   3000

ggcaatgccc gcgcagacga tctggtacgc aataacggct atgccgccaa cgccatccag   3060

ctgcatcagg atcatatcgt cgggtctttt ttccggctca gtcatcgccc aagctggcgc   3120

tatctgggca tcggggagga agaagcccgt gccttttccc gcgaggttga agcggcatgg   3180

aaagagtttg ccgaggatga ctgctgctgc attgacgttg agcgaaaacg cacgtttacc   3240

atgatgattc gggaaggtgt ggccatgcac gcctttaacg gtgaactgtt cgttcaggcc   3300

acctgggata ccagttcgtc gcggcttttc cggacacagt tccggatggt cagcccgaag   3360

cgcatcagca acccgaacaa taccggcgac agccggaact gccgtgccgg tgtgcagatt   3420

aatgacagcg gtgcggcgct gggatattac gtcagcgagg acgggtatcc tggctggatg   3480

ccgcagaaat ggacatggat accccgtgag ttacccggcg ggcgcgcctc gttcattcac   3540

gtttttgaac ccgtggagga cgggcagact cgcggtgcaa atgtgtttta cagcgtgatg   3600

gagcagatga agatgctcga cacgctgcag aacacgcagc tgcagagcgc cattgtgaag   3660

gcgatgtatg ccgccaccat tgagagtgag ctggatacgc agtcagcgat ggattttatt   3720

ctgggcgcga acagtcagga gcagcgggaa aggctgaccg gctggattgg tgaaattgcc   3780

gcgtattacg ccgcagcgcc ggtccggctg ggaggcgcaa aagtaccgca cctgatgccg   3840

ggtgactcac tgaacctgca gacggctcag gatacggata acggctactc cgtgtttgag   3900

cagtcactgc tgcggtatat cgctgccggg ctgggtgtct cgtatgagca gctttcccgg   3960

aattacgccc agatgagcta ctccacggca cgggccagtg cgaacgagtc gtgggcgtac   4020

tttatggggc ggcgaaaatt cgtcgcatcc cgtcaggcga gccagatgtt tctgtgctgg   4080

ctggaagagg ccatcgttcg ccgcgtggtg acgttacctt caaaagcgcg cttcagtttt   4140

caggaagccc gcagtgcctg gggggaactgc gactggatag gctccggtcg tatggccatc   4200

gatggtctga aagaagttca ggaagcggtg atgctgatag aagccggact gagtacctac   4260

gagaaagagt gcgcaaaacg cggtgacgac tatcaggaaa tttttgccca gcaggtccgt   4320

gaaacgatgg agcgccgtgc agccggtctt aaaccgcccg cctgggcggc tgcagcattt   4380

gaatccgggc tgcgacaatc aacagaggag gagaagagtg acagcagagc tgcgtaatct   4440

cccgcatatt gccagcatgg cctttaatga gccgctgatg cttgaacccg cctatgcgcg   4500

ggttttcttt tgtgcgcttg caggccagct tgggatcagc agcctgacgg atgcggtgtc   4560
```

cggcgacagc ctgactgccc aggaggcact cgcgacgctg gcattatccg gtgatgatga 4620
cggaccacga caggcccgca gttatcaggt catgaacggc atcgccgtgc tgccggtgtc 4680
cggcacgctg gtcagccgga cgcgggcgct gcagccgtac tcggggatga ccggttacaa 4740
cggcattatc gcccgtctgc aacaggctgc cagcgatccg atggtggacg gcattctgct 4800
cgatatggac acgcccggcg ggatggtggc gggggcattt gactgcgctg acatcatcgc 4860
ccgtgtgcgt gacataaaac cggtatgggc gcttgccaac gacatgaact gcagtgcagg 4920
tcagttgctt gccagtgccg cctcccggcg tctggtcacg cagaccgccc ggacaggctc 4980
catcggcgtc atgatggctc acagtaatta cggtgctgcg ctggagaaac agggtgtgga 5040
aatcacgctg atttacagcg gcagccataa ggtggatggc aacccctaca gccatcttcc 5100
ggatgacgtc cgggagacac tgcagtcccg gatggacgca acccgccaga tgtttgcgca 5160
gaaggtgtcg gcatataccg gcctgtccgt gcaggttgtg ctggataccg aggctgcagt 5220
gtacagcggt caggaggcca ttgatgccgg actggctgat gaacttgtta acagcaccga 5280
tgcgatcacc gtcatgcgtg atgcactgga tgcacgtaaa tcccgtctct caggagggcg 5340
aatgaccaaa gagactcaat caacaactgt ttcagccact gcttcgcagg ctgacgttac 5400
tgacgtggtg ccagcgacgg agggcgagaa cgccagcgcg gcgcagccgg acgtgaacgc 5460
gcagatcacc gcagcggttg cggcagaaaa cagccgcatt atggggatcc tcaactgtga 5520
ggaggctcac ggacgcgaag aacaggcacg cgtgctggca gaaacccccg gtatgaccgt 5580
gaaaacggcc cgccgcattc tggccgcagc accacagagt gcacaggcgc gcagtgacac 5640
tgcgctggat cgtctgatgc aggggggcacc ggcaccgctg gctgcaggta acccggcatc 5700
tgatgccgtt aacgatttgc tgaacacacc agtgtaaggg atgtttatga cgagcaaaga 5760
aacctttacc cattaccagc cgcagggcaa cagtgacccg gctcataccg caaccgcgcc 5820
cctagacctt catcactaaa ggccgcctgt gcggcttttt ttacgggatt tttttatgtc 5880
gatgtacaca accgcccaac tgctggcggc aaatgagcag aaatttaagt ttgatccgct 5940
gtttctgcgt ctctttttcc gtgagagcta tcccttcacc acggagaaag tctatctctc 6000
acaaattccg ggactggtaa acatggcgct gtacgtttcg ccgattgttt ccggtgaggt 6060
tatccgttcc cgtggcggct ccacctctga atttacgccg ggatatgtca agccgaagca 6120
tgaagtgaat ccgcagatga ccctgcgtcg cctgccggat gaagatccgc agaatctggc 6180
ggacccggct taccgccgcc gtcgcatcat catgcagaac atgcgtgacg aagagctggc 6240
cattgctcag gtcgaagaga tgcaggcagt ttctgccgtg cttaagggca aatacaccat 6300
gaccggtgaa gccttcgatc cggttgaggt ggatatgggc cgcagtgagg agaataacat 6360
cacgcagtcc ggcggcacgg agtggagcaa gcgtgacaag tccacgtatg acccgaccga 6420
cgatatcgaa gcctacgcgc tgaacgccag cggtgtggtg aatatcatcg tgttcgatcc 6480
gaaaggctgg gcgctgttcc gttccttcaa agccgtcaag gagaagctgg atacccgtcg 6540
tggctctaat tccgagctgg agacagcggt gaaagacctg ggcaaagcgg tgtcctataa 6600
ggggatgtat ggcgatgtgg ccatcgtcgt gtattccgga cagtacgtgg aaaacggcgt 6660
caaaaagaac ttcctgccgg acaacacgat ggtgctgggg aacactcagg cacgcggtct 6720
gcgcacctat ggctgcattc aggatgcgga cgcacagcgc gaaggcatta acgcctctgc 6780
ccgttacccg aaaaactggg tgaccaccgg cgatccggcg cgtgagttca ccatgattca 6840
gtcagcaccg ctgatgctgc tggctgaccc tgatgagttc gtgtccgtac aactggcgta 6900
atcatggccc ttcggggcca ttgtttctct gtggaggagt ccatgacgaa agatgaactg 6960
attgcccgtc tccgctcgct gggtgaacaa ctgaaccgtg atgtcagcct gacggggacg 7020
aaagaagaac tggcgctccg tgtggcagag ctgaaagagg agcttgatga cacggatgaa 7080
actgccggtc aggacacccc tctcagccgg gaaaatgtgc tgaccggaca tgaaaatgag 7140
gtgggatcag cgcagccgga taccgtgatt ctggatacgt ctgaactggt cacggtcgtg 7200
gcactggtga agctgcatac tgatgcactt cacgccacgc gggatgaacc tgtggcattt 7260
gtgctgccgg gaacggcgtt tcgtgtctct gccggtgtgg cagccgaaat gacagagcgc 7320
ggcctggcca gaatgcaata acgggaggcg ctgtggctga tttcgataac ctgttcgatg 7380
ctgccattgc ccgcgccgat gaaacgatac gcgggtacat gggaacgtca gccaccatta 7440
catccggtga gcagtcaggt gcggtgatac gtggtgtttt tgatgaccct gaaaatatca 7500
gctatgccgg acagggcgtg cgcgttgaag gctccagccc gtccctgttt gtccggactg 7560
atgaggtgcg gcagctgcgg cgtggagaca cgctgaccat cggtgaggaa aatttctggg 7620
tagatcgggt ttcgccggat gatggcggaa gttgtcatct ctggcttgga cggggcgtac 7680
cgcctgccgt taaccgtcgc cgctgaaagg gggatgtatg gccataaaag gtcttgagca 7740
ggccgttgaa aacctcagcc gtatcagcaa aacggcggtg cctggtgccg ccgcaatggc 7800
cattaaccgc gttgcttcat ccgcgatatc gcagtcggcg tcacaggttg cccgtgagac 7860
aaaggtacgc cggaaactgg taaaggaaag ggccaggctg aaaagggcca cggtcaaaaa 7920
tccgcaggcc agaatcaaag ttaaccgggg ggatttgccc gtaatcaagc tgggtaatgc 7980
gcgggttgtc ctttcgcgcc gcaggcgtcg taaaaagggg cagcgttcat ccctgaaagg 8040
tggcggcagc gtgcttgtgg tgggtaaccg tcgtattccc ggcgcgttta ttcagcaact 8100
gaaaaatggc cggtggcatg tcatgcagcg tgtggctggg aaaaaccgtt accccattga 8160
tgtggtgaaa atcccgatgg cggtgccgct gaccacggcg tttaaacaaa atattgagcg 8220
gatacggcgt gaacgtcttc cgaaagagct gggctatgcg ctgcagcatc aactgaggat 8280
ggtaataaag cgatgaaaca tactgaactc cgtgcagccg tactggatgc actggagaag 8340
catgacaccg gggcgacgtt ttttgatggt cgccccgctg tttttgatga ggcggatttt 8400
ccggcagttg ccgtttatct caccggcgct gaatacacgg gcgaagagct ggacagcgat 8460
acctggcagg cggagctgca tatcgaagtt ttcctgcctg ctcaggtgcc ggattcagag 8520
ctggatgcgt ggatggagtc ccggatttat ccggtgatga gcgatatccc ggcactgtca 8580
gatttgatca ccagtatggt ggccagcggc tatgactacc ggcgcgacga tgatgcgggc 8640
ttgtggagtt cagccgatct gacttatgtc attacctatg aaatgtgagg acgctatgcc 8700
tgtaccaaat cctacaatgc cggtgaaagg tgccgggacc accctgtggg tttataaggg 8760
gagcggtgac ccttacgcga atccgctttc agacgttgac tggtcgcgtc tggcaaaagt 8820
taaagacctg acgcccggcg aactgaccgc tgagtcctat gacgacagct atctcgatga 8880
tgaagatgca gactggactg cgaccgggca ggggcagaaa tctgccggag ataccagctt 8940
cacgctggcg tggatgcccg gagagcaggg gcagcaggcg ctgctggcgt ggtttaatga 9000
aggcgatacc cgtgcctata aaatccgctt cccgaacggc acggtcgatg tgttccgtgg 9060
ctgggtcagc agtatcggta aggcggtgac ggcgaaggaa gtgatcaccc gcacggtgaa 9120
agtcaccaat gtgggacgtc cgtcgatggc agaagatcgc agcacggtaa cagcggcaac 9180
cggcatgacc gtgacgcctg ccagcacctc ggtggtgaaa gggcagagca ccacgctgac 9240
cgtggccttc cagccggagg gcgtaaccga caagagcttt cgtgcggtgt ctgcggataa 9300

-continued

```
aacaaaagcc accgtgtcgg tcagtggtat gaccatcacc gtgaacggcg ttgctgcagg   9360
caaggtcaac attccggttg tatccggtaa tggtgagttt gctgcggttg cagaaattac   9420
cgtcaccgcc agttaatccg gagagtcagc gatgttcctg aaaaccgaat catttgaaca   9480
taacggtgtg accgtcacgc tttctgaact gtcagccctg cagcgcattg agcatctcgc   9540
cctgatgaaa cggcaggcag aacaggcgga gtcagacagc aaccggaagt ttactgtgga   9600
agacgccatc agaaccggcg cgtttctggt ggcgatgtcc ctgtggcata accatccgca   9660
gaagacgcag atgccgtcca tgaatgaagc cgttaaacag attgagcagg aagtgcttac   9720
cacctggccc acggaggcaa tttctcatgc tgaaaacgtg gtgtaccggc tgtctggtat   9780
gtatgagttt gtggtgaata atgcccctga acagacagag gacgccgggc ccgcagagcc   9840
tgtttctgcg ggaaagtgtt cgacggtgag ctgagttttg ccctgaaact ggcgcgtgag   9900
atggggcgac ccgactggcg tgccatgctt gccgggatgt catccacgga gtatgccgac   9960
tggcaccgct tttacagtac ccattatttt catgatgttc tgctggatat gcacttttcc  10020
gggctgacgt acaccgtgct cagcctgttt ttcagcgatc cggatatgca tccgctggat  10080
ttcagtctgc tgaaccggcg cgaggctgac gaagagcctg aagatgatgt gctgatgcag  10140
aaagcggcag ggcttgccgg aggtgtccgc tttggcccgg acgggaatga agttatcccc  10200
gcttccccgg atgtggcgga catgacggag gatgacgtaa tgctgatgac agtatcagaa  10260
gggatcgcag gaggagtccg gtatggctga accggtaggc gatctggtcg ttgatttgag  10320
tctggatgcg gccagatttg acgagcagat ggccagagtc aggcgtcatt tttctggtac  10380
ggaaagtgat gcgaaaaaaa cagcggcagt cgttgaacag tcgctgagcc gacaggcgct  10440
ggctgcacag aaagcgggga tttccgtcgg gcagtataaa gccgccatgc gtatgctgcc  10500
tgcacagttc accgacgtgg ccacgcagct tgcaggcggg caaagtccgt ggctgatcct  10560
gctgcaacag ggggggcagg tgaaggactc cttcggcggg atgatcccca tgttcagggg  10620
gcttgccggt gcgatcaccc tgccgatggt gggggccacc tcgctggcgg tggcgaccgg  10680
tgcgctggcg tatgcctggt atcagggcaa ctcaaccctg tccgatttca acaaaacgct  10740
ggtcctttcc ggcaatcagg cgggactgac ggcagatcgt atgctggtcc tgtccagagc  10800
cgggcaggcg gcagggctga cgtttaacca gaccagcgag tcactcagcg cactggttaa  10860
ggcgggggta agcggtgagg ctcagattgc gtccatcagc cagagtgtgg cgcgtttctc  10920
ctctgcatcc ggcgtggagg tggacaaggt cgctgaagcc ttcgggaagc tgaccacaga  10980
cccgacgtcg gggctgacgg cgatggctcg ccagttccat aacgtgtcgg cggagcagat  11040
tgcgtatgtt gctcagttgc agcgttccgg cgatgaagcc ggggcattgc aggcggcgaa  11100
cgaggccgca acgaaagggt ttgatgacca gacccgccgc ctgaaagaga acatgggcac  11160
gctggagacc tgggcagaca ggactgcgcg ggcattcaaa tccatgtggg atgcggtgct  11220
ggatattggt cgtcctgata ccgcgcagga gatgctgatt aaggcagagg ctgcgtataa  11280
gaaagcagac gacatctgga atctgcgcaa ggatgattat tttgttaacg atgaagcgcg  11340
ggcgcgttac tgggatgatc gtgaaaaggc ccgtcttgcg cttgaagccg cccgaaagaa  11400
ggctgagcag cagactcaac aggacaaaaa tgcgcagcag cagagcgata ccgaagcgtc  11460
acggctgaaa tataccgaag aggcgcagaa ggcttacgaa cggctgcaga cgccgctgga  11520
gaaatatacc gcccgtcagg aagaactgaa caaggcactg aaagacggga aaatcctgca  11580
ggcggattac aacacgctga tggcggcggc gaaaaaggat tatgaagcga cgctgaaaaa  11640
```

-continued gccgaaacag tccagcgtga aggtgtctgc gggcgatcgt caggaagaca gtgctcatgc 11700
tgccctgctg acgcttcagg cagaactccg gacgctggag aagcatgccg gagcaaatga 11760
gaaaatcagc cagcagcgcc gggatttgtg gaaggcggag agtcagttcg cggtactgga 11820
ggaggcggcg caacgtcgcc agctgtctgc acaggagaaa tccctgctgg cgcataaaga 11880
tgagacgctg gagtacaaac gccagctggc tgcacttggc gacaaggtta cgtatcagga 11940
gcgcctgaac gcgctggcgc agcaggcgga taaattcgca cagcagcaac gggcaaaacg 12000
ggccgccatt gatgcgaaaa gccgggggct gactgaccgg caggcagaac gggaagccac 12060
ggaacagcgc ctgaaggaac agtatggcga taatccgctg gcgctgaata acgtcatgtc 12120
agagcagaaa aagacctggg cggctgaaga ccagcttcgc gggaactgga tggcaggcct 12180
gaagtccggc tggagtgagt gggaagagag cgccacggac agtatgtcgc aggtaaaaag 12240
tgcagccacg cagacctttg atggtattgc acagaatatg gcggcgatgc tgaccggcag 12300
tgagcagaac tggcgcagct tcacccgttc cgtgctgtcc atgatgacag aaattctgct 12360
taagcaggca atggtgggga ttgtcgggag tatcggcagc gccattggcg gggctgttgg 12420
tggcggcgca tccgcgtcag gcggtacagc cattcaggcc gctgcggcga aattccattt 12480
tgcaaccgga ggatttacgg gaaccggcgg caaatatgag ccagcgggga ttgttcaccg 12540
tggtgagttt gtcttcacga aggaggcaac cagccggatt ggcgtgggga atctttaccg 12600
gctgatgcgc ggctatgcca ccggcggtta tgtcggtaca ccgggcagca tggcagacag 12660
ccggtcgcag gcgtccggga cgtttgagca gaataaccat gtggtgatta acaacgacgg 12720
cacgaacggg cagataggtc cggctgctct gaaggcggtg tatgacatgg cccgcaaggg 12780
tgcccgtgat gaaattcaga cacagatgcg tgatggtggc ctgttctccg gaggtggacg 12840
atgaagacct tccgctggaa agtgaaaccc ggtatggatg tggcttcggt cccttctgta 12900
agaaaggtgc gctttggtga tggctattct cagcgagcgc ctgccgggct gaatgccaac 12960
ctgaaaacgt acagcgtgac gctttctgtc ccccgtgagg aggccacggt actggagtcg 13020
tttctggaag agcacggggg ctggaaatcc tttctgtgga cgccgcctta tgagtggcgg 13080
cagataaagg tgacctgcgc aaaatggtcg tcgcgggtca gtatgctgcg tgttgagttc 13140
agcgcagagt ttgaacaggt ggtgaactga tgcaggatat ccggcaggaa acactgaatg 13200
aatgcacccg tgcggagcag tcggccagcg tggtgctctg ggaaatcgac ctgacagagg 13260
tcggtggaga acgttatttt ttctgtaatg agcagaacga aaaaggtgag ccggtcacct 13320
ggcaggggcg acagtatcag ccgtatccca ttcaggggag cggttttgaa ctgaatggca 13380
aaggcaccag tacgcgcccc acgctgacgg tttctaacct gtacggtatg gtcaccggga 13440
tggcggaaga tatgcagagt ctggtcggcg gaacggtggt ccggcgtaag gtttacgccc 13500
gttttctgga tgcggtgaac ttcgtcaacg gaaacagtta cgccgatccg gagcaggagg 13560
tgatcagccg ctggcgcatt gagcagtgca gcgaactgag cgcggtgagt gcctcctttg 13620
tactgtccac gccgacggaa acggatggcg ctgtttttcc gggacgtatc atgctggcca 13680
acacctgcac ctggacctat cgcggtgacg agtgcggtta tagcggtccg gctgtcgcgg 13740
atgaatatga ccagccaacg tccgatatca cgaaggataa atgcagcaaa tgcctgagcg 13800
gttgtaagtt ccgcaataac gtcggcaact ttggcggctt cctttccatt aacaaacttt 13860
cgcagtaaat cccatgacac agacagaatc agcgattctg gcgcacgccc ggcgatgtgc 13920
gccagcggag tcgtgcggct tcgtggtaag cacgccggag gggaaagat atttcccctg 13980 cgtgaatatc tccggtgagc cggaggctat ttccgtatgt cgccggaaga ctggctgcag 14040
gcagaaatgc agggtgagat tgtggcgctg gtccacagcc accccggtgg tctgccctgg 14100
ctgagtgagg ccgaccggcg gctgcaggtg cagagtgatt tgccgtggtg gctggtctgc 14160
cgggggacga ttcataagtt ccgctgtgtg ccgcatctca ccgggcggcg ctttgagcac 14220
ggtgtgacgg actgttacac actgttccgg gatgcttatc atctggcggg gattgagatg 14280
ccggactttc atcgtgagga tgactggtgg cgtaacggcc agaatctcta tctggataat 14340
ctggaggcga cggggctgta tcaggtgccg ttgtcagcgg cacagccggg cgatgtgctg 14400
ctgtgctgtt ttggttcatc agtgccgaat cacgccgcaa tttactgcgg cgacggcgag 14460
ctgctgcacc atattcctga acaactgagc aaacgagaga ggtacaccga caaatggcag 14520
cgacgcacac actccctctg gcgtcaccgg gcatggcgcg catctgcctt tacggggatt 14580
tacaacgatt tggtcgccgc atcgaccttc gtgtgaaaac gggggctgaa gccatccggg 14640
cactggccac acagctcccg gcgtttcgtc agaaactgag cgacggctgg tatcaggtac 14700
ggattgccgg gcgggacgtc agcacgtccg ggttaacggc gcagttacat gagactctgc 14760
ctgatggcgc tgtaattcat attgttccca gagtcgccgg ggccaagtca ggtggcgtat 14820
tccagattgt cctgggggct gccgccattg ccggatcatt ctttaccgcc ggagccaccc 14880
ttgcagcatg gggggcagcc attggggccg gtggtatgac cggcatcctg ttttctctcg 14940
gtgccagtat ggtgctcggt ggtgtggcgc agatgctggc accgaaagcc agaactcccc 15000
gtatacagac aacggataac ggtaagcaga acacctattt ctcctcactg gataacatgg 15060
ttgcccaggg caatgttctg cctgttctgt acggggaaat gcgcgtgggg tcacgcgtgg 15120
tttctcagga gatcagcacg gcagacgaag ggacggtgg tcaggttgtg gtgattggtc 15180
gctgatgcaa aatgttttat gtgaaaccgc ctgcgggcgg ttttgtcatt tatggagcgt 15240
gaggaatggg taaaggaagc agtaaggggc ataccccgcg cgaagcgaag gacaacctga 15300
agtccacgca gttgctgagt gtgatcgatg ccatcagcga agggccgatt gaaggtccgg 15360
tggatggctt aaaaagcgtg ctgctgaaca gtacgccggt gctggacact gaggggaata 15420
ccaacatatc cggtgtcacg gtggtgttcc gggctggtga gcaggagcag actccgccgg 15480
agggatttga atcctccggc tccgagacgg tgctgggtac ggaagtgaaa tatgacacgc 15540
cgatcacccg caccattacg tctgcaaaca tcgaccgtct gcgctttacc ttcggtgtac 15600
aggcactggt ggaaaccacc tcaaagggtg acaggaatcc gtcggaagtc cgcctgctgg 15660
ttcagataca acgtaacggt ggctgggtga cggaaaaaga catcaccatt aagggcaaaa 15720
ccacctcgca gtatctggcc tcggtggtga tgggtaacct gccgccgcgc ccgtttaata 15780
tccggatgcg caggatgacg ccggacagca ccacagacca gctgcagaac aaaacgctct 15840
ggtcgtcata cactgaaatc atcgatgtga aacagtgcta cccgaacacg gcactggtcg 15900
gcgtgcaggt ggactcggag cagttcggca gccagcaggt gagccgtaat tatcatctgc 15960
gcgggcgtat tctgcaggtg ccgtcgaact ataacccgca gacgcggcaa tacagcggta 16020
tctgggacgg aacgtttaaa ccggcataca gcaacaacat ggcctggtgt ctgtgggata 16080
tgctgaccca tccgcgctac ggcatgggga aacgtcttgg tgcggcggat gtggataaat 16140
gggcgctgta tgtcatcggc cagtactgcg accagtcagt gccggacggc tttggcggca 16200
cggagccgcg catcacctgt aatgcgtacc tgaccacaca gcgtaaggcg tgggatgtgc 16260
tcagcgattt ctgctcggcg atgcgctgta tgccggtatg gaacgggcag acgctgacgt 16320
tcgtgcagga ccgaccgtcg gataagacgt ggacctataa ccgcagtaat gtggtgatgc 16380

-continued

```
cggatgatgg cgcgccgttc cgctacagct tcagcgccct gaaggaccgc cataatgccg  16440
ttgaggtgaa ctggattgac ccgaacaacg gctgggagac ggcgacagag cttgttgaag  16500
atacgcaggc cattgcccgt tacggtcgta atgttacgaa gatggatgcc tttggctgta  16560
ccagccgggg gcaggcacac cgcgccgggc tgtggctgat taaaacagaa ctgctggaaa  16620
cgcagaccgt ggatttcagc gtcggcgcag aagggcttcg ccatgtaccg ggcgatgtta  16680
ttgaaatctg cgatgatgac tatgccggta tcagcaccgg tggtcgtgtg ctggcggtga  16740
acagccagac ccggacgctg acgctcgacc gtgaaatcac gctgccatcc tccggtaccg  16800
cgctgataag cctggttgac ggaagtggca atccggtcag cgtggaggtt cagtccgtca  16860
ccgacggcgt gaaggtaaaa gtgagccgtg ttcctgacgg tgttgctgaa tacagcgtat  16920
gggagctgaa gctgccgacg ctgcgccagc gactgttccg ctgcgtgagt atccgtgaga  16980
acgacgacgg cacgtatgcc atcaccgccg tgcagcatgt gccggaaaaa gaggccatcg  17040
tggataacgg ggcgcacttt gacggcgaac agagtggcac ggtgaatggt gtcacgccgc  17100
cagcggtgca gcacctgacc gcagaagtca ctgcagacag cggggaatat caggtgctgg  17160
cgcgatggga cacaccgaag gtggtgaagg gcgtgagttt cctgctccgt ctgaccgtaa  17220
cagcggacga cggcagtgag cggctggtca gcacggcccg gacgacggaa accacatacc  17280
gcttcacgca actggcgctg ggaactaca ggctgacagt ccgggcggta aatgcgtggg  17340
ggcagcaggg cgatccggcg tcggtatcgt tccggattgc cgcaccggca gcaccgtcga  17400
ggattgagct gacgccgggc tattttcaga taaccgccac gccgcatctt gccgtttatg  17460
acccgacggt acagtttgag ttctggttct cggaaaagca gattgcggat atcagacagg  17520
ttgaaaccag cacgcgttat cttggtacgg cgctgtactg gatagccgcc agtatcaata  17580
tcaaaccggg ccatgattat tacttttata tccgcagtgt gaacaccgtt ggcaaatcgg  17640
cattcgtgga ggccgtcggt cgggcgagcg atgatgcgga aggttacctg gatttttca  17700
aaggcaagat aaccgaatcc catctcggca aggagctgct ggaaaaagtc gagctgacgg  17760
aggataacgc cagcagactg gaggagtttt cgaaagagtg gaaggatgcc agtgataagt  17820
ggaatgccat gtgggctgtc aaaattgagc agaccaaaga cggcaaacat tatgtcgcgg  17880
gtattggcct cagcatggag gacacggagg aaggcaaact gagccagttt ctggttgccg  17940
ccaatcgtat cgcatttatt gacccggcaa acgggaatga aacgccgatg tttgtggcgc  18000
agggcaacca gatattcatg aacgacgtgt tcctgaagcg cctgacggcc cccaccatta  18060
ccagcggcgg caatcctccg gccttttccc tgacaccgga cggaaagctg accgctaaaa  18120
atgcggatat cagtggcagt gtgaatgcga actccgggac gctcagtaat gtgacgatag  18180
ctgaaaactg tacgataaac ggtacgctga gggcggaaaa aatcgtcggg gacattgtaa  18240
aggcggcgag cgcggctttt ccgcgccagc gtgaaagcag tgtggactgg ccgtcaggta  18300
cccgtactgt caccgtgacc gatgaccatc cttttgatcg ccagatagtg gtgcttccgc  18360
tgacgtttcg cggaagtaag cgtactgtca gcggcaggac aacgtattcg atgtgttatc  18420
tgaaagtact gatgaacggt gcggtgattt atgatggcgc ggcgaacgag gcggtacagg  18480
tgttctcccg tattgttgac atgccagcgg gtcggggaaa cgtgatcctg acgttcacgc  18540
ttacgtccac acggcattcg gcagatattc cgccgtatac gtttgccagc gatgtgcagg  18600
ttatggtgat taagaaacag gcgctgggca tcagcgtggt ctgagtgtgt tacagaggtt  18660
cgtccgggaa cgggcgtttt attataaaac agtgagaggt gaacgatgcg taatgtgtgt  18720
attgccgttg ctgtctttgc cgcacttgcg gtgacagtca ctccggcccg tgcggaaggt  18780
```

ggacatggta cgtttacggt gggctatttt caagtgaaac cgggtacatt gccgtcgttg 18840
tcgggcgggg ataccggtgt gagtcatctg aaagggatta acgtgaagta ccgttatgag 18900
ctgacggaca gtgtgggggt gatggcttcc ctggggttcg ccgcgtcgaa aaagagcagc 18960
acagtgatga ccggggagga tacgtttcac tatgagagcc tgcgtggacg ttatgtgagc 19020
gtgatggccg gaccggtttt acaaatcagt aagcaggtca gtgcgtacgc catggccgga 19080
gtggctcaca gtcggtggtc cggcagtaca atggattacc gtaagacgga aatcactccc 19140
gggatcctct agagtcgacc tgcaggcatg caagcttggc gtaatcatgg tcatagctgt 19200
ttcctgtgtg aaattgttat ccgctcacaa ttccacacaa catacgagcc ggaagcataa 19260
agtgtaaagc ctggggtgcc taatgagtga gctaactcac attaattgcg ttgcgctcac 19320
tgcccgcttt ccagtcggga aacctgtcgt gccagctgca ttaatgaatc ggccaacgcg 19380
cggggagagg cggtttgcgt attgggcgct cttccgcttc ctcgctcact gactcgctgc 19440
gctcggtcgt tcggctgcgg cgagcggtat cagctcactc aaaggcggta atacggttat 19500
ccacagaatc aggggataac gcaggaaaga acatgtgagc aaaaggccag caaaaggcca 19560
ggaaccgtaa aaaggccgcg ttgctggcgt ttttccatag gctccgcccc cctgacgagc 19620
atcacaaaaa tcgacgctca agtcagaggt ggcgaaaccc gacaggacta taaagatacc 19680
aggcgtttcc ccctggaagc tccctcgtgc gctctcctgt tccgaccctg ccgcttaccg 19740
gatacctgtc cgcctttctc ccttcgggaa gcgtggcgct ttctcatagc tcacgctgta 19800
ggtatctcag ttcggtgtag gtcgttcgct ccaagctggg ctgtgtgcac gaaccccccg 19860
ttcagcccga ccgctgcgcc ttatccggta actatcgtct tgagtccaac ccggtaagac 19920
acgacttatc gccactggca gcagccactg gtaacaggat tagcagagcg aggtatgtag 19980
gcggtgctac agagttcttg aagtggtggc ctaactacgg ctacactaga aggacagtat 20040
ttggtatctg cgctctgctg aagccagtta ccttcggaaa aagagttggt agctcttgat 20100
ccggcaaaca aaccaccgct ggtagcggtg gtttttttgt ttgcaagcag cagattacgc 20160
gcagaaaaaa aggatctcaa gaagatcctt tgatcttttc tacggggtct gacgctcagt 20220
ggaacgaaaa ctcacgttaa gggattttgg tcatgagatt atcaaaaagg atcttcacct 20280
agatcctttt aaattaaaaa tgaagtttta aatcaatcta aagtatatat gagtaaactt 20340
ggtctgacag ttaccaatgc ttaatcagtg aggcacctat ctcagcgatc tgtctatttc 20400
gttcatccat agttgcctga ctccccgtcg tgtagataac tacgatacgg gagggcttac 20460
catctggccc cagtgctgca atgataccgc gagacccacg ctcaccggct ccagatttat 20520
cagcaataaa ccagccagcc ggaagggccg agcgcagaag tggtcctgca actttatccg 20580
cctccatcca gtctattaat tgttgccggg aagctagagt aagtagttcg ccagttaata 20640
gtttgcgcaa cgttgttgcc attgctacag gcatcgtggt gtcacgctcg tcgtttggta 20700
tggcttcatt cagctccggt tcccaacgat caaggcgagt tacatgatcc cccatgttgt 20760
gcaaaaaagc ggttagctcc ttcggtcctc cgatcgttgt cagaagtaag ttggccgcag 20820
tgttatcact catggttatg gcagcactgc ataattctct tactgtcatg ccatccgtaa 20880
gatgcttttc tgtgactggt gagtactcaa ccaagtcatt ctgagaatag tgtatgcggc 20940
gaccgagttg ctcttgcccg gcgtcaatac gggataatac cgcgccacat agcagaactt 21000
taaaagtgct catcattgga aaacgttctt cggggcgaaa actctcaagg atcttaccgc 21060
tgttgagatc cagttcgatg taacccactc gtgcacccaa ctgatcttca gcatctttta 21120

-continued

```
ctttcaccag cgtttctggg tgagcaaaaa caggaaggca aaatgccgca aaaaagggaa  21180
taagggcgac acggaaatgt tgaatactca tactcttcct ttttcaatat tattgaagca  21240
tttatcaggg ttattgtctc atgagcggat acatatttga atgtatttag aaaaataaac  21300
aaataggggt tccgcgcaca tttccccgaa aagtgccacc tgacgtctaa gaaaccatta  21360
ttatcatgac attaacctat aaaaataggc gtatcacgag gccctttcgt ctcgcgcgtt  21420
tcggtgatga cggtgaaaac ctctgacaca tgcagctccc ggagacggtc acagcttgtc  21480
tgtaagcgga tgccgggagc agacaagccc gtcagggcgc gtcagcgggt gttggcgggt  21540
gtcggggctg gcttaactat gcggcatcag agcagattgt actgagagtg caccatatgc  21600
ggtgtgaaat accgcacaga tgcgtaagga gaaaataccg catcaggcgc cattcgccat  21660
tcaggctgcg caactgttgg gaagggcgat cggtgcgggc ctcttcgcta ttacgccagc  21720
tggcgaaagg gggatgtgct gcaaggcgat taagttgggt aacgccaggg ttttcccagt  21780
cacgacgttg taaaacgacg gccagtgaat tcgattttaa gatacattga tgagtttgga  21840
caaaccacaa ctagaatgca gtgaaaaaaa tgctttattt gtgaaatttg tgatgctatt  21900
gctttatttg taaccattat aagctgcaat aaacaagtta acaacaacaa ttgcattcat  21960
tttatgtttc aggttcaggg ggaggtgtgg gaggtttttt aaagcaagta aaacctctac  22020
aaatgtggta tggctgatta tgatcagtta tctagagtcg cggccgcttt acttgtacag  22080
ctcgtccatg ccgagagtga tcccggcggc ggtcacgaac tccagcagga ccatgtgatc  22140
gcgcttctcg ttggggtctt tgctcagggc ggactgggtg ctcaggtagt ggttgtcggg  22200
cagcagcacg gggccgtcgc cgatgggggt gttctgctgg tagtggtcgg cgagctgcac  22260
gctgccgtcc tcgatgttgt ggcggatctt gaagttcacc ttgatgccgt tcttctgctt  22320
gtcggccatg atatagacgt tgtggctgtt gtagttgtac tccagcttgt gccccaggat  22380
gttgccgtcc tccttgaagt cgatgccctt cagctcgatg cggttcacca gggtgtcgcc  22440
ctcgaacttc acctcggcgc gggtcttgta gttgccgtcg tccttgaaga agatggtgcg  22500
ctcctggacg tagccttcgg gcatggcgga cttgaagaag tcgtgctgct tcatgtggtc  22560
ggggtagcgg ctgaagcact gcacgccgta ggtcagggtg gtcacgaggg tgggccaggg  22620
cacgggcagc ttgccggtgg tgcagatgaa cttcagggtc agcttgccgt aggtggcatc  22680
gccctcgccc tcgccggaca cgctgaactt gtggccgttt acgtcgccgt ccagctcgac  22740
caggatgggc accaccccgg tgaacagctc ctcgcccttg ctcaccatgg tggcgaccgg  22800
tggatcgatc ctagcggatc tgacggttca ctaaaccagc tctgcttata tagacctccc  22860
accgtacacg cctaccgccc atttgcgtca atggggcgga gttgttacga cattttggaa  22920
agtcccgttg attttggtgc caaaacaaac tcccattgac gtcaatgggg tggagacttg  22980
gaaatccccg tgagtcaaac cgctatccac gcccattgat gtactgccaa aaccgcatca  23040
ccatggtaat agcgatgact aatacgtaga tgtactgcca agtaggaaag tcccataagg  23100
tcatgtactg ggcataatgc caggcgggcc atttaccgtc attgacgtca atagggggcg  23160
tacttggcat atgatacact tgatgtactg ccaagtgggc agtttaccgt aaatactcca  23220
cccattgacg tcaatggaaa gtccctattg gcgttactat gggaacatac gtcattattg  23280
acgtcaatgg gcgggggtcg ttgggcggtc agccaggcgg gccatttacc gtaagttatg  23340
taacgcggaa ctccatatat gggctatgaa ctaatgaccc cgtaattgat tactattaaa  23400
tcactagtga attcgattaa agcgacggca cagctcgcgg aaaatatcaa agtcgttgcg  23460
cgcctcgaac tgcggcggca ccacctgttt catggcgata atgccacggt tggagtggtt  23520
```

gccgtactgg tcgagatcgt tacgctcaaa ctgcgtggtc gcaggcagca cgatatcggc 23580
aaagcggcag gttgaggtcc actggttatc tatggcgata accgtttcca gcttgcgcca 23640
gccttcaata atgcggttga tctgctgatg gcgatggaat gggttagttc cggcaaaaat 23700
acacattttc agcggcggca gttttaccga tttaccgttc cagttgatca ctttccccgg 23760
ttcgaggatc gcatcgataa aacgggcaat cggaatggtg ctgctgtagc ctttgtaatc 23820
actgttgtcg tgaacaggcg gaatcgacgt agagccggag aaaccactca gaataacgcc 23880
tttacgcccc ggcgtgcctg cgccgttata gtgccagcca aaaccaaagc caccacctgg 23940
caggccaatt tgccccagca tcgccgccag aaccacaatc atccacgccc actgttcacc 24000
gtgctgcata cgctgcacgc accagccagc aataatttgc gttctgttcg ccgccatctg 24060
ccgcgccagc ccacgaatgg tttcggcatc aatgccggtc agtttttcag cccatgcggc 24120
atctttcggc tgaccgtctt tctcacccag caggtacggc aggaactgct caaaacccac 24180
acagtagtta gcgaggaagt ttttgtcgta caggttttca ctgtacagcg tatacgccag 24240
cgccagttgc agcggcacat cagtttgcgg gttaaccgca atgtgcttca catgctcgcg 24300
ccccagatac tcatgggtgg atgtgacaac cggatcgatg ctgatgacct caatttcacc 24360
ggcggtgact ttcgctttta gctgcgcgta atattcataa acatcgtgat ccgggcacca 24420
ccagttcgct tgctggtttt tcagcaaatc agagccccac agcacaatgg ttttgctgtt 24480
ctgcaatacc agcggccagg aggtttgctg ttcatacact tccattgagc caaccacgcg 24540
cggcaggatc acctgcgcag caccggtaga gtaatctccg cccgtaccaa cgctattacc 24600
atgcaaggca atagctttcg ccagcatccc cgaagcgtta tggaacatcc ccgtcgattg 24660
ccaaccactg gcggtcagca aggcactcgg cccgtgagtt ttctgcacgc gttccagttc 24720
ttcatagaac atgtcgaggg cttcatccca gctcacgcgc acaaaacggt tatcaccgcg 24780
ctgggaggta tcgctgagat ggcgcttacg cagccagtcc acgcgtacca tcggataacg 24840
aatacgcgcc gcgttgtgta cgtgatccgg caatccggca atcattttcg acggatattt 24900
atccagttcg aacggttttg ccgccacaaa gcgaccatcc ttcaccgtcg cgcggatagc 24960
cccccagtgc gacccggtaa gaatgccctc tttcgagatg acagcctcag tcgccgcttg 25020
cgccgcagtc gcacggcgcg gcgttaacaa tgacggcccc agcatcccgg cgacggttaa 25080
gccgccgagt tgtgccagaa aacgccgacg tgatgcctga aagagatcgt tattgttcat 25140
tatttttctt ccttcttatc gccgtgagcc ttacctgcgg tgtcagacgc attcatttgc 25200
agatatttca acaaagtgcg ttcttcacgt ttatcgagac tggtaaagcc aatcatgccg 25260
ttgagcgtgc cgatccaacc gttagcgtca aagtgggcga tttccggtgc gccgtggcac 25320
tggttacagg tgccgttgta caacgaatcc gcataagccc agatcggttt gatatcgttc 25380
accatgtcgc ctttcttcat ccacgcagtg gcctgcaact tgctccactc ggtattggtg 25440
tcggcaacgg tggttttctc cagcgttttt acctgctgct gcacatcacc acgaatcgag 25500
gcaacaaaga tgcgtttacc tgggaattgg gtgagtacac gctgacgtcc ggcgctttcc 25560
gtccagccgg taatttcaat ttgcagccag tcgccgtcac gtttaaggac tttcacttcc 25620
gaagcaggca gcagagaacc agaggcttct ttatcgcctt tcgccgcata aattggctta 25680
atatcaatag agtacagcgt gtcaccactg tcattagcac tggcgcgcag ctcatcgaac 25740
tgcttacgga agccgctact catatccggt aactggtggg caatatcttt atgacagtcg 25800
atgcaggatt gattatcttt cgctgccacc ttcatctgac gtgccgcttc aggatgctgc 25860

-continued

```
ttcgcatgat ccatcgcatc gtagttatgg caggagcggc aggttgccga gttgttttct  25920
ttcattcgcg cccattcacg ctcggcaagt tccgcgcgtt tggcttcgaa tttttcaggt  25980
gtatcaatgg agtgagcaat aaaggtctgg tagatatcat tgctcgcttc cagtttgcgc  26040
ttcaccatgc ctggaatatc cggcgggata tgacagtcat ggcattcagc tcgcacgccg  26100
gaggcgttct ggaaatgcac cgactgttta tattcttcat acaccggttg catactgtgg  26160
caactgacac aaaattcggt tgtgctggtg actttgatcc caacgtgtgg caatacaatc  26220
agcgcaatgc caatcacaat cccaattgcg accagcgcca gtaccgacca acgagcactg  26280
ggtcggcgta gcgcgttcca gagtttccgc ataatagccc ctgtaaaatt atggtttagt  26340
gaagcgatct taatgagcaa atatgaacag cggcactggt caggatgaac ggcttacggc  26400
agaatatgaa cagatatgaa cagaatgagt aaaaccctct gatgccacat cacattgtta  26460
ttgttgaaga tgagccggtt acccaggcgc gattacaatc ttacttcact caggaggggt  26520
ataccgtttc cgttacagcg agcggtgccg ggctgcggga aattatgcag aatcagccgg  26580
tagatttaat tctgctggat atcaacttac ccgatgaaaa tggcctgatg ttaacccgcg  26640
ccctgcgaga acgctcaacg gtggggatta ttctggttac cggacgcagc gatcggattg  26700
accgtattgt tgggctggaa atgggcgcag acgattacgt caccaaaccg ctggaactgc  26760
gcgaactggt agtacgggtg aaaaatctgc tctggcgaat cgacctcgcg cgacaagctc  26820
aaccgcacac tcaggacaac tgctatcgct ttgccggtta ttgcctgaat gtgtcgcgcc  26880
atacgctgga gcgggatggc gagccgatta aactgacccg cgcagagtat gaaatgttgg  26940
tggcatttgt gacgaatccg ggcgaaattc tcagccgtga acgtctgcta cgtatgcttt  27000
ctgcgcgtcg ggtggaaaac cctgacctgc gcaccgtcga tgtgttaatt cgtcgtttac  27060
gtcataaact cagcgcggat ttactggtga cgcaacatgg tgaaggttat ttcttagccg  27120
ctgatgtgtg ctgataaaaa tagaccggac gaaatccccc tggtgacagc gagcggcgga  27180
tatgttctcg gtcggcattt ttcggcgtca gaactaaaat cggtgggctg acattatcag  27240
acaccgattg cccctgtaat tgcctgatgg cctgctcaac tgccagttcc ccctgccaga  27300
ccatttgatc gctggcagcc ataatcactc ttccccgctt cagcccgcga tacacctgat  27360
gtgaaagata aaacgacacc acggtaagcg gcgttttcag gttacgccct tcacccattg  27420
ccgcctctgc cgcaatggcc gttccggcaa cgacgtcaat ttctgggtgg cgttccagca  27480
tctcctgcaa caggttacgc tggatttcaa tatcgttatc accaagcgca atatcaacaa  27540
tacgcaccgg gcttccggca atggctgcgc gaaaaccctc gaccatctct ttactgcccc  27600
cggcattatc gggtccgggc atcaacagca cgttcagtgg tttaccgtgc gcccattgca  27660
ccaaatatcg cccaggttga tagcccatct gaaaccaggg tacaccaacg cggcttttca  27720
cctggggagc atcaatagca tttaccagtt cgatcaccgg cagacttgct acctgctttt  27780
gcagatcggg aaatgaggtc gtgctactac cgagtaaaat ggcctctgcg ccccactgtt  27840
tacactggtc gatttgtgct tgctgggtag ccaactggct gtagccgcct gcctccagca  27900
cttttaaatc cacaccatag cggcgagctg cctcctgcat accatagttc aacgataacc  27960
agtatgaatc tttcaggctg ggataaagcg cgcacagttt ccatgcgcgt ttggctttaa  28020
gcggcataga ggcttgcacc gtgaaatgct gcgcatcatg ccagcgcaac aggttatcag  28080
ccgaaaatgc cggcaacatg aaaagggaaa gaagtaaaaa tagcagtacg cgcatgatag  28140
cctcatcaat aataaggctt tatgctagat gcattccgct ttgcgactca acctttttca  28200
ccttaagtgc accgaccgtg aatttaaccc tgacccgaag actctggatg ggctttgccc  28260
```

-continued tgatggcgct gttaaccctg accagtaccc tggtgggatg gtacaacctg cgctttatca 28320
gccaggtgga aaaagacaac actcaggcat tgattcctac catgaatatg gcgcgccagt 28380
tgagcgaagc cagcgcctgg gaacttttcg ccgcgcagaa cctgaccagt gccgataacg 28440
aaaagatgtg gcaggcgcag ggcgaatgc tcaccgcaca aagcctgaag attaatgcgt 28500
tgctgcaagc gttacgggaa caaggttttg ataccaccgc tattgaacaa caggagcagg 28560
agatctcccg ttcattacgt cagcaagggg aactggtggg gcggcgtctg caactacgcc 28620
agcaacaacg gcaactcagt cagcagatag tcgctgccgc cgatgagatc gcacgcctgg 28680
cgcaaggtca ggcgaataat gcgacaactt ccgctggagc gacccaggcc gggatttacg 28740
atttgatcga acaagatcag cgtcaggctg ctgaaagtgc actcgatcgg ctgattgata 28800
tcgatcttga gtatgttaac cagatgaatg aactgcgcct tagcgctctg cgggtgcagc 28860
aaatggtgat gaatctgggg ctggagcaga tccagaaaaa tgcaccaacg ctggaaaagc 28920
agctcaataa tgcggtgaaa attctgcaac gtcggcaaat acgcattgaa gatccgggtg 28980
ttcgtgcgca ggtcgcaaca acgttaacta ccgttagcca atatagcgat ttgctggcgc 29040
tgtatcagca ggacagtgaa atcagcaatc acctacaaac tctcgcacaa aataacatcg 29100
cccagttcgc gcagtttagt agcgaagtca gtcagctggt cgactcggta cccggggatc 29160
cactcgttat tctcggacga gtgttcagta atgaacctct ggagagaacc atgtatatga 29220
tcgttatctg ggttggactt ctgcttttaa gcccagataa ctggcctgaa tatgttaatg 29280
agagaatcgg tattcctcat gtgtggcatg ttttcgtctt tgctcttgca ttttcgctag 29340
caattaatgt gcatcgatta tcagctattg ccagcgccag atataagcga tttaagctaa 29400
gaaaacgcat taagatgcaa aacgataaag tgcgatcagt aattcaaaac cttacagaag 29460
agcaatctat ggttttgtgc gcagccctta atgaaggcag gaagtatgtg gttacatcaa 29520
aacaattccc atacattagt gagttgattg agcttggtgt gttgaacaaa actttttccc 29580
gatggaatgg aaagcatata ttattcccta ttgaggatat ttactggact gaattagttg 29640
ccagctatga tccatataat attgagataa agccaaggcc aatatctaag taactagata 29700
agaggaatcg attttccctt aattttctgg cgtccactgc atgttatgcc gcgttcgcca 29760
ggcttgctgt accatgtgcg ctgattcttg cgctcaatac gttgcaggtt gctttcaatc 29820
tgtttgtggt attcagccag cactgtaagg tctatcggat ttagtgcgct ttctactcgt 29880
gatttcggtt tgcgattcag cgagagaata gggcggttaa ctggttttgc gcttacccca 29940
accaacaggg gatttgctgc tttccattga gcctgtttct ctgcgcgacg ttcgcggcgg 30000
cgtgtttgtg catccatctg gattctcctg tcagttagct ttggtggtgt gtggcagttg 30060
tagtcctgaa cgaaaacccc ccgcgattgg cacattggca gctaatccgg aatcgcactt 30120
acggccaatg cttcgtttcg tatcacacac cccaaagcct tctgctttga atgctgccct 30180
tcttcagggc ttaattttta agagcgtcac cttcatggtg gtcagtgcgt cctgctgatg 30240
tgctcagtat caccgccagt ggtatttatg tcaacaccgc cagagataat ttatcaccgc 30300
agatggttat ctgtatgttt tttatatgaa tttatttttt gcagggggc attgtttggt 30360 aggtgagaga tctgaattgc tatgtttagt gagttgtatc tatttatttt tcaataaata 30420
caattggtta tgtgttttgg gggcgatcgt gaggcaaaga aaacccggcg ctgaggccgg 30480
gttattcttg ttctctggtc aaattatata gttggaaaac aaggatgcat atatgaatga 30540
acgatgcaga ggcaatgccg atggcgatag tgggtatcat gtagccgctt atgctggaaa 30600
gaagcaataa cccgcagaaa aacaaagctc caagctcaac aaaactaagg gcatagacaa 30660
taactaccga tgtcatatac ccatactctc taatcttggc cagtcggcgc gttctgcttc 30720
cgattagaaa cgtcaaggca gcaatcagga ttgcaatcat ggttcctgca tatgatgaca 30780
atgtcgcccc aagaccatct ctatgagctg aaaaagaaac accaggaatg tagtggcgga 30840
aaaggagata gcaaatgctt acgataacgt aaggaattat tactatgtaa acaccaggca 30900
tgattctgtt ccgcataatt actcctgata attaatcctt aactttgccc acctgccttt 30960
taaaacattc cagtatatca cttttcattc ttgcgtagca atatgccatc tcttcagcta 31020
tctcagcatt ggtgaccttg ttcagaggcg ctgagagatg gcctttttct gatagataat 31080
gttctgttaa aatatctccg gcctcatctt ttgcccgcag gctaatgtct gaaaattgag 31140
gtgacgggtt aaaaataata tccttggcaa cctttttat atccctttta aattttggct 31200
taatgactat atccaatgag tcaaaaagct ccccttcaat atctgttgcc cctaagacct 31260
ttaatatatc gccaaataca ggtagcttgg cttctacctt caccgttgtt cggccgatga 31320
aatgcatatg cataacatcg tctttggtgg ttcccctcat cagtggctct atctgaacgc 31380
gctctccact gcttaatgac attcctttcc cgattaaaaa atctgtcaga tcggatgtgg 31440
tcggcccgaa aacagttctg gcaaaaccaa tggtgtcgcc ttcaacaaac aaaaaagatg 31500
ggaatcccaa tgattcgtca tctgcgaggc tgttcttaat atcttcaact gaagctttag 31560
agcgatttat cttctgaacc agactcttgt catttgtttt ggtaaagaga aaagtttttc 31620
catcgatttt atgaatatac aaataattgg agccaacctg caggtgatga ttatcagcca 31680
gcagagaatt aaggaaaaca gacaggttta ttgagcgctt atctttccct ttatttttgc 31740
tgcggtaagt cgcataaaaa ccattcttca taattcaatc catttactat gttatgttct 31800
gaggggagtg aaaattcccc taattcgatg aagattcttg ctcaattgtt atcagctatg 31860
cgccgaccag aacaccttgc cgatcagcca aacgtctctt caggccactg actagcgata 31920
actttcccca caacggaaca actctcattg catgggatca ttgggtactg tgggtttagt 31980
ggttgtaaaa acacctgacc gctatccctg atcagtttct tgaaggtaaa ctcatcaccc 32040
ccaagtctgg ctatgcagaa atcacctggc tcaacagcct gctcagggtc aacgagaatt 32100
aacattccgt caggaaagct tggcttggag cctgttggtg cggtcatgga attaccttca 32160
acctcaagcc agaatgcaga atcactggct tttttggttg tgcttaccca tctctccgca 32220
tcacctttgg taaaggttct aagctcaggt gagaacatcc ctgcctgaac atgagaaaaa 32280
acagggtact catactcact tctaagtgac ggctgcatac taaccgcttc atacatctcg 32340
tagatttctc tggcgattga agggctaaat tcttcaacgc taactttgag aatttttgca 32400
agcaatgcgg cgttataagc atttaatgca ttgatgccat taaataaagc accaacgcct 32460
gactgcccca tccccatctt gtctgcgaca gattcctggg ataagccaag ttcatttttc 32520
ttttttcat aaattgcttt aaggcgacgt gcgtcctcaa gctgctcttg tgttaatggt 32580
ttcttttttg tgctcatacg ttaaatctat caccgcaagg gataaatatc taacaccgtg 32640
cgtgttgact attttacctc tggcggtgat aatggttgca tgtactaagg aggttgtatg 32700
gaacaacgca taaccctgaa agattatgca atgcgctttg ggcaaaccaa gacagctaaa 32760
gatctcggcg tatatcaaag cgcgatcaac aaggccattc atgcaggccg aaagattttt 32820
ttaactataa acgctgatgg aagcgtttat gcggaagagg taaagccctt cccgagtaac 32880
aaaaaaacaa cagcataaat aaccccgctc ttacacattc cagccctgaa aaagggcatc 32940
aaattaaacc acacctatgg tgtatgcatt tatttgcata cattcaatca attgttatct 33000

```
aaggaaatac ttacatatgg ttcgtgcaaa caaacgcaac gaggctctac gaatcgagag  33060
tgcgttgctt aacaaaatcg caatgcttgg aactgagaag acagcggaag ctgtgggcgt  33120
tgataagtcg cagatcagca ggtggaagag ggactggatt ccaaagttct caatgctgct  33180
tgctgttctt gaatgggggg tcgttgacga cgacatggct cgattggcgc gacaagttgc  33240
tgcgattctc accaataaaa aacgcccggc ggcaaccgag cgttctgaac aaatccagat  33300
ggagttctga ggtcattact ggatctatca acaggagtca ttatgacaaa tacagcaaaa  33360
atactcaact tcggcagagg taactttgcc ggacaggagc gtaatgtggc agatctcgat  33420
gatggttacg ccagactatc aaatatgctg cttgaggctt attcgggcgc agatctgacc  33480
aagcgacagt ttaaagtgct gcttgccatt ctgcgtaaaa cctatgggtg gaataaacca  33540
atggacagaa tcaccgattc tcaacttagc gagattacaa agttacctgt caaacggtgc  33600
aatgaagcca agttagaact cgtcagaatg aatattatca agcagcaagg cggcatgttt  33660
ggaccaaata aaaacatctc agaatggtgc atccctcaaa acgagggaaa atcccctaaa  33720
acgagggata aaacatccct caaattgggg gattgctatc cctcaaaaca gggggacaca  33780
aaagacacta ttacaaaaga aaaaagaaaa gattattcgt cagannnnnn tggcgaatcc  33840
tctgaccagc cagaaaacga cctttctgtg gtgaaaccgg atgctgcaat tcagagcggc  33900
agcaagtggg ggacagcaga agacctgacc gccgcagagt ggatgtttga catggtgaag  33960
actatcgcac catcagccag aaaaccgaat tttgctgggt gggctaacga tatccgcctg  34020
atgcgtgaac gtgacggacg taaccaccgc gacatgtgtg tgctgttccg ctgggcatgc  34080
caggacaact tctggtccgg taacgtgctg agcccggcca aactccgcga taagtggacc  34140
caactcgaaa tcaaccgtaa caagcaacag gcaggcgtga cagccagcaa accaaaactc  34200
gacctgacaa acacagactg gatttacggg gtggatctat gaaaaacatc gccgcacaga  34260
tggttaactt tgaccgtgag cagatgcgtc ggatcgccaa caacatgccg gaacagtacg  34320
acgaaaagcc gcaggtacag caggtagcgc agatcatcaa cggtgtgttc agccagttac  34380
tggcaacttt cccggcgagc ctggctaacc gtgaccagaa cgaagtgaac gaaatccgtc  34440
gccagtgggt tctggctttt cgggaaaacg ggatcaccac gatggaacag gttaacgcag  34500
gaatgcgcgt agcccgtcgg cagaatcgac catttctgcc atcacccggg cagtttgttg  34560
catggtgccg ggaagaagca tccgttaccg ccggactgcc aaacgtcagc gagctggttg  34620
atatggttta cgagtattgc cggaagcgag gcctgtatcc ggatgcggag tcttatccgt  34680
ggaaatcaaa cgcgcactac tggctggtta ccaacctgta tcagaacatg cgggccaatg  34740
cgcttactga tgcggaatta cgccgtaagg ccgcagatga gcttgtccat atgactgcga  34800
gaattaaccg tggtgaggcg atccctgaac cagtaaaaca acttcctgtc atgggcggta  34860
gacctctaaa tcgtgcacag gctctggcga agatcgcaga aatcaaagct aagttcggac  34920
tgaaaggagc aagtgtatga cgggcaaaga ggcaattatt cattacctgg ggacgcataa  34980
tagcttctgt gcgccggacg ttgccgcgct aacaggcgca acagtaacca gcataaatca  35040
ggccgcggct aaaatggcac gggcaggtct tctggttatc gaaggtaagg tctggcgaac  35100
ggtgtattac cggtttgcta ccagggaaga acgggaagga aagatgagcg atgaacaaac  35160
tggatacgat tggattcgac aacaaaaaag acctgcttat ctcggtgggc gatttggttg  35220
atcgtggtgc agagaacgtt gaatgcctgg aattaatcac attcccctgg ttcagagctg  35280
tacgtggaaa ccatgagcaa atgatgattg atggcttatc agagcgtgga aacgttaatc  35340
```

```
actggctgct taatggcggt ggctggttct ttaatctcga ttacgacaaa gaaattctgg  35400
ctaaagctct tgcccataaa gcagatgaac ttccgttaat catcgaactg gtgagcaaag  35460
ataaaaaata tgttatctgc cacgccgatt atccctttga cgaatacgag tttggaaagc  35520
cagttgatca tcagcaggta atctggaacc gcgaacgaat cagcaactca caaaacggga  35580
tcgtgaaaga aatcaaaggc gcggacacgt tcatctttgg tcatacgcca gcagtgaaac  35640
cactcaagtt tgccaaccaa atgtatatcg ataccggcgc agtgttctgc ggaaacctaa  35700
cattgattca ggtacaggga gaaggcgcat gagactcgaa agcgtagcta aatttcattc  35760
gccaaaaagc ccgatgatga gcgactcacc acgggccacg gcttctgact ctctttccgg  35820
tactgatgtg atggctgcta tggggatggc gcaatcacaa gccggattcg gtatggctgc  35880
attctgcggt aagcacgaac tcagccagaa cgacaaacaa aaggctatca actatctgat  35940
gcaatttgca cacaaggtat cggggaaata ccgtggtgtg gcaaagcttg aaggaaatac  36000
taaggcaaag gtactgcaag tgctcgcaac attcgcttat gcggattatt gccgtagtgc  36060
cgcgacgccg gggggcaagat gcagagattg ccatggtaca ggccgtgcgg ttgatattgc  36120
caaaacagag ctgtggggga gagttgtcga gaaagagtgc ggaagatgca aaggcgtcgg  36180
ctattcaagg atgccagcaa gcgcagcata tcgcgctgtg acgatgctaa tcccaaacct  36240
tacccaaccc acctggtcac gcactgttaa gccgctgtat gacgctctgg tggtgcaatg  36300
ccacaaagaa gagtcaatcg cagacaacat tttgaatgcg gtcacacgtt agcagcatga  36360
ttgccacgga tggcaacata ttaacggcat gatattgact tattgaataa aattgggtaa  36420
atttgactca acgatgggtt aattcgctcg ttgtggtagt gagatgaaaa gaggcggcgc  36480
ttactaccga ttccgcctag ttggtcactt cgacgtatcg tctggaactc caaccatcgc  36540
aggcagagag gtctgcaaaa tgcaatcccg aaacagttcg caggtaatag ttagagcctg  36600
cataacggtt tcgggatttt ttatatctgc acaacaggta agagcattga gtcgataatc  36660
gtgaagagtc ggcgagcctg gttagccagt gctctttccg ttgtgctgaa ttaagcgaat  36720
accggaagca gaaccggatc accaaatgcg tacaggcgtc atcgccgccc agcaacagca  36780
caacccaaac tgagccgtag ccactgtctg tcctnnnnnn attagtaata gttacgctgc  36840
ggccttttac acatgacctt cgtgaaagcg ggtggcagga ggtcgcgcta acaacctcct  36900
gccgttttgc ccgtgcatat cggtcacgaa caaatctgat tactaaacac agtagcctgg  36960
atttgttcta tcagtaatcg accttattcc taattaaata gagcaaatcc ccttattggg  37020
ggtaagacat gaagatgcca gaaaaacatg acctgttggc cgccattctc gcggcaaagg  37080
aacaaggcat cggggcaatc cttgcgtttg caatggcgta ccttcgcggc agatataatg  37140
gcggtgcgtt tacaaaaaca gtaatcgacg caacgatgtg cgccattatc gcctggttca  37200
ttcgtgacct tctcgacttc gccggactaa gtagcaatct cgcttatata acgagcgtgt  37260
ttatcggcta catcggtact gactcgattg gttcgcttat caaacgcttc gctgctaaaa  37320
aagccggagt agaagatggt agaaatcaat aatcaacgta aggcgttcct cgatatgctg  37380
gcgtggtcgg agggaactga taacggacgt cagaaaacca gaaatcatgg ttatgacgtc  37440
attgtaggcg gagagctatt tactgattac tccgatcacc ctcgcaaact tgtcacgcta  37500
aacccaaaac tcaaatcaac aggcgccgga cgctaccagc ttctttcccg ttggtgggat  37560
gcctaccgca agcagcttgg cctgaaagac ttctctccga aaagtcagga cgctgtggca  37620
ttgcagcaga ttaaggagcg tggcgcttta cctatgattg atcgtggtga tatccgtcag  37680
gcaatcgacc gttgcagcaa tatctgggct tcactgccgg gcgctggtta tggtcagttc  37740
```

-continued gagcataagg ctgacagcct gattgcaaaa ttcaaagaag cgggcggaac ggtcagagag 37800
attgatgtat gagcagagtc accgcgatta tctccgctct ggttatctgc atcatcgtct 37860
gcctgtcatg ggctgttaat cattaccgtg ataacgccat tacctacaaa gcccagcgcg 37920
acaaaaatgc cagagaactg aagctggcga acgcggcaat tactgacatg cagatgcgtc 37980
agcgtgatgt tgctgcgctc gatgcaaaat acacgaagga gttagctgat gctaaagctg 38040
aaaatgatgc tctgcgtgat gatgttgccg ctggtcgtcg tcggttgcac atcaaagcag 38100
tctgtcagtc agtgcgtgaa gccaccaccg cctccggcgt ggataatgca gcctccccc 38160 gactggcaga caccgctgaa cgggattatt tcaccctcag agagaggctg atcactatgc 38220
aaaaacaact ggaaggaacc cagaagtata ttaatgagca gtgcagatag agttgcccat 38280
atcgatgggc aactcatgca attattgtga gcaatacaca cgcgcttcca gcggagtata 38340
aatgcctaaa gtaataaaac cgagcaatcc atttacgaat gtttgctggg tttctgtttt 38400
aacaacattt tctgcgccgc cacaaatttt ggctgcatcg acagttttct tctgcccaat 38460
tccagaaacg aagaaatgat gggtgatggt ttcctttggt gctactgctg ccggtttgtt 38520
ttgaacagta aacgtctgtt gagcacatcc tgtaataagc agggccagcg cagtagcgag 38580
tagcattttt ttcatggtgt tattcccgat gctttttgaa gttcgcagaa tcgtatgtgt 38640
agaaaattaa acaaacccta aacaatgagt tgaaatttca tattgttaat atttattaat 38700
gtatgtcagg tgcgatgaat cgtcattgta ttcccggatt aactatgtcc acagccctga 38760
cggggaactt ctctgcggga gtgtccggga ataattaaaa cgatgcacac agggtttagc 38820
gcgtacacgt attgcattat gccaacgccc cggtgctgac acggaagaaa ccggacgtta 38880
tgatttagcg tggaaagatt tgtgtagtgt tctgaatgct ctcagtaaat agtaatgaat 38940
tatcaaaggt atagtaatat cttttatgtt catggatatt tgtaacccat cggaaaactc 39000
ctgctttagc aagattttcc ctgtattgct gaaatgtgat ttctcttgat ttcaacctat 39060
cataggacgt ttctataaga tgcgtgtttc ttgagaattt aacatttaca accttttttaa 39120 gtccttttat taacacggtg ttatcgtttt ctaacacgat gtgaatatta tctgtggcta 39180
gatagtaaat ataatgtgag acgttgtgac gttttagttc agaataaaac aattcacagt 39240
ctaaatcttt tcgcacttga tcgaatattt ctttaaaaat ggcaacctga gccattggta 39300
aaaccttcca tgtgatacga gggcgcgtag tttgcattat cgtttttatc gtttcaatct 39360
ggtctgacct ccttgtgttt tgttgatgat ttatgtcaaa tattaggaat gttttcactt 39420
aatagtattg gttgcgtaac aaagtgcggt cctgctggca ttctggaggg aaatacaacc 39480
gacagatgta tgtaaggcca acgtgctcaa atcttcatac agaaagattt gaagtaatat 39540
tttaaccgct agatgaagag caagcgcatg gagcgacaaa atgaataaag aacaatctgc 39600
tgatgatccc tccgtggatc tgattcgtgt aaaaaaatatg cttaatagca ccatttctat 39660
gagttaccct gatgttgtaa ttgcatgtat agaacataag gtgtctctgg aagcattcag 39720
agcaattgag gcagcgttgg tgaagcacga taataatatg aaggattatt ccctggtggt 39780
tgactgatca ccataactgc taatcattca aactatttag tctgtgacag agccaacacg 39840
cagtctgtca ctgtcaggaa agtggtaaaa ctgcaactca attactgcaa tgccctcgta 39900
attaagtgaa tttacaatat cgtcctgttc ggagggaaga acgcgggatg ttcattcttc 39960
atcactttta attgatgtat atgctctctt ttctgacgtt agtctccgac ggcaggcttc 40020
aatgacccag gctgagaaat tcccggaccc tttttgctca agagcgatgt taatttgttc 40080
aatcatttgg ttaggaaagc ggatgttgcg ggttgttgtt ctgcgggttc tgttcttcgt 40140
tgacatgagg ttgccccgta ttcagtgtcg ctgatttgta ttgtctgaag ttgtttttac 40200
gttaagttga tgcagatcaa ttaatacgat acctgcgtca taattgatta tttgacgtgg 40260
tttgatggcc tccacgcacg ttgtgatatg tagatgataa tcattatcac tttacgggtc 40320
ctttccggtg atccgacagg ttacg 40345

<210> SEQ ID NO 34
<211> LENGTH: 5793
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 34
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgacagct gtctcttata cacatctcaa ccatcatcga tgaattttct cgggtaggga 360
taacagggta atgaattgaa attacgcccc gccctgccac tcatcgcagt actgttgtaa 420
ttcattaagc attctgccga catggaagcc atcacagacg gcatgatgaa cctgaatcgc 480
cagcggcatc agcaccttgt cgccttgcgt ataatatttg cccatggtga aaacgggggc 540
gaagaagttg tccatattgg ccacgtttaa atcaaaactg gtgaaactca cccagggatt 600
ggctgagacg aaaaacatat tctcaataaa ccctttaggg aaataggcca ggttttcacc 660
gtaacacgcc acatcttgcg aatatatgtg tagaaactgc cggaaatcgt cgtggtattc 720
actccagagc gatgaaaacg tttcagtttg ctcatggaaa acggtgtaac aagggtgaac 780
actatcccat atcaccagct caccgtcttt cattgccata cggaattccg gatgagcatt 840
catcaggcgg gcaagaatgt gaataaaggc cggataaaac ttgtgcttat ttttctttac 900
ggtctttaaa aaggccgtaa tatccagctg aacggtctgg ttataggtac attgagcaac 960
tgactgaaat gcctcaaaat gttctttacg atgccattgg gatatatcaa cggtggtata 1020
tccagtgatt tttttctcca ttttagcttc cttagctcca gatctatgga tcgctcgaaa 1080
aaatcaaatc atcaatttct gagcttgctg taatttcttg tttatcaaca tatgaagtca 1140
tacctgtttt actcctcaag ataatattag aaagtatggc agcactgctg tcatactctt 1200 ttatacccttt catctttcaa gctgctgctt tgttggctgc tttcactcac cccagtcaca 1260
tagttatcta tgctcctggg gattcgttca cttgccgcct cgctgcaact cgaaatctat 1320
taggtatatt ccatgtggta cttcttaata ttatcatcaa caatattgat tacatttttt 1380
tggctcatca aatcattcat tggttcaaag gacagcaata cacttttcgc accacacttt 1440
tcaattgcca acttagccgc agttatacac tccgtataat ttccgacagc gttttctgca 1500
attatttctt caagtttatt ttcgaaattt tcattagggt gcatttcaag aacataatca 1560
ctaataaatg cacgcgtctc ttgtttagct ttattactat cttcgttata gttaactaat 1620
atcattaact gatggtctat ctctgatagg tcaacgtcat atttatccgc aacggcttta 1680
tatctttcag catattcata tctaacatca ttagaatcat cccacttaaa gatgagagga 1740

-continued atacctttt tggccgccca ctcaacaata tgatgactgg ttgctgttac atatttccga 1800
ggtccgcctg gcgtataagc atggggattt acagatattt tagggaagct ataaaaatcg 1860
ttatctggat tacaatagcc tgttgttaaa gcatcgttaa tgatttcata acactcttca 1920
aatagttgct gttgatattc aaccgggcga ttaaaaaaat gcatttcatc tttttttttcg 1980 caatcactaa accctaaaat aaatctccct tcacttaact gatccaataa gcaagcttcc 2040
tccgctatgg cgacaggatg atgagttgta atgatgtgat ttaatgaacc aattttaatt 2100
ttctctgtta aaccgagcag aaaaccagaa acagtcagag gagcgccgac aacaccatta 2160
tctgaaaaat gatttcata cactaaaatc tgttcaaaat tcaacttatc aacatactcc 2220
gttatttcct gcatgcgaac tatactttgt tcttgaacag ttgttgaatt gatgaagtta 2280
aggaagaaca atccaaattt catttctttc tccttagcta atataatagc gaacgttgtt 2340
tttctttaag aaatggcatg acatcagact ggaagagctt catggaagca ataatttcgt 2400
ctactgttcc attagcttca aatccacaac aaatatttga tattcctgta gcatcaatgt 2460
ctttttgaat tatgtcaata cattcctgcg gcgttcccac gggattgatt tcgtaactgt 2520
aatcaatacg gcgattagta tctttatgtc cttttaatac aaagtcacgc cactgccctt 2580
tattgaaatc ataacctctt gtttggtctg aatcatcaaa aatagtcgta gcattcacat 2640
aagaatcata ccaatgcccc agaaatttcc ggcaaatctc tttcgcttta attgagtcat 2700
gatctacaga tgttatatat gataagcaat ggtcgatatt atgaatatcg tgcccatatt 2760
cttgagccac ttcattataa agctcaagtt gtgctttctt ttcgttagta tttataatcc 2820
aacttaatat catcggtagg ccaaattgag cagcccactc agtcgtcgaa gctgattcag 2880
ccaccacata aaccggtgcg ccacctctgc tatacgccgc ggggtttact tttaccttat 2940
ggaacttgat atgttcatta tcagcttcca tatatccctc tgtcatgcca ttctttatca 3000
gcccgtacca gcattccgct aaggcgcgac tgttattcat atctgtgccg aatacgcgaa 3060
agtccttgtt gtaaagccct cggcaaatac caaaccgaaa tcgtcctttt gacatttgat 3120
ccaataaatt cacatcttca agttggcgta ctggatgggc tgtgggaaga acaatagcgg 3180
cagttcctac attcaatttt ttagtcgcgc caagtaaata tgcagcagcg acataagggt 3240
taccaagcaa accaaactcc gtgaaatgat gctccagtaa ccatacggta tcaaaaccac 3300
actcctcaga gatgcgacct aatttaacca aacgtttcat tacctctgtt tgagaaaatt 3360
ggggaggttg gtatgtaagc aaaaagtttc caaatttcat agagagtcct tatattgcta 3420
tttgagtgat agaatatctc aatagatttt aagacagaga aattgcttga ttttcaatct 3480
caattctcat tcggcgttca ttgactgtcg caatagttaa atgttcaaat gacggttcag 3540
taatatcaac atcaatatcc agatgatcat tatccatcgt actgcgcgaa ttataacata 3600
attttttata aaattcaaat ttatgcaggc atgcaagtcg acattaccct gttatcccta 3660
ctgcaggcat gcaagcttgc caacgactac gcactagcca acaagagctt cagggttgag 3720
atgtgtataa gagacagctg tcttaatgaa tcggccaacg cgcggggaga ggcggtttgc 3780
gtattgggcg ctcttccgct tcctcgctca ctgactcgct gcgctcggtc gttcggctgc 3840
ggcgagcggt atcagctcac tcaaaggcgg taatacggtt atccacagaa tcaggggata 3900
acgcaggaaa gaacatgtga gcaaaaggcc agcaaaaggc caggaaccgt aaaaaggccg 3960
cgttgctggc gtttttccat aggctccgcc cccctgacga gcatcacaaa aatcgacgct 4020
caagtcagag gtggcgaaac ccgacaggac tataaagata ccaggcgttt ccccctggaa 4080
gctccctcgt gcgctctcct gttccgaccc tgccgcttac cggatacctg tccgcctttc 4140

-continued

```
tcccttcggg aagcgtggcg ctttctcata gctcacgctg taggtatctc agttcggtgt   4200

aggtcgttcg ctccaagctg ggctgtgtgc acgaaccccc cgttcagccc gaccgctgcg   4260

ccttatccgg taactatcgt cttgagtcca acccggtaag acacgactta tcgccactgg   4320

cagcagccac tggtaacagg attagcagag cgaggtatgt aggcggtgct acagagttct   4380

tgaagtggtg gcctaactac ggctacacta gaaggacagt atttggtatc tgcgctctgc   4440

tgaagccagt taccttcgga aaaagagttg gtagctcttg atccggcaaa caaaccaccg   4500

ctggtagcgg tggttttttt gtttgcaagc agcagattac gcgcagaaaa aaaggatctc   4560

aagaagatcc tttgatcttt tctacggggt ctgacgctca gtggaacgaa aactcacgtt   4620

aagggatttt ggtcatgaga ttatcaaaaa ggatcttcac ctagatcctt ttaaattaaa   4680

aatgaagttt taaatcaatc taaagtatat atgagtaaac ttggtctgac agttaccaat   4740

gcttaatcag tgaggcacct atctcagcga tctgtctatt tcgttcatcc atagttgcct   4800

gactccccgt cgtgtagata actacgatac gggagggctt accatctggc cccagtgctg   4860

caatgatacc gcgagaccca cgctcaccgg ctccagattt atcagcaata aaccagccag   4920

ccggaagggc cgagcgcaga agtggtcctg caactttatc cgcctccatc cagtctatta   4980

attgttgccg ggaagctaga gtaagtagtt cgccagttaa tagtttgcgc aacgttgttg   5040

ccattgctac aggcatcgtg gtgtcacgct cgtcgtttgg tatggcttca ttcagctccg   5100

gttcccaacg atcaaggcga gttacatgat cccccatgtt gtgcaaaaaa gcggttagct   5160

ccttcggtcc tccgatcgtt gtcagaagta agttggccgc agtgttatca ctcatggtta   5220

tggcagcact gcataattct cttactgtca tgccatccgt aagatgcttt tctgtgactg   5280

gtgagtactc aaccaagtca ttctgagaat agtgtatgcg gcgaccgagt tgctcttgcc   5340

cggcgtcaat acgggataat accgcgccac atagcagaac tttaaaagtg ctcatcattg   5400

gaaaacgttc ttcggggcga aaactctcaa ggatcttacc gctgttgaga tccagttcga   5460

tgtaacccac tcgtgcaccc aactgatctt cagcatcttt tactttcacc agcgtttctg   5520

ggtgagcaaa aacaggaagg caaaatgccg caaaaaaggg aataagggcg acacggaaat   5580

gttgaatact catactcttc ctttttcaat attattgaag catttatcag ggttattgtc   5640

tcatgagcgg atacatattt gaatgtattt agaaaaataa acaaataggg gttccgcgca   5700

catttccccg aaaagtgcca cctgacgtct aagaaaccat tattatcatg acattaacct   5760

ataaaaatag gcgtatcacg aggccctttc gtc                                 5793
```

METHODS USING A MODIFIED BACTERIOPHAGE FOR THE DETECTION OF TARGET MOLECULES

CROSS-REFERENCE TO RELATED APPLICATIONS

This application claims the benefit of U.S. Provisional Application No. 61/643,534, filed May 7, 2012, the entire contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Jul. 11, 2013, is named 099523-0104 SL.txt and is 271,735 bytes in size.

FIELD OF TECHNOLOGY

This technology relates generally to the field of biotechnology, and in particular to the field of molecular detection.

BACKGROUND

Enzyme-linked immunosorbent assay (ELISA) has been used as a versatile and powerful tool both in basic science and clinical diagnostics since the mid-1960s. This assay makes use of the physical connection established between an antigen-recognizing moiety and device capable of generating a visual signal. The specificity of the assay is mostly determined by the first component while the sensitivity is determined by the second. Traditionally, as the antigen-recognizing moiety in ELISA, monoclonal or polyclonal antibodies are used and enzymes such as alkaline phosphatase or horse radish peroxidase serve as the device generating the visual signal.

Often, conventional ELISA is not sensitive enough and a wide range of labeling and signal-enhancement strategies have been developed in an attempt to increase its sensitivity. A so-called DNA-enhanced immunoassay strategy stands out as the most sensitive one. This strategy employs antigen-recognizing molecules carrying DNA tags and relies on the ability of DNA polymerases to exponentially amplify these tags. Because of this amplification, the sensitivity of the assay becomes 10-10,000-fold higher than the sensitivity of traditional antigen detection methods. Originally, this strategy was described by Sano et al. in 1992 and was called immuno-PCR (IPCR). Later, a number of modifications of this strategy were developed that targeted two major areas: 1) coupling of immunoassay reagents and DNA markers, and 2) assay readout.

While the original Sano's IPCR was modular and utilized a linker protein that allowed the binding of the Fc part of an IgG and subsequent tagging with biotinylated dsDNA, it has been demonstrated that the performance of pre-assembled antibody-DNA conjugates exceeds that of the stepwise assembled complexes in the modular approach. Several approaches have been proposed that allow direct coupling of DNA tags with antigen-recognizing molecules. For example, Guo et al. described a phage display-mediated IPCR assay that makes use of filamentous bacteriophage M13 to expose on its surface single chain variable fragments (scFv) of IgG antibodies. In this assay, entire phage particles were used for binding to the target antigen and simultaneously their DNA served as a tag that was amplified by PCR upon completion of the antigen-binding portion of the reaction.

Among approaches that try to improve assay readout, the approach termed Expression Immunoassay deserves special attention. It takes advantage of a biotinylated DNA tag which encodes the firefly luciferase. In this approach, formation of the immuno-complex is followed by a one-step, cell-free translation expression step, which enables the detection of 3000 DNA molecules or 50 000 antigen molecules, respectively.

While being substantially more sensitive than conventional ELISA, DNA-enhanced immunoassays turn out to be significantly more difficult to perform and more expensive than conventional ELISA.

SUMMARY

In one aspect, the present disclosure provides a method for detecting a target molecule, comprising: contacting an immobilized target molecule with a modified bacteriophage encoding a luciferase, wherein the bacteriophage specifically binds the target molecule, under conditions that promote binding of the bacteriophage to the target molecule, to produce an target molecule-bacteriophage complex; contacting the target molecule-bacteriophage complex with a bacterial strain susceptible to infection by the bacteriophage; incubating the target molecule-bacteriophage complex with the bacterial strain under conditions that promote the propagation of the bacteriophage in the bacteria and expression of the luciferase, to produce a bacteriophage-infected culture; adding to the bacteriophage-infected culture a substrate for the luciferase; and measuring the presence and/or magnitude of fluorescence produced from the action of the luciferase on its substrate.

In some embodiments, the target molecule comprises a first affinity tag and the bacteriophage comprises a second affinity tag, wherein the first and second affinity tags specifically bind. In some embodiments, the first and second affinity tags are enzymatically or chemically coupled to the target molecule and the bacteriophage. In some embodiments, the first affinity tag is streptavidin and the second affinity tag is biotin. In some embodiments, the bacteriophage is engineered to bind directly to the target molecule using phage display.

In some embodiments, the modified bacteriophage is derived from an M13, T, T7, or λ bacteriophage. In some embodiments, the modified bacteriophage comprises SEQ ID NO:1, SEQ ID NO:2, SEQ ID NO:3, or SEQ ID NO:4.

In another aspect, the present disclosure provides a method for detecting a target molecule, comprising: contacting an immobilized target molecule with a first affinity ligand that specifically binds the target molecule, under conditions that promote target molecule-affinity ligand binding, to form a target molecule-first affinity ligand complex, and optionally contacting the target molecule-first affinity ligand complex with one or more additional antibodies under conditions that promote affinity ligand-affinity ligand binding, to produce a target molecule-first affinity ligand-additional affinity ligand complex, wherein the one or more antibodies are added sequentially, and wherein each successive affinity ligand specifically binds to the affinity ligand added immediately previous; contacting the target molecule-first affinity ligand complex or the target molecule-first affinity ligand-additional affinity ligand complex with a modified bacteriophage encoding a luciferase, wherein the bacteriophage binds to the first affinity ligand, or if one or more additional antibodies are used, binds to the ultimate affinity ligand, to form a target molecule-affinity ligand-bacteriophage complex; contacting the target molecule-affinity ligand-bacteriophage complex with a bacterial strain susceptible to infection by the bacteriophage; incubating the target molecule-affinity ligand-bacteriophage complex with the bacterial strain under conditions that promote the propagation of the bacteriophage in the bacteria and expression of the luciferase, to produce a bacteriophage-infected culture; adding to the bacteriophage-infected culture a substrate for the luciferase; and measuring the presence and/or magnitude of fluorescence produced from the action the luciferase on its substrate.

In some embodiments, the first affinity ligand, or if one or more additional antibodies are used, the ultimate affinity ligand, comprises a first affinity tag, and the bacteriophage comprises a second affinity tag, wherein the first and second affinity tags specifically bind. In some embodiments, the first and second affinity tags are enzymatically or chemically coupled to the affinity ligand and the bacteriophage. In some embodiments, the first affinity tag is streptavidin and the second affinity tag is biotin. In some embodiments, the bacteriophage is engineered to bind directly to the affinity ligand using phage display.

In some embodiments, the modified bacteriophage is derived from an M13, T, T7, or λ bacteriophage. In some embodiments, the modified bacteriophage comprises SEQ ID NO:1, SEQ ID NO:2, SEQ ID NO:3, or SEQ ID NO:4.

In one aspect, the present disclosure provides a nucleic acid comprising a modified bacteriophage encoding a luciferase. In some embodiments, the modified bacteriophage is selected from the group consisting of SEQ ID NO:1, SEQ ID NO:2, SEQ ID NO:3, and SEQ ID NO:4. In some embodiments, the nucleic acid comprises an affinity tag. In some embodiments, the affinity tag is enzymatically or chemically coupled to the bacteriophage. In some embodiments, the bacteriophage is engineered to bind directly to an affinity ligand or to a target molecule using phage display.

DETAILED DESCRIPTION

Figure 1A:
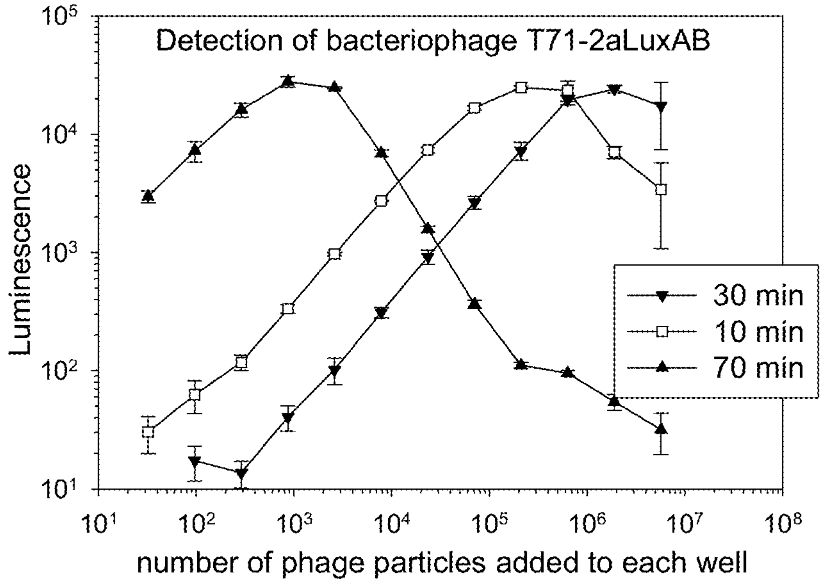
FIGS. 1A and 1B show the detection of luciferase-encoding derivatives of phages T7 and λk. Different amounts of phage particles were incubated with 100 μl of overnight culture of the appropriate host diluted in LB. Upon completion of incubation, 50 μl of 0.004% of decanal in water was added to each well containing pSL-LuxAB and measurements of luminescence were performed on Veritas luminometer. In the case of the T7 derivative, decanal was present in the mixture during incubation time and measurements were taken automatically. Bacteriophage cultures were incubated for 10, 30, 45, 65, or 70 minutes prior to fluorescence measurement.

The present disclosure provides compositions and methods for the detection of molecules. In some embodiments, the methods comprise the use of bacteriophages engineered to express a bacterial luciferase and to comprise an affinity tag or other label. In some embodiments, the bacteriophage is chemically conjugated with an affinity tag or other label. In some embodiments, expression of a bacteriophage-encoded bacterial luciferase is used to detect the presence of a molecule of interest.

To create an assay that offers high sensitivity in combination with simplicity of performance and low cost, here, we introduced a new type of engineered bacteriophage that exposes antigen-recognizing moieties on the surface of its particles and simultaneously encodes bacterial luciferase. Earlier, it was demonstrated that, in addition to proteins III and V that are traditionally used for exposing foreign proteins on the surface of capsids of filamentous *E. coli* phage M13, protein VII can also be used for such a role. Unlike protein III, protein VII is not involved in the recognition of bacterial receptors. Here, we demonstrated that phages exposing antigen-recognizing polypeptides as part of protein VII can be attached to immobilized antigens and retain their ability to infect host bacterial cells. Also, we demonstrated that phages exposing antigen-recognizing moieties on the surface of their particles can be generated via chemical conjugation of these particles with corresponding antigen-recognizing moieties.

It has also been determined that several marine (*Vibrio harveyi* and *Vibrio fischeri*) and terrestrial (*Photorhabdus luminescence*) species of bacteria produce homologous luciferases that catalyze the oxidation of long-chain aldehydes and produce photons as one of the reaction products. In all species, sequences encoding subunits of these enzymes (luxA and luxB) are expressed as part of a larger operon that also encodes proteins responsible for synthesis of long-chain aldehydes. The luxA and luxB genes in all of these operons, however, are located next to each other, allowing their separation from the rest of the operon and isolation on a relatively short DNA fragment. Luciferase produced by *P. luminescence* has substantially higher thermostability than homologous enzymes from *V. harveyi* and *V. fischeri*. Also, it has a higher thermostability than firefly luciferase, which was used in the herein-described Expression Immunoassay.

It is to be understood that the present methods may be practiced using any luciferase enzyme, whether derived from a bacterial or a non-bacterial source. However, luciferase from *P. luminescence* presents certain advantages for expression in *E. coli* as compared to non-bacterial luciferases. For example, the substrate for *P. luminescence* luciferase is substantially less expensive than the substrate for firefly luciferase and, unlike the latter, is capable of penetrating through the cell membrane. This eliminates the need for lysis of cells that is required when activity of firefly luciferase in cells has to be measured. Thus, bacterial luciferase may be selected for the current methods, depending on operator preference.

By introducing *P. luminescence* genes for luciferase into genomes of phages and exposing antigen-recognizing polypeptides on the surface of phage particles (as part of capsid protein VII or via chemical conjugation of such polypeptides with phage particles) we created new tools for detection of molecules of interest. These tools can be used in a phage-linked immunosorbent assay (PLISA), which is similar to the conventional ELISA. While being less expensive than reagents used in conventional ELISA, these tools allow the sensitivity of detection to exceed the sensitivity of conventional ELISA by 10-1000 times and makes it comparable to that of IPCR.

As used herein, "bacteriophage" means a virus that infects and replicates within bacteria, composed of proteins that encapsulate a DNA or RNA genome. In some embodiments, the bacteriophage comprises an M13 bacteriophage. In some embodiments, the bacteriophage comprises a T or T7 bacteriophage. In some embodiments, the bacteriophage comprises a λ bacteriophage. In some embodiments, the bacteriophage comprises SEQ ID NO: 1, SEQ ID NO: 2, SEQ ID NO:3, or SEQ ID NO: 4. In some embodiments, the bacteriophage is engineered to encode an affinity tag or other label. In some embodiments, the bacteriophage is enzymatically or chemically labeled with an affinity tag or other label. In some embodiments, the bacteriophage is engineered to express an affinity tag or other label using phage display.

As used herein, "affinity tag" means a label that is appended to a protein or other molecule for purposes of purification or detection. Non-limiting examples of affinity tags commonly used in the art include chitin binding protein (CBP), maltose binding protein (MBP), and glutathione-S-transferase (GST), poly-histidine (HIS), streptavidin, and biotin. In some embodiments, the affinity tag is streptavidin. In some embodiments, the affinity tag is biotin. In some embodiments, the affinity tag is a hybrid of staphylococcal protein A and streptococcal protein. As used herein "affinity ligand" means any molecule that binds with high affinity to a target molecule of interest. In some embodiments, the affinity ligand is an antibody.

In some embodiments, the target molecule of interest comprises a first affinity tag, and the bacteriophage comprises a second affinity tag, wherein the first and second affinity tags interact. In some embodiments, the bacteriophage is engineered bind directly to a target molecule or an affinity ligand, in the absence of an affinity tag on the bacteriophage, target molecule, or affinity ligand. In some embodiments, the affinity ligand is an antibody.

In some embodiments, a target molecule of interest and an engineered bacteriophage bind via the use of affinity tags. In some embodiments, a target molecule of interest and an engineered bacteriophage bind via the use of other labels, such as a compatible binding pairs, including, but not limited to, antibody-antigen pairs, complementary nucleic acids, enzyme-substrate pairs, aptamer-protein pairs, nucleic acid-protein pairs, hormone-ligand pairs, and receptor-ligand pairs. One of skill in the art will understand that the methods described herein may be practiced using any means to bind the target molecule of interest to the engineered bacteriophage.

In some embodiments, the target molecule of interest and the bacteriophage bind directly, such as through the biding of affinity tags present on the target molecule and the bacteriophage. In some embodiments, the target molecule of interest and the bacteriophage bind indirectly, such as through the use of one or more antibody intermediates. In some embodiments, an target molecule of interest is contacted by an antibody comprising a first affinity tag, which is in turn contacted by a bacteriophage comprising a second affinity tag that binds to the first affinity tag. In some embodiments, the target molecule of interest is contacted by an antibody, which is in turn contacted by an additional antibody, comprising the second affinity tag. In some embodiments, the target molecule of interest is contacted by an antibody, followed by a series of antibodies added sequentially, wherein each successive antibody specifically binds to the antibody added previously, and wherein the final antibody comprises a first affinity tag that binds to a second affinity tag present on a bacteriophage. In some embodiments, the bacteriophage is engineered to bind directly to a target molecule or an antibody.

As used herein, "bacterial luciferase" refers to the luciferase enzyme encoded by one of various bacterial species. In some embodiments, the bacterial species are of the genus *Photorhabdus*. In some embodiments, the bacterial species are of the genus *Vibrio*. In some embodiments, the bacterial species are of the genus *Photobacterium*. In some embodiments, the bacterial luciferase is that of *Photorhabdus luminescence*. In some embodiments, the bacterial luciferase is that of *Vibrio harveyi*. In some embodiments, the bacterial luciferase is that of *Vibrio fischeri*. In some embodiments, the bacterial luciferase comprises all the subunits of the bacterial lux operon. In some embodiments, the bacterial luciferase comprises a subset of the subunits of the bacterial lux operon. In some embodiments, methods described herein comprise the use of a bacterial luciferase substrate. In some embodiments, the bacterial luciferase substrate is decanal As used herein, "modified bacteriophage" refers to a bacteriophage that has been modified to express a detectable marker. In some embodiments, the detectable marker is a fluorescent protein. In some embodiments the detectable marker is green fluorescent protein (GFP) or a variant of GFP. In some embodiments the detectable marker is an enzyme. In some embodiments, the detectable marker is a luciferase. In some embodiments, the modified bacteriophage has been further engineered to comprise an affinity tag. In some embodiments, the modified bacteriophage has been further engineered to specifically bind to a target molecule or an antibody or other affinity ligand, such as, for example, using phage display. In some embodiments, the luciferase is a bacterial luciferase. In some embodiments, the luciferase is derived from non-bacterial sources, such as, for example, firefly, click beetle, sea pansy, dinoflagellates, or copepod.

As used herein "target molecule" refers to a molecule of interest, i.e., a molecule to be detected or quantified. The methods and compositions disclosed herein are not intended to be limited by the type of target molecule. The methods may be used, for example, for the detection of any kind of polypeptide, polysaccharide, lipid, or nucleic acid for which interacting molecules are available which could be directly or indirectly attached to bacteriophage particles. In some embodiments, the target molecule is a protein. In some embodiments, the target molecule is a polypeptide. In some embodiments, the target molecule is a native polypeptide. In some embodiments, the target molecule is a modified polypeptide. In some embodiments, the target molecule is a polysaccharide. In some embodiments, the target molecule is a lipid. In some embodiments, the target molecule is a nucleic acid. In some embodiments the target molecule is a chimeric protein. In some embodiments, the target molecule is an antigen.

Methods

In one aspect, the present disclosure provides methods for the detection of molecules. In some embodiments, the methods comprise the use of a bacteriophage engineered to express a bacterial luciferase and to comprise an affinity tag or other label.

In some embodiments, the bacteriophage comprises an M13, T, T7, or λ bacteriophage. In some embodiments, the bacteriophage encodes a *Photorhabdus luminescence* luciferase. In some embodiments, the bacterial luciferase comprises all the subunits of the bacterial lux operon. In some embodiments, the bacterial luciferase comprises a subset of the subunits of the bacterial lux operon. In some embodiments, the bacteriophage encodes one or more of the A, B, and E subunits of the lux operon. In some embodiments, the bacteriophage encodes one or more of the A, B, and E subunits of the lux operon.

In some embodiments, the bacteriophage is enzymatically or chemically coupled to an affinity tag or other label. In some embodiments, the affinity tag is biotin. In some embodiments, the affinity tag is encoded by the bacteriophage. In some embodiments, the bacteriophage is engineered to express a protein sequence (i.e. an affinity tag) that specifically binds to a specific protein using phage display. In some embodiments, the bacteriophage is engineered to display a protein that specifically binds to a particular affinity tag or label of interest. In some embodiments, the bacteriophage comprise SEQ ID NO: 1, SEQ ID NO: 2, SEQ ID NO: 3, or SEQ ID NO: 4.

In some embodiments, the method comprises a) contacting an immobilized molecule with a modified bacteriophage encoding a bacterial luciferase, wherein the molecule comprises a first affinity tag and the bacteriophage comprises a second affinity tag, and wherein the first and second affinity tags specifically bind, under conditions that promote binding of the first and second affinity tags, to produce an molecule-bacteriophage complex; b) contacting the molecule-bacteriophage complex with a bacterial strain susceptible to infection by the bacteriophage; c) incubating the molecule-bacteriophage complex with the bacterial strain under conditions that promote the propagation of the bacteriophage in the bacteria and expression of the bacterial luciferase, to produce a bacteriophage culture; d) adding to the bacteriophage culture a substrate for the bacterial luciferase; and e) measuring the presence and/or magnitude of fluorescence produced from the action of the bacterial luciferase on its substrate.

In some embodiments, the method comprises a) contacting an immobilized molecule with a first antibody that specifically binds the molecule, under conditions that promote molecule-antibody binding, to form a molecule-first antibody complex, and optionally contacting the molecule-first antibody complex with one or more additional antibodies under conditions that promote antibody-antibody binding, to produce a molecule-first antibody-additional antibody complex, wherein the one or more antibodies are added sequentially, and wherein each successive antibody specifically binds to the antibody added immediately previous, and wherein either the first antibody comprises a first affinity tag, or if one or more additional antibodies are added, the ultimate antibody comprises a first affinity tag; b) contacting the molecule-first antibody complex or the molecule-first antibody-additional antibody complex of a) with a modified bacteriophage encoding a bacterial luciferase and comprising a second affinity tag that specifically binds to the first affinity tag, under conditions that promote binding of the first and second affinity tags, to form a molecule-antibody-bacteriophage complex; c) contacting the molecule-antibody-bacteriophage complex of b) with a bacterial strain susceptible to infection by the bacteriophage; d) incubating the molecule-antibody-bacteriophage complex with the bacterial strain under conditions that promote the propagation of the bacteriophage in the bacteria and expression of the bacterial luciferase, to produce a bacteriophage culture; e) adding to the bacteriophage culture of d) a substrate for the bacterial luciferase; and f) measuring the presence and/or magnitude of fluorescence produced from the action the bacterial luciferase on its substrate.

Compositions

In one aspect, the present disclosure provides compositions for the detection of molecules.

In some embodiments, the compositions comprise one or more nucleic acids comprising a bacteriophage engineered to express a bacterial luciferase. In some embodiments, the modified bacteriophage is selected from the group consisting of SEQ ID NO:1, SEQ ID NO:2, SEQ ID NO:3, and SEQ ID NO:4. In some embodiments, the nucleic acid comprises an affinity tag. In some embodiments, the affinity tag is encoded by the bacteriophage or is enzymatically or chemically coupled to the bacteriophage. In some embodiments, the bacteriophage is engineered to express the second affinity tag by phage display.

Kits

In one aspect, the present disclosure provides kits for the detection of molecules.

In some embodiments, the kits comprise one or more nucleic acids comprising a bacteriophage engineered to express a bacterial luciferase. In some embodiments, the modified bacteriophage is selected from the group consisting of SEQ ID NO:1, SEQ ID NO:2, SEQ ID NO:3, and SEQ ID NO:4. In some embodiments, the nucleic acid comprises an affinity tag. In some embodiments, the affinity tag is encoded by the bacteriophage or is enzymatically or chemically coupled to the bacteriophage. In some embodiments, the bacteriophage is engineered to express the second affinity tag by phage display.

In some embodiments, the kits comprise one or more positive and/or negative control samples, and instructions for use.

EXAMPLES

This example demonstrates the compositions and methods comprising the use of engineered bacteriophages for the detection of molecules.

Materials and Methods

Cells—The *Escherichia coli* DH5αF strain and its derivative AU-DH10, carrying F'-factor with tetracycline resistance marker, were used for routine propagation of plasmids and derivatives of phage M13. Strains BLT5615 and LE392 were used propagate derivatives of phages T7 and λ, respectively. Strain BL21(DE3) was used for expression of plasmids encoding recombinant proteins. Strain AU-SE2 was used for generation of MD12™ phage display. This strain was constructed on the basis of strain MC1061 via conjugation with strain ER2738 followed by P1-mediated transduction of mutS201::Tn5(KmR) from ES1301 mutS. Strain ER2738 was used for propagation of luciferase-encoding phages in PLISA.

Production of Recombinant Proteins—BL21(DE3) cells carrying plasmids for streptavidin were grown in LB media at 37° C. with aeration until culture reached $OD_{600}$~0.4 and expression was induced via addition of IPTG. After induction, cultures were kept aerated at 37° C. for 3 hours and then cells were harvested by centrifugation, resuspended in PBS and stored at −84° C. until further use. BL21(DE3) cells carrying plasmids for *E. coli* biotin ligase (BirA), a hybrid between staphylococcal protein A and streptococcal protein G (SpAG) or the receptor-recognizing domain of botulinum neurotoxin serotype A (BoNT/A-CH5) were treated similarly, except for that they were grown until $OD_{600}$~0.6 before induction and they were grown overnight at 16° C. after induction. Plasmids encoding all of these proteins were constructed in our lab earlier and possess Ni-affinity tag incorporated in their structure. Streptavidin that accumulated inside cells in the form of inclusion bodies was purified via denaturation in 6 M guanidine followed by renaturation in PBS. BirA, SpAG and BoNT/A-CH5 were accumulated inside cells in the soluble form and were purified via affinity chromatography on Ni-NTA Superflow (Qiagen). The amino acid sequence of the SpAG polypeptide is given in Table 2. The amino acid sequence of the BoNT/A-CH5 polypeptide is given in Table 3.

DNA Modifying Enzymes—All restriction endonucleases, as well as T4 DNA-polymerase, Rapid DNA Ligation Kit and Expand™ High Fidelity PCR System were supplied by Fermentas.

Oligonucleotides—Oligonucleotides used for polymerase chain reaction, as well as oligonucleotides used for cloning are listed in Table 1. All of these oligonucleotides were synthesized at Integrated DNA Technologies.

Construction of Phages and Plasmids—M13Δlinker5 was constructed by treating DNA of M13tg130 (GenBank Accession No. L08828) with restriction endonucleases PstI and EcoRI, followed by treatment with DNA polymerase T4 and DNA ligase.

M13Cm3 was constructed by cloning a fragment of the chloramphenicol acetyl transferase-encoding fragment plasmid pACYC184 (GenBank Accession No. X06403) PCR-amplified with primers Cm-Bsp119I and Cm-NatrI (Table 1) and treated with restriction endonucleases Bsp119I and NarI into the DNA of M13Δlinker5 treated with restriction endonuclease NarI.

M13CmSompbioVII8 was constructed by substituting the 461 by PagI-Bsp1407I fragment in M12 Cm3 with a PCR-amplified fragment of DNA that was created via PCR-mediated joining and amplification of four fragments. The first and the fourth of the four fragments were amplified from M13Cm3 using pairs of primers VII-N5', VII-N3' and VII-C5', VII-C3', respectively. The second fragment encoding signal peptide of *E. coli*, OmpA, was amplified from *E. coli* chromosome DNA using primers S-5' and S-3'. The third fragment, encoding a biotinylatable peptide, was amplified from plasmid pParaBAD-bio6 with primers Bio-52' and Bio-3'.

Plasmid pParaBAD-bio6 was created earlier in our lab and contains a synthetic fragment encoding biotinylatable peptide and formed by oligonucleotides Bio-Nco, Bio-Nco-P, Bio-Nde and Bio-Nde-P. The sequence of pParaBAD-bio6 is given in Table 4.

M13CmSompbioTAGVII-1 was constructed by substitution of the 33 by NotI-I-SceI fragment in DNA of M13CmSompbioVII8 with a DNA fragment formed by oligonucleotides SompTAG5' and SompTAG-3'.

M13CmSompbioTAGVII1mut1 was generated via site specific mutagenesis of M13CmSompbioTAGVII-1 with primers TAG-I and TAG-II2.

M13CmSompΔTAGVII10 was constructed by substitution of the 98 by XhoI-Cfr42I fragment in M13CmSompbioTAGVII1mut1 with DNA formed by oligonucleotides M13delBio-5' and M13delBio-3'.

Plasmid pGEM-LuxC2 was constructed by cloning a fragment amplified from *Photorhabdus luminescence* chromosome (GenBank Accession No. AF403784) by PCR with primers P.luc-5'C and P.luc-3'-Hb into pGEM-T Easy Vector (Promega). Luciferase-encoding sequences in this plasmid are placed under control of a lactose promoter.

M13LuxABE2 was constructed by cloning a 3725 by EcoRI fragment of plasmid pGEM-LuxC2 into the EcoRI site of vector M13tg130. Luciferase-encoding sequences in this construct are under control of the lactose promoter.

M13LuxABElink15 was generated by substitution of the 1171 by Bsp1407I-CaiI fragment of M13LuxABE2 with a Bsp1407I-CaiI fragment of the same phage that was generated via a two-step process. First, two separate fragments were amplified by PCR using two pairs of primers: VII-N5', S-IIIC and IIIN, VII-N3', respectively. Second, two amplified fragments were joined together and amplified in a separate PCR using primers VII-N5' and VII-N3'.

M13LuxABESstrep25-1 was constructed by joining a 1117 by CaiI-Bsp1407I fragment of M13LuxABE2 with a 1303 by CaiI-Bsp1407I fragment of M13CmSstrepVII25, which was isolated from phage display MD12™ and has an affinity to streptavidin.

M13LuxABESspAGVII1 was constructed by joining the 1171 by CaiI-Bsp1407I fragment of M13LuxABE2 with the 1303 by CaiI-Bsp1407I fragment of M13CmSspAGVII12, which was isolated from phage display MD12™ and has an affinity to streptococcal protein G.

M13LuxABElink-SompbioVII3 was constructed by joining the 9000 by Eco105I-Bsu36I fragment of M13LuxABElink15 with the 2194 by Bsu36I-Eco105I fragment of M13CmSompbioVII8.

pParaBAD-bioLuxABE2 was constructed by joining the 3626 by luciferase-encoding Bsp68I-PstI fragment of phage M13LuxABE2 and the 4813 by SmaI-PstI fragment of plasmid pParaBAD-bio6.

pParaBAD-bioLuxAB7 was generated by treating pParaBAD-bioLuxABE2 DNA with restriction endonucleases Ecl136II and BstXI, followed by treatment with DNA polymerase T4 and ligase.

T71-2aLuxAB was constructed by combining fragments of phage T7Select1-2b (Novagen) and plasmid pParaBAD-bioLuxAB7. The fragment of phage T7Select1-2b was generated as a result of treatment of the phage DNA with restriction endonuclease BamHI and DNA polymerase T4, followed by treatment with EcoRI. The fragment of plasmid pParaBAD-bioLuxAB7 was generated as a result of treatment of the plasmid DNA with restriction endonuclease XhoI and DNA polymerase T4, followed by treatment with restriction endonuclease EcoRI.

pSL-LuxABE10 was constructed by inserting the luciferase-encoding PvuII fragment of plasmid pGEM-LuxC2 into the DNA of plasmid pSL-EGFP2, which had been treated with restriction endonuclease Pf123II and DNA polymerase T4. Phasmid pSL-EGFP2 was constructed earlier in our lab and contains the origin of replication of plasmid pMB1, the sequence encoding β-lactamase, and a fragment of bacteriophage lambda genome that encodes proteins required for maintenance of the phage's lysogenic state, as well as proteins required for propagation via lytic state. The sequence of pSL-EGFP2 is given in Table 5.

pTn-I-Sce2-PsapLuxAB-Cm1 was constructed earlier in our lab on the basis of commercially available vector pMOD-2<MCS>EZ::TN. This plasmid contains a hybrid operon encoding both subunits of luciferase from *P. luminescence* and chloramphenicol acetyl transferase and controlled by sapA promoter of the *Campylobacter fetus*. This operon is positioned between inverted repeats that are recognized by transposase Tn5 and, together with these repeats, forms a mini-transposon. The sequence of pTn-I-Sce2-PsapLuxAB-Cm1 is given in Table 6.

λ::Tn-I-Sce2-PsapLuxAB-Cm5 was generated by in vitro transposition of the luciferase-encoding mini-transposon into the genome of phage λCI857Sam7. The mini-transposon was excised from plasmid pTn-I-Sce2-PsapLuxAB-Cm1 using restriction endonuclease BoxI. After completion of the in vitro transposition reaction using EZ-Tn5™ Transposase as suggested by the manufacturer (Epicentre, Madison), the mixture was packaged using MaxPlax™ Lambda Packaging Extract (Epicentre, Madison). The packaged DNA was introduced into *E. coli* LE392. This strain was used as a host for further propagation of λ::Tn-I-Sce2-PsapLuxAB-Cm5.

Conjugation of T71-2aLuxAB with spAG

Phage T71-2aLuxAB, purified on Cs-gradient, was dialyzed against 20 mM sodium phosphate, 150 mM NaCl, and 1 mM EDTA, pH7.5 (PBS-EDTA). 100 μl of such a suspension, containing $2\times10^{12}$ plaque forming units, were combined with 5 μl of 20 mM Sulfo-LC-SPDP (Thermo Scientific) and the mixture was incubated for 30 min at room temperature. Then, reaction byproducts were removed from the reaction mixture by passing the reaction mixture through a desalting column equilibrated with PBS-EDTA. The collected sample of Sulfo-LC-SPDP modified T71-2aLuxAB was combined with an equal volume of solution containing 2.1 mg/ml of hybrid protein spAG. This protein was constructed earlier in our lab and includes immunoglobulin binding domains of staphylococcal protein A and streptococcal protein G, as well as a single cysteine residue per molecule in its structure. After overnight incubation at room temperature, the reaction mixture was subjected to ultrafiltration on Centricon® Ultracel YM-100 (Millipore) to separate the T71-2aLuxAB-spAG conjugate from free spAG.

Construction of MD12™ Phage Display and its Screening—M13 phage-based display MD12™ was constructed via site-specific mutagenesis of M13CmSompΔTAGVII10 using the primer and procedure of Scholle, et al. The length of the randomized sequence was 12 amino acid residues and the resulting diversity of the library was $10^{11}$. This library was used for selection of sequences with an affinity to streptavidin and the hybrid between staphylococcal protein A and streptococcal protein G. Both of these proteins had Ni affinity tags incorporated into their structure. Therefore, for the purpose of biopanning, these proteins were immobilized on Ni-carrying magnetic beads—MagneHis™ (Promega) and in this form were exposed to MD12™ display. Otherwise, the biopanning was carried out according to standard procedure described by Smith.

Biotinylation of Phage M13LuxABElink-SompbioVII3

The reaction containing $10^{12}$ phage particles and 5 μg of recombinant biotin ligase was carried out in a buffer containing 40 mM TrisHCl, pH 8.0, 100 mM KCl, 3 mM ATP, 5.5 mM $MgCl_2$ and 5 mM biotin. The total volume was 500 μl and the reaction mixture was incubated overnight at 37° C. Upon completion of the reaction, the mixture was dialyzed against three changes of PBS to remove unincorporated biotin, as well as ATP.

PLISA—subsequent dilutions of analyzed recombinant proteins (streptavidin, BoNT/A-CH5 or SpAG) in PBS were loaded into wells of a 96-well plate and plates were incubated at 4° C. overnight. Then, the solution was removed from wells and wells were filled with corresponding blocking solution. In the case of streptavidin and BoNT/A-CH, 5 we used normal horse serum from VectaStain ABC kit (Vector Laboratories Inc., CA). In the case of SpAG, we used BSA. Blocking was conducted at 37° C. for 1 hour. Then, wells were washed three times with PBS containing 0.1% Tween20 (PBST) and 50 μl aliquots of PBST containing the appropriate detector phage at concentration $10^9$ phage particles per milliliter were added to each well. After a 1 hour-long incubation at 37° C., the liquid was removed from wells and wells were washed ten times with PBST and one time with PBS. Then, 200 μl of overnight ER2738 culture diluted in fresh LB media supplemented with IPTG were added to each well and plates were placed in the 37° C. incubator. At appropriate time points, 50 μaliquots were transferred into wells of an opaque 96-well Microlite™ 2 plate (Thermo Scientific) and supplemented with 25 μl of 0.004% of decanal in water. Luminescence was detected using Veritas luminometer (Promega).

Results

Construction and Properties of the Luciferase-Encoding Phage. To demonstrate that bacterial luciferase can be used to speed up detection of phages, we created luciferase-encoding derivatives of three different *E. coli* phages: M13, T7 and λ.

As a donor for the luciferase-encoding sequence, we used plasmid pGEM-LuxABE2. This plasmid was constructed in our lab and, in addition to sequences luxA and B, encodes subunits of bacterial luciferase containing luxE from *P. luminescence*. Previously, we found that the presence of luxE stimulates luminescence of *E. coli* cells possessing luxA and B (unpublished data).

Derivatives of three chosen phages, named M13LuxABE2, T71-2aLuxAB, and pSL-LuxABE10, respectively, were generated using known structure of phages' genomes and conventional genetic engineering techniques as described in Materials and Methods. Phages M13LuxABE2 and pSL-LuxABE10 carry the luxABE portion of the lux operon. At the same time, because of the limitations caused by the size of the genome of the used phage T7 derivatives and capacity of phage capsid we had to limit portion of the lux operon present in T71-2aLuxAB just to luxAB. The sequences of M13LuxABE2 (SEQ ID NO:1), T71-2aLuxAB (SEQ ID NO:2), and pSL-LuxABE10 (SEQ ID NO:3) are given in Table 7, Table 8, and Table 9, respectively.

Also, we constructed a luciferase-encoding derivative of bacteriophage λ called λ::Tn-I-Sce2-PsapLuxAB-Cm5, using transposition in vitro. Construction of this derivative may serve as a demonstration of how the luciferase-encoding form of any DNA-containing phage can be developed even when knowledge of its genome structure is limited or not available. The sequence of λ::Tn-I-Sce2-PsapLuxAB-Cm5 (SEQ ID NO:4) is given in Table 10.

Figure 1B:
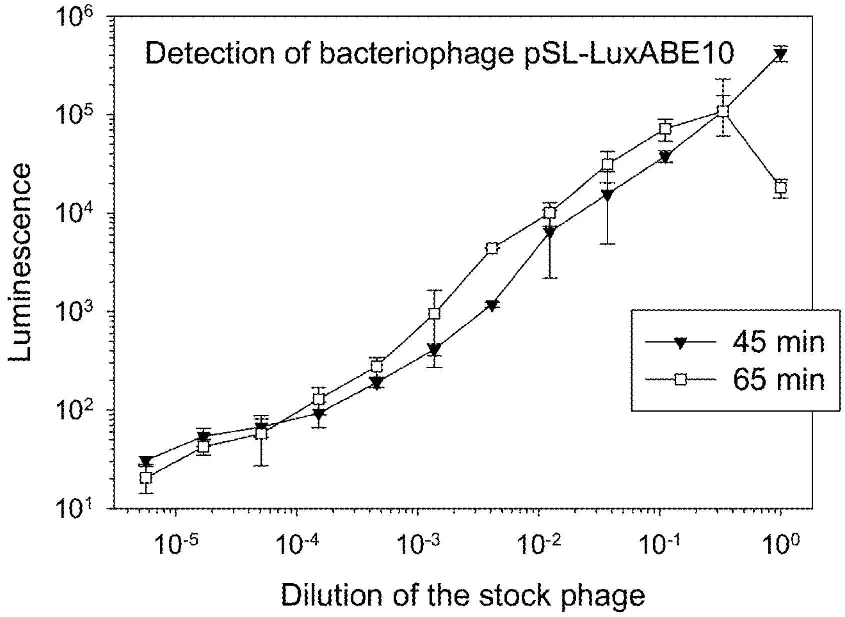
Figure 2A:
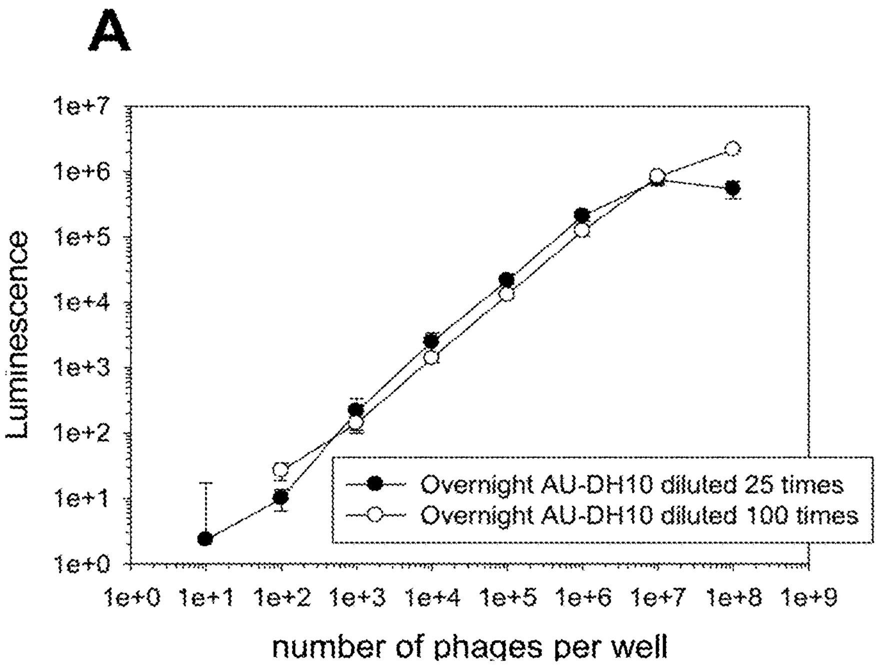
FIGS. 2A and 2B show the accumulation of luciferase in cells infected with M13LuxABE2. Dilutions of overnight culture were infected with different amounts of M12LuxABE2 and allowed to grow in LB media supplemented with IPTG for 4 hours at 37° C. with aeration prior to measuring luciferase activity. The luciferase activity of 50 μl aliquots was determined after addition of 25 μl of 0.004% decanal on Veritas luminometer. 450 μl aliquots of bacterial cultures diluted 100 times with LB supplemented with IPTG were infected with $10^6$ particles of M13LuxABE2 and were incubated for 3 hours at 37° C. without aeration prior to measuring luciferase activity. Then, the luciferase activity was determined as described herein.
Figure 2B:
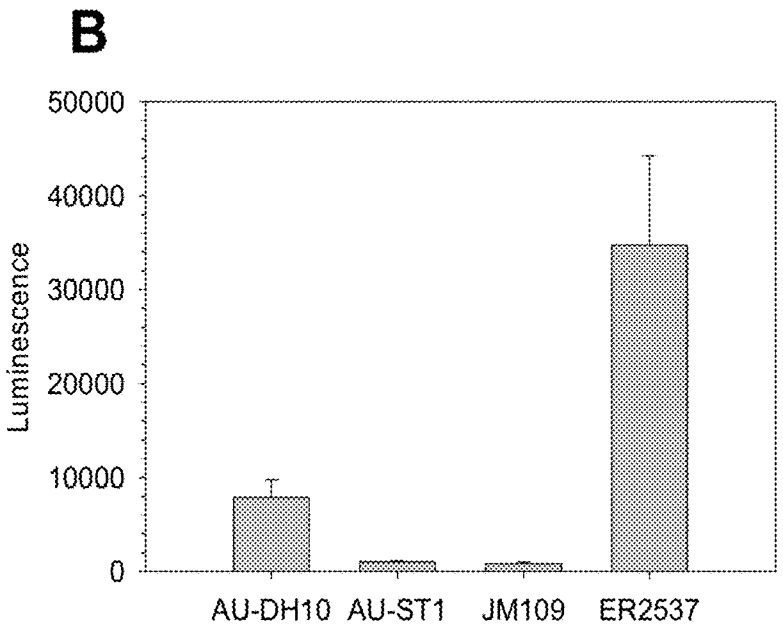

Analysis revealed that all developed luciferase-encoding phages cause production of light whose intensities are proportional to the number of phage particles used in the experiment (FIGS. 1 and 2). However, in the case of phage T7 derivatives, after a relatively short period during which the light intensity grows, the second period starts during which the light intensity begins to decrease. This occurs because, in the course of its development, phage T7 kills host cells and causes their lysis. Consequently, the amount of luciferase accumulated by the cell population stops growing and the efficiency of the luciferase itself starts to decrease, probably, because the concentration of $FMNH_2$ outside the cell is lower than that required for the reaction.

The derivative of phage λ used in the experiment presented in FIG. 1 is capable of propagating either through lytic or lysogenic pathways. It contains a temperature-sensitive repressor CI. The experiment reported in FIG. 1 was conducted at 37° C. At this temperature, the phage predominantly propagates via lytic pathway. However, lysis of host cells by this phage occurs less efficiently and takes more time than that caused by the phage T71-2aLuxAB. Consequently, light emission curves produced by pSL10-LuxABE10 are more stable over time and therefore more suitable for quantitative analysis.

To demonstrate that luciferase-encoding derivatives even of lytic phages such as T7 can be used as signal amplifying devices in immunologic reactions, we conjugated T71-2aLuxAB with a hybrid protein composed of immunoglobulin-binding domains of staphylococcal protein A and streptococcal protein G (spAG). Data presented in FIG. 3 demonstrate that this conjugate (T71-2aLuxAB-spAG) can detect the presence of rabbit serum diluted $10^6$-$10^7$ times.

Among all tested luciferase-encoding phages, M13LuxABE2 generated the most suitable light emission curves for quantitative analysis. This phage that does not kill host cells and light emission by cultures infected with this phage does not experience dramatic drops characteristic of cultures infected with lytic phages. As demonstrated in FIG. 2 panel A, less than 100 phage particles of M13LuxABE2 can be detected using AU-DH10 culture within 4 hours of incubation. The luminescence emitted by the infected culture is proportional to the number of phages used for the initial infection. The number of phages that can be reliably quantified under used conditions spans between $10^2$ and $10^7$ and the results of quantification are not dramatically affected by the original dilution of the host culture. Also, we tested four F-factor-carrying cultures for the ability to serve as hosts for the M13LuxABE2 phage. Data presented in FIG. 2 panel B demonstrate that all tested strains were capable of supporting growth of M13LuxABE2 and accumulated enzymatically active luciferase. However, in different strains, this accumulation occurred with different speed. Among all tested strains ER2738 had the highest speed of luciferase accumulation. This strain was used as a host in all further PLISA.

Construction of MD12™ Phage Display and Generation of Detectors for Streptavidin and SpAG. To create phages capable of detecting target molecules of interest, we had to incorporate antigen-recognizing moieties into the structure of the phage capsid. Phage display technology allows to do this, but the most commonly used approach through exposure of antigen-specific sequences as part of protein III requires dissociation of the phage particle from the antigen prior to infection of the host cell. Our goal was to create phages that could infect host cells while being attached to the antigen. For this reason, we decided to use protein VII—not involved in receptor recognition—as a carrier of antigen-recognizing polypeptides. Through the set of cloning experiments described in Materials and Methods, we assembled a derivative of vector M13tg130 called M13CmSompΔTAGVII10. This derivative has sequences for chloramphenicol acetyl transferase, α-peptide of β-galactosidase and hybrid protein VII. The latter encodes sequences for the signal peptide of *E. coli* OmpA and protein VII. These two sequences are separated by a linker possessing the TAG codon. Using the inability of M13CmSompΔTAGVII10 to propagate on $sup^-$ strains, we constructed a phage display library of dodekapeptides by the procedure described by Scholle and coauthors.

The resulting MD12™ phage display was used for biopanning with SpAG and streptavidin and produced a number of phages targeted at the corresponding protein. We used two of them: M13CmSspAGVII12 and M13CmSstrepVII25 targeted at SpAG and streptavidin, respectively. These two phages were further modified as is described in Materials and Methods to produce phages targeted either at SpAG or streptavidin and simultaneously carry luxABE sequence (M13LuxABESspAGVII1 and M13LuxABESstrep25-1, respectively).

Figure 4A:
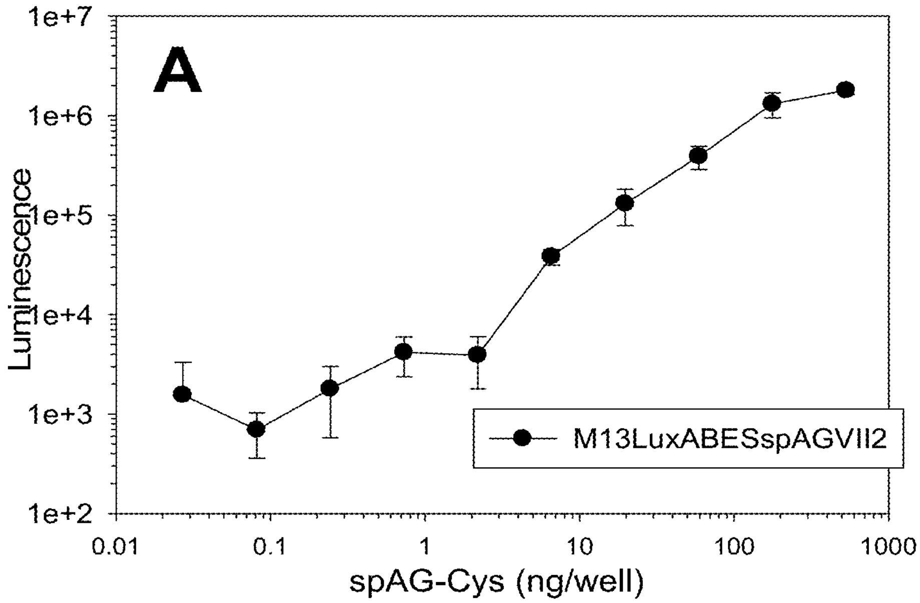
FIGS. 4A and 4B show the detection of SpAG and streptavidin with luciferase-encoding phages. Different quantities of immobilized SpAG were incubated with M13LuxABESspAGVII2 for one hour and then the immobilized phage was detected via addition of overnight culture ER2738 diluted 1:100 with LB supplemented with IPTG to wells. Incubation was conducted for 4 hours at 37° C. without aeration. Different quantities of immobilized streptavidin were incubated with M13LuxABESstrepVII25-1 for either 16 hours at room temperature or for 1 hours at 37° C. After completion of incubation and removal of unbound phage, 50 μl of either PBS alone or PBS containing 5 mM of biotin were added to each set of wells and plates were incubated for 30 min at 37° C. prior to addition of 1:100 diluted overnight culture of ER2738. After 4 hours of incubation at 37° C. without aeration, luciferase activity was determined as described in FIG. 1.
Figure 4B:
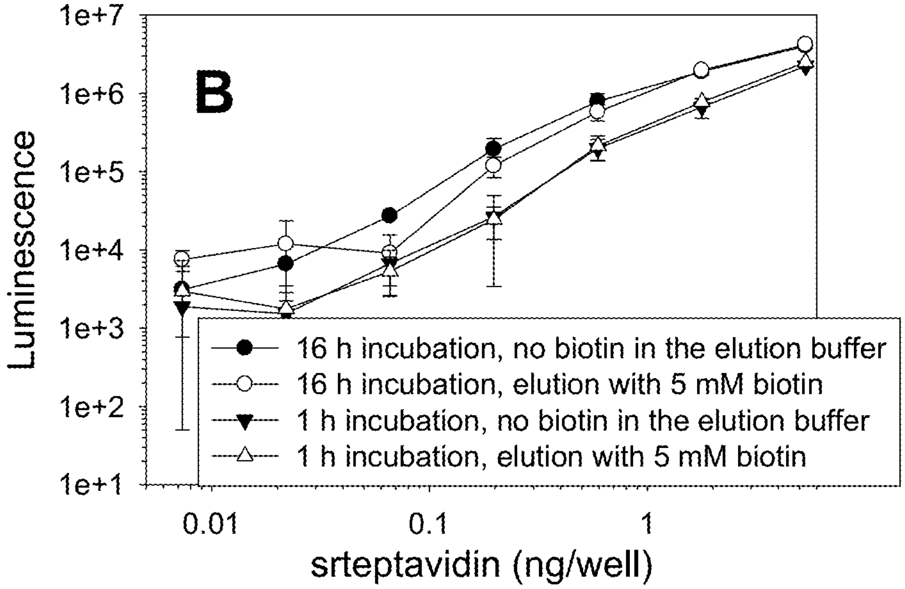

Data presented in FIG. 4 demonstrate that both phages were able to function as detectors of corresponding proteins. Sensitivities of the phages were slightly different, but both were in the range of 0.1-2 ng of target per well. We used phage M13LuxABESstrep25-1 to test whether the binding to immobilized antigen interferes with the phage's ability to infect host cells or not. First, we determined that a phage attached to immobilized streptavidin can be effectively released by addition of 5 mM biotin to wells. Then, we tested whether treatment of wells containing the immobilized streptavidin-phage sandwich with 5 mM biotin prior to addition of host cells changes results of the PLISA. As shown in FIG. 4 panel B, experiments with and without biotin give practically the same results, suggesting that release from the antigen is not required for infection to occur. The length of incubation of the phage with antigen, on the other hand, does matter. As depicted in FIG. 4 panel B, overnight incubation resulted in a stronger signal than 1 hour-long incubation, even at higher temperature. However, the observed difference was not dramatic enough to suggest that the protocol should include overnight incubation rather than a shorter one.

Construction and Detector Properties of Biotinylated Form of the Luciferase-Encoding Phage.

Figure 5:
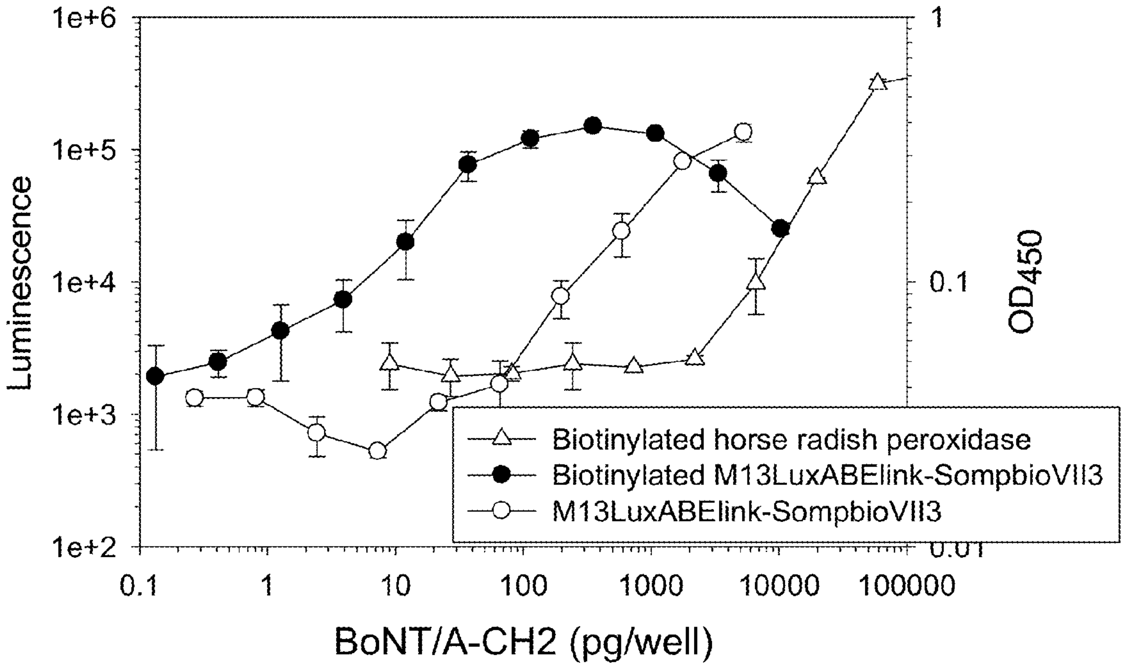
FIG. 5 shows the detection of streptavidin by PLISA and ELISA. Wells with immobilized streptavidin were incubated with either non-biotinylated or biotinylated M13LuxABElink-SompbioVII3 or biotinylated horse radish peroxidase for 1 hour at 37° C. Then, the unbound material was washed away and the immobilized phage was detected as described in FIG. 2 while the horse radish peroxidase was detected by addition of 1-Step™ Slow TMB-ELISA (Thermo Scientific) into wells.

Data presented in FIG. 4 panel B and FIG. 5 demonstrate that PLISA utilizing phage M13LuxABESstrep25-1 for detection of streptavidin is about 20-100 times more sensitive than ELISA utilizing biotinylated horse radish peroxidase for detection of streptavidin. However, the affinity of peptide exposed on the capsid of phage M13LuxABESstrep25-1 to streptavidin is substantially lower than that of biotin. To compare sensitivities of PLISA and ELISA in comparable conditions, we assembled phage M13LuxABElink-SompbioVII3 (see Materials and Methods). This phage exposes on its capsid a polypeptide that serves as a substrate for biotin ligase (BirA). Although *E. coli* strain AU-DH10 has birA gene, it seems that the majority of phage particles produced in this strain remain unmodified. The ratio of biotinylated phage particles increased dramatically after incubation of these phages with purified BirA in the presence of free biotin and ATP. The sensitivity of streptavidin detection grows along with this increase. As shown in FIG. 5, the biotinylated form of M13LuxABElink-SompbioVII3 can detect as little as 1 pg loaded in the well (the amount immobilized is probably lower).

Figure 6A:
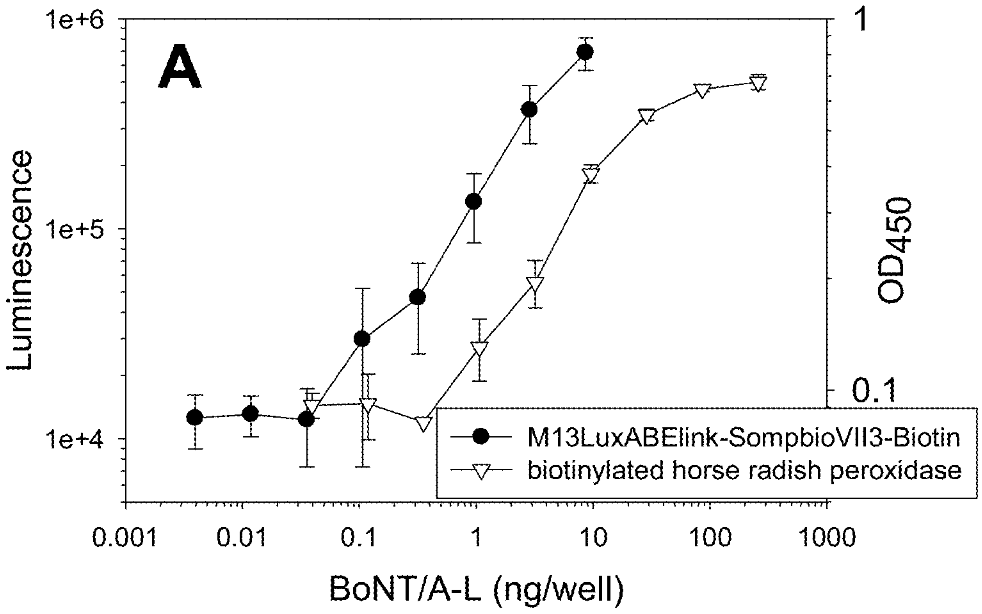
FIGS. 6A and 6B show the detection of fragments of botulinum neurotoxin by PLISA and ELISA. Wells covered with either BoNT/A-L (Panel A) or BoNT/A-CH (Panel B) were subsequently blocked with normal goat serum, incubated with rabbit antibodies raised to botulinum neurotoxin A, incubated with horse biotinylated anti-rabbit antibodies, peroxidase, and either biotinylated M13LuxABElink-SompbioVII3 or biotinylated horse radish peroxidase. Except for BoNT/A fragments, anti-BoNT and phage, all other components come from VectaStain ABC kit (Vector Laboratories Inc., CA). Detection of phage and horse radish peroxidase was done as described in the legend of FIG. 3.
Figure 6B:
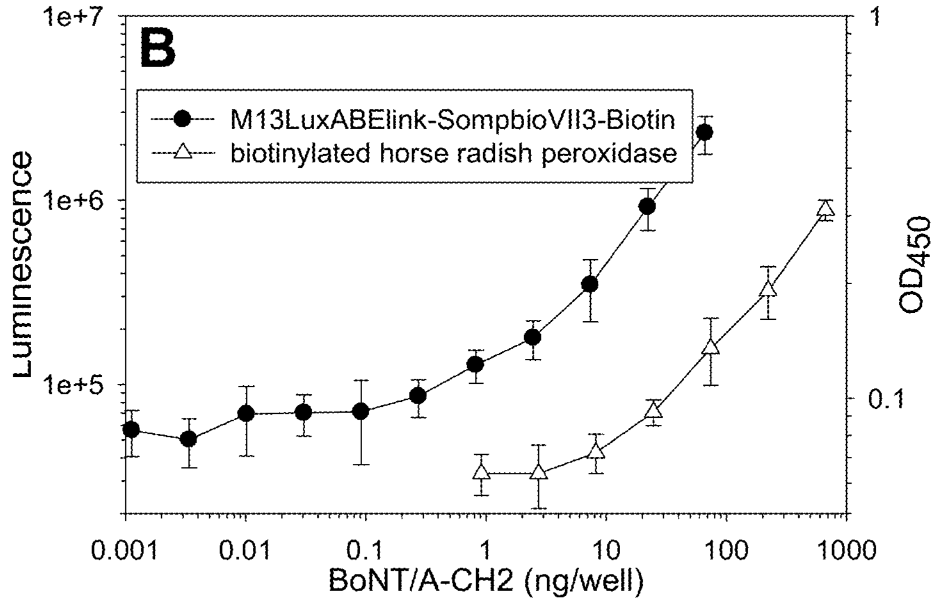

To test whether use of M13LuxABElink-SompbioVII3 can increase sensitivity of detection of molecules other than streptavidin, we tested it in the system for detection of fragments of botulinum neurotoxin. This system includes rabbit antibodies specific to botulinum neurotoxin A, biotinylated anti-rabbit antibodies, streptavidin and biotinylated horse radish peroxidase used in consecutive order. As shown in FIG. 6, substitution of the last element in this system with biotinylated M13LuxABElink-SompbioVII3 allowed to increase sensitivity of detection by at least 10 times.

Figure 3:
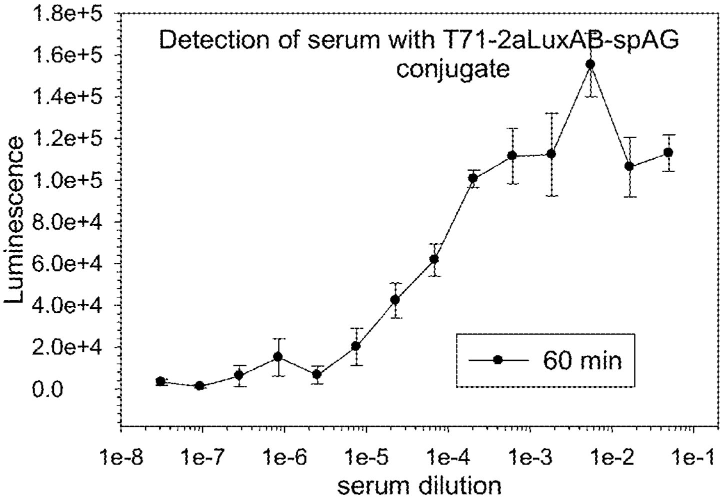
FIG. 3 shows the detection of rabbit serum with T71-2aLuxAB-spAG conjugate. Subsequent dilutions of rabbit serum were attached to wells of a 96-well plate and the remaining centers for nonspecific sorption were blocked with 1% BSA dissolved in PBS with 0.1% Tween 20 (PBST). Then, wells were filled with PBST containing diluted T71-2aLuxAB-spAG conjugate and the plate was incubated for 1 hour at 37° C. After completion of incubation, wells were washed ten times with PBST and filled with 100 μl of overnight *E. coli* BLT5615 culture diluted 1:50 in LB. They were subsequently incubated for 1 hour at 37° C. without aeration. Then, 50 μl of 0.004% of decanal in water was added to each well and measurements of luminescence were performed on Veritas luminometer. The bacteriophage culture was incubated for 60 minutes prior to fluorescence measurement.

Luciferase-encoding phages have numerous advantages of a signal amplification device. They are capable of exponential amplification while producing an easily detectable and quantifiable light signal. Also, the cost of their production and use is substantially lower than that of any enzyme-based signal amplifying device currently used in immuno assays. Data presented herein demonstrate that via physical connection with antigen-recognizing moieties, such phages can be converted into very sensitive and simple to use detectors. Even with relatively low affinity ligands, such as peptides isolated from a phage display library, it is possible to build phage-based detector systems that will have higher sensitivity than conventional systems, despite the fact that conventional systems utilize ligands with higher affinity to the antigen (FIG. 4 panel B and FIG. 3). The higher affinity to the antigen of the moiety exposed on the phage surface, the higher the sensitivity of the resulting construct will be. Accordingly, in some embodiments short polypeptides having higher affinity to a chosen antigen are employed, and/or 2) chemical coupling or coupling via chimeras, such as streptavidin-SpAG, of conventional antibodies or their derivatives to phage particles are utilized, and/or 3) single chain antibodies or variable domains of heavy chain only camelidae antibodies that can be incorporated into the phage capsid as a result of genetic modifications of the phage genome are used.

In some embodiments, phage derivatives that can directly target antigens of interest are provided. In some embodiments, this approach will not only increase sensitivity of PLISA, but will simplify it and make it less expensive. Although both lytic and temperate phages can be used as signal amplifying devices, phages that can propagate without causing lysis of host cells will have an advantage, in some embodiments, because of a more stable signal whose changes are easier to interpret. Data presented in FIG. 2 demonstrate that in the case of M13 derivatives, the range of quantitative response spans over five logarithms of phage concentrations. This range is substantially wider than that of enzymes traditionally used in immono assays. The less inclined slope of the PLISA curve than that of ELISA in FIG. 5 may serve as a demonstration of an additional advantage that use of luciferase-encoding derivatives of M13 devices in immuno assay may provide.

TABLE 1

List of oligonucleotides used in the project.

| Name | Sequence | Used for |
|---|---|---|
| Cm-Bsp119I | 5'-gctttcgaatttctgccattcatcc (SEQ ID NO: 5) | Construction of |
| Cm-NarI | 5'-ttgggcgccatctccttgggccaacttttggcgaaaatg (SEQ ID NO: 6) | M13Cm3 |
| S-5' | 5'-cgttccggctaagtaacatgaaaaagacagctatcgcgattgcagtg (SEQ ID NO: 7) | Construction of M13CmSompbio |
| S-3' | 5'-tgcccgcggcctgcg (SEQ ID NO: 8) | VII8 |
| VII-N5' | 5'-gcgcctggtctgtacaccgttcatctg (SEQ ID NO: 9) | |
| VII-N3' | 5'-catgttacttagccggaacg (SEQ ID NO: 10) | |
| Bio-52' | 5'-cgcaggccgcgggcgcaagcagcctgagaca (SEQ ID NO: 11) | |
| Bio-3' | 5'-tgcggccgcctgggccccct (SEQ ID NO: 12) | |
| VII-C5' | 5'-agggggcccaggcggccgcagagcaggtcgcggatt (SEQ ID NO: 13) | |
| VII-C3' | 5'-aagcgcagtctctgaattta (SEQ ID NO: 14) | |
| Bio-Nco | 5'-catggcaagcagcctgagacagattctggactcccagaaaatggagtgga (SEQ ID NO: 15) | Assembly of sequence |
| Bio-Nco-P | 5'-ggtccaacgccgggggcagcggtagggataacagggtaatcca (SEQ ID NO: 16) | encoding biotinylatable |
| Bio-Nde | 5'-tatggattaccctgttatccctaccgctgcccccggcgttg (SEQ ID NO: 17) | peptide |

TABLE 1-continued

| List of oligonucleotides used in the project. | | |
|---|---|---|
| Name | Sequence | Used for |
| Bio-Nde-P | 5'-gacctccactccattttctgggagtccagaatctgtctcaggctgcttgc (SEQ ID NO: 18) | |
| TAG-I | 5'-ctattttgcacccagctacaattttatcctgaatcttaccaacgc (SEQ ID NO: 19) | Construction of M13CmSompbio TAGVII1mut1 |
| TAG-II2 | 5'-ggcttagagcttaattgctgaatctggtgctgtagctca (SEQ ID NO: 20) | |
| M13delBio-5' | 5'-ggggagctctgggggcagcggtagggataacccctcaggctagatgc (SEQ ID NO: 21) | Construction of M13CmSompΔ TAGVII10 |
| M13delBio-3' | 5'-tcgagcatctagcctgaggggttatccctaccgctgcccccagagctccccgc (SEQ ID NO: 22) | Construction of pGEM-LuxC2 |
| P.luc-5'C | 5'-atggtaaagcaagatgaagttatcacattgt (SEQ ID NO: 23) | |
| P.luc-3'-Hb | 5'-atgtcaactattaaatgcttggtttaag (SEQ ID NO: 24) | Construction of M13LuxABElin k15 |
| VII-N5' | 5'-gcgcctggtctgtacaccgttcatctg (SEQ ID NO: 25) | |
| S-IIIC | 5'-ctcgagtcggccgcccatggcaacagtttcagcggagtga (SEQ ID NO: 26) | Construction of MD12$^{Tm}$ |
| IIIN | 5'-ccatgggcggccgactcgaggaaagttgtttagcaaaacccc (SEQ ID NO: 2) | |
| VII-N3' | 5'-catgttacttagccggaacg (SEQ ID NO: 28) | |
| VII-N12cor | 5'-cgacctgctctgcggccgccga(N)$_{36}$accgctgccccc (SEQ ID NO: 29) | |

This example demonstrates that the methods and compositions described herein are useful in the detection of molecules.

TABLE 2

| Sequence of SpAG. (SEQ ID NO: 30) |
|---|
| mgsshhhhhhssglvprgshrstledpsqstnvlgeakklnesqapkadnnfnkeqqnafyeilnmpnlneeqrngfiqslkddp |
| sqsanllaeakklnesqapkadnkfnkeqqnafyeilhlpnlneeqrngfiqslkddpsqsanllaeakklndaqapkadnkfnke |
| qqnafyeilhlpnlteeqrngfiqslkddprstlaaasgastdtyklilngktlkgetttteavdaataekvfkqyandngvdgewtydd |
| atktftvtekpevidaseltpavttyklvingktlkgetttkavdaetaekafkqyandngvdgvwtyddatktftvtemvtevpvvr |
| ggscg |

TABLE 3

| Sequence of BoNT/A-CH5. (SEQ ID NO: 31) |
|---|
| msackgmgsshhhhhhssglvprgshmarivdnqrllstfteyikniintsilnlryesnhlidlsryaskinigskvnfdpidknqiq |
| lfnlesskievilknaivynsmyenfstsfwiripkyfnsislnneytiincmennsgwkvslnygeiiwtlqdtqeikqrvvfkysq |
| minisdyinrwifvtitnnrlnnskiyingrlidqkpisnlgnihasnnimfkldgcrdthryiwikyfnlfdkelnekeikdlydnqs |
| nsgilkdfwgdylqydkpyymlnlydpnkyvdvnnvgirgymylkgprgsvmttniylnsslyrgtkfiikkyasgnkdnivrn |
| ndrvyinvvvknkeyrlatnasqagvekilsaleipdvgnlsqvvvmksknd qgitnkckmnlqdnngndigfigfhqfnniakl |
| vasnwynrqierssrtlgcswefipvddgwgerpl |

TABLE 4

| Sequence of pParaBAD-bio6. (SEQ ID NO: 32) |
|---|
| agatctgcaagtcttgcataatgtgcctgtcaaatggacgaagcagggattctgcaaaccctatgctactccgtcaagccgtcaattgtctg |
| attcgttaccaattatgacaacttgacggctacatcattcactttttcttcacaaccggcacggaactcgctcgggctggccccggtgcatttt |

TABLE 4-continued

| Sequence of pParaBAD-bio6. (SEQ ID NO: 32) |
|---|
| ttaaatacccgcgagaaatagagttgatcgtcaaaaccaacattgcgaccgacggtggcgataggcatccgggtggtgctcaaaagca |
| gcttcgcctggctgatacgttggtcctcgcgccagcttaagacgctaatccctaactgctggcggaaaagatgtgacagacgcgacggc |
| gacaagcaaacatgctgtgcgacgctggcgatatcaaaattgctgtctgccaggtgatcgctgatgtactgacaagcctcgcgtacccg |
| attatccatcggtggatggagcgactcgttaatcgcttccatgcgccgcagtaacaattgctcaagcagatttatcgccagcagctccgaa |
| tagcgcccttccccttgcccggcgttaatgatttgcccaaacaggtcgctgaaatgcggctggtgcgcttcatccgggcgaaagaaccc |
| cgtattggcaaatattgacggccagttaagccattcatgccagtaggcgcgcggacgaaagtaaacccactggtgataccattcgcgag |
| cctccggatgacgaccgtagtgatgaatctctcctggcgggaacagcaaaatatcacccggtcggcaaacaaattctcgtccctgatttt |
| caccaccccctgaccgcgaatggtgagattgagaatataacctttcattcccagcggtcggtcgataaaaaaatcgagataaccgttggc |
| ctcaatcggcgttaaacccgccaccagatgggcattaaacgagtatcccggcagcaggggatcattttgcgcttcagccatacttttcata |
| ctcccgccattcagagaagaaaccaattgtccatattgcatcagacattgccgtcactgcgtcttttactggctcttctcgctaaccaaaccg |
| gtaaccccgcttattaaaagcattctgtaacaaagcgggaccaaagccatgacaaaaacgcgtaacaaaagtgtctataatcacggcagaaa |
| agtccacattgattatttgcacggcgtcacactttgctatgccatagcatttttatccataagattagcggatcctacctgacgctttttatc |
| gcaactctctactgtttctccatacccgtttttttggatggagtgaaacgatggcgattgcaatttctagcgccattcgccattcaggctgcgc |
| aactgttgggaagggcgatcggtgcgggcctcttcgctattacgccagctggcgaaaggggggatgtgctgcaaggcgattaagttggg |
| taacgccagggttttcccagtcacgacgttgtaaaacgacggccagtgaattcgagctagaaataattttgtttaactttaagaaggagata |
| taccatggcaagcagcctgagacagattctggactcccagaaaatggagtggaggtccaacgccgggggcagcggtagggataaca |
| gggtaatccatatgctcgagggggcccaggcggccgcactcgactcggtacccggggatcctctagagtcgacctgcaggcatgcaa |
| gcttggcgtaatcatggtcatagctgtttcctgtgtgaaattgttatccgctcacaattccacacaacatacgagccggaagcataaagtgta |
| aagcctggggtgcctaatgagtgagctaactcacattaattgcgttgcgctcactgcccgctttccagtcgggaaacctgtcgtgccagc |
| gagctcgaattcggctgctaacaaagcccgaaaggaagctgagttggctgctgccaccgctgagcaataactagcataaccccttggg |
| cctctaaacgggtcttgaggggttttttgctgaaaggaggaactatatccggatcggagatcaattctggcgtaatagcgaagaggcccg |
| caccgatcgcccttcccaacagttgcgtagcctgaatggcgaatgggacgcgccctgtagcggcgcattaagcgcggcgggtgtggt |
| ggttacgcgcagcgtgaccgctacacttgccagcgccctagcgcccgctcctttcgctttcttcccttcctttctcgccacgttcgccggctt |
| tccccgtcaagctctaaatcgggggctccctttagggttccgatttagtgctttacggcacctcgaccccaaaaaacttgattagggtgatgg |
| ttcacgtagtgggccatcgccctgatagacggtttttcgccctttgacgttggagtccacgttctttaatagtggactcttgttccaaactgga |
| acaacactcaaccctatctcggtctattcttttgatttataagggattttgccgatttcggcctattggttaaaaaatgagctgatttaacaaaa |
| atttaacgcgaattttaacaaaatattaacgtttacaatttcaggtggcacttttcggggaaatgtgcgcggaacccctatttgtttatttttct |
| aaatacattcaaatatgtatccgctcatgagacaataaccctgataaatgcttcaataatattgaaaaaggaagagtatgagtattcaacatttc |
| cgtgtcgcccttattcccttttttgcggcattttgccgtcctgtttttgctcacccagaaacgctggtgaaagtaaaagatgctgaagatcagtt |
| gggtgcacgagtgggttacatcgaactggatctcaacagcggtaagatccttgagagttttcgccccgaagaacgttttccaatgatgagc |
| acttttaaagttctgctatgtggcgcggtattatcccgtattgacgccgggcaagagcaactcggtcgccgcatacactattctcagaatga |
| cttggttgagtactcaccagtcacagaaaagcatcttacggatggcatgacagtaagagaattatgcagtgctgccataagcatgagtgat |
| aacactgcggccaacttacttctgacaacgatcggaggaccgaaggagctaaccgcttttttcacaacatgggggatcatgtaactcgc |
| cttgatcgttgggaaccggagctgaatgaagccataccaaacgacgagcgtgacaccacgatgcctgtagcaatggcaacaacgttgc |
| gcaaactattaactggcgaactacttactctagcttcccggcaacaattaatagactggatggaggcggataaagttgcaggaccacttct |
| gcgctcggcccttccggctggctggtttattgctgataaatctggagccggtgagcgtgggtctcgcggtatcattgcagcactggggcc |
| agatggtaagccctcccgtatcgtagttatctacacgacgggcagtcaggcaactatggatgaacgaaatagacagatcgctgagataggtgc |
| ctcactgattaagcattggtaactgtcagaccaagtttactcatatatactttagattgatttaaaacttcatttttaatttaaaaggatcta |
| ggtgaagatcctttttgataatctcatgaccaaaatcccttaacgtgagttttcgttccactgagcgtcagaccccgtagaaaagatcaaag |

TABLE 4-continued

| Sequence of pParaBAD-bio6. (SEQ ID NO: 32) |
| --- |
| gatcttcttgagatcctttttttctgcgcgtaatctgctgcttgcaaacaaaaaaaccaccgctaccagcggtggtttgtttgccggatcaaga |
| gctaccaactctttttccgaaggtaactggcttcagcagagcgcagataccaaatactgtccttctagtgtagccgtagttaggccaccact |
| tcaagaactctgtagcaccgcctacatacctcgctctgctaatcctgttaccagtggctgctgccagtggcgataagtcgtgtcttaccggg |
| ttggactcaagacgatagttaccggataaggcgcagcggtcgggctgaacggggggttcgtgcacacagcccagcttggagcgaacg |
| acctacaccgaactgagatacctacagcgtgagcattgagaaagcgccacgcttcccgaagggagaaaggcggacaggtatccggta |
| agcggcagggtcggaacaggagagcgcacgagggagcttccagggggaaacgcctggtatctttatagtcctgtcgggtttcgccac |
| ctctgacttgagcgtcgatttttgtgatgctcgtcaggggggcgagcctatggaaaaacgccagcaacgcggcctttttacggttcctggcc |
| ttttgctggccttttgctcacatgttctttcctgcgttatcccctgattctgtggataaccgtattaccgcctttgagtgagctgataccgctc |
| gccgcagccgaacgaccgagcgcagcgagtcagtgagcgaggaagcggaagagcgcctgatgcggtattttctccttacgcatctgt |
| gcggtatttcacaccgcatatatggtgcactctcagtacaatctgctctgatgccgcatagttaagccagtatacactccgctatcgctacgt |
| gactgcaaggagatggcgcccaacagtcccccggccacggggcctgccaccatacccacgccgaaacaagcgctcatgagcccga |
| agtggcgagcccgatcttccccatcggtgatgtcggcgatataggcgccagcaaccgcacctgtggcgccggtgatgccggccacga |
| tgcgtccggcgtagaggatcttg |

TABLE 5

| Sequence of pSL-EGFP2. (SEQ ID NO: 33) |
| --- |
| gggcggcgacctcgcgggttttcgctatttatgaaaattttccggtttaaggcgtttccgttcttcttcgtcataacttaatgtttttatttaaaataccc |
| tctgaaaagaaaggaaacgacaggtgctgaaagcgaggctttttggcctctgtcgtttcctttctctgtttttgtccgtggaatgaacaa |
| tggaagtcaacaaaaagcagctggctgacattttcggtgcgagtatccgtaccattcagaactggcaggaacagggaatgcccgttctg |
| cgaggcggtggcaagggtaatgaggtgctttatgactctgccgccgtcataaaatggtatgccgaaagggatgctgaaattgagaacga |
| aaagctgcgccgggaggttgaagaactgcggcaggccagcgaggcagatctccagccaggaactattgagtacgaacgccatcgac |
| ttacgcgtgcgcaggccgacgcacaggaactgaagaatgccagagactccgctgaagtggtggaaaccgcattctgtactttcgtgctg |
| tcgcggatcgcaggtgaaattgccagtattctcgacgggctcccccctgtcggtgcagcggcgttttccggaactggaaaaccgacatgtt |
| gatttcctgaaacgggatatcatcaaagccatgaacaaagcagccgcgctggatgaactgataccggggttgctgagtgaatatatcga |
| acagtcaggttaacaggctgcggcattttgtccgcgccgggcttcgctcactgttcaggccggagccacagaccgccgttgaatgggc |
| ggatgctaattactatctcccgaaagaatccgcataccaggaagggcgctgggaaacactgccctttcagcgggccatcatgaatgcga |
| tgggcagcgactacatccgtgaggtgaatgtggtgaagtctgcccgtgtcggttattccaaaatgctgctgggtgtttatgcctactttatag |
| agcataagcagcgcaacacccttatctggttgccgacggatggtgatgccgagaactttatgaaaacccacgttgagccgactattcgtg |
| atattccgtcgctgctggcgctggccccgtggtatggcaaaaagcaccgggataacacgctcaccatgaagcgtttcactaatgggcgt |
| ggcttctggtgcctgggcggtaaagcggcaaaaaactaccgtgaaaagtcggtggatgtggcgggttatgatgaacttgctgcttttgat |
| gatgatattgaacaggaaggctctccgacgttcctgggtgacaagcgtattgaaggctcggtctggccaaagtccatccgtggctccac |
| gccaaaagtgagaggcacctgtcagattgagcgtgcagccagtgaatccccgcattttatgcgttttcatgttgcctgcccgcattgcggg |
| gaggagcagtatcttaaatttggcgacaaagagacgccgtttggcctcaaatggacgccggatgacccctccagcgtgttttatctctgc |
| gagcataatgcctgcgtcatccgccagcaggagctggactttactgatgcccgttatatctgcgaaaagaccgggatctggacccgtgat |
| ggcattctctggttttcgtcatccggtgaagagattgagccacctgacagtgtgacctttcacatctggacagcgtacagcccgttcaccac |
| ctgggtgcagattgtcaaagactggatgaaaacgaaaggggatacgggaaaacgtaaaaccttcgtaaacaccacgctcggtgagac |
| gtgggaggcgaaaattggcgaacgtccggatgctgaagtgatggcagagcggaaagagcattattcagcgcccgttcctgaccgtgtg |
| gcttacctgaccgccggtatcgactcccagctggaccgctacgaaatgcgcgtatggggatgggggccgggtgaggaaagctggctg |
| attgaccggcagattattatgggccgccacgacgatgaacagacgctgctgcgtgtggatgaggccatcaataaaacctatacccgccg |

TABLE 5-continued

| Sequence of pSL-EGFP2. (SEQ ID NO: 33) |
| --- |
| gaatggtgcagaaatgtcgatatcccgtatctgctgggatactggcgggattgacccgaccattgtgtatgaacgctcgaaaaaacatgg |
| gctgttccgggtgatccccattaaaggggcatccgtctacggaaagccggtggccagcatgccacgtaagcgaaacaaaaacggggtt |
| taccttaccgaaatcggtacggataccgcgaaagagcagatttataaccgcttcacactgacgccggaaggggatgaaccgcttcccg |
| gtgccgttcacttcccgaataacccggatatttttgatctgaccgaagcgcagcagctgactgctgaagagcaggtcgaaaaatgggtgg |
| atggcaggaaaaaaatactgtgggacagcaaaaagcgacgcaatgaggcactcgactgcttcgtttatgcgctggcggcgctgcgcat |
| cagtatttcccgctggcagctggatctcagtgcgctgctggcgagcctgcaggaagaggatggtgcagcaaccaacaagaaaacactg |
| gcagattacgcccgtgccttatccggagaggatgaatgacgcgacaggaagaacttgccgctgcccgtgcggcactgcatgacctgat |
| gacaggtaaacgggtggcaacagtacagaaagacggacgaagggtggagtttacggccacttccgtgtctgacctgaaaaaatatatt |
| gcagagctggaagtgcagaccggcatgacacagcgacgcaggggacctgcaggattttatgtatgaaaacgcccaccattcccaccct |
| tctggggccggacggcatgacatcgctgcgcgaatatgccggttatcacggcggtggcagcggatttggagggcagttgcggtcgtg |
| gaacccaccgagtgaaagtgtggatgcagccctgttgcccaactttacccgtggcaatgcccgcgcagacgatctggtacgcaataac |
| ggctatgccgccaacgccatccagctgcatcaggatcatatcgtcgggtctttttttccggctcagtcatcgcccaagctggcgctatctgg |
| gcatcggggaggaagaagcccgtgccttttcccgcgaggttgaagcggcatggaaagagtttgccgaggatgactgctgctgcattga |
| cgttgagcgaaaacgcacgtttaccatgatgattcgggaaggtgtggccatgcacgcctttaacggtgaactgttcgttcaggccacctg |
| ggataccagttcgtcgcggcttttccggacacagttccggatggtcagcccgaagcgcatcagcaacccgaacaataccggcgacagc |
| cggaactgccgtgccggtgtgcagattaatgacagcggtgcggcgctgggatattacgtcagcgaggacgggtatcctggctggatgc |
| cgcagaaatggacatggataccccgtgagttacccggcgggcgcgcctcgttcattcacgtttttgaacccgtggaggacgggcagact |
| cgcggtgcaaatgtgttttacagcgtgatggagcagatgaagatgctcgacacgctgcagaacacgcagctgcagagcgccattgtga |
| aggcgatgtatgccgccaccattgagagtgagctggatacgcagtcagcgatggatttattctgggcgcgaacagtcaggagcagcg |
| ggaaaggctgaccggctggattggtgaaattgccgcgtattacgccgcagcgccggtccggctgggaggcgcaaaagtaccgcacct |
| gatgccgggtgactcactgaacctgcagacggctcaggatacggataacggctactccgtgtttgagcagtcactgctgcggtatatcg |
| ctgccgggctgggtgtctcgtatgagcagctttcccggaattacgcccagatgagctactccacggcacgggccagtgcgaacgagtc |
| gtgggcgtactttatggggcggcgaaaattcgtcgcatcccgtcaggcgagccagatgtttctgtgctggctggaagaggccatcgttcg |
| ccgcgtggtgacgttaccttcaaaagcgcgcttcagttttcaggaagcccgcagtgcctgggggaactgcgactggataggctccggtc |
| gtatggccatcgatggtctgaaagaagttcaggaagcggtgatgctgatagaagccggactgagtacctacgagaaagagtgcgcaaa |
| acgcggtgacgactatcaggaaatttttgcccagcaggtccgtgaaacgatggagcgccgtgcagccggtcttaaaccgcccgcctgg |
| gcggctgcagcatttgaatccgggctgcgacaatcaacagaggaggagaagagtgacagcagagctgcgtaatctcccgcatattgcc |
| agcatggcctttaatgagccgctgatgcttgaacccgcctatgcgcgggttttcttttgtgcgcttgcaggccagcttgggatcagcagcct |
| gacggatgcggtgtccggcgacagcctgactgcccaggaggcactcgcgacgctggcattatccggtgatgatgacggaccacgac |
| aggcccgcagttatcaggtcatgaacggcatcgccgtgctgccggtgtccggcacgctggtcagccggacgcgggcgctgcagccgt |
| actcggggatgaccggttacaacggcattatcgcccgtctgcaacaggctgccagcgatccgatggtggacggcattctgctcgatatg |
| gacacgcccggcgggatggtggcgggggcatttgactgcgctgacatcatcgcccgtgtgcgtgacataaaaccggtatgggcgcttg |
| ccaacgacatgaactgcagtgcaggtcagttgcttgccagtgccgcctcccggcgtctggtcacgcagaccgcccggacaggctccat |
| cggcgtcatgatggctcacagtaattacggtgctgcgctggagaaacagggtgtggaaatcacgctgatttacagcggcagccataag |
| gtggatggcaacccctacagccatcttccggatgacgtccgggagacactgcagtcccggatggacgcaacccgccagatgtttgcgc |
| agaaggtgtcggcatataccggcctgtccgtgcaggttgtgctggataccgaggctgcagtgtacagcggtcaggaggccattgatgc |
| cggactggctgatgaacttgttaacagcaccgatgcgatcaccgtcatgcgtgatgcactggatgcacgtaaatcccgtctctcaggagg |
| gcgaatgaccaaagagactcaatcaacaactgtttcagccactgcttcgcaggctgacgttactgacgtggtgccagcgacggagggc |
| gagaacgccagcgcggcgcagccggacgtgaacgcgcagatcaccgcagcggttgcggcagaaaacagccgcattatggggatcc |

TABLE 5-continued

| Sequence of pSL-EGFP2. (SEQ ID NO: 33) |
| --- |
| tcaactgtgaggaggctcacggacgcgaagaacaggcacgcgtgctggcagaaacccccggtatgaccgtgaaaacggcccgccg |
| cattctggccgcagcaccacagagtgcacaggcgcgcagtgacactgcgctggatcgtctgatgcaggggcaccggcaccgctgg |
| ctgcaggtaacccggcatctgatgccgttaacgatttgctgaacacaccagtgtaagggatgtttatgacgagcaaagaaacctttaccca |
| ttaccagccgcagggcaacagtgacccggctcataccgcaaccgcgcccctagaccttcatcactaaaggccgcctgtgcggcttttttt |
| acgggatttttttatgtcgatgtacacaaccgcccaactgctggcggcaaatgagcagaaatttaagtttgatccgctgtttctgcgtctctttt |
| tccgtgagagctatcccttcaccacggagaaagtctatctctcacaaattccgggactggtaaacatggcgctgtacgtttcgccgattgtt |
| tccggtgaggttatccgttcccgtggcggctccacctctgaatttacgccgggatatgtcaagccgaagcatgaagtgaatccgcagatg |
| accctgcgtcgcctgccggatgaagatccgcagaatctggcggacccggcttaccgccgccgtcgcatcatcatgcagaacatgcgtg |
| acgaagagctggccattgctcaggtcgaagagatgcaggcagtttctgccgtgcttaagggcaaatacaccatgaccggtgaagccttc |
| gatccggttgaggtggatatgggccgcagtgaggagaataacatcacgcagtccggcggcacggagtggagcaagcgtgacaagtc |
| cacgtatgacccgaccgacgatatcgaagcctacgcgctgaacgccagcggtgtggtgaatatcatcgtgttcgatccgaaaggctgg |
| gcgctgttccgttccttcaaagccgtcaaggagaagctggatacccgtcgtggctctaattccgagctggagacagcggtgaaagacct |
| gggcaaagcggtgtcctataaggggatgtatggcgatgtggccatcgtcgtgtattccggacagtacgtggaaaacggcgtcaaaaag |
| aacttcctgccggacaacacgatggtgctggggaacactcaggcacgcggtctgcgcacctatggctgcattcaggatgcggacgcac |
| agcgcgaaggcattaacgcctctgcccgttacccgaaaaactgggtgaccaccggcgatccggcgcgtgagttcaccatgattcagtc |
| agcaccgctgatgctgctggctgaccctgatgagttcgtgtccgtacaactggcgtaatcatggcccttcggggccattgtttctctgtgga |
| ggagtccatgacgaaagatgaactgattgcccgtctccgctcgctgggtgaacaactgaaccgtgatgtcagcctgacggggacgaaa |
| gaagaactggcgctccgtgtggcagagctgaaagaggagcttgatgacacggatgaaactgccggtcaggacacccctctcagccgg |
| gaaaatgtgctgaccggacatgaaaatgaggtgggatcagcgcagccggataccgtgattctggatacgtctgaactggtcacggtcgt |
| ggcactggtgaagctgcatactgatgcacttcacgccacgcgggatgaacctgtggcatttgtgctgccgggaacggcgtttcgtgtctc |
| tgccggtgtggcagccgaaatgacagagcgcggcctggccagaatgcaataacgggaggcgctgtggctgatttcgataacctgttcg |
| atgctgccattgcccgcgccgatgaaacgatacgcgggtacatgggaacgtcagccaccattacatccggtgagcagtcaggtgcggt |
| gatacgtggtgtttttgatgaccctgaaaatatcagctatgccggacagggcgtgcgcgttgaaggctccagcccgtccctgtttgtccgg |
| actgatgaggtgcggcagctgcggcgtggagacacgctgaccatcggtgaggaaaatttctgggtagatcgggtttcgccggatgatg |
| gcggaagttgtcatctctggcttggacggggcgtaccgcctgccgttaaccgtcgccgctgaaaggggggatgtatggccataaaaggtc |
| ttgagcaggccgttgaaaacctcagccgtatcagcaaaacggcggtgcctggtgccgccgcaatggccattaaccgcgttgcttcatcc |
| gcgatatcgcagtcggcgtcacaggttgcccgtgagacaaaggtacgccggaaactggtaaaggaaagggccaggctgaaaagggc |
| cacggtcaaaaatccgcaggccagaatcaaagttaaccgggggggatttgcccgtaatcaagctgggtaatgcgcgggttgtcctttcgc |
| gccgcaggcgtcgtaaaaaggggcagcgttcatccctgaaaggtggcggcagcgtgcttgtggtgggtaaccgtcgtattcccggcgc |
| gtttattcagcaactgaaaaatggccggtggcatgtcatgcagcgtgtggctgggaaaaaccgttaccccattgatgtggtgaaaatccc |
| gatggcggtgccgctgaccacggcgtttaaacaaaatattgagcggatacggcgtgaacgtcttccgaaagagctgggctatgcgctg |
| cagcatcaactgaggatggtaataaagcgatgaaacatactgaactccgtgcagccgtactggatgcactggagaagcatgacaccgg |
| ggcgacgtttttgatggtcgccccgctgtttttgatgaggcggattttccggcagttgccgtttatctcaccggcgctgaatacacgggcg |
| aagagctggacagcgatacctggcaggcggagctgcatatcgaagttttcctgcctgctcaggtgccggattcagagctggatgcgtgg |
| atggagtcccggatttatccggtgatgagcgatatcccggcactgtcagatttgatcaccagtatggtggccagcggctatgactaccgg |
| cgcgacgatgatgcgggcttgtggagttcagccgatctgacttatgtcattacctatgaaatgtgaggacgctatgcctgtaccaaatccta |
| caatgccggtgaaaggtgccgggaccaccctgtgggtttataaggggagcggtgacccttacgcgaatccgctttcagacgttgactgg |
| tcgcgtctggcaaaagttaaagacctgacgcccggcgaactgaccgctgagtcctatgacgacagctatctcgatgatgaagatgcaga |
| ctggactgcgaccgggcaggggcagaaatctgccggagataccagcttcacgctggcgtggatgcccggagagcaggggcagcag |

TABLE 5-continued

| Sequence of pSL-EGFP2. (SEQ ID NO: 33) |
|---|
| gcgctgctggcgtggtttaatgaaggcgatacccgtgcctataaaatccgcttcccgaacggcacggtcgatgtgttccgtggctgggtc |
| agcagtatcggtaaggcggtgacggcgaaggaagtgatcacccgcacggtgaaagtcaccaatgtgggacgtccgtcgatggcaga |
| agatcgcagcacggtaacagcggcaaccggcatgaccgtgacgcctgccagcacctcggtggtgaaagggcagagcaccacgctg |
| accgtggccttccagccggagggcgtaaccgacaagagctttcgtgcggtgtctgcggataaaacaaaagccaccgtgtcggtcagtg |
| gtatgaccatcaccgtgaacggcgttgctgcaggcaaggtcaacattccggttgtatccggtaatggtgagtttgctgcggttgcagaaat |
| taccgtcaccgccagttaatccggagagtcagcgatgttcctgaaaaccgaatcatttgaacataacggtgtgaccgtcacgctttctgaa |
| ctgtcagccctgcagcgcattgagcatctcgccctgatgaaacggcaggcagaacaggcggagtcagacagcaaccggaagtttact |
| gtggaagacgccatcagaaccggcgcgtttctggtggcgatgtccctgtggcataaccatccgcagaagacgcagatgccgtccatga |
| atgaagccgttaaacagattgagcaggaagtgcttaccacctggcccacggaggcaatttctcatgctgaaaacgtggtgtaccggctgt |
| ctggtatgtatgagtttgtggtgaataatgcccctgaacagacagaggacgccgggcccgcagagcctgtttctgcgggaaagtgttcg |
| acggtgagctgagttttgccctgaaactggcgcgtgagatggggcgacccgactggcgtgccatgcttgccgggatgtcatccacgga |
| gtatgccgactggcaccgcttttacagtacccattattttcatgatgttctgctggatatgcacttttccgggctgacgtacaccgtgctcagc |
| ctgtttttcagcgatccggatatgcatccgctggatttcagtctgctgaaccggcgcgaggctgacgaagagcctgaagatgatgtgctg |
| atgcagaaagcggcagggcttgccggaggtgtccgctttggcccggacgggaatgaagttatccccgcttccccggatgtggcggac |
| atgacggaggatgacgtaatgctgatgacagtatcagaagggatcgcaggaggagtccggtatggctgaaccggtaggcgatctggtc |
| gttgatttgagtctggatgcggccagatttgacgagcagatggccagagtcaggcgtcatttttctggtacggaaagtgatgcgaaaaaa |
| acagcggcagtcgttgaacagtcgctgagccgacaggcgctggctgcacagaaagcggggatttccgtcgggcagtataaagccgc |
| catgcgtatgctgcctgcacagttcaccgacgtggccacgcagcttgcaggcgggcaaagtccgtggctgatcctgctgcaacagggg |
| gggcaggtgaaggactccttcggcgggatgatccccatgttcaggggggcttgccggtgcgatcaccctgccgatggtgggggccacc |
| tcgctggcggtggcgaccggtgcgctggcgtatgcctggtatcagggcaactcaaccctgtccgatttcaacaaaacgctggtcctttcc |
| ggcaatcaggcgggactgacggcagatcgtatgctggtcctgtccagagccgggcaggcggcagggctgacgtttaaccagaccag |
| cgagtcactcagcgcactggttaaggcgggggtaagcggtgaggctcagattgcgtccatcagccagagtgtggcgcgtttctcctctg |
| catccggcgtggaggtggacaaggtcgctgaagccttcgggaagctgaccacagacccgacgtcggggctgacggcgatggctcgc |
| cagttccataacgtgtcggcggagcagattgcgtatgttgctcagttgcagcgttccggcgatgaagccggggcattgcaggcggcga |
| acgaggccgcaacgaaagggtttgatgaccagacccgccgcctgaaagagaacatgggcacgctggagacctgggcagacaggac |
| tgcgcgggcattcaaatccatgtgggatgcggtgctggatattggtcgtcctgataccgcgcaggagatgctgattaaggcagaggctg |
| cgtataagaaagcagacgacatctggaatctgcgcaaggatgattattttgttaacgatgaagcgcgggcgcgttactgggatgatcgtg |
| aaaaggcccgtcttgcgcttgaagccgcccgaaagaaggctgagcagcagactcaacaggacaaaaatgcgcagcagcagagcgat |
| accgaagcgtcacggctgaaatataccgaagaggcgcagaaggcttacgaacggctgcagacgccgctggagaaatataccgcccg |
| tcaggaagaactgaacaaggcactgaaagacgggaaaatcctgcaggcggattacaacacgctgatggcggcggcgaaaaaggatt |
| atgaagcgacgctgaaaaagccgaaacagtccagcgtgaaggtgtctgcgggcgatcgtcaggaagacagtgctcatgctgccctgc |
| tgacgcttcaggcagaactccggacgctggagaagcatgccggagcaaatgagaaaatcagccagcagcgccgggatttgtggaag |
| gcggagagtcagttcgcggtactggaggaggcggcgcaacgtcgccagctgtctgcacaggagaaatccctgctggcgcataaagat |
| gagacgctggagtacaaacgccagctggctgcacttggcgacaaggttacgtatcaggagcgcctgaacgcgctggcgcagcaggc |
| ggataaattcgcacagcagcaacgggcaaaacgggccgccattgatgcgaaaagccgggggctgactgaccggcaggcagaacgg |
| gaagccacggaacagcgcctgaaggaacagtatggcgataatccgctggcgctgaataacgtcatgtcagagcagaaaaagacctgg |
| gcggctgaagaccagcttcgcgggaactggatggcaggcctgaagtccggctggagtgagtgggaagagagcgccacggacagta |
| tgtcgcaggtaaaaagtgcagccacgcagacctttgatggtattgcacagaatatggcggcgatgctgaccggcagtgagcagaactg |
| gcgcagcttcacccgttccgtgctgtccatgatgacagaaattctgcttaagcaggcaatggtggggattgtcgggagtatcggcagcgc |

TABLE 5-continued

| Sequence of pSL-EGFP2. (SEQ ID NO: 33) |
| --- |
| cattggcggggctgttggtggcggcgcatccgcgtcaggcggtacagccattcaggccgctgcggcgaaattccattttgcaaccgga |
| ggatttacgggaaccggcggcaaatatgagccagcggggattgttcaccgtggtgagtttgtcttcacgaaggaggcaaccagccgga |
| ttggcgtggggaatctttaccggctgatgcgcggctatgccaccggcggttatgtcggtacaccgggcagcatggcagacagccggtc |
| gcaggcgtccgggacgtttgagcagaataaccatgtggtgattaacaacgacggcacgaacgggcagataggtccggctgctctgaa |
| ggcggtgtatgacatggcccgcaagggtgcccgtgatgaaattcagacacagatgcgtgatggtggcctgttctccggaggtggacga |
| tgaagaccttccgctggaaagtgaaacccggtatggatgtggcttcggtcccttctgtaagaaaggtgcgctttggtgatggctattctcag |
| cgagcgcctgccgggctgaatgccaacctgaaaacgtacagcgtgacgctttctgtccccgtgaggaggccacggtactggagtcgt |
| ttctggaagagcacgggggctggaaatcctttctgtggacgccgccttatgagtggcggcagataaaggtgacctgcgcaaaatggtcg |
| tcgcgggtcagtatgctgcgtgttgagttcagcgcagagtttgaacaggtggtgaactgatgcaggatatccggcaggaaacactgaat |
| gaatgcacccgtgcggagcagtcggccagcgtggtgctctgggaaatcgacctgacagaggtcggtggagaacgttatttttctgtaat |
| gagcagaacgaaaaaggtgagccggtcacctggcaggggcgacagtatcagccgtatcccattcaggggagcggttttgaactgaat |
| ggcaaaggcaccagtacgcgccccacgctgacggtttctaacctgtacggtatggtcaccgggatggcggaagatatgcagagtctgg |
| tcggcggaacggtggtccggcgtaaggtttacgcccgttttctggatgcggtgaacttcgtcaacggaaacagttacgccgatccggag |
| caggaggtgatcagccgctggcgcattgagcagtgcagcgaactgagcgcggtgagtgcctcctttgtactgtccacgccgacggaaa |
| cggatggcgctgtttttccgggacgtatcatgctggccaacacctgcacctggacctatcgcggtgacgagtgcggttatagcggtccg |
| gctgtcgcggatgaatatgaccagccaacgtccgatatcacgaaggataaatgcagcaaatgcctgagcggttgtaagttccgcaataa |
| cgtcggcaactttggcggcttcctttccattaacaaactttcgcagtaaatcccatgacacagacagaatcagcgattctggcgcacgccc |
| ggcgatgtgcgccagcggagtcgtgcggcttcgtggtaagcacgccggagggggaaagatatttcccctgcgtgaatatctccggtga |
| gccggaggctatttccgtatgtcgccggaagactggctgcaggcagaaatgcagggtgagattgtggcgctggtccacagccacccc |
| ggtggtctgccctggctgagtgaggccgaccggcggctgcaggtgcagagtgatttgccgtggtggctggtctgccgggggacgattc |
| ataagttccgctgtgtgccgcatctcaccgggcggcgctttgagcacggtgtgacggactgttacacactgttccgggatgcttatcatct |
| ggcggggattgagatgccggactttcatcgtgaggatgactggtggcgtaacggccagaatctctatctggataatctggaggcgacgg |
| ggctgtatcaggtgccgttgtcagcggcacagccgggcgatgtgctgctgtgctgttttggttcatcagtgccgaatcacgccgcaattta |
| ctgcggcgacggcgagctgctgcaccatattcctgaacaactgagcaaacgagagaggtacaccgacaaatggcagcgacgcacac |
| actccctctggcgtcaccgggcatggcgcgcatctgcctttacggggatttacaacgatttggtcgccgcatcgaccttcgtgtgaaaac |
| gggggctgaagccatccgggcactggccacacagctcccggcgtttcgtcagaaactgagcgacggctggtatcaggtacggattgc |
| cgggcgggacgtcagcacgtccgggttaacggcgcagttacatgagactctgcctgatggcgctgtaattcatattgttcccagagtcgc |
| cggggccaagtcaggtggcgtattccagattgtcctgggggctgccgccattgccggatcattctttaccgccggagccacccttgcag |
| catgggggcagccattggggccggtggtatgaccggcatcctgttttctctcggtgccagtatggtgctcggtggtgtggcgcagatg |
| ctggcaccgaaagccagaactccccgtatacagacaacggataacggtaagcagaacacctatttctcctcactggataacatggttgc |
| ccagggcaatgttctgcctgttctgtacggggaaatgcgcgtggggtcacgcgtggtttctcaggagatcagcacggcagacgaaggg |
| gacggtggtcaggttgtggtgattggtcgctgatgcaaaatgttttatgtgaaaccgcctgcgggcggttttgtcatttatggagcgtgagg |
| aatgggtaaaggaagcagtaaggggcataccccgcgcgaagcgaaggacaacctgaagtccacgcagttgctgagtgtgatcgatgc |
| catcagcgaagggccgattgaaggtccggtggatggcttaaaaagcgtgctgctgaacagtacgccggtgctggacactgaggggaa |
| taccaacatatccggtgtcacggtggtgttccgggctggtgagcaggagcagactccgccggagggatttgaatcctccggctccgag |
| acggtgctgggtacggaagtgaaatatgacacgccgatcacccgcaccattacgtctgcaaacatcgaccgtctgcgctttaccttcggt |
| gtacaggcactggtggaaaccacctcaaagggtgacaggaatccgtcggaagtccgcctgctggttcagatacaacgtaacggtggct |
| gggtgacggaaaaagacatcaccattaagggcaaaaccacctcgcagtatctggcctcggtggtgatgggtaacctgccgccgcgcc |
| cgtttaatatccggatgcgcaggatgacgccggacagcaccacagaccagctgcagaacaaaacgctctggtcgtcatacactgaaat |

TABLE 5-continued

| Sequence of pSL-EGFP2. (SEQ ID NO: 33) |
| --- |
| catcgatgtgaaacagtgctacccgaacacggcactggtcggcgtgcaggtggactcggagcagttcggcagccagcaggtgagcc |
| gtaattatcatctgcgcgggcgtattctgcaggtgccgtcgaactataacccgcagacgcggcaatacagcggtatctgggacggaacg |
| tttaaaccggcatacagcaacaacatggcctggtgtctgtgggatatgctgacccatccgcgctacggcatggggaaacgtcttggtgc |
| ggcggatgtggataaatgggcgctgtatgtcatcggccagtactgcgaccagtcagtgccggacggctttggcggcacggagccgcg |
| catcacctgtaatgcgtacctgaccacacagcgtaaggcgtgggatgtgctcagcgatttctgctcggcgatgcgctgtatgccggtatg |
| gaacgggcagacgctgacgttcgtgcaggaccgaccgtcggataagacgtggacctataaccgcagtaatgtggtgatgccggatgat |
| ggcgcgccgttccgctacagcttcagcgccctgaaggaccgccataatgccgttgaggtgaactggattgacccgaacaacggctgg |
| gagacggcgacagagcttgttgaagatacgcaggccattgcccgttacggtcgtaatgttacgaagatggatgcctttggctgtaccagc |
| cgggggcaggcacaccgcgccgggctgtggctgattaaacagaactgctggaaacgcagaccgtggatttcagcgtcggcgcaga |
| agggcttcgccatgtaccgggcgatgttattgaaatctgcgatgatgactatgccggtatcagcaccggtggtcgtgtgctggcggtgaa |
| cagccagacccggacgctgacgctcgaccgtgaaatcacgctgccatcctccggtaccgcgctgataagcctggttgacggaagtgg |
| caatccggtcagcgtggaggttcagtccgtcaccgacggcgtgaaggtaaaagtgagccgtgttcctgacggtgttgctgaatacagcg |
| tatgggagctgaagctgccgacgctgcgccagcgactgttccgctgcgtgagtatccgtgagaacgacgacggcacgtatgccatcac |
| cgccgtgcagcatgtgccggaaaaagaggccatcgtggataacggggcgcactttgacggcgaacagagtggcacggtgaatggtg |
| tcacgccgccagcggtgcagcacctgaccgcagaagtcactgcagacagcggggaatatcaggtgctggcgcgatgggacacacc |
| gaaggtggtgaagggcgtgagtttcctgctccgtctgaccgtaacagcggacgacggcagtgagcggctggtcagcacggcccgga |
| cgacggaaaccacataccgcttcacgcaactggcgctggggaactacaggctgacagtccgggcggtaaatgcgtgggggcagcag |
| ggcgatccggcgtcggtatcgttccggattgccgcaccggcagcaccgtcgaggattgagctgacgccgggctattttcagataaccg |
| ccacgccgcatcttgccgtttatgacccgacggtacagtttgagttctggttctcggaaaagcagattgcggatatcagacaggttgaaac |
| cagcacgcgttatcttggtacggcgctgtactggatagccgccagtatcaatatcaaaccgggccatgattattacttttatatccgcagtgt |
| gaacaccgttggcaaatcggcattcgtggaggccgtcggtcgggcgagcgatgatgcggaaggttacctggatttttttcaaaggcaaga |
| taaccgaatcccatctcggcaaggagctgctggaaaaagtcgagctgacggaggataacgccagcagactggaggagttttcgaaag |
| agtggaaggatgccagtgataagtggaatgccatgtgggctgtcaaaattgagcagaccaaagacggcaaacattatgtcgcgggtatt |
| ggcctcagcatggaggacacggaggaaggcaaactgagccagtttctggttgccgccaatcgtatcgcatttattgacccggcaaacg |
| ggaatgaaacgccgatgtttgtggcgcagggcaaccagatattcatgaacgacgtgttcctgaagcgcctgacggcccccaccattacc |
| agcggcggcaatcctccggccttttccctgacaccggacggaaagctgaccgctaaaaatgcggatatcagtggcagtgtgaatgcga |
| actccgggacgctcagtaatgtgacgatagctgaaaactgtacgataaacggtacgctgagggcggaaaaaatcgtcggggacattgt |
| aaaggcggcgagcgcggcttttccgcgccagcgtgaaagcagtgtggactggccgtcaggtacccgtactgtcaccgtgaccgatga |
| ccatccttttgatcgccagatagtggtgcttccgctgacgtttcgcggaagtaagcgtactgtcagcggcaggacaacgtattcgatgtgtt |
| atctgaaagtactgatgaacggtgcggtgatttatgatggcgcggcgaacgaggcggtacaggtgttctcccgtattgttgacatgccag |
| cgggtcggggaaacgtgatcctgacgttcacgcttacgtccacacggcattcggcagatattccgccgtatacgtttgccagcgatgtgc |
| aggttatggtgattaagaaacaggcgctgggcatcagcgtggtctgagtgtgttacagaggttcgtccgggaacgggcgttttattataaa |
| acagtgagaggtgaacgatgcgtaatgtgtgtattgccgttgctgtctttgccgcacttgcggtgacagtcactccggcccgtgcggaag |
| gtggacatggtacgtttacggtgggctattttcaagtgaaaccgggtacattgccgtcgttgtcgggcggggataccggtgtgagtcatct |
| gaaagggattaacgtgaagtaccgttatgagctgacggacagtgtgggggtgatggcttccctggggttcgccgcgtcgaaaaagagc |
| agcacagtgatgaccggggaggatacgtttcactatgagagcctgcgtggacgttatgtgagcgtgatggccggaccggttttacaaat |
| cagtaagcaggtcagtgcgtacgccatggccggagtggctcacagtcggtggtccggcagtacaatggattaccgtaagacggaaatc |
| actcccgggatcctctagagtcgacctgcaggcatgcaagcttggcgtaatcatggtcatagctgtttcctgtgtgaaattgttatccgctca |
| caattccacacaacatacgagccggaagcataaagtgtaaagcctggggtgcctaatgagtgagctaactcacattaattgcgttgcgct |

TABLE 5-continued

| Sequence of pSL-EGFP2. (SEQ ID NO: 33) |
|---|
| cactgcccgctttccagtcgggaaacctgtcgtgccagctgcattaatgaatcggccaacgcgcggggagaggcggtttgcgtattggg |
| cgctcttccgcttcctcgctcactgactcgctgcgctcggtcgttcggctgcggcgagcggtatcagctcactcaaaggcggtaatacgg |
| ttatccacagaatcaggggataacgcaggaaagaacatgtgagcaaaaggccagcaaaaggccaggaaccgtaaaaaggccgcgtt |
| gctggcgtttttccataggctccgcccccctgacgagcatcacaaaaatcgacgctcaagtcagaggtggcgaaacccgacaggactat |
| aaagataccaggcgtttccccctggaagctccctcgtgcgctctcctgttccgaccctgccgcttaccggatacctgtccgcctttctccct |
| tcgggaagcgtggcgctttctcatagctcacgctgtaggtatctcagttcggtgtaggtcgttcgctccaagctgggctgtgtgcacgaac |
| cccccgttcagcccgaccgctgcgccttatccggtaactatcgtcttgagtccaacccggtaagacacgacttatcgccactggcagcag |
| ccactggtaacaggattagcagagcgaggtatgtaggcggtgctacagagttcttgaagtggtggcctaactacggctacactagaagg |
| acagtatttggtatctgcgctctgctgaagccagttaccttcggaaaaagagttggtagctcttgatccggcaaacaaaccaccgctggta |
| gcggtggtttttttgtttgcaagcagcagattacgcgcagaaaaaaaggatctcaagaagatcctttgatcttttctacggggtctgacgctc |
| agtggaacgaaaactcacgttaagggattttggtcatgagattatcaaaaaggatcttcacctagatccttttaaattaaaaatgaagttttaa |
| atcaatctaaagtatatatgagtaaacttggtctgacagttaccaatgcttaatcagtgaggcacctatctcagcgatctgtctatttcgttcat |
| ccatagttgcctgactccccgtcgtgtagataactacgatacgggagggcttaccatctggccccagtgctgcaatgataccgcgagacc |
| cacgctcaccggctccagatttatcagcaataaaccagccagccggaagggccgagcgcagaagtggtcctgcaactttatccgcctc |
| catccagtctattaattgttgccgggaagctagagtaagtagttcgccagttaatagtttgcgcaacgttgttgccattgctacaggcatcgt |
| ggtgtcacgctcgtcgtttggtatggcttcattcagctccggttcccaacgatcaaggcgagttacatgatcccccatgttgtgcaaaaaag |
| cggttagctccttcggtcctccgatcgttgtcagaagtaagttggccgcagtgttatcactcatggttatggcagcactgcataattctcttac |
| tgtcatgccatccgtaagatgcttttctgtgactggtgagtactcaaccaagtcattctgagaatagtgtatgcggcgaccgagttgctcttg |
| cccggcgtcaatacgggataataccgcgccacatagcagaactttaaaagtgctcatcattggaaaacgttcttcggggcgaaaactctc |
| aaggatcttaccgctgttgagatccagttcgatgtaacccactcgtgcacccaactgatcttcagcatcttttactttcaccagcgtttctggg |
| tgagcaaaaacaggaaggcaaaatgccgcaaaaaagggaataagggcgacacggaaatgttgaatactcatactcttcctttttcaatat |
| tattgaagcatttatcagggttattgtctcatgagcggatacatatttgaatgtatttagaaaaataaacaaataggggttccgcgcacatttcc |
| ccgaaaagtgccacctgacgtctaagaaaccattattatcatgacattaacctataaaaataggcgtatcacgaggccctttcgtctcgcgc |
| gtttcggtgatgacggtgaaaacctctgacacatgcagctcccggagacggtcacagcttgtctgtaagcggatgccgggagcagaca |
| agcccgtcagggcgcgtcagcgggtgttggcgggtgtcggggctggcttaactatgcggcatcagagcagattgtactgagagtgcac |
| catatgcggtgtgaaataccgcacagatgcgtaaggagaaaataccgcatcaggcgccattcgccattcaggctgcgcaactgttggga |
| agggcgatcggtgcgggcctcttcgctattacgccagctggcgaaagggggatgtgctgcaaggcgattaagttgggtaacgccagg |
| gttttcccagtcacgacgttgtaaaacgacggccagtgaattcgattttaagatacattgatgagtttggacaaaccacaactagaatgcag |
| tgaaaaaaatgctttatttgtgaaatttgtgatgctattgctttatttgtaaccattataagctgcaataaacaagttaacaacaacaattgcattc |
| attttatgtttcaggttcagggggaggtgtgggaggttttttaaagcaagtaaaacctctacaaatgtggtatggctgattatgatcagttatct |
| agagtcgcggccgctttacttgtacagctcgtccatgccgagagtgatcccggcggcggtcacgaactccagcaggaccatgtgatcg |
| cgcttctcgttggggtctttgctcagggcggactgggtgctcaggtagtggttgtcgggcagcagcacggggccgtcgccgatgggg |
| tgttctgctggtagtggtcggcgagctgcacgctgccgtcctcgatgttgtggcggatcttgaagttcaccttgatgccgttcttctgcttgtc |
| ggccatgatatagacgttgtggctgttgtagttgtactccagcttgtgccccaggatgttgccgtcctccttgaagtcgatgcccttcagctc |
| gatgcggttcaccagggtgtcgccctcgaacttcacctcggcgcgggtcttgtagttgccgtcgtccttgaagaagatggtgcgctcctg |
| gacgtagccttcgggcatggcggacttgaagaagtcgtgctgcttcatgtggtcggggtagcggctgaagcactgcacgccgtaggtc |
| agggtggtcacgagggtgggccagggcacgggcagcttgccggtggtgcagatgaacttcagggtcagcttgccgtaggtggcatcg |
| ccctcgccctcgccggacacgctgaacttgtggccgtttacgtcgccgtccagctcgaccaggatgggcaccaccccggtgaacagct |
| cctcgcccttgctcaccatggtggcgaccggtggatcgatcctagcggatctgacggttcactaaaccagctctgcttatatagacctccc |

TABLE 5-continued

| Sequence of pSL-EGFP2. (SEQ ID NO: 33) |
|---|
| accgtacacgcctaccgcccatttgcgtcaatggggcggagttgttacgacattttggaaagtcccgttgattttggtgccaaaacaaactc |
| ccattgacgtcaatggggtggagacttggaaatccccgtgagtcaaaccgctatccacgcccattgatgtactgccaaaaccgcatcacc |
| atggtaatagcgatgactaatacgtagatgtactgccaagtaggaaagtcccataaggtcatgtactgggcataatgccaggcgggccat |
| ttaccgtcattgacgtcaatagggggcgtacttggcatatgatacacttgatgtactgccaagtgggcagtttaccgtaaatactccaccca |
| ttgacgtcaatggaaagtccctattggcgttactatgggaacatacgtcattattgacgtcaatgggcgggggtcgttgggcggtcagcca |
| ggcgggccatttaccgtaagttatgtaacgcggaactccatatatgggctatgaactaatgaccccgtaattgattactattaaatcactagt |
| gaattcgattaaagcgacggcacagctcgcggaaaatatcaaagtcgttgcgcgcctcgaactgcggcggcaccacctgtttcatggcg |
| ataatgccacggttggagtggttgccgtactggtcgagatcgttacgctcaaactgcgtggtcgcaggcagcacgatatcggcaaagcg |
| gcaggttgaggtccactggttatctatggcgataaccgtttccagcttgcgccagccttcaataatgcggttgatctgctgatggcgatgga |
| atgggttagttccggcaaaaatacacattttcagcggcggcagttttaccgatttaccgttccagttgatcactttccccggttcgaggatcg |
| catcgataaaacgggcaatcggaatggtgctgctgtagcctttgtaatcactgttgtcgtgaacaggcggaatcgacgtagagccggag |
| aaaccactcagaataacgcctttacgccccggcgtgcctgcgccgttatagtgccagccaaaaccaaagccaccacctggcaggccaa |
| tttgccccagcatcgccgccagaaccacaatcatccacgcccactgttcaccgtgctgcatacgctgcacgcaccagccagcaataattt |
| gcgttctgttcgccgccatctgccgcgccagcccacgaatggtttcggcatcaatgccggtcagtttttcagcccatgcggcatctttcgg |
| ctgaccgtctttctcacccagcaggtacggcaggaactgctcaaaacccacacagtagttagcgaggaagtttttgtcgtacaggttttca |
| ctgtacagcgtatacgccagcgccagttgcagcggcacatcagtttgcgggttaaccgcaatgtgcttcacatgctcgcgccccagatac |
| tcatgggtggatgtgacaaccggatcgatgctgatgacctcaatttcaccggcggtgactttcgcttttagctgcgcgtaatattcataaaca |
| tcgtgatccgggcaccaccagttcgcttgctggtttttcagcaaatcagagccccacagcacaatggttttgctgttctgcaataccagcgg |
| ccaggaggtttgctgttcatacacttccattgagccaaccacgcgcggcaggatcacctgcgcagcaccggtagagtaatctccgcccg |
| taccaacgctattaccatgcaaggcaatagctttcgccagcatccccgaagcgttatggaacatccccgtcgattgccaaccactggcgg |
| tcagcaaggcactcggcccgtgagttttctgcacgcgttccagttcttcatagaacatgtcgagggcttcatcccagctcacgcgcacaaa |
| acggttatcaccgcgctgggaggtatcgctgagatggcgcttacgcagccagtccacgcgtaccatcggataacgaatacgcgccgcg |
| ttgtgtacgtgatccggcaatccggcaatcattttcgacggatatttatccagttcgaacggttttgccgccacaaagcgaccatccttcacc |
| gtcgcgcggatagcccccagtgcgacccggtaagaatgccctctttcgagatgacagcctcagtcgccgcttgcgccgcagtcgcac |
| ggcgcggcgttaacaatgacggccccagcatcccggcgacggttaagccgccgagttgtgccagaaaacgccgacgtgatgcctga |
| aagagatcgttattgttcattatttttcttccttcttatcgccgtgagccttacctgcggtgtcagacgcattcatttgcagatatttcaacaaagt |
| gcgttcttcacgtttatcgagactggtaaagccaatcatgccgttgagcgtgccgatccaaccgttagcgtcaaagtgggcgatttccggt |
| gcgccgtggcactggttacaggtgccgttgtacaacgaatccgcataagcccagatcggtttgatatcgttcaccatgtcgcctttcttcat |
| ccacgcagtggcctgcaacttgctccactcggtattggtgtcggcaacggtggttttctccagcgtttttacctgctgctgcacatcaccac |
| gaatcgaggcaacaaagatgcgtttacctgggaattgggtgagtacacgctgacgtccggcgctttccgtccagccggtaatttcaatttg |
| cagccagtcgccgtcacgtttaaggactttcacttccgaagcaggcagcagagaaccagaggcttctttatcgcctttcgccgcataaatt |
| ggcttaatatcaatagagtacagcgtgtcaccactgtcattagcactggcgcgcagctcatcgaactgcttacggaagccgctactcatat |
| ccggtaactggtgggcaatacctttatgacagtcgatgcaggattgattatctttcgctgccaccttcatctgacgtgccgcttcaggatgct |
| gcttcgcatgatccatcgcatcgtagttatggcaggagcggcaggttgccgagttgttttctttcattcgcgcccattcacgctcggcaagtt |
| ccgcgcgtttggcttcgaatttttcaggtgtatcaatggagtgagcaataaaggtctggtagatatcattgctcgcttccagtttgcgcttcac |
| catgcctggaatatccggcgggatatgacagtcatggcattcagctcgcacgccggaggcgttctggaaatgcaccgactgtttatattct |
| tcatacaccggttgcatactgtggcaactgacacaaaattcggttgtgctggtgactttgatcccaacgtgtggcaatacaatcagcgcaat |
| gccaatcacaatcccaattgcgaccagcgccagtaccgaccaacgagcactgggtcggcgtagcgcgttccagagtttccgcataata |
| gcccctgtaaaattatggtttagtgaagcgatcttaatgagcaaatatgaacagcggcactggtcaggatgaacggcttacggcagaatat |

TABLE 5-continued

| Sequence of pSL-EGFP2. (SEQ ID NO: 33) |
| --- |
| gaacagatatgaacagaatgagtaaaaccctctgatgccacatcacattgttattgttgaagatgagccggttacccaggcgcgattacaa |
| tcttacttcactcaggaggggtataccgtttccgttacagcgagcggtgccgggctgcgggaaattatgcagaatcagccggtagatttaa |
| ttctgctggatatcaacttacccgatgaaaatggcctgatgttaacccgcgccctgcgagaacgctcaacggtggggattattctggttac |
| cggacgcagcgatcggattgaccgtattgttgggctggaaatgggcgcagacgattacgtcaccaaaccgctggaactgcgcgaactg |
| gtagtacgggtgaaaaatctgctctggcgaatcgacctcgcgcgacaagctcaaccgcacactcaggacaactgctatcgctttgccgg |
| ttattgcctgaatgtgtcgcgccatacgctggagcgggatggcgagccgattaaactgacccgcgcagagtatgaaatgttggtggcatt |
| tgtgacgaatccgggcgaaattctcagccgtgaacgtctgctacgtatgctttctgcgcgtcgggtggaaaaccctgacctgcgcaccgt |
| cgatgtgttaattcgtcgtttacgtcataaactcagcgcggatttactggtgacgcaacatggtgaaggttatttcttagccgctgatgtgtgc |
| tgataaaaatagaccggacgaaatcccccctggtgacagcgagcggcggatatgttctcggtcggcatttttcggcgtcagaactaaaatc |
| ggtgggctgacattatcagacaccgattgcccctgtaattgcctgatggcctgctcaactgccagttcccccctgccagaccatttgatcgct |
| ggcagccataatcactcttccccgcttcagcccgcgatacacctgatgtgaaagataaaacgacaccacggtaagcggcgttttcaggtt |
| acgcccttcacccattgccgcctctgccgcaatggccgttccggcaacgacgtcaatttctgggtggcgttccagcatctcctgcaacag |
| gttacgctggatttcaatatcgttatcaccaagcgcaatatcaacaatacgcaccgggcttccggcaatggctgcgcgaaaaccctcgac |
| catctctttactgcccccggcattatcgggtccgggcatcaacagcacgttcagtggtttaccgtgcgcccattgcaccaaatatcgccca |
| ggttgatagcccatctgaaaccagggtacaccaacgcggcttttcacctggggagcatcaatagcatttaccagttcgatcaccggcaga |
| cttgctacctgcttttgcagatcgggaaatgaggtcgtgctactaccgagtaaaatggcctctgcgccccactgtttacactggtcgatttgt |
| gcttgctgggtagccaactggctgtagccgcctgcctccagcacttttaaatccacaccatagcggcgagctgcctcctgcataccatagt |
| tcaacgataaccagtatgaatctttcaggctgggataaagcgcgcacagtttccatgcgcgtttggctttaagcggcatagaggcttgcac |
| cgtgaaatgctgcgcatcatgccagcgcaacaggttatcagccgaaaatgccggcaacatgaaaagggaaagaagtaaaaatagcag |
| tacgcgcatgatagcctcatcaataataaggctttatgctagatgcattccgctttgcgactcaacctttttcaccttaagtgcaccgaccgtg |
| aatttaaccctgacccgaagactctggatgggctttgccctgatggcgctgttaaccctgaccagtaccctggtgggatggtacaacctgc |
| gctttatcagccaggtggaaaaagacaacactcaggcattgattcctaccatgaatatggcgcgccagttgagcgaagccagcgcctgg |
| gaacttttcgccgcgcagaacctgaccagtgccgataacgaaaagatgtggcaggcgcaggggcgaatgctcaccgcacaaagcctg |
| aagattaatgcgttgctgcaagcgttacgggaacaaggttttgataccaccgctattgaacaacaggagcaggagatctcccgttcattac |
| gtcagcaaggggaactggtggggcggcgtctgcaactacgccagcaacaacggcaactcagtcagcagatagtcgctgccgccgat |
| gagatcgcacgcctggcgcaaggtcaggcgaataatgcgacaacttccgctggagcgacccaggccgggatttacgatttgatcgaac |
| aagatcagcgtcaggctgctgaaagtgcactcgatcggctgattgatatcgatcttgagtatgttaaccagatgaatgaactgcgccttag |
| cgctctgcgggtgcagcaaatggtgatgaatctggggctggagcagatccagaaaaatgcaccaacgctggaaaagcagctcaataat |
| gcggtgaaaattctgcaacgtcggcaaatacgcattgaagatccgggtgttcgtgcgcaggtcgcaacaacgttaactaccgttagcca |
| atatagcgatttgctggcgctgtatcagcaggacagtgaaatcagcaatcacctacaaactctcgcacaaaataacatcgcccagttcgc |
| gcagtttagtagcgaagtcagtcagctggtcgactcggtacccggggatccactcgttattctcggacgagtgttcagtaatgaacctctg |
| gagagaaccatgtatatgatcgttatctgggttggacttctgcttttaagcccagataactggcctgaatatgttaatgagagaatcggtattc |
| ctcatgtgtggcatgttttcgtctttgctcttgcattttcgctagcaattaatgtgcatcgattatcagctattgccagcgccagatataagcgat |
| ttaagctaagaaaacgcattaagatgcaaaacgataaagtgcgatcagtaattcaaaaccttacagaagagcaatctatggttttgtgcgc |
| agcccttaatgaaggcaggaagtatgtggttacatcaaaacaattcccatacattagtgagttgattgagcttggtgtgttgaacaaaactttt |
| tcccgatggaatggaaagcatatattattccctattgaggatatttactggactgaattagttgccagctatgatccatataatattgagataaa |
| gccaaggccaatatctaagtaactagataagaggaatcgatttcccttaatttctggcgtccactgcatgttatgccgcgttcgccaggct |
| tgctgtaccatgtgcgctgattcttgcgctcaatacgttgcaggttgctttcaatctgtttgtggtattcagccagcactgtaaggtctatcgga |
| tttagtgcgctttctactcgtgatttcggtttgcgattcagcgagagaatagggcggttaactggttttgcgcttaccccaaccaacaggga |

TABLE 5-continued

| Sequence of pSL-EGFP2. (SEQ ID NO: 33) |
| --- |
| tttgctgctttccattgagcctgtttctctgcgcgacgttcgcggcggcgtgtttgtgcatccatctggattctcctgtcagttagctttggtggt |
| gtgtggcagttgtagtcctgaacgaaaaccccccgcgattggcacattggcagctaatccggaatcgcacttacggccaatgcttcgtttc |
| gtatcacacaccccaaagccttctgctttgaatgctgcccttcttcagggcttaatttttaagagcgtcaccttcatggtggtcagtgcgtcct |
| gctgatgtgctcagtatcaccgccagtggtatttatgtcaacaccgccagagataatttatcaccgcagatggttatctgtatgtttttatatg |
| aatttatttttttgcaggggggcattgtttggtaggtgagagatctgaattgctatgtttagtgagttgtatctatttatttttcaataaatacaattg |
| gttatgtgttttgggggcgatcgtgaggcaaagaaaacccggcgctgaggccgggttattcttgttctctggtcaaattatatagttggaaa |
| acaaggatgcatatatgaatgaacgatgcagaggcaatgccgatggcgatagtgggtatcatgtagccgcttatgctggaaagaagcaa |
| taacccgcagaaaaacaaagctccaagctcaacaaaactaagggcatagacaataactaccgatgtcatatacccatactctctaatcttg |
| gccagtcggcgcgttctgcttccgattagaaacgtcaaggcagcaatcaggattgcaatcatggttcctgcatatgatgacaatgtcgccc |
| caagaccatctctatgagctgaaaaagaaacaccaggaatgtagtggcggaaaaggagatagcaaatgcttacgataacgtaaggaatt |
| attactatgtaaacaccaggcatgattctgttccgcataattactcctgataattaatccttaactttgcccacctgccttttaaaacattccagt |
| atatcacttttcattcttgcgtagcaatatgccatctcttcagctatctcagcattggtgaccttgttcagaggcgctgagagatggcctttttct |
| gatagataatgttctgttaaaatatctccggcctcatcttttgcccgcaggctaatgtctgaaaattgaggtgacgggttaaaaataatatcctt |
| ggcaaccttttttatatcccttttaaattttggcttaatgactatatccaatgagtcaaaaagctccccttcaatatctgttgcccctaagaccttt |
| aatatatcgccaaatacaggtagcttggcttctaccttcaccgttgttcggccgatgaaatgcatatgcataacatcgtctttggtggttcccc |
| tcatcagtggctctatctgaacgcgctctccactgcttaatgacattcctttcccgattaaaaaatctgtcagatcggatgtggtcggcccga |
| aaacagttctggcaaaaccaatggtgtcgccttcaacaaacaaaaaagatgggaatcccaatgattcgtcatctgcgaggctgttcttaat |
| atcttcaactgaagctttagagcgatttatcttctgaaccagactcttgtcatttgttttggtaaagagaaaagtttttccatcgattttatgaatat |
| acaaataattggagccaacctgcaggtgatgattatcagccagcagagaattaaggaaaacagacaggtttattgagcgcttatctttccc |
| tttatttttgctgcggtaagtcgcataaaaaccattcttcataattcaatccatttactatgttatgttctgaggggagtgaaaattcccctaattc |
| gatgaagattcttgctcaattgttatcagctatgcgccgaccagaacaccttgccgatcagccaaacgtctcttcaggccactgactagcg |
| ataactttccccacaacggaacaactctcattgcatgggatcattgggtactgtgggtttagtggttgtaaaaacacctgaccgctatccctg |
| atcagtttcttgaaggtaaactcatcacccccaagtctggctatgcagaaatcacctggctcaacagcctgctcagggtcaacgagaatta |
| acattccgtcaggaaagcttggcttggagcctgttggtgcggtcatggaattaccttcaacctcaagccagaatgcagaatcactggctttt |
| ttggttgtgcttacccatctctccgcatcacctttggtaaaggttctaagctcaggtgagaacatccctgcctgaacatgagaaaaaacagg |
| gtactcatactcacttctaagtgacggctgcatactaaccgcttcatacatctcgtagatttctctggcgattgaagggctaaattcttcaacg |
| ctaactttgagaatttttgcaagcaatgcggcgttataagcatttaatgcattgatgccattaaataaagcaccaacgcctgactgccccatc |
| cccatcttgtctgcgacagattcctgggataagccaagttcatttttctttttttcataaattgctttaaggcgacgtgcgtcctcaagctgctctt |
| gtgttaatggtttctttttttgtgctcatacgttaaatctatcaccgcaagggataaatatctaacaccgtgcgtgttgactattttacctctggcg |
| gtgataatggttgcatgtactaaggaggttgtatggaacaacgcataaccctgaaagattatgcaatgcgctttgggcaaaccaagacag |
| ctaaagatctcggcgtatatcaaagcgcgatcaacaaggccattcatgcaggccgaaagatttttttaactataaacgctgatggaagcgt |
| ttatgcggaagaggtaaagcccttcccgagtaacaaaaaaacaacagcataaataaccccgctcttacacattccagccctgaaaaagg |
| gcatcaaattaaaccacacctatggtgtatgcatttatttgcatacattcaatcaattgttatctaaggaaatacttacatatggttcgtgcaaac |
| aaacgcaacgaggctctacgaatcgagagtgcgttgcttaacaaaatcgcaatgcttggaactgagaagacagcggaagctgtgggcg |
| ttgataagtcgcagatcagcaggtggaagagggactggattccaaagttctcaatgctgcttgctgttcttgaatgggggtcgttgacga |
| cgacatggctcgattggcgcgacaagttgctgcgattctcaccaataaaaaacgcccggcggcaaccgagcgttctgaacaaatccag |
| atggagttctgaggtcattactggatctatcaacaggagtcattatgacaaatacagcaaaaatactcaacttcggcagaggtaactttgcc |
| ggacaggagcgtaatgtggcagatctcgatgatggttacgccagactatcaaatatgctgcttgaggcttattcgggcgcagatctgacc |
| aagcgacagtttaaagtgctgcttgccattctgcgtaaaacctatgggtggaataaaccaatggacagaatcaccgattctcaacttagcg |

TABLE 5-continued

| Sequence of pSL-EGFP2. (SEQ ID NO: 33) |
| --- |
| agattacaaagttacctgtcaaacggtgcaatgaagccaagttagaactcgtcagaatgaatattatcaagcagcaaggcggcatgtttg |
| gaccaaataaaaacatctcagaatggtgcatccctcaaaacgagggaaaatcccctaaaacgagggataaaacatccctcaaattggg |
| ggattgctatccctcaaaacagggggacacaaaagacactattacaaaagaaaaaagaaaagattattcgtcagannnnnntggcgaa |
| tcctctgaccagccagaaaacgacctttctgtggtgaaaccggatgctgcaattcagagcggcagcaagtgggggacagcagaagac |
| ctgaccgccgcagagtggatgtttgacatggtgaagactatcgcaccatcagccagaaaaccgaattttgctgggtgggctaacgatatc |
| cgcctgatgcgtgaacgtgacggacgtaaccaccgcgacatgtgtgtgctgttccgctgggcatgccaggacaacttctggtccggtaa |
| cgtgctgagcccggccaaactccgcgataagtggacccaactcgaaatcaaccgtaacaagcaacaggcaggcgtgacagccagca |
| aaccaaaactcgacctgacaaacacagactggatttacggggtggatctatgaaaaacatcgccgcacagatggttaactttgaccgtga |
| gcagatgcgtcggatcgccaacaacatgccggaacagtacgacgaaaagccgcaggtacagcaggtagcgcagatcatcaacggtg |
| tgttcagccagttactggcaactttcccggcgagcctggctaaccgtgaccagaacgaagtgaacgaaatccgtcgccagtgggttctg |
| gcttttcgggaaaacgggatcaccacgatggaacaggttaacgcaggaatgcgcgtagcccgtcggcagaatcgaccatttctgccatc |
| acccgggcagtttgttgcatggtgccgggaagaagcatccgttaccgccggactgccaaacgtcagcgagctggttgatatggtttacg |
| agtattgccggaagcgaggcctgtatccggatgcggagtcttatccgtggaaatcaaacgcgcactactggctggttaccaacctgtatc |
| agaacatgcgggccaatgcgcttactgatgcggaattacgccgtaaggccgcagatgagcttgtccatatgactgcgagaattaaccgt |
| ggtgaggcgatccctgaaccagtaaaacaacttcctgtcatgggcggtagacctctaaatcgtgcacaggctctggcgaagatcgcaga |
| aatcaaagctaagttcggactgaaaggagcaagtgtatgacgggcaaagaggcaattattcattacctggggacgcataatagcttctgt |
| gcgccggacgttgccgcgctaacaggcgcaacagtaaccagcataaatcaggccgcggctaaaatggcacgggcaggtcttctggtt |
| atcgaaggtaaggtctggcgaacggtgtattaccggtttgctaccagggaagaacgggaaggaaagatgagcgatgaacaaactggat |
| acgattggattcgacaacaaaaaagacctgcttatctcggtgggcgatttggttgatcgtggtgcagagaacgttgaatgcctggaattaa |
| tcacattcccctggttcagagctgtacgtggaaaccatgagcaaatgatgattgatggcttatcagagcgtggaaacgttaatcactggct |
| gcttaatggcggtggctggttctttaatctcgattacgacaaagaaattctggctaaagctcttgcccataaagcagatgaacttccgttaat |
| catcgaactggtgagcaaagataaaaaatatgttatctgccacgccgattatccctttgacgaatacgagtttggaaagccagttgatcatc |
| agcaggtaatctggaaccgcgaacgaatcagcaactcacaaaacgggatcgtgaaagaaatcaaaggcgcggacacgttcatctttgg |
| tcatacgccagcagtgaaaccactcaagtttgccaaccaaatgtatatcgataccggcgcagtgttctgcggaaacctaacattgattcag |
| gtacagggagaaggcgcatgagactcgaaagcgtagctaaatttcattcgccaaaaagcccgatgatgagcgactcaccacgggcca |
| cggcttctgactctctttccggtactgatgtgatggctgctatggggatggcgcaatcacaagccggattcggtatggctgcattctgcggt |
| aagcacgaactcagccagaacgacaaacaaaaggctatcaactatctgatgcaatttgcacacaaggtatcggggaaataccgtggtgt |
| ggcaaagcttgaaggaaatactaaggcaaaggtactgcaagtgctcgcaacattcgcttatgcggattattgccgtagtgccgcgacgc |
| cgggggcaagatgcagagattgccatggtacaggccgtgcggttgatattgccaaaacagagctgtgggggagagttgtcgagaaag |
| agtgcggaagatgcaaaggcgtcggctattcaaggatgccagcaagcgcagcatatcgcgctgtgacgatgctaatcccaaaccttac |
| ccaacccacctggtcacgcactgttaagccgctgtatgacgctctggtggtgcaatgccacaaagaagagtcaatcgcagacaacatttt |
| gaatgcggtcacacgttagcagcatgattgccacggatggcaacatattaacggcatgatattgacttattgaataaaattgggtaaatttg |
| actcaacgatgggttaattcgctcgttgtggtagtgagatgaaaagaggcggcgcttactaccgattccgcctagttggtcacttcgacgt |
| atcgtctggaactccaaccatcgcaggcagagaggtctgcaaaatgcaatcccgaaacagttcgcaggtaatagttagagcctgcataa |
| cggtttcgggatttttttatatctgcacaacaggtaagagcattgagtcgataatcgtgaagagtcggcgagcctggttagccagtgctctttc |
| cgttgtgctgaattaagcgaataccggaagcagaaccggatcaccaaatgcgtacaggcgtcatcgccgcccagcaacagcacaacc |
| caaactgagccgtagccactgtctgtcctnnnnnnattagtaatagttacgctgcggccttttacacatgaccttcgtgaaagcgggtggc |
| aggaggtcgcgctaacaacctcctgccgttttgcccgtgcatatcggtcacgaacaaatctgattactaaacacagtagcctggatttgttc |
| tatcagtaatcgaccttattcctaattaaatagagcaaatccccttattgggggtaagacatgaagatgccagaaaaacatgacctgttggc |

TABLE 5-continued

| Sequence of pSL-EGFP2. (SEQ ID NO: 33) |
|---|
| cgccattctcgcggcaaaggaacaaggcatcggggcaatccttgcgtttgcaatggcgtaccttcgcggcagatataatggcggtgcgt |
| ttacaaaaacagtaatcgacgcaacgatgtgcgccattatcgcctggttcattcgtgaccttctcgacttcgccggactaagtagcaatctc |
| gcttatataacgagcgtgtttatcggctacatcggtactgactcgattggttcgcttatcaaacgcttcgctgctaaaaaagccggagtaga |
| agatggtagaaatcaataatcaacgtaaggcgttcctcgatatgctggcgtggtcggagggaactgataacggacgtcagaaaaccag |
| aaatcatggttatgacgtcattgtaggcggagagctatttactgattactccgatcaccctcgcaaacttgtcacgctaaacccaaaactca |
| aatcaacaggcgccggacgctaccagcttctttcccgttggtgggatgcctaccgcaagcagcttggcctgaaagacttctctccgaaaa |
| gtcaggacgctgtggcattgcagcagattaaggagcgtggcgctttacctatgattgatcgtggtgatatccgtcaggcaatcgaccgttg |
| cagcaatatctgggcttcactgccgggcgctggttatggtcagttcgagcataaggctgacagcctgattgcaaaattcaaagaagcgg |
| gcggaacggtcagagagattgatgtatgagcagagtcaccgcgattatctccgctctggttatctgcatcatcgtctgcctgtcatgggct |
| gttaatcattaccgtgataacgccattacctacaaagcccagcgcgacaaaaatgccagagaactgaagctggcgaacgcggcaattac |
| tgacatgcagatgcgtcagcgtgatgttgctgcgctcgatgcaaaatacacgaaggagttagctgatgctaaagctgaaaatgatgctct |
| gcgtgatgatgttgccgctggtcgtcgtcggttgcacatcaaagcagtctgtcagtcagtgcgtgaagccaccaccgcctccggcgtgg |
| ataatgcagcctccccccgactggcagacaccgctgaacgggattatttcaccctcagagagaggctgatcactatgcaaaaacaactg |
| gaaggaacccagaagtatattaatgagcagtgcagatagagttgcccatatcgatgggcaactcatgcaattattgtgagcaatacacac |
| gcgcttccagcggagtataaatgcctaaagtaataaaaccgagcaatccatttacgaatgtttgctgggtttctgttttaacaacattttctgc |
| gccgccacaaatttggctgcatcgacagttttcttctgcccaattccagaaacgaagaaatgatgggtgatggtttcctttggtgctactgc |
| tgccggtttgttttgaacagtaaacgtctgttgagcacatcctgtaataagcagggccagcgcagtagcgagtagcatttttttcatggtgtt |
| attcccgatgctttttgaagttcgcagaatcgtatgtgtagaaaattaaacaaaccctaaacaatgagttgaaatttcatattgttaatatttatta |
| atgtatgtcaggtgcgatgaatcgtcattgtattcccggattaactatgtccacagccctgacggggaacttctctgcgggagtgtccggg |
| aataattaaaacgatgcacacagggtttagcgcgtacacgtattgcattatgccaacgccccggtgctgacacggaagaaaccggacgt |
| tatgatttagcgtggaaagatttgtgtagtgttctgaatgctctcagtaaatagtaatgaattatcaaaggtatagtaatatcttttatgttcatgg |
| atatttgtaacccatcggaaaactcctgctttagcaagattttccctgtattgctgaaatgtgatttctcttgatttcaacctatcataggacgttt |
| ctataagatgcgtgtttcttgagaatttaacatttacaaccttttttaagtccttttattaacacggtgttatcgttttctaacacgatgtgaatattat |
| ctgtggctagatagtaaatataatgtgagacgttgtgacgttttagttcagaataaaacaattcacagtctaaatcttttcgcacttgatcgaat |
| atttctttaaaaatggcaacctgagccattggtaaaaccttccatgtgatacgagggcgcgtagtttgcattatcgtttttatcgtttcaatctgg |
| tctgacctccttgtgttttgttgatgatttatgtcaaatattaggaatgttttcacttaatagtattggttgcgtaacaaagtgcggtcctgctggc |
| attctggagggaaatacaaccgacagatgtatgtaaggccaacgtgctcaaatcttcatacagaaagatttgaagtaatattttaaccgcta |
| gatgaagagcaagcgcatggagcgacaaaatgaataaagaacaatctgctgatgatccctccgtggatctgattcgtgtaaaaaatatgc |
| ttaatagcaccatttctatgagttaccctgatgttgtaattgcatgtatagaacataaggtgtctctggaagcattcagagcaattgaggcagc |
| gttggtgaagcacgataataatatgaaggattattccctggtggttgactgatcaccataactgctaatcattcaaactatttagtctgtgaca |
| gagccaacacgcagtctgtcactgtcaggaaagtggtaaaactgcaactcaattactgcaatgccctcgtaattaagtgaatttacaatatc |
| gtcctgttcggagggaagaacgcgggatgttcattcttcatcacttttaattgatgtatatgctctcttttctgacgttagtctccgacggcagg |
| cttcaatgacccaggctgagaaattcccggacccttttttgctcaagagcgatgttaatttgttcaatcatttggttaggaaagcggatgttgc |
| gggttgttgttctgcgggttctgttcttcgttgacatgaggttgccccgtattcagtgtcgctgatttgtattgtctgaagttgtttttacgttaagt |
| tgatgcagatcaattaatacgatacctgcgtcataattgattatttgacgtggtttgatggcctccacgcacgttgtgatatgtagatgataatcattatc |
| actttacgggtcctttccggtgatccgacaggttacg |

TABLE 6

| Sequence of pTn-I-Sce2-PsapLuxAB-Cm1. (SEQ ID NO: 34) |
|---|
| tcgcgcgtttcggtgatgacggtgaaaacctctgacacatgcagctcccggagacggtcacagcttgtctgtaagcggatgccgggag |
| cagacaagcccgtcagggcgcgtcagcgggtgttggcgggtgtcggggctggcttaactatgcggcatcagagcagattgtactgag |
| agtgcaccatatgcggtgtgaaataccgcacagatgcgtaaggagaaaataccgcatcaggcgccattcgccattcaggctgcgcaac |
| tgttgggaagggcgatcggtgcgggcctcttcgctattacgacagctgtctcttatacacatctcaaccatcatcgatgaattttctcgggta |
| gggataacagggtaatgaattgaaattacgccccgccctgccactcatcgcagtactgttgtaattcattaagcattctgccgacatggaa |
| gccatcacagacggcatgatgaacctgaatcgccagcggcatcagcaccttgtcgccttgcgtataatatttgcccatggtgaaaacggg |
| ggcgaagaagttgtccatattggccacgtttaaatcaaaactggtgaaactcacccagggattggctgagacgaaaaacatattctcaata |
| aaccctttagggaaataggccaggttttcaccgtaacacgccacatcttgcgaatatatgtgtagaaactgccggaaatcgtcgtggtattc |
| actccagagcgatgaaaacgtttcagtttgctcatggaaaacggtgtaacaagggtgaacactatcccatatcaccagctcaccgtctttc |
| attgccatacggaattccggatgagcattcatcaggcgggcaagaatgtgaataaaggccggataaaacttgtgcttatttttctttacggtc |
| tttaaaaaggccgtaatatccagctgaacggtctggttataggtacattgagcaactgactgaaatgcctcaaaatgttctttacgatgccat |
| tgggatatatcaacggtggtatatccagtgatttttttctccattttagcttccttagctccagatctatggatcgctcgaaaaaatcaaatcatc |
| aatttctgagcttgctgtaatttcttgtttatcaacatatgaagtcatacctgttttactcctcaagataatattagaaagtatggcagcactgctgtcata |
| ctcttttataccctttcatctttcaagctgctgctttgttggctgctttcactcaccccagtcacatagttatctatgctcctggggattcgtt |
| cacttgccgcctcgctgcaactcgaaatctattaggtatattccatgtggtacttcttaatattatcatcaacaatattgattacatttttttggctc |
| atcaaatcattcattggttcaaaggacagcaatacacttttcgcaccacacttttcaattgccaacttagccgcagttatacactccgtataatt |
| tccgacagcgttttctgcaattatttcttcaagtttattttcgaaattttcattagggtgcatttcaagaacataatcactaataaatgcacgcgtc |
| tcttgtttagctttattactatcttcgttatagttaactaatatcattaactgatggtctatctctgataggtcaacgtcatatttatccgcaacggct |
| ttatatctttcagcatattcatatctaacatcattagaatcatcccacttaaagatgagaggaatacctttttttggccgcccactcaacaatatga |
| tgactggttgctgttacatatttccgaggtccgcctggcgtataagcatggggatttacagatattttagggaagctataaaaatcgttatctg |
| gattacaatagcctgttgttaaagcatcgttaatgatttcataacactcttcaaatagttgctgttgatattcaaccgggcgattaaaaaaatgc |
| atttcatctttttttttcgcaatcactaaaccctaaaataaatctcccttcacttaactgatccaataagcaagcttcctccgctatggcgacagg |
| atgatgagttgtaatgatgtgatttaatgaaccaattttaattttctctgttaaaccgagcagaaaaccagaaacagtcagaggagcgccga |
| caacaccattatctgaaaaatgattttcatacactaaaatctgttcaaaattcaacttatcaacatactccgttatttcctgcatgcgaactatac |
| tttgttcttgaacagttgttgaattgatgaagttaaggaagaacaatccaaatttcatttctttctccttagctaatataatagcgaacgttgtttttt |
| ctttaagaaatggcatgacatcagactggaagagcttcatggaagcaataatttcgtctactgttccattagcttcaaatccacaacaaatatt |
| tgatattcctgtagcatcaatgtctttttgaattatgtcaatacattcctgcggcgttcccacgggattgatttcgtaactgtaatcaatacggcg |
| attagtatctttatgtccttttaatacaaagtcacgccactgccctttattgaaatcataacctcttgtttggtctgaatcatcaaaaatagtcgta |
| gcattcacataagaatcataccaatgccccagaaatttccggcaaatctctttcgctttaattgagtcatgatctacagatgttatatatgataa |
| gcaatggtcgatattatgaatatcgtgcccatattcttgagccacttcattataaagctcaagttgtgctttcttttcgttagtatttataatccaac |
| ttaatatcatcggtaggccaaattgagcagcccactcagtcgtcgaagctgattcagccaccacataaaccggtgcgccacctctgctata |
| cgccgcggggtttacttttaccttatggaacttgatatgttcattatcagcttccatatatccctctgtcatgccattctttatcagcccgtacca |
| gcattccgctaaggcgcgactgttattcatatctgtgccgaatacgcgaaagtccttgttgtaaagccctcggcaaataccaaaccgaaat |
| cgtccttttgacatttgatccaataaattcacatcttcaagttggcgtactggatgggctgtgggaagaacaatagcggcagttcctacattc |
| aatttttagtcgcgccaagtaaatatgcagcagcgacataagggttaccaagcaaaccaaactccgtgaaatgatgctccagtaaccata |
| cggtatcaaaaccacactcctcagagatgcgacctaatttaaccaaacgtttcattacctctgtttgagaaaattggggaggttggtatgtaa |
| gcaaaaagtttccaaatttcatagagagtccttatattgctatttgagtgatagaatatctcaatagattttaagacagagaaattgcttgatttt |
| caatctcaattctcattcggcgttcattgactgtcgcaatagttaaatgttcaaatgacggttcagtaatatcaacatcaatatccagatgatca |
| ttatccatcgtactgcgcgaattataacataatttttttataaaattcaaatttatgcaggcatgcaagtcgacattaccctgttatccctactgca |

TABLE 6-continued

| Sequence of pTn-I-Sce2-PsapLuxAB-Cm1. (SEQ ID NO: 34) |
| --- |
| ggcatgcaagcttgccaacgactacgcactagccaacaagagcttcagggttgagatgtgtataagagacagctgtcttaatgaatcgg |
| ccaacgcgcggggagaggcggtttgcgtattgggcgctcttccgcttcctcgctcactgactcgctgcgctcggtcgttcggctgcggc |
| gagcggtatcagctcactcaaaggcggtaatacggttatccacagaatcaggggataacgcaggaaagaacatgtgagcaaaaggcc |
| agcaaaaggccaggaaccgtaaaaaggccgcgttgctggcgtttttccataggctccgcccccctgacgagcatcacaaaaatcgacg |
| ctcaagtcagaggtggcgaaacccgacaggactataaagataccaggcgtttccccctggaagctccctcgtgcgctctcctgttccga |
| ccctgccgcttaccggatacctgtccgcctttctcccttcgggaagcgtggcgctttctcatagctcacgctgtaggtatctcagttcggtgt |
| aggtcgttcgctccaagctgggctgtgtgcacgaaccccccgttcagcccgaccgctgcgccttatccggtaactatcgtcttgagtcca |
| acccggtaagacacgacttatcgccactggcagcagccactggtaacaggattagcagagcgaggtatgtaggcggtgctacagagtt |
| cttgaagtggtggcctaactacggctacactagaaggacagtatttggtatctgcgctctgctgaagccagttaccttcggaaaaagagtt |
| ggtagctcttgatccggcaaacaaaccaccgctggtagcggtggtttttttgtttgcaagcagcagattacgcgcagaaaaaaaggatctc |
| aagaagatcctttgatcttttctacggggtctgacgctcagtggaacgaaaactcacgttaagggattttggtcatgagattatcaaaaagg |
| atcttcacctagatccttttaaattaaaaatgaagttttaaatcaatctaaagtatatatgagtaaacttggtctgacagttaccaatgcttaatca |
| gtgaggcacctatctcagcgatctgtctatttcgttcatccatagttgcctgactccccgtcgtgtagataactacgatacgggagggcttac |
| catctggccccagtgctgcaatgataccgcgagacccacgctcaccggctccagatttatcagcaataaaccagccagccggaagggc |
| cgagcgcagaagtggtcctgcaactttatccgcctccatccagtctattaattgttgccgggaagctagagtaagtagttcgccagttaata |
| gtttgcgcaacgttgttgccattgctacaggcatcgtggtgtcacgctcgtcgtttggtatggcttcattcagctccggttcccaacgatcaa |
| ggcgagttacatgatcccccatgttgtgcaaaaaagcggttagctccttcggtcctccgatcgttgtcagaagtaagttggccgcagtgtta |
| tcactcatggttatggcagcactgcataattctcttactgtcatgccatccgtaagatgcttttctgtgactggtgagtactcaaccaagtcatt |
| ctgagaatagtgtatgcggcgaccgagttgctcttgcccggcgtcaatacgggataataccgcgccacatagcagaactttaaaagtgct |
| catcattggaaaacgttcttcggggcgaaaactctcaaggatcttaccgctgttgagatccagttcgatgtaacccactcgtgcacccaact |
| gatcttcagcatcttttactttcaccagcgtttctgggtgagcaaaaacaggaaggcaaaatgccgcaaaaaagggaataagggcgaca |
| cggaaatgttgaatactcatactcttcctttttcaatattattgaagcatttatcagggttattgtctcatgagcggatacatatttgaatgtattta |
| gaaaaataaacaaataggggttccgcgcacatttccccgaaaagtgccacctgacgtctaagaaaccattattatcatgacattaacctataaaa |
| ataggcgtatcacgaggccctttcgtc |

TABLE 7

| Sequence of M13LuxABE2 (SEQ ID NO: 1). Sequences encoding luciferase subunits are shown in underline. |
| --- |
| aatgctactactattagtagaattgatgccaccttttcagctcgcgccccaaatgaaaatatagctaaacaggttattgaccatttgcgaaat |
| gtatctaatggtcaaactaaatctactcgttcgcagaattgggaatcaactgttacatggaatgaaacttccagacaccgtactttagttgcat |
| atttaaaacatgttgagctacagcaccagattcagcaattaagctctaagccatccgcaaaaatgacctcttatcaaaaggagcaattaaa |
| ggtactctctaatcctgacctgttggagtttgcttccggtctggttcgctttgaagctcgaattaaaacgcgatatttgaagtctttcgggcttc |
| ctcttaatctttttgatgcaatccgctttgcttctgactataatagtcagggtaaagacctgatttttgatttatggtcattctcgttttctgaactgtt |
| taaagcatttgaggggattcaatgaatatttatgacgattccgcagtattggacgctatccagtctaaacattttactattaccccctctggc |
| aaaacttcttttgcaaaagcctctcgctattttggtttttatcgtcgtctggtaaacgagggttatgatagtgttgctcttactatgcctcgtaattc |
| cttttggcgttatgtatctgcattagttgaatgtggtattcctaaatctcaactgatgaatctttctacctgtaataatgttgttccgttagttcgtttt |
| attaacgtagatttttcttcccaacgtcctgactggtataatgagccagttcttaaaatcgcataaggtaattcacaatgattaaagttgaaatt |
| aaaccatctcaagcccaatttactactcgttctggtgtttctcgtcagggcaagccttattcactgaatgagcagctttgttacgttgatttggg |
| taatgaatatccggttcttgtcaagattactcttgatgaaggtcagccagcctatgcgcctggtctgtacaccgttcatctgtcctctttcaaag |

TABLE 7-continued

| Sequence of M13LuxABE2 (SEQ ID NO: 1). Sequences encoding luciferase subunits are shown in underline. |
|---|
| ttggtcagttcggttcccttatgattgaccgtctgcgcctcgttccggctaagtaacatggagcaggtcgcggatttcgacacaatttatcag |
| gcgatgatacaaatctccgttgtactttgtttcgcgcttggtataatcgctgggggtcaaagatgagtgttttagtgtattctttcgcctctttcgt |
| tttaggttggtgccttcgtagtggcattacgtattttacccgtttaatggaaacttcctcatgaaaaagtctttagtcctcaaagcctctgtagcc |
| gttgctaccctcgttccgatgctgtctttcgctgctgagggtgacgatcccgcaaaagcggcctttaactccctgcaagcctcagcgaccg |
| aatatatcggttatgcgtgggcgatggttgttgtcattgtcggcgcaactatcggtatcaagctgtttaagaaattcacctcgaaagcaagct |
| gataaaccgatacaattaaaggctccttttggagcctttttttttggagattttcaacgtgaaaaaattattattcgcaattcctttagttgttccttt |
| ctattctcactccgctgaaactgttgaaagttgtttagcaaaaccccatacagaaaattcatttactaacgtctggaaagacgacaaaacttt |
| agatcgttacgctaactatgagggttgtctgtggaatgctacaggcgttgtagtttgtactggtgacgaaactcagtgttacggtacatgggt |
| tcctattgggcttgctatccctgaaaatgagggtggtggctctgagggtggcggttctgagggtggcggttctgagggtggcggtactaa |
| acctcctgagtacggtgatacacctattccgggctatacttatatcaaccctctcgacggcacttatccgcctggtactgagcaaaacccc |
| gctaatcctaatccttctcttgaggagtctcagcctcttaatactttcatgtttcagaataataggttccgaaataggcagggggcattaactgt |
| ttatacgggcactgttactcaaggcactgaccccgttaaaacttattaccagtacactcctgtatcatcaaaagccatgtatgacgcttactg |
| gaacggtaaattcagagactgcgctttccattctggctttaatgaagatccattcgtttgtgaatatcaaggccaatcgtctgacctgcctca |
| acctcctgtcaatgctggcggcggctctggtggtggttctggtggcggctctgagggtggtggctctgagggtggcggttctgagggtg |
| gcggctctgagggaggcggttccggtggtggctctggttccggtgattttgattatgaaaagatggcaaacgctaataagggggctatga |
| ccgaaaatgccgatgaaaacgcgctacagtctgacgctaaaggcaaacttgattctgtcgctactgattacggtgctgctatcgatggtttc |
| attggtgacgtttccggccttgctaatggtaatggtgctactggtgattttgctggctctaattcccaaatggctcaagtcggtgacggtgata |
| attcacctttaatgaataatttccgtcaatatttaccttccctccctcaatcggttgaatgtcgcccttttgtctttagcgctggtaaaccatatga |
| attttctattgattgtgacaaaataaacttattccgtggtgtctttgcgtttcttttatatgttgccacctttatgtatgtattttctacgtttgctaacat |
| actgcgtaataaggagtcttaatcatgccagttcttttgggtattccgttattattgcgtttcctcggtttccttctggtaactttgttcggctatct |
| gcttacttttcttaaaaagggcttcggtaagatagctattgctatttcattgtttcttgctcttattattgggcttaactcaattcttgtgggttatctc |
| tctgatattagcgctcaattaccctctgactttgttcagggtgttcagttaattctcccgtctaatgcgcttccctgtttttatgttattctctctgta |
| aaggctgctattttcatttttgacgttaaacaaaaaatcgtttcttatttggattgggataaataatatggctgtttattttgtaactggcaaattag |
| gctctggaaagacgctcgttagcgttggtaagattcaggataaaattgtagctgggtgcaaaatagcaactaatcttgatttaaggcttcaa |
| aacctcccgcaagtcgggaggttcgctaaaacgcctcgcgttcttagaataccggataagccttctatatctgatttgcttgctattgggcg |
| cggtaatgattcctacgatgaaaataaaaacggcttgcttgttctcgatgagtgcggtacttggtttaatacccgttcttggaatgataagga |
| aagacagccgattattgattggtttctacatgctcgtaaattaggatgggatattatttttcttgttcaggacttatctattgttgataaacaggcg |
| cgttctgcattagctgaacatgttgtttattgtcgtcgtctggacagaattactttaccttttgtcggtactttatattctcttattactggctcgaaa |
| atgcctctgcctaaattacatgttggcgttgttaaatatggcgattctcaattaagccctactgttgagcgttggctttatactggtaagaatttg |
| tataacgcatatgatactaaacaggctttttctagtaattatgattccggtgtttattcttatttaacgccttatttatcacacggtcggtatttcaaa |
| ccattaaatttaggtcagaagatgaaattaactaaaatatatttgaaaaagttttctcgcgttctttgtcttgcgattggatttgcatcagcattta |
| catatagttatataacccaacctaagccggaggttaaaaaggtagtctctcagacctatgattttgataaattcactattgactcttctcagcgt |
| cttaatctaagctatcgctatgttttcaaggattctaagggaaaattaattaatagcgacgatttacagaagcaaggttattcactcacatatat |
| tgatttatgtactgtttccattaaaaaaggtaattcaaatgaaattgttaaatgtaattaattttgttttcttgatgtttgtttcatcatcttcttttgctc |
| aggtaattgaaatgaataattcgcctctgcgcgattttgtaacttggtattcaaagcaatcaggcgaatccgttattgtttctcccgatgtaaaa |
| ggtactgttactgtatattcatctgacgttaaacctgaaaatctacgcaatttctttatttctgttttacgtgctaataattttgatatggttggttca |
| attccttccataattcagaagtataatccaaacaatcaggattatattgatgaattgccatcatctgataatcaggaatatgatgataattccgc |
| tccttctggtggtttctttgttccgcaaaatgataatgttactcaaacttttaaaattaataacgttcgggcaaaggatttaatacgagttgtcga |
| attgtttgtaaagtctaatacttctaaatcctcaaatgtattatctattgacggctctaatctattagttgttagtgcacctaaagatattttagataa |

TABLE 7-continued

Sequence of M13LuxABE2 (SEQ ID NO: 1). Sequences encoding luciferase subunits are shown in underline.

ccttcctcaattcctttctactgttgatttgccaactgaccagatattgattgagggtttgatatttgaggttcagcaaggtgatgctttagatttttt catttgctgctggctctcagcgtggcactgttgcaggcggtgttaatactgaccgcctcacctctgttttatcttctgctggtggttcgttcggt atttttaatggcgatgttttagggctatcagttcgcgcattaaagactaatagccattcaaaaatattgtctgtgccacgtattcttacgctttca ggtcagaagggttctatctctgttggccagaatgtcccttttattactggtcgtgtgactggtgaatctgccaatgtaaataatccatttcagac gattgagcgtcaaaatgtaggtatttccatgagcgtttttcctgttgcaatggctggcggtaatattgttctggatattaccagcaaggccgat agtttgagttcttctactcaggcaagtgatgttattactaatcaaagaagtattgctacaacggttaatttgcgtgatggacagactcttttactc ggtggcctcactgattataaaaacacttctcaagattctggcgtaccgttcctgtctaaaatccctttaatcggcctcctgtttagctcccgctc tgattccaacgaggaaagcacgttatacgtgctcgtcaaagcaaccatagtacgcgccctgtagcggcgcattaagcgcggcgggtgt ggtggttacgcgcagcgtgaccgctacacttgccagcgccctagcgcccgctcctttcgctttcttcccttcctttctcgccacgttcgccg gctttccccgtcaagctctaaatcgggggctccctttagggttccgatttagtgctttacggcacctcgaccccaaaaaacttgatttgggtg atggttcacgtagtgggccatcgccctgatagacggtttttcgccctttgacgttggagtccacgttctttaatagtggactcttgttccaaac tggaacaacactcaaccctatctcgggctattcttttgatttataagggattttgccgatttcggaaccaccatcaaacaggattttcgcctgc tggggcaaaccagcgtggaccgcttgctgcaactctctcagggccaggcggtgaagggcaatcagctgttgcccgtctcgctggtgaa aagaaaaaccaccctggcgcccaatacgcaaaccgcctctccccgcgcgttggccgattcattaatgcagctggcacgacaggtttccc gactggaaagcgggcagtgagcgcaacgcaattaatgtgagttagctcactcattaggcaccccaggctttacactttatgcttccggctc gtatgttgtgtggaattgtgagcggataacaatttcacacaggaaacagctatgaccatgattacgaattcactagtgattatggtaaagca agatgaagttatcacattgttatcaaatattcgtagtaatcgatgcaagatatattctttgttaggaagttcgcatgacttgagtgaaaatttagt ggtcctgcgcaatttttatcaatcggttacgaaagccgctatcgcgatggataatgatcatctggatattgatgttgatattactgaaccgtca tttgaacatttaactattgcgacagtcaatgaacgccgaatgagaattgagattgaaaatcaagcaatttctctgtcttaaaatctattgagata ttctatcactcaaatagcaatataaggactctctatgaaatttggaaactttttgcttacataccaacctccccaatttctcaaacagaggtaat gaaacgtttggttaaattaggtcgcatctctgaggagtgtggttttgataccgtatggttactggagcatcatttcacggagtttggtttgcttg gtaacccttatgtcgctgctgcatatttacttggcgcgactaaaaaattgaatgtaggaactgccgctattgttcttcccacagcccatccagt acgccaacttgaagatgtgaatttattggatcaaatgtcaaaaggacgatttcggtttggtatttgccgagggctttacaacaaggactttcg cgtattcggcacagatatgaataacagtcgcgccttagcggaatgctggtacgggctgataaagaatggcatgacagagggatatatgg aagctgataatgaacatatcaagttccataaggtaaaagtaaaccccgcggcgtatagcagaggtggcgcaccggtttatgtggtggctg aatcagcttcgacgactgagtgggctgctcaatttggcctaccgatgatattaagttggattataaatactaacgaaaagaaagcacaactt gagctttataatgaagtggctcaagaatatgggcacgatattcataatatcgaccattgcttatcatatataacatctgtagatcatgactcaat taaagcgaaagagatttgccggaaatttctggggcattggtatgattcttatgtgaatgctacgactatttttgatgattcagaccaaacaag aggttatgatttcaataaagggcagtggcgtgactttgtattaaaaggacataaagatactaatcgccgtattgattacagttacgaaatcaa tcccgtgggaacgccgcaggaatgtattgacataattcaaaaagacattgatgctacaggaatatcaaatatttgttgtggatttgaagcta atggaacagtagacgaaattattgcttccatgaagctcttccagtctgatgtcatgccatttcttaaagaaaaacaacgttcgctattatattag ctaaggagaaagaaatgaaatttggattgttcttccttaacttcatcaattcaacaactgttcaagaacaaagtatagttcgcatgcaggaaa taacggagtatgttgataagttgaattttgaacagattttagtgtatgaaaatcatttttcagataatggtgttgtcggcgctcctctgactgtttc tggttttctgctcggtttaacagagaaaattaaaattggttcattaaatcacatcattacaactcatcatcctgtcgccatagcggaggaagct tgcttattggatcagttaagtgaagggagatttattttagggtttagtgattgcgaaaaaaaagatgaaatgcatttttttaatcgcccggttga atatcaacagcaactatttgaagagtgttatgaaatcattaacgatgctttaacaacaggctattgtaatccagataacgattttttatagcttcc ctaaaatatctgtaaatccccatgcttatacgccaggcggacctcggaaatatgtaacagcaaccagtcatcatattgttgagtgggcggc caaaaaaggtattcctctcatctttaagtgggatgattctaatgatgttagatatgaatatgctgaaagatataaagccgttgcggataaatat gacgttgacctatcagagatagaccatcagttaatgatattagttaactataacgaagatagtaataaagctaaacaagagacgcgtgcatt TABLE 7-continued

| Sequence of M13LuxABE2 (SEQ ID NO: 1). Sequences encoding luciferase subunits are shown in underline. |
|---|
| tattagtgattatgttcttgaaatgcaccctaatgaaaatttcgaaaataaacttgaagaaataattgcagaaaacgctgtcggaaattatacg |
| gagtgtataactgcggctaagttggcaattgaaaagtgtggtgcgaaaagtgtattgctgtcctttgaaccaatgaatgatttgatgagcca |
| aaaaaatgtaatcaatattgttgatgataatattaagaagtaccacatggaatatacctaatagatttcgagttgcagcgaggcggcaagtg |
| aacgaatccccaggagcatagataactatgtgactggggtgagtgaaagcagccaacaaagcagcagcttgaaagatgaagggtata |
| aaagagtatgacagcagtgctgccatactttctaatattatcttgaggagtaaaacaggtatgacttcatatgttgataaacaagaaattaca |
| gcaagctcagaaattgatgatttgatttttcgagcgatccattagtgtggtcttacgacgagcaggaaaaaatcagaaagaaacttgtgctt |
| gatgcatttcgtaatcattataaacattgtcgagaatatcgtcactactgtcaggcacacaaagtagatgacaatattacggaaattgatgac |
| atacctgtattcccaacatcggtttttaagtttactcgcttattaacttctcaggaaaacgagattgaaagttggtttaccagtagcggcacga |
| atggtttaaaaagtcaggtggcgcgtgacagattaagtattgagagactcttaggctctgtgagttatggcatgaaatatgttggtagttggt |
| ttgatcatcaaatagaattagtcaatttgggaccagatagatttaatgctcataatatttggtttaaatatgttatgagtttggtggaattgttatat |
| cctacgacatttaccgtaacagaagaacgaatagatttgttaaaacattgaatagtcttgaacgaataaaaaatcaagggaaagatctttgt |
| cttattggttcgccatactttatttatttactctgccattatatgaaagataaaaaaatctcattttctggagataaaagcctttatatcataaccgg |
| aggcggctggaaaagttacgaaaaagaatctctgaaacgtgatgatttcaatcatcttttatttgatactttcaatctcagtgatattagtcaga |
| tccgagatatatttaatcaagttgaactcaacacttgtttctttgaggatgaaatgcagcgtaaacatgttccgccgtgggtatatgcgcgag |
| cgcttgatcctgaaacgttgaaacctgtacctgatggaacgccggggttgatgagttatatggatgcgtcagcaaccagttatccagcattt |
| attgttaccgatgatgtcgggataattagcagagaatatggtaagtatcccggcgtgctcgttgaaattttacgtcgcgtcaatacgaggac |
| gcagaaagggtgtgctttaagcttaaaccaagcatttaatagttgacataatcgaattcccgggagagctcgatatcgcatgcggtacctct |
| agaagaagcttgggatccgtcgacctgcagcaattcactggccgtcgttttacaacgtcgtgactgggaaaaccctggcgttacccaact |
| taatcgccttgcagcacatccccctttcgccagctggcgtaatagcgaagaggcccgcaccgatcgcccttcccaacagttgcgcagcc |
| tgaatggcgaatggcgctttgcctggtttccggcaccagaagcggtgccggaaagctggctggagtgcgatcttcctgaggccgatac |
| ggtcgtcgtcccctcaaactggcagatgcacggttacgatgcgcccatctacaccaacgtaacctatcccattacggtcaatccgccgttt |
| gttcccacggagaatccgacgggttgttactcgctcacatttaatgttgatgaaagctggctacaggaaggccagacgcgaattatttttga |
| tggcgttcctattggttaaaaaatgagctgatttaacaaaaatttaacgcgaattttaacaaaatattaacgtttacaatttaaatatttgcttata |
| caatcttcctgtttttggggcttttctgattatcaaccggggtacatatgattgacatgctagttttacgattaccgttcatcgattctcttgtttgct |
| ccagactctcaggcaatgacctgatagcctttgtagatctctcaaaaatagctaccctctccggcattaatttatcagctagaacggttgaat |
| atcatattgatggtgatttgactgtctccggcctttctcacccttttgaatctttacctacacattactcaggcattgcatttaaaatatatgaggg |
| ttctaaaaatttttatccttgcgttgaaataaaggcttctcccgcaaaagtattacagggtcataatgtttttggtacaaccgatttagctttatgc |
| tctgaggctttattgcttaattttgctaattctttgccttgcctgtatgatttattggatgtt |

TABLE 8

| Sequence of T71-2aLuxAB (SEQ ID NO: 2). Sequences encoding luciferase subunits are shown in underline. |
|---|
| tctcacagtgtacggacctaaagttcccccatagggggtacctaaagcccagccaatcacctaaagtcaaccttcggttgaccttgaggg |
| ttccctaagggttggggatgacccttgggtttgtctttgggtgttaccttgagtgtctctctgtgtccctatctgttacagtctcctaaagtatcct |
| cctaaagtcacctcctaacgtccatcctaaagccaacacctaaagcctacacctaaagacccatcaagtcaacgcctatcttaaagtttaa |
| acataaagaccagacctaaagaccagacctaaagacactacataaagaccagacctaaagacgccttgttgttagccataaagtgataa |
| cctttaatcattgtctttattaatacaactcactataaggagagacaacttaaagagacttaaaagattaatttaaaatttatcaaaaagagtatt |
| gacttaaagtctaacctataggatacttacagccatcgagagggacacggcgaatagccatcccaatcgacaccggggtcaaccggat |
| aagtagacagcctgataagtcgcacgacagaaagaaattgaccgcgctaaggcccgtaaagaacgtcacgaggggcgcttagaggc |

TABLE 8-continued

| Sequence of T71-2aLuxAB (SEQ ID NO: 2). Sequences encoding luciferase subunits are shown in underline. |
|---|
| acgcagattcaaacgtcgcaaccgcaaggcacgtaaagcacacaaagctaagcgcgaaagaatgcttgctgcgtggcgatgggctga |
| acgtcaagaacggcgtaaccatgaggtagctgtagatgtactaggaagaaccaataacgctatgctctgggtcaacatgttctctgggga |
| ctttaaggcgcttgaggaacgaatcgcgctgcactggcgtaatgctgaccggatggctatcgctaatggtcttacgctcaacattgataag |
| caacttgacgcaatgttaatgggctgatagtcttatcttacaggtcatctgcgggtggcctgaataggtacgatttactaactggaagaggc |
| actaaatgaacacgattaacatcgctaagaacgacttctctgacatcgaactggctgctatcccgttcaacactctggctgaccattacggt |
| gagcgtttagctcgcgaacagttggcccttgagcatgagtcttacgagatgggtgaagcacgcttccgcaagatgtttgagcgtcaactta |
| aagctggtgaggttgcggataacgctgccgccaagcctctcatcactaccctactccctaagatgattgcacgcatcaacgactggtttga |
| ggaagtgaaagctaagcgcggcaagcgcccgacagccttccagttcctgcaagaaatcaagccggaagccgtagcgtacatcaccat |
| taagaccactctggcttgcctaaccagtgctgacaatacaaccgttcaggctgtagcaagcgcaatcggtcgggccattgaggacgagg |
| ctcgcttcggtcgtatccgtgaccttgaagctaagcacttcaagaaaaacgttgaggaacaactcaacaagcgcgtagggcacgtctac |
| aagaaagcatttatgcaagttgtcgaggctgacatgctctctaagggtctactcggtggcgaggcgtggtcttcgtggcataaggaagac |
| tctattcatgtaggagtacgctgcatcgagatgctcattgagtcaaccggaatggttagcttacaccgccaaaatgctggcgtagtaggtc |
| aagactctgagactatcgaactcgcacctgaatacgctgaggctatcgcaacccgtgcaggtgcgctggctggcatctctccgatgttcc |
| aaccttgcgtagttcctcctaagccgtggactggcattactggtggtggctattgggctaacggtcgtcgtcctctggcgctggtgcgtact |
| cacagtaagaaagcactgatgcgctacgaagacgtttacatgcctgaggtgtacaaagcgattaacattgcgcaaaacaccgcatggaa |
| aatcaacaagaaagtcctagcggtcgccaacgtaatcaccaagtggaagcattgtccggtcgaggacatccctgcgattgagcgtgaa |
| gaactcccgatgaaaccggaagacatcgacatgaatcctgaggctctcaccgcgtggaaacgtgctgccgctgctgtgtaccgcaagg |
| acaaggctcgcaagtctcgccgtatcagccttgagttcatgcttgagcaagccaataagtttgctaaccataaggccatctggttcccttac |
| aacatggactggcgcggtcgtgtttacgctgtgtcaatgttcaacccgcaaggtaacgatatgaccaaaggactgcttacgctggcgaaa |
| ggtaaaccaatcggtaaggaaggttactactggctgaaaatccacggtgcaaactgtgcgggtgtcgataaggttccgttccctgagcg |
| catcaagttcattgaggaaaaccacgagaacatcatggcttgcgctaagtctccactggagaacacttggtgggctgagcaagattctcc |
| gttctgcttccttgcgttctgctttgagtacgctggggtacagcaccacggcctgagctataactgctcccttccgctggcgtttgacgggtc |
| ttgctctggcatccagcacttctccgcgatgctccgagatgaggtaggtggtcgcgcggttaacttgcttcctagtgaaaccgttcaggac |
| atctacgggattgttgctaagaaagtcaacgagattctacaagcagacgcaatcaatgggaccgataacgaagtagttaccgtgaccgat |
| gagaacactggtgaaatctctgagaaagtcaagctgggcactaaggcactggctggtcaatggctggcttacggtgttactcgcagtgtg |
| actaagcgttcagtcatgacgctggcttacgggtccaaagagttcggcttccgtcaacaagtgctggaagataccattcagccagctattg |
| attccggcaagggtctgatgttcactcagccgaatcaggctgctggatacatggctaagctgatttgggaatctgtgagcgtgacggtggt |
| agctgcggttgaagcaatgaactggcttaagtctgctgctaagctgctggctgctgaggtcaaagataagaagactggagagattcttcg |
| caagcgttgcgctgtgcattgggtaactcctgatggtttccctgtgtggcaggaatacaagaagcctattcagacgcgcttgaacctgatg |
| ttcctcggtcagttccgcttacagcctaccattaacaccaacaaagatagcgagattgatgcacacaaacaggagtctggtatcgctccta |
| actttgtacacagccaagacggtagccaccttcgtaagactgtagtgtgggcacacgagaagtacggaatcgaatcttttgcactgattca |
| cgactccttcggtaccattccggctgacgctgcgaacctgttcaaagcagtgcgcgaaactatggttgacacatatgagtcttgtgatgta |
| ctggctgatttctacgaccagttcgctgaccagttgcacgagtctcaattggacaaaatgccagcacttccggctaaaggtaacttgaacc |
| tccgtgacatcttagagtcggacttcgcgttcgcgtaacgccaaatcaatacgactcactatagagggacaaactcaaggtcattcgcaa |
| gagtggcctttatgattgaccttcttccggttaatacgactcactataggagaaccttaaggtttaactttaagacccttaagtgttaattagag |
| atttaaattaaagaattactaagagaggactttaagtatgcgtaacttcgaaaagatgaccaaacgttctaaccgtaatgctcgtgacttcga |
| ggcaaccaaaggtcgcaagttgaataagactaagcgtgaccgctctcacaagcgtagctgggagggtcagtaagatgggacgtttatat |
| agtggtaatctggcagcattcaaggcagcaacaaacaagctgttccagttagacttagcggtcatttatgatgactggtatgatgcctatac |
| aagaaaagattgcatacggttacgtattgaggacaggagtggaaacctgattgatactagcaccttctaccaccacgacgaggacgttct |

TABLE 8-continued

| Sequence of T71-2aLuxAB (SEQ ID NO: 2). Sequences encoding luciferase subunits are shown in underline. |
|---|
| gttcaatatgtgtactgattggttgaaccatatgtatgaccagttgaaggactggaagtaatacgactcagtatagggacaatgcttaaggt |
| cgctctctaggagtggccttagtcatttaaccaataggagataaacattatgatgaacattaagactaacccgtttaaagccgtgtctttcgta |
| gagtctgccattaagaaggctctggataacgctgggtatcttatcgctgaaatcaagtacgatggtgtacgcgggaacatctgcgtagac |
| aatactgctaacagttactggctctctcgtgtatctaaaacgattccggcactggagcacttaaacgggtttgatgttcgctggaagcgtcta |
| ctgaacgatgaccgttgcttctacaaagatggctttatgcttgatggggaactcatggtcaagggcgtagactttaacacagggtccggcc |
| tactgcgtaccaaatggactgacacgaagaaccaagagttccatgaagagttattcgttgaaccaatccgtaagaaagataaagttccctt |
| taagctgcacactggacaccttcacataaaactgtacgctatcctcccgctgcacatcgtggagtctggagaagactgtgatgtcatgacg |
| ttgctcatgcaggaacacgttaagaacatgctgcctctgctacaggaatacttccctgaaatcgaatggcaagcggctgaatcttacgag |
| gtctacgatatggtagaactacagcaactgtacgagcagaagcgagcagaaggccatgagggtctcattgtgaaagacccgatgtgtat |
| ctataagcgcggtaagaaatctggctggtggaaaatgaaacctgagaacgaagctgacggtatcattcagggtctggtatggggtacaa |
| aaggtctggctaatgaaggtaaagtgattggttttgaggtgcttcttgagagtggtcgtttagttaacgccacgaatatctctcgcgccttaat |
| ggatgagttcactgagacagtaaaagaggccaccctaagtcaatggggattctttagcccatacggtattggcgacaacgatgcttgtact |
| attaacccttacgatggctgggcgtgtcaaattagctacatggaggaaacacctgatggctctttgcggcacccatcgttcgtaatgttccg |
| tggcaccgaggacaaccctcaagagaaaatgtaatcacactggctcaccttcgggtgggcctttctgcgtttataaggagacactttatgtt |
| taagaaggttggtaaattccttgcggctttggcagctatcctgacgcttgcgtatattcttgcggtataccctcaagtagcactagtagtagtt |
| ggcgcttgttacttagcggcagtgtgtgcttgcgtgtggagtatagttaactggtaatacgactcactaaaggaggtacacaccatgatgta |
| cttaatgccattactcatcgtcattgtaggatgccttgcgctccactgtagcgatgatgatatgccagatggtcacgcttaatacgactcact |
| aaaggagacactatatgtttcgacttcattacaacaaaagcgttaagaatttcacggttcgccgtgctgaccgttcaatcgtatgtgcgagc |
| gagcgccgagctaagatacctcttattggtaacacagttcctttggcaccgagcgtccacatcattatcacccgtggtgactttgagaaag |
| caatagacaagaaacgtccggttcttagtgtggcagtgacccgcttcccgttcgtccgtctgttactcaaacgaatcaaggaggtgttctg |
| atgggactgttagatggtgaagcctgggaaaaagaaaacccgccagtacaagcaactgggtgtatagcttgcttagagaaagatgacc |
| gttatccacacacctgtaacaaaggagctaacgatatgaccgaacgtgaacaagagatgatcattaagttgatagacaataatgaaggtc |
| gcccagatgatttgaatggctgcggtattctctgctccaatgtcccttgccacctctgccccgcaaataacgatcaaaagataaccttaggt |
| gaaatccgagcgatggacccacgtaaaccacatctgaataaacctgaggtaactcctacagatgaccagccttccgctgagacaatcga |
| aggtgtcactaagccttcccactacatgctgtttgacgacattgaggctatcgaagtgattgctcgttcaatgaccgttgagcagttcaagg |
| gatactgcttcggtaacatcttaaagtacagactacgtgctggtaagaagtcagagttagcgtacttagagaaagacctagcgaaagcag |
| acttctataaagaactctttgagaaacataaggataaatgttatgcataacttcaagtcaaccccacctgccgacagcctatctgatgacttc |
| acatcttgctcagagtggtgccgaaagatgtgggaagagacattcgacgatgcgtacatcaagctgtatgaactttggaaatcgagaggt |
| caatgactatgtcaaacgtaaatacaggttcacttagtgtggacaataagaagttttgggctaccgtagagtcctcggagcattccttcgag |
| gttccaatctacgctgagaccctagacgaagctctggagttagccgaatggcaatacgttccggctggctttgaggttactcgtgtgcgtc |
| cttgtgtagcaccgaagtaatacgactcactattagggaagactccctctgagaaaccaaacgaaacctaaaggagattaacattatggct |
| aagaagattttcacctctgcgctgggtaccgctgaaccttacgcttacatcgccaagccggactacggcaacgaagagcgtggctttgg |
| gaaccctcgtggtgtctataaagttgacctgactattcccaacaaagacccgcgctgccagcgtatggtcgatgaaatcgtgaagtgtca |
| cgaagaggcttatgctgctgccgttgaggaatacgaagctaatccacctgctgtagctcgtggtaagaaaccgctgaaaccgtatgagg |
| gtgacatgccgttcttcgataacggtgacggtacgactacctttaagttcaaatgctacgcgtctttccaagacaagaagaccaaagagac |
| caagcacatcaatctggttgtggttgactcaaaaggtaagaagatggaagacgttccgattatcggtggtggctctaagctgaaagttaaa |
| tattctctggttccatacaagtggaacactgctgtaggtgcgagcgttaagctgcaactggaatccgtgatgctggtcgaactggctacctt |
| tggtggcggtgaagacgattgggctgacgaagttgaagagaacggctatgttgcctctggttctgccaaagcgagcaaaccacgcgac |
| gaagaaagctgggacgaagacgacgaagagtccgaggaagcagacgaagacggagacttctaagtggaactgcgggagaaaatcc |

TABLE 8-continued

Sequence of T71-2aLuxAB (SEQ ID NO: 2). Sequences encoding luciferase subunits are shown in underline.

ttgagcgaatcaaggtgacttcctctgggtgttgggagtggcagggcgctacgaacaataaagggtacgggcaggtgtggtgcagcaa taccggaaaggttgtctactgtcatcgcgtaatgtctaatgctccgaaaggttctaccgtcctgcactcctgtgataatccattatgttgtaac cctgaacacctatccataggaactccaaaagagaactccactgacatggtaaataagggtcgctcacacaaggggtataaactttcagac gaagacgtaatggcaatcatggagtccagcgagtccaatgtatccttagctcgcacctatggtgtctcccaacagactatttgtgatatacg caaagggaggcgacatggcaggttacggcgctaaaggaatccgaaaggttggagcgtttcgctctggcctagaggacaaggtttcaaa gcagttggaatcaaaaggtattaaattcgagtatgaagagtggaaagtgccttatgtaattccggcgagcaatcacacttacactccagac ttcttacttccaaacggtatattcgttgagacaaagggtctgtgggaaagcgatgatagaaagaagcacttattaattagggagcagcacc ccgagctagacatccgtattgtcttctcaagctcacgtactaagttatacaaaggttctccaacgtcttatggagagttctgcgaaaagcatg gtattaagttcgctgataaactgatacctgctgagtggataaaggaacccaagaaggaggtcccctttgatagattaaaaaggaaaggag gaaagaaataatggctcgtgtacagtttaaacaacgtgaatctactgacgcaatctttgttcactgctcggctaccaagccaagtcagaatg ttggtgtccgtgagattcgccagtggcacaaagagcagggttggctcgatgtgggataccactttatcatcaagcgagacggtactgtgg aggcaggacgagatgagatggctgtaggctctcacgctaagggttacaaccacaactctatcggcgtctgccttgttggtggtatcgacg ataaaggtaagttcgacgctaactttacgccagcccaaatgcaatcccttcgctcactgcttgtcacactgctggctaagtacgaaggcgc tggtcttcgcgcccatcatgaggtggcgccgaaggcttgcccttcgttcgaccttaagcgttggtgggagaagaacgaactggtcacttc tgaccgtggataatgatctattggaagtcgttgcgtggatttatagaactaggagggaattgcatggacaattcgcacgattccgatagtgt atttctttaccacattccttgtgacaactgtgggagtagtgatgggaactcgctgttctctgacggacacacgttctgctacgtatgcgagaa gtggactgctggtaatgaagacactaaagagagggcttcaaaacggaaaccctcaggaggtaaaccaatgacttacaacgtgtggaac ttcggggaatccaatggacgctactccgcgttaactgcgagaggaatctccaaggaaacctgtcagaaggctggctactggattgccaa agtagacggtgtgatgtaccaagtggctgactatcgggaccagaacggcaacattgtgagtcagaaggttcgagataaagataagaact ttaagaccactggtagtcacaagagtgacgctctgttcgggaagcacttgtggaatggtggtaagaagattgtcgttacagaaggtgaaa tcgacatgcttaccgtgatggaacttcaagactgtaagtatcctgtagtgtcgttgggtcacggtgcctctgccgctaagaagacatgcgct gccaactacgaatactttgaccagttcgaacagattatcttaatgttcgatatggacgaagcagggcgcaaagcagtcgaagaggctgca caggttctacctgctggtaaggtacgagtggcagttcttccgtgtaaggatgcaaacgagtgtcacctaaatggtcacgaccgtgaaatc atggagcaagtgtggaatgctggtccttggattcctgatggtgtggtatcggctctttcgttacgtgaacgaatccgtgagcacctatcgtc cgaggaatcagtaggtttacttttcagtggctgcactggtatcaacgataagaccttaggtgcccgtggtggtgaagtcattatggtcacttc cggttccggtatgggtaagtcaacgttcgtccgtcaacaagctctacaatggggcacagcgatgggcaagaaggtaggcttagcgatg cttgaggagtccgttgaggagaccgctgaggaccttataggtctacacaaccgtgtccgactgagacaatccgactcactaaagagaga gattattgagaacggtaagttcgaccaatggttcgatgaactgttcggcaacgatacgttccatctatatgactcattcgccgaggctgaga cggatagactgctcgctaagctggcctacatgcgctcaggcttgggctgtgacgtaatcattctagaccacatctcaatcgtcgtatccgct tctggtgaatccgatgagcgtaagatgattgacaacctgatgaccaagctcaaagggttcgctaagtcaactggggtggtgctggtcgta atttgtcaccttaagaacccagacaaaggtaaagcacatgaggaaggtcgccccgtttctattactgacctacgtggttctggcgcactac gccaactatctgatactattattgcccttgagcgtaatcagcaaggcgatatgcctaaccttgtcctcgttcgtattctcaagtgccgctttact ggtgatactggtatcgctggctacatggaatacaacaaggaaaccggatggcttgaaccatcaagttactcaggggaagaagagtcaca ctcagagtcaacagactggtccaacgacactgacttctgacaggattcttgacagttgtttcatatgaagagattgttaagtcacgataatca ataggagaaatcaatatgatcgtttctgacatcgaagctaacgccctcttagagagcgtcactaagttccactgcggggttatctacgacta ctccaccgctgagtacgtaagctaccgtccgagtgacttcggtgcgtatctggatgcgctggaagccgaggttgcacgaggcggtcttat tgtgttccacaacggtcacaagtatgacgttcctgcattgaccaaactggcaaagttgcaattgaaccgagagttccaccttcctcgtgag aactgtattgacacccttgtgttgtcacgtttgattcattccaacctcaaggacaccgatatgggtcttctgcgttccggcaagttgcccgga TABLE 8-continued

| Sequence of T71-2aLuxAB (SEQ ID NO: 2). Sequences encoding luciferase subunits are shown in underline. |
|---|
| aaacgctttgggtctcacgctttggaggcgtggggttatcgcttaggcgagatgaagggtgaatacaaagacgactttaagcgtatgcttg |
| aagagcagggtgaagaatacgttgacggaatggagtggtggaacttcaacgaagagatgatggactataacgttcaggacgttgtggta |
| actaaagctctccttgagaagctactctctgacaaacattacttccctcctgagattgactttacggacgtaggatacactacgttctggtca |
| gaatcccttgaggccgttgacattgaacatcgtgctgcatggctgctcgctaaacaagagcgcaacgggttcccgtttgacacaaaagca |
| atcgaagagttgtacgtagagttagctgctcgccgctctgagttgctccgtaaattgaccgaaacgttcggctcgtggtatcagcctaaag |
| gtggcactgagatgttctgccatccgcgaacaggtaagccactacctaaataccctcgcattaagacacctaaagttggtggtatctttaa |
| gaagcctaagaacaaggcacagcgagaaggccgtgagccttgcgaacttgatacccgcgagtacgttgctggtgctccttacacccca |
| gttgaacatgttgtgtttaacccttcgtctcgtgaccacattcagaagaaactccaagaggctgggtgggtcccgaccaagtacaccgata |
| agggtgctcctgtggtggacgatgaggtactcgaaggagtacgtgtagatgaccctgagaagcaagccgctatcgacctcattaaaga |
| gtacttgatgattcagaagcgaatcggacagtctgctgagggagacaaagcatggcttcgttatgttgctgaggatggtaagattcatggt |
| tctgttaaccctaatggagcagttacgggtcgtgcgacccatgcgttcccaaaccttgcgcaaattccgggtgtacgttctccttatggaga |
| gcagtgtcgcgctgcttttggcgctgagcaccatttggatgggataactggtaagccttgggttcaggctggcatcgacgcatccggtctt |
| gagctacgctgcttggctcacttcatggctcgctttgataacggcgagtacgctcacgagattcttaacggcgacatccacactaagaacc |
| agatagctgctgaactacctacccgagataacgctaagacgttcatctatgggttcctctatggtgctggtgatgagaagattggacagatt |
| gttggtgctggtaaagagcgcggtaaggaactcaagaagaaattccttgagaacacccccgcgattgcagcactccgcgagtctatcca |
| acagacacttgtcgagtcctctcaatgggtagctggtgagcaacaagtcaagtggaaacgccgctggattaaaggtctggatggtcgta |
| aggtacacgttcgtagtcctcacgctgccttgaatacccactgcaatctgctggtgctctcatctgcaaactgtggattatcaagaccgaa |
| gagatgctcgtagagaaaggcttgaagcatggctgggatggggactttgcgtacatggcatgggtacatgatgaaatccaagtaggctg |
| ccgtaccgaagagattgctcaggtggtcattgagaccgcacaagaagcgatgcgctgggttggagaccactggaacttccggtgtcttc |
| tggataccgaaggtaagatgggtcctaattgggcgatttgccactgatacaggaggctactcatgaacgaaagacacttaacaggtgctg |
| cttctgaaatgctagtagcctacaaatttaccaaagctgggtacactgtctattaccctatgctgactcagagtaaagaggacttggttgtat |
| gtaaggatggtaaatttagtaaggttcaggttaaaacagccacaacggttcaaaccaacacaggagatgccaagcaggttaggctaggt |
| ggatgcggtaggtccgaatataaggatggagactttgacattcttgcggttgtggttgacgaagatgtgcttattttcacatgggacgaagt |
| aaaaggtaagacatccatgtgtgtcggcaagagaaacaaaggcataaaactataggagaaattattatggctatgacaaagaaatttaaa |
| gtgtccttcgacgttaccgcaaagatgtcgtctgacgttcaggcaatcttagagaaagatatgctgcatctatgtaagcaggtcggctcag |
| gtgcgattgtccccaatggtaaacagaaggaaatgattgtccagttcctgacacacggtatggaaggattgatgacattcgtagtacgtac |
| atcatttcgtgaggccattaaggacatgcacgaagagtatgcagataaggactctttcaaacaatctcctgcaacagtacggaggtgttc |
| tgatgtctgactacctgaaagtgctgcaagcaatcaaaagttgccctaagactttccagtccaactatgtacggaacaatgcgagcctcgt |
| agcggaggccgcttcccgtggtcacatctcgtgcctgactactagtggacgtaacggtggcgcttgggaaatcactgcttccggtactcg |
| ctttctgaaacgaatgggaggatgtgtctaatgtctcgtgaccttgtgactattccacgcgatgtgtggaacgatatacagggctacatcga |
| ctctctggaacgtgagaacgatagccttaagaatcaactaatggaagctgacgaatacgtagcggaactagaggagaaacttaatggca |
| cttcttgaccttaaacaattctatgagttacgtgaaggctgcgacgacaagggtatccttgtgatggacggcgactggctggtcttccaagc |
| tatgagtgctgctgagtttgatgcctcttgggaggaagagatttggcaccgatgctgtgaccacgctaaggcccgtcagattcttgaggat |
| tccattaagtcctacgagacccgtaagaaggcttgggcaggtgctccaattgtccttgcgttcaccgatagtgttaactggcgtaaagaac |
| tggttgacccgaactataaggctaaccgtaaggccgtgaagaaacctgtagggtactttgagttccttgatgctctctttgagcgcgaaga |
| gttctattgcatccgtgagcctatgcttgagggtgatgacgttatgggagttattgcttccaatccgtctgccttcggtgctcgtaaggctgta |
| atcatctcttgcgataaggactttaagaccatccctaactgtgacttcctgtggtgtaccactggtaacatcctgactcagaccgaagagtc |
| cgctgactggtggcacctcttccagaccatcaagggtgacatcactgatggttactcagggattgctggatggggtgataccgccgagg |
| acttcttgaataacccgttcataaccgagcctaaaacgtctgtgcttaagtccggtaagaacaaaggccaagaggttactaaatgggttaa |

TABLE 8-continued

| Sequence of T71-2aLuxAB (SEQ ID NO: 2). Sequences encoding luciferase subunits are shown in underline. |
|---|
| acgcgaccctgagcctcatgagacgctttgggactgcattaagtccattggcgcgaaggctggtatgaccgaagaggatattatcaagc |
| agggccaaatggctcgaatcctacggttcaacgagtacaactttattgacaaggagatttacctgtggagaccgtagcgtatattggtctg |
| ggtctttgtgttctcggagtgtgcctcatttcgtggggcctttgggacttagccagaataatcaagtcgttacacgacactaagtgataaact |
| caaggtccctaaattaatacgactcactatagggagataggggcctttacgattattactttaagatttaactctaagaggaatctttattatgtt |
| aacacctattaaccaattacttaagaaccctaacgatattccagatgtacctcgtgcaaccgctgagtatctacaggttcgattcaactatgc |
| gtacctcgaagcgtctggtcatataggacttatgcgtgctaatggttgtagtgaggcccacatcttgggtttcattcagggcctacagtatgc |
| ctctaacgtcattgacgagattgagttacgcaaggaacaactaagagatgatggggaggattgacactatgtgtttctcaccgaaaattaa |
| aactccgaagatggataccaatcagattcgagccgttgagccagcgcctctgacccaagaagtgtcaagcgtggagttcggtgggtctt |
| ctgatgagacggataccgagggcaccgaagtgtctggacgcaaaggcctcaaggtcgaacgtgatgattccgtagcgaagtctaaag |
| ccagcggcaatggctccgctcgtatgaaatcttccatccgtaagtccgcatttggaggtaagaagtgatgtctgagttcacatgtgtggag |
| gctaagagtcgcttccgtgcaatccggtggactgtggaacaccttgggttgcctaaaggattcgaaggacactttgtgggctacagcctct |
| acgtagacgaagtgatggacatgtctggttgccgtgaagagtacattctggactctaccggaaaacatgtagcgtacttcgcgtggtgcg |
| taagctgtgacattcaccacaaaggagacattctggatgtaacgtccgttgtcattaatcctgaggcagactctaagggcttacagcgattc |
| ctagcgaaacgctttaagtaccttgcggaactccacgattgcgattgggtgtctcgttgtaagcatgaaggcgagacaatgcgtgtatactt |
| taaggaggtataagttatgggtaagaaagttaagaaggccgtgaagaaagtcaccaagtccgttaagaaagtcgttaaggaaggggctc |
| gtccggttaaacaggttgctggcggtctagctggtctggctggtggtactggtgaagcacagatggtggaagtaccacaagctgccgca |
| cagattgttgacgtacctgagaaagaggtttccactgaggacgaagcacagacagaaagcggacgcaagaaagctcgtgctggcggt |
| aagaaatccttgagtgtagcccgtagctccggtggcggtatcaacatttaatcaggaggttatcgtggaagactgcattgaatggaccgg |
| aggtgtcaactctaagggttatggtcgtaagtgggttaatggtaaacttgtgactccacataggcacatctatgaggagacatatggtcca |
| gttccaacaggaattgtggtgatgcatatctgcgataaccctaggtgctataacataaagcaccttacgcttggaactccaaaggataattc |
| cgaggacatggttaccaaaggtagacaggctaaaggagaggaactaagcaagaaacttacagagtcagacgttctcgctatacgctctt |
| caaccttaagccaccgctccttaggagaactgtatggagtcagtcaatcaaccataacgcgaatactacagcgtaagacatggagacac |
| atttaatggctgagaaacgaacaggacttgcggaggatggcgcaaagtctgtctatgagcgtttaaagaacgaccgtgctccctatgaga |
| cacgcgctcagaattgcgctcaatataccatcccatcattgttccctaaggactccgataacgcctctacagattatcaaactccgtggcaa |
| gccgtgggcgctcgtggtctgaacaatctagcctctaagctcatgctggctctattccctatgcagacttggatgcgacttactatatctgaa |
| tatgaagcaaagcagttactgagcgaccccgatggactcgctaaggtcgatgagggcctctcgatggtagagcgtatcatcatgaacta |
| cattgagtctaacagttaccgcgtgactctctttgaggctctcaaacagttagtcgtagctggtaacgtcctgctgtacctaccggaaccgg |
| aagggtcaaactataatcccatgaagctgtaccgattgtcttcttatgtggtccaacgagacgcattcggcaacgttctgcaaatggtgact |
| cgtgaccagatagcttttggtgctctccctgaggacatccgtaaggctgtagaaggtcaaggtggtgagaagaaagctgatgagacaat |
| cgacgtgtacactcacatctatctggatgaggactcaggtgaatacctccgatacgaagaggtcgagggtatggaagtccaaggctccg |
| atgggacttatcctaaagaggcttgcccatacatcccgattcggatggtcagactagatggtgaatcctacggtcgttcgtacattgagga |
| atacttaggtgacttacggtcccttgaaaatctccaagaggctatcgtcaagatgtccatgattagctctaaggttatcggcttagtgaatcct |
| gctggtatcacccagccacgccgactgaccaaagctcagactggtgacttcgttactggtcgtccagaagacatctcgttcctccaactg |
| gagaagcaagcagactttactgtagctaaagccgtaagtgacgctatcgaggctcgcctttcgtttgcctttatgttgaactctgcggttca |
| gcgtacaggtgaacgtgtgaccgccgaagagattcggtatgtagcttctgaacttgaagatactttaggtggtgtctactctatcctttctca |
| agaattacaattgcctctggtacgagtgctcttgaagcaactacaagccacgcaacagattcctgagttacctaaggaagccgtagagcc |
| aaccattagtacaggtctggaagcaattggtcgaggacaagaccttgataagctggagcggtgtgtcactgcgtgggctgcactggcac |
| ctatgcgggacgaccctgatattaaccttgcgatgattaagttacgtattgccaacgctatcggtattgacacttctggtattctactcaccga |
| agaacagaagcaacagaagatggcccaacagtctatgcaaatgggtatggataatggtgctgctgcgctggctcaaggtatggctgca |

TABLE 8-continued

| Sequence of T71-2aLuxAB (SEQ ID NO: 2). Sequences encoding luciferase subunits are shown in underline. |
| --- |
| caagctacagcttcacctgaggctatggctgctgccgctgattccgtaggtttacagccgggaatttaatacgactcactatagggagacc |
| tcatctttgaaatgagcgatgacaagaggttggagtcctcggtcttcctgtagttcaactttaaggagacaataataatggctgaatctaatg |
| cagacgtatatgcatcttttggcgtgaactccgctgtgatgtctggtggttccgttgaggaacatgagcagaacatgctggctcttgatgttg |
| ctgcccgtgatggcgatgatgcaatcgagttagcgtcagacgaagtggaaacagaacgtgacctgtatgacaactctgacccgttcggt |
| caagaggatgacgaaggccgcattcaggttcgtatcggtgatggctctgagccgaccgatgtggacactggagaagaaggcgttgag |
| ggcaccgaaggttccgaagagtttaccccactgggcgagactccagaagaactggtagctgcctctgagcaacttggtgagcacgaag |
| agggcttccaagagatgattaacattgctgctgagcgtggcatgagtgtcgagaccattgaggctatccagcgtgagtacgaggagaac |
| gaagagttgtccgccgagtcctacgctaagctggctgaaattggctacacgaaggctttcattgactcgtatatccgtggtcaagaagctc |
| tggtggagcagtacgtaaacagtgtcattgagtacgctggtggtcgtgaacgttttgatgcactgtataaccaccttgagacgcacaaccc |
| tgaggctgcacagtcgctggataatgcgttgaccaatcgtgacttagcgaccgttaaggctatcatcaacttggctggtgagtctcgcgct |
| aaggcgttcggtcgtaagccaactcgtagtgtgactaatcgtgctattccggctaaacctcaggctaccaagcgtgaaggctttgcggac |
| cgtagcgagatgattaaagctatgagtgaccctcggtatcgcacagatgccaactatcgtcgtcaagtcgaacagaaagtaatcgattcg |
| aacttctaactagatctcattatcatatggctagcatgactggtggacagcaaatgggtactaaccaaggtaaaggtgtagttgctgctgga |
| gataaactggcgttgttcttgaaggtatttggcggtgaagtcctgactgcgttcgctcgtacctccgtgaccacttctcgccacatggtacgt |
| tccatctccagcggtaaatccgctcagttccctgttctgggtcgcactcaggcagcgtatctggctccgggcgagaacctcgacgataaa |
| cgtaaggacatcaaacacaccgagaaggtaatcaccattgacggtctcctgacggctgacgttctgatttatgatattgaggacgcgatg |
| aaccactacgacgttcgctctgagtatacctctcagttgggtgaatctctggcgatggctgcggatggtgcggttctggctgagattgccg |
| gtctgtgtaacgtggaaagcaaatataatgagaacatcgagggcttaggtactgctaccgtaattgagaccactcagaacaaggccgca |
| cttaccgaccaagttgcgctgggtaaggagattattgcggctctgactaaggctcgtgcggctctgaccaagaactatgttccggctgctg |
| accgtgtgttctactgtgacccagatagctactctgcgattctggcagcactgatgccgaacgcagcaaactacgctgctctgattgaccc |
| tgagaagggttctatccgcaacgttatgggctttgaggttgtagaagttccgcacctcaccgctggtggtgctggtaccgctcgtgaggg |
| cactactggtcagaagcacgtcttccctgccaataaaggtgagggtaatgtcaaggttgctaaggacaacgttatcggcctgttcatgcac |
| cgctctgcggtaggtactgttaagctgcgtgacttggctctggagcgcgctcgccgtgctaacttccaagcggaccagattatcgctaagt |
| acgcaatgggccacggtggtcttcgcccagaagctgcaggagctgtcgtattccagtcaggtgtgatgctcggggatctcgagggggc |
| ccaggcggccgcactcgactcggtaccccgatggataatgatcatctggatattgatgttgatattactgaaccgtcatttgaacatttaact |
| attgcgacagtcaatgaacgccgaatgagaattgagattgaaaatcaagcaatttctctgtcttaaaatctattgagatattctatcactcaaa |
| tagcaatataaggactctctatgaaatttggaaactttttgcttacataccaacctccccaatttctcaaacagaggtaatgaaacgtttggtt |
| aaattaggtcgcatctctgaggagtgtggttttgataccgtatggttactggagcatcatttcacggagtttggtttgcttggtaacccttatgt |
| cgctgctgcatatttacttggcgcgactaaaaaattgaatgtaggaactgccgctattgttcttcccacagcccatccagtacgccaacttg |
| aagatgtgaatttattggatcaaatgtcaaaaggacgatttcggtttggtatttgccgagggctttacaacaaggactttcgcgtattcggca |
| cagatatgaataacagtcgcgccttagcggaatgctggtacgggctgataaagaatggcatgacagagggatatatggaagctgataat |
| gaacatatcaagttccataaggtaaaagtaaaccccgcggcgtatagcagaggtggcgcaccggtttatgtggtggctgaatcagcttcg |
| acgactgagtgggctgctcaatttggcctaccgatgatattaagttggattataaatactaacgaaaagaaagcacaacttgagctttataat |
| gaagtggctcaagaatatgggcacgatattcataatatcgaccattgcttatcatatataacatctgtagatcatgactcaattaaagcgaaa |
| gagatttgccggaaatttctggggcattggtatgattcttatgtgaatgctacgactattttgatgattcagaccaaacaagaggttatgattt |
| caataaagggcagtggcgtgactttgtattaaaaggacataaagatactaatcgccgtattgattacagttacgaaatcaatcccgtggga |
| acgccgcaggaatgtattgacataattcaaaaagacattgatgctacaggaatatcaaatatttgttgtggatttgaagctaatggaacagta |
| gacgaaattattgcttccatgaagctcttccagtctgatgtcatgccatttcttaaagaaaaacaaacgttcgctattatattagctaaggagaa |

TABLE 8-continued

| Sequence of T71-2aLuxAB (SEQ ID NO: 2). Sequences encoding luciferase subunits are shown in underline. |
|---|
| agaaatgaaatttggattgttcttccttaacttcatcaattcaacaactgttcaagaacaaagtatagttcgcatgcaggaaataacggagtat |
| gttgataagttgaattttgaacagattttagtgtatgaaaatcatttttcagataatggtgttgtcggcgctcctctgactgtttctggttttctgct |
| cggtttaacagagaaaattaaaattggttcattaaatcacatcattacaactcatcatcctgtcgccatagcggaggaagcttgcttattggat |
| cagttaagtgaagggagatttattttagggtttagtgattgcgaaaaaaaagatgaaatgcatttttttaatcgcccggttgaatatcaacagc |
| aactatttgaagagtgttatgaaatcattaacgatgctttaacaacaggctattgtaatccagataacgatttttatagcttccctaaaatatctg |
| taaatccccatgcttatacgccaggcggacctcggaaatatgtaacagcaaccagtcatcatattgttgagtgggcggccaaaaaaggta |
| ttcctctcatctttaagtgggatgattctaatgatgttagatatgaatatgctgaaagatataaagccgttgcggataaatatgacgttgaccta |
| tcagagatagaccatcagttaatgatattagttaactataacgaagatagtaataaagctaaacaagagacgcgtgcatttattagtgattat |
| gttcttgaaatgcaccctaatgaaaatttcgaaaataaacttgaagaaataattgcagaaaacgctgtcggaaattatacggagtgtataact |
| gcggctaagttggcaattgaaaagtgtggtgcgaaaagtgtattgctgtcctttgaaccaatgaatgatttgatgagccaaaaaaatgtaat |
| caatattgttgatgataatattaagaagtaccacatggaatatacctaatagatttcgagttgcagcgaggcggcaagtgaacgaatcccc |
| aggagcatagataactatgtgactggggtgagtgaaagcagccaacaaagcagcagcttgaaagatgaagggtataaaagagtatgac |
| agcagtgctgccatactttctaatattatcttgaggagtaaaacaggtatgacttcatatgttgataaacaagaaattacagcaagctcagaa |
| attgatgatttgatttttcgagcgatccatctcgaattcgagctccgtcgacaagcttgcggccgcactcgagtaactagttaaccccttgg |
| ggcctctaaacgggtcttgaggggttttttgctgaaaggaggaactatatgcgctcatacgatatgaacgttgagactgccgctgagttatc |
| agctgtgaacgacattctggcgtctatcggtgaacctccggtatcaacgctggaaggtgacgctaacgcagatgcagcgaacgctcgg |
| cgtattctcaacaagattaaccgacagattcaatctcgtggatggacgttcaacattgaggaaggcataacgctactacctgatgtttactc |
| caacctgattgtatacagtgacgactatttatccctaatgtctacttccggtcaatccatctacgttaaccgaggtggctatgtgtatgaccga |
| acgagtcaatcagaccgctttgactctggtattactgtgaacattattcgtctccgcgactacgatgagatgcctgagtgcttccgttactgg |
| attgtcaccaaggcttcccgtcagttcaacaaccgattctttggggcaccggaagtagagggtgtactccaagaagaggaagatgaggc |
| tagacgtctctgcatggagtatgagatggactacggtgggtacaatatgctggatggagatgcgttcacttctggtctactgactcgctaac |
| attaataaataaggaggctctaatggcactcattagccaatcaatcaagaacttgaagggtggtatcagccaacagcctgacatccttcgtt |
| atccagaccaagggtcacgccaagttaacggttggtcttcggagaccgagggcctccaaaagcgtccacctcttgttttcttaaatacact |
| tggagacaacggtgcgttaggtcaagctccgtacatccacctgattaaccgagatgagcacgaacagtattacgctgtgttcactggtag |
| cggaatccgagtgttcgacctttctggtaacgagaagcaagttaggtatcctaacggttccaactacatcaagaccgctaatccacgtaac |
| gacctgcgaatggttactgtagcagactatacgttcatcgttaaccgtaacgttgttgcacagaagaacacaaagtctgtcaacttaccgaa |
| ttacaaccctaatcaagacggattgattaacgttcgtggtggtcagtatggtagggaactaattgtacacattaacggtaaagacgttgcga |
| agtataagataccagatggtagtcaacctgaacacgtaaacaatacggatgcccaatggttagctgaagagttagccaagcagatgcgc |
| actaacttgtctgattggactgtaaatgtagggcaagggttcatccatgtgaccgcacctagtggtcaacagattgactccttcacgactaa |
| agatggctacgcagaccagttgattaaccctgtgacccactacgctcagtcgttctctaagctgccacctaatgctcctaacggctacatg |
| gtgaaaatcgtaggggacgcctctaagtctgccgaccagtattacgttcggtatgacgctgagcggaaagtttggactgagactttaggtt |
| ggaacactgaggaccaagttctatgggaaaccatgccacacgctcttgtgcgagccgctgacggtaatttcgacttcaagtggcttgagt |
| ggtctcctaagtcttgtggtgacgttgacaccaacccttggccttcttttgttggttcaagtattaacgatgtgttcttcttccgtaaccgcttag |
| gattccttagtggggagaacatcatattgagtcgtacagccaaatacttcaacttctaccctgcgtccattgcgaaccttagtgatgacgac |
| cctatagacgtagctgtgagtaccaaccgaatagcaatccttaagtacgccgttccgttctcagaagagttactcatctggtccgatgaag |
| cacaattcgtcctgactgcctcgggtactctcacatctaagtcggttgagttgaacctaacgacccagtttgacgtacaggaccgagcga |
| gaccttttgggattgggcgtaatgtctactttgctagtccgaggtccagcttcacgtccatccacaggtactacgctgtgcaggatgtcagtt |
| ccgttaagaatgctgaggacattacatcacacgttcctaactacatccctaatggtgtgttcagtatttgcggaagtggtacggaaaacttct |
| gttcggtactatctcacggggaccctagtaaaatcttcatgtacaaattcctgtacctgaacgaagagttaaggcaacagtcgtggtctcatt |

TABLE 8-continued

| Sequence of T71-2aLuxAB (SEQ ID NO: 2). Sequences encoding luciferase subunits are shown in underline. |
|---|
| gggactttggggaaaacgtacaggttctagcttgtcagagtatcagctcagatatgtatgtgattcttcgcaatgagttcaatacgttcctag |
| ctagaatctctttcactaagaacgccattgacttacagggagaaccctatcgtgcctttatggacatgaagattcgatacacgattcctagtg |
| gaacatacaacgatgacacattcactacctctattcatattccaacaatttatggtgcaaacttcgggaggggcaaaatcactgtattggag |
| cctgatggtaagataaccgtgtttgagcaacctacggctgggtggaatagcgacccttggctgagactcagcggtaacttggagggacg |
| catggtgtacattgggttcaacattaacttcgtatatgagttctctaagttcctcatcaagcagactgccgacgacgggtctacctccacgga |
| agacattgggcgcttacagttacgccgagcgtgggttaactacgagaactctggtacgtttgacatttatgttgagaaccaatcgtctaact |
| ggaagtacacaatggctggtgcccgattaggctctaacactctgagggctgggagactgaacttagggaccggacaatatcgattccct |
| gtggttggtaacgccaagttcaacactgtatacatcttgtcagatgagactacccctctgaacatcattgggtgtggctgggaaggtaacta |
| cttacggagaagttccggtatttaattaaatattctccctgtggtggctcgaaattaatacgactcactatagggagaacaatacgactacgg |
| gagggttttcttatgatgactataagacctactaaaagtacagactttgaggtattcactccggctcaccatgacattcttgaagctaaggct |
| gctggtattgagccgagtttccctgatgcttccgagtgtgtcacgttgagcctctatgggttccctctagctatcggtggtaactgcgggga |
| ccagtgctggttcgttacgagcgaccaagtgtggcgacttagtggaaaggctaagcgaaagttccgtaagttaatcatggagtatcgcga |
| taagatgcttgagaagtatgatactctttggaattacgtatgggtaggcaatacgtcccacattcgtttcctcaagactatcggtgcggtattc |
| catgaagagtacacacgagatggtcaatttcagttatttacaatcacgaaaggaggataaccatatgtgttgggcagccgcaatacctatc |
| gctatatctggcgctcaggctatcagtggtcagaacgctcaggccaaaatgattgccgctcagaccgctgctggtcgtcgtcaagctatg |
| gaaatcatgaggcagacgaacatccagaatgctgacctatcgttgcaagctcgaagtaaacttgaggaagcgtccgccgagttgacctc |
| acagaacatgcagaaggtccaagctattgggtctatccgagcggctatcggagagagtatgcttgaaggttcctcaatggaccgcattaa |
| gcgagtcacagaaggacagttcattcgggaagccaatatggtaactgagaactatcgccgtgactaccaagcaatcttcgcacagcaac |
| ttggtggtactcaaagtgctgcaagtcagattgacgaaatctataagagcgaacagaaacagaagagtaagctacagatggttctggac |
| ccactggctatcatggggtcttccgctgcgagtgcttacgcatccggtgcgttcgactctaagtccacaactaaggcacctattgttgccg |
| ctaaaggaaccaagacggggaggtaatgagctatgagtaaaattgaatctgcccttcaagcggcacaaccgggactctctcggttacgt |
| ggtggtgctggaggtatgggctatcgtgcagcaaccactcaggccgaacagccaaggtcaagcctattggacaccattggtcggttcg |
| ctaaggctggtgccgatatgtataccgctaaggaacaacgagcacgagacctagctgatgaacgctctaacgagattatccgtaagctg |
| acccctgagcaacgtcgagaagctctcaacaacgggacccttctgtatcaggatgacccatacgctatggaagcactccgagtcaaga |
| ctggtcgtaacgctgcgtatcttgtggacgatgacgttatgcagaagataaaagagggtgtcttccgtactcgcgaagagatggaagagt |
| atcgccatagtcgccttcaagagggcgctaaggtatacgctgagcagttcggcatcgaccctgaggacgttgattatcagcgtggtttca |
| acggggacattaccgagcgtaacatctcgctgtatggtgcgcatgataacttcttgagccagcaagctcagaagggcgctatcatgaac |
| agccgagtggaactcaacggtgtccttcaagaccctgatatgctgcgtcgtccagactctgctgacttctttgagaagtatatcgacaacg |
| gtctggttactggcgcaatcccatctgatgctcaagccacacagcttataagccaagcgttcagtgacgcttctagccgtgctggtggtgc |
| tgacttcctgatgcgagtcggtgacaagaaggtaacacttaacggagccactacgacttaccgagagttgattggtgaggaacagtgga |
| acgctctcatggtcacagcacaacgttctcagtttgagactgacgcgaagctgaacgagcagtatcgcttgaagattaactctgcgctga |
| accaagaggacccaaggacagcttgggagatgcttcaaggtatcaaggctgaactagataaggtccaacctgatgagcagatgacacc |
| acaacgtgagtggctaatctccgcacaggaacaagttcagaatcagatgaacgcatggacgaaagctcaggccaaggctctggacgat |
| tccatgaagtcaatgaacaaacttgacgtaatcgacaagcaattccagaagcgaatcaacggtgagtgggtctcaacggattttaaggat |
| atgccagtcaacgagaacactggtgagttcaagcatagcgatatggttaactacgccaataagaagctcgctgagattgacagtatggac |
| attccagacggtgccaaggatgctatgaagttgaagtaccttcaagcggactctaaggacggagcattccgtacagccatcggaaccat |
| ggtcactgacgctggtcaagagtggtctgccgctgtgattaacggtaagttaccagaacgaaccccagctatggatgctctgcgcagaat |
| ccgcaatgctgaccctcagttgattgctgcgctatacccagaccaagctgagctattcctgacgatggacatgatggacaagcagggtat |

TABLE 8-continued

| Sequence of T71-2aLuxAB (SEQ ID NO: 2). Sequences encoding luciferase subunits are shown in underline. |
|---|
| tgaccctcaggttattcttgatgccgaccgactgactgttaagcggtccaaagagcaacgctttgaggatgataaagcattcgagtctgca |
| ctgaatgcatctaaggctcctgagattgcccgtatgccagcgtcactgcgcgaatctgcacgtaagatttatgactccgttaagtatcgctc |
| ggggaacgaaagcatggctatggagcagatgaccaagttccttaaggaatctacctacacgttcactggtgatgatgttgacggtgatac |
| cgttggtgtgattcctaagaatatgatgcaggttaactctgacccgaaatcatgggagcaaggtcgggatattctggaggaagcacgtaa |
| gggaatcattgcgagcaacccttggataaccaataagcaactgaccatgtattctcaaggtgactccatttaccttatggacaccacaggt |
| caagtcagagtccgatacgacaaagagttactctcgaaggtctggagtgagaaccagaagaaactcgaagagaaagctcgtgagaag |
| gctctggctgatgtgaacaagcgagcacctatagttgccgctacgaaggcccgtgaagctgctgctaaacgagtccgagagaaacgta |
| aacagactcctaagttcatctacggacgtaaggagtaactaaaggctacataaggaggccctaaatggataagtacgataagaacgtac |
| caagtgattatgatggtctgttccaaaaggctgctgatgccaacggggtctcttatgaccttttacgtaaagtcgcttggacagaatcacgat |
| ttgtgcctacagcaaaatctaagactggaccattaggcatgatgcaatttaccaaggcaaccgctaaggccctcggtctgcgagttaccg |
| atggtccagacgacgaccgactgaaccctgagttagctattaatgctgccgctaagcaacttgcaggtctggtagggaagtttgatggcg |
| atgaactcaaagctgcccttgcgtacaaccaaggcgagggacgcttgggtaatccacaacttgaggcgtactctaagggagacttcgca |
| tcaatctctgaggagggacgtaactacatgcgtaaccttctggatgttgctaagtcacctatggctggacagttggaaacttttggtggcat |
| aaccccaaagggtaaaggcattccggctgaggtaggattggctggaattggtcacaagcagaaagtaacacaggaacttcctgagtcc |
| acaagttttgacgttaagggtatcgaacaggaggctacggcgaaaccattcgccaaggacttttgggagacccacggagaaacacttga |
| cgagtacaacagtcgttcaaccttcttcggattcaaaaatgctgccgaagctgaactctccaactcagtcgctgggatggctttccgtgctg |
| gtcgtctcgataatggttttgatgtgtttaaagacaccattacgccgactcgctggaactctcacatctggactccagaggagttagagaag |
| attcgaacagaggttaagaaccctgcgtacatcaacgttgtaactggtggttcccctgagaacctcgatgacctcattaaattggctaacg |
| agaactttgagaatgactcccgcgctgccgaggctggcctaggtgccaaactgagtgctggtattattggtgctggtgtggacccgctta |
| gctatgttcctatggtcggtgtcactggtaagggctttaagttaatcaataaggctcttgtagttggtgccgaaagtgctgctctgaacgttgc |
| atccgaaggtctccgtacctccgtagctggtggtgacgcagactatgcgggtgctgccttaggtggctttgtgtttggcgcaggcatgtct |
| gcaatcagtgacgctgtagctgctggactgaaacgcagtaaaccagaagctgagttcgacaatgagttcatcggtcctatgatgcgattg |
| gaagcccgtgagacagcacgaaacgccaactctgcggacctctctcggatgaacactgagaacatgaagtttgaaggtgaacataatg |
| gtgtcccttatgaggacttaccaacagagagaggtgccgtggtgttacatgatggctccgttctaagtgcaagcaacccaatcaacccta |
| agactctaaaagagttctccgaggttgaccctgagaaggctgcgcgaggaatcaaactggctgggttcaccgagattggcttgaagacc |
| ttggggtctgacgatgctgacatccgtagagtggctatcgacctcgttcgctctcctactggtatgcagtctggtgcctcaggtaagttcgg |
| tgcaacagcttctgacatccatgagagacttcatggtactgaccagcgtacttataatgacttgtacaaagcaatgtctgacgctatgaaag |
| accctgagttctctactggcggcgctaagatgtcccgtgaagaaactcgatacactatctaccgtagagcggcactagctattgagcgtc |
| cagaactacagaaggcactcactccgtctgagagaatcgttatggacatcattaagcgtcactttgacaccaagcgtgaacttatggaaa |
| acccagcaatattcggtaacacaaaggctgtgagtatcttccctgagagtcgccacaaaggtacttacgttcctcacgtatatgaccgtcat |
| gccaaggcgctgatgattcaacgctacggtgccgaaggtttgcaggaagggattgcccgctcatggatgaacagctacgtctccagac |
| ctgaggtcaaggccagagtcgatgagatgcttaaggaattacacggggtgaaggaagtaacaccagagatggtagagaagtacgctat |
| ggataaggcttatggtatctcccactcagaccagttcaccaacagttccataatagaagagaacattgagggcttagtaggtatcgagaat |
| aactcattccttgaggcacgtaacttgtttgattcggacctatccatcactatgccagacggacagcaattctcagtgaatgacctaaggga |
| cttcgatatgttccgcatcatgccagcgtatgaccgccgtgtcaatggtgacatcgccatcatggggtctactggtaaaaccactaaggaa |
| cttaaggatgagattttggctctcaaagcgaaagctgagggagacggtaagaagactggcgaggtacatgctttaatggataccgttaag |
| attcttactggtcgtgctagacgcaatcaggacactgtgtgggaaacctcactgcgtgccatcaatgacctagggttcttcgctaagaacg |
| cctacatgggtgctcagaacattacggagattgctgggatgattgtcactggtaacgttcgtgctctagggcatggtatcccaattctgcgt |
| gatacactctacaagtctaaaccagtttcagctaaggaactcaaggaactccatgcgtctctgttcgggaaggaggtggaccagttgattc |

TABLE 8-continued

| Sequence of T71-2aLuxAB (SEQ ID NO: 2). Sequences encoding luciferase subunits are shown in underline. |
|---|
| ggcctaaacgtgctgacattgtgcagcgcctaagggaagcaactgataccggacctgccgtggcgaacatcgtagggaccttgaagta |
| ttcaacacaggaactggctgctcgctctccgtggactaagctactgaacggaaccactaactaccttctggatgctgcgcgtcaaggtat |
| gcttggggatgttattagtgccaccctaacaggtaagactacccgctgggagaaagaaggcttccttcgtggtgcctccgtaactcctga |
| gcagatggctggcatcaagtctctcatcaaggaacatatggtacgcggtgaggacgggaagtttaccgttaaggacaagcaagcgttct |
| ctatggacccacgggctatggacttatggagactggctgacaaggtagctgatgaggcaatgctgcgtccacataaggtgtccttacag |
| gattcccatgcgttcggagcactaggtaagatggttatgcagtttaagtctttcactatcaagtcccttaactctaagttcctgcgaaccttcta |
| tgatggatacaagaacaaccgagcgattgacgctgcgctgagcatcatcacctctatgggtctcgctggtggtttctatgctatggctgca |
| cacgtcaaagcatacgctctgcctaaggagaaacgtaaggagtacttggagcgtgcactggacccaaccatgattgcccacgctgcgtt |
| atctcgtagttctcaattgggtgctcctttggctatggttgacctagttggtggtgttttagggttcgagtcctccaagatggctcgctctacga |
| ttctacctaaggacaccgtgaaggaacgtgacccaaacaaaccgtacacctctagagaggtaatgggcgctatgggttcaaaccttctg |
| gaacagatgccttcggctggctttgtggctaacgtaggggctaccttaatgaatgctgctggcgtggtcaactcacctaataaagcaacc |
| gagcaggacttcatgactggtcttatgaactccacaaaagagttagtaccgaacgacccattgactcaacagcttgtgttgaagatttatga |
| ggcgaacggtgttaacttgagggagcgtaggaaataatacgactcactatagggagaggcgaaataatcttctccctgtagtctcttagat |
| ttactttaaggaggtcaaatggctaacgtaattaaaaccgttttgacttaccagttagatggctccaatcgtgattttaatatcccgtttgagtat |
| ctagcccgtaagttcgtagtggtaactcttattggtgtagaccgaaaggtccttacgattaatacagactatcgctttgctacacgtactacta |
| tctctctgacaaaggcttggggtccagccgatggctacacgaccatcgagttacgtcgagtaacctccactaccgaccgattggttgactt |
| tacggatggttcaatcctccgcgcgtatgaccttaacgtcgctcagattcaaacgatgcacgtagcggaagaggcccgtgacctcactac |
| ggatactatcggtgtcaataacgatggtcacttggatgctcgtggtcgtcgaattgtgaacctagcgaacgccgtggatgaccgcgatgc |
| tgttccgtttggtcaactaaagaccatgaaccagaactcatggcaagcacgtaatgaagccttacagttccgtaatgaggctgagactttc |
| agaaaccaagcggagggctttaagaacgagtccagtaccaacgctacgaacacaaagcagtggcgcgatgagaccaagggtttccg |
| agacgaagccaagcggttcaagaatacggctggtcaatacgctacatctgctgggaactctgcttccgctgcgcatcaatctgaggtaaa |
| cgctgagaactctgccacagcatccgctaactctgctcatttggcagaacagcaagcagaccgtgcggaacgtgaggcagacaagctg |
| gaaaattacaatggattggctggtgcaattgataaggtagatggaaccaatgtgtactggaaaggaaatattcacgctaacgggcgccttt |
| acatgaccacaaacggttttgactgtggccagtatcaacagttctttggtggtgtcactaatcgttactctgtcatggagtggggagatgag |
| aacggatggctgatgtatgttcaacgtagagagtggacaacagcgataggcggtaacatccagttagtagtaaacggacagatcatcac |
| ccaaggtggagccatgaccggtcagctaaaattgcagaatgggcatgttcttcaattagagtccgcatccgacaaggcgcactatattct |
| atctaaagatggtaacaggaataactggtacattggtagagggtcagataacaacaatgactgtaccttccactcctatgtacatggtacg |
| accttaacactcaagcaggactatgcagtagttaacaaacacttccacgtaggtcaggccgttgtggccactgatggtaatattcaaggta |
| ctaagtggggaggtaaatggctggatgcttacctacgtgacagcttcgttgcgaagtccaaggcgtggactcaggtgtggtctggtagtg |
| ctggcggtggggtaagtgtgactgtttcacaggatctccgcttccgcaatatctggattaagtgtgccaacaactcttggaacttcttccgta |
| ctggccccgatggaatctacttcatagcctctgatggtggatggttacgattccaaatacactccaacggtctcggattcaagaatattgca |
| gacagtcgttcagtacctaatgcaatcatggtggagaacgagtaattggtaaatcacaaggaaagacgtgtagtccacggatggactctc |
| aaggaggtacaaggtgctatcattagactttaacaacgaattgattaaggctgctccaattgttgggacgggtgtagcagatgttagtgctc |
| gactgttctttgggttaagccttaacgaatggttctacgttgctgctatcgcctacacagtggttcagattggtgccaaggtagtcgataaga |
| tgattgactggaagaaagccaataaggagtgatatgtatggaaaaggataagagccttattacattcttagagatgttggacactgcgatg |
| gctcagcgtatgcttgcggacctttcggaccatgagcgtcgctctccgcaactctataatgctattaacaaactgttagaccgccacaagtt |
| ccagattggtaagttgcagccggatgttcacatcttaggtggccttgctggtgctcttgaagagtacaaagagaaagtcggtgataacggt |
| cttacggatgatgatatttacacattacagtgatatactcaaggccactacagatagtggtctttatggatgtcattgtctatacgagatgctcc |

TABLE 8-continued

| Sequence of T71-2aLuxAB (SEQ ID NO: 2). Sequences encoding luciferase subunits are shown in underline. |
| --- |
| tacgtgaaatctgaaagttaacgggaggcattatgctagaattttttacgtaagctaatcccttgggttctcgctgggatgctattcgggttag |
| gatggcatctagggtcagactcaatggacgctaaatggaaacaggaggtacacaatgagtacgttaagagagttgaggctgcgaagag |
| cactcaaagagcaatcgatgcggtatctgctaagtatcaagaagaccttgccgcgctggaagggagcactgataggattatttctgatttg |
| cgtagcgacaataagcggttgcgcgtcagagtcaaaactaccggaacctccgatggtcagtgtggattcgagcctgatggtcgagccg |
| aacttgacgaccgagatgctaaacgtattctcgcagtgacccagaagggtgacgcatggattcgtgcgttacaggatactattcgtgaact |
| gcaacgtaagtaggaaatcaagtaaggaggcaatgtgtctactcaatccaatcgtaatgcgctcgtagtggcgcaactgaaaggagact |
| tcgtggcgttcctattcgtcttatggaaggcgctaaacctaccggtgcccactaagtgtcagattgacatggctaaggtgctggcgaatgg |
| agacaacaagaagttcatcttacaggctttccgtggtatcggtaagtcgttcatcacatgtgcgttcgttgtgtggtccttatggagagaccc |
| tcagttgaagatacttatcgtatcagcctctaaggagcgtgcagacgctaactccatctttattaagaacatcattgacctgctgccattccta |
| tctgagttaaagccaagacccggacagcgtgactcggtaatcagctttgatgtaggcccagccaatcctgaccactctcctagtgtgaaat |
| cagtaggtatcactggtcagttaactggtagccgtgctgacattatcattgcggatgacgttgagattccgtctaacagcgcaactatgggt |
| gcccgtgagaagctatggactctggttcaggagttcgctgcgttacttaaaccgctgccttcctctcgcgttatctaccttggtacacctcag |
| acagagatgactctctataaggaacttgaggataaccgtgggtacacaaccattatctggcctgctctgtacccaaggacacgtgaagag |
| aacctctattactcacagcgtcttgctcctatgttacgcgctgagtacgatgagaaccctgaggcacttgctgggactccaacagacccag |
| tgcgctttgaccgtgatgacctgcgcgagcgtgagttggaatacggtaaggctggctttacgctacagttcatgcttaaccctaaccttagt |
| gatgccgagaagtacccgctgaggcttcgtgacgctatcgtagcggccttagacttagagaaggccccaatgcattaccagtggcttcc |
| gaaccgtcagaacatcattgaggaccttcctaacgttggccttaagggtgatgacctgcatacgtaccacgattgttccaacaactcaggt |
| cagtaccaacagaagattctggtcattgaccctagtggtcgcggtaaggacgaaacaggttacgctgtgctgtacacactgaacggttac |
| atctaccttatggaagctggaggtttccgtgatggctactccgataagacccttgagttactcgctaagaaggcaaagcaatggggagtc |
| cagacggttgtctacgagagtaacttcggtgacggtatgttcggtaaggtattcagtcctatccttcttaaacaccacaactgtgcgatgga |
| agagattcgtgcccgtggtatgaaagagatgcgtatttgcgatacccttgagccagtcatgcagactcaccgccttgtaattcgtgatgag |
| gtcattagggccgactaccagtccgctcgtgacgtagacggtaagcatgacgttaagtactcgttgttctaccagatgacccgtatcactc |
| gtgagaaaggcgctctggctcatgatgaccgattggatgcccttgcgttaggcattgagtatctccgtgagtccatgcagttggattccgtt |
| aaggtcgagggtgaagtacttgctgacttccttgaggaacacatgatgcgtcctacggttgctgctacgcatatcattgagatgtctgtggg |
| aggagttgatgtgtactctgaggacgatgagggttacggtacgtctttcattgagtggtgatttatgcattaggactgcatagggatgcact |
| atagaccacggatggtcagttctttaagttactgaaaagacacgataaattaatacgactcactatagggagaggagggacgaaaggtta |
| ctatatagatactgaatgaatacttatagagtgcataaagtatgcataatggtgtacctagagtgacctctaagaatggtgattatattgtatta |
| gtatcaccttaacttaaggaccaacataaagggaggagactcatgttccgcttattgttgaacctactgcggcatagagtcacctaccgatt |
| tcttgtggtactttgtgctgcccttgggtacgcatctcttactggagacctcagttcactggagtctgtcgtttgctctatactcacttgtagcga |
| ttagggtcttcctgaccgactgatggctcaccgagggattcagcggtatgattgcatcacaccacttcatccctatagagtcaagtcctaag |
| gtatacccataaagagcctctaatggtctatcctaaggtctatacctaaagataggccatcctatcagtgtcacctaaagagggtcttagag |
| agggcctatggagttcctatagggtcctttaaaatataccataaaaatctgagtgactatctcacagtgtacggacctaaagttcccccata |
| gggggtacctaaagcccagccaatcacctaaagtcaaccttcggttgaccttgagggttccctaagggttggggatgacccttgggtttgtctttgggtgtta |
| ccttgagtgtctctctgtgtccct |

TABLE 9

Sequence of pSL-LuxABE10 (SEQ ID NO: 3). Sequences encoding luciferase subunits are shown in underline.

gggcggcgacctcgcgggttttcgctatttatgaaaattttccggtttaaggcgtttccgttcttcttcgtcataacttaatgtttttatttaaaata ccctctgaaaagaaaggaaacgacaggtgctgaaagcgaggctttttggcctctgtcgtttcctttctctgtttttgtccgtggaatgaacaa tggaagtcaacaaaaagcagctggctgacattttcggtgcgagtatccgtaccattcagaactggcaggaacagggaatgcccgttctg cgaggcggtggcaagggtaatgaggtgctttatgactctgccgccgtcataaaatggtatgccgaaagggatgctgaaattgagaacga aaagctgcgccgggaggttgaagaactgcggcaggccagcgaggcagatctccagccaggaactattgagtacgaacgccatcgac ttacgcgtgcgcaggccgacgcacaggaactgaagaatgccagagactccgctgaagtggtggaaaccgcattctgtactttcgtgctg tcgcggatcgcaggtgaaattgccagtattctcgacgggctcccccctgtcggtgcagcggcgttttccggaactggaaaaccgacatgtt gatttcctgaaacgggatatcatcaaagccatgaacaaagcagccgcgctggatgaactgataccggggttgctgagtgaatatatcga acagtcaggttaacaggctgcggcattttgtccgcgccgggcttcgctcactgttcaggccggagccacagaccgccgttgaatgggc ggatgctaattactatctcccgaaagaatccgcataccaggaagggcgctgggaaacactgccctttcagcgggccatcatgaatgcga tgggcagcgactacatccgtgaggtgaatgtggtgaagtctgcccgtgtcggttattccaaaatgctgctgggtgtttatgcctactttatag agcataagcagcgcaacacccttatctggttgccgacggatggtgatgccgagaactttatgaaaacccacgttgagccgactattcgtg atattccgtcgctgctggcgctggccccgtggtatggcaaaaagcaccgggataacacgctcaccatgaagcgtttcactaatgggcgt ggcttctggtgcctgggcggtaaagcggcaaaaaactaccgtgaaaagtcggtggatgtggcgggttatgatgaacttgctgcttttgat gatgatattgaacaggaaggctctccgacgttcctgggtgacaagcgtattgaaggctcggtctggccaaagtccatccgtggctccac gccaaaagtgagaggcacctgtcagattgagcgtgcagccagtgaatccccgcattttatgcgttttcatgttgcctgcccgcattgcggg gaggagcagtatcttaaatttggcgacaaagagacgccgtttggcctcaaatggacgccggatgacccctccagcgtgttttatctctgc gagcataatgcctgcgtcatccgccagcaggagctggactttactgatgcccgttatatctgcgaaaagaccgggatctggacccgtgat ggcattctctggttttcgtcatccggtgaagagattgagccacctgacagtgtgacctttcacatctggacagcgtacagcccgttcaccac ctgggtgcagattgtcaaagactggatgaaaacgaaaggggatacgggaaaacgtaaaaccttcgtaaacaccacgctcggtgagac gtgggaggcgaaaattggcgaacgtccggatgctgaagtgatggcagagcggaaagagcattattcagcgcccgttcctgaccgtgtg gcttacctgaccgccggtatcgactcccagctggaccgctacgaaatgcgcgtatggggatgggggccgggtgaggaaagctggctg attgaccggcagattattatgggccgccacgacgatgaacagacgctgctgcgtgtggatgaggccatcaataaaacctatacccgccg gaatggtgcagaaatgtcgatatcccgtatctgctgggatactggcgggattgacccgaccattgtgtatgaacgctcgaaaaaacatgg gctgttccgggtgatccccattaaaggggcatccgtctacggaaagccggtggccagcatgccacgtaagcgaaacaaaaacggggtt taccttaccgaaatcggtacggataccgcgaaagagcagatttataaccgcttcacactgacgccggaaggggatgaaccgcttcccg gtgccgttcacttcccgaataacccggatatttttgatctgaccgaagcgcagcagctgactgctgaagagcaggtcgaaaaatgggtgg atggcaggaaaaaaatactgtgggacagcaaaaagcgacgcaatgaggcactcgactgcttcgtttatgcgctggcggcgctgcgcat cagtatttcccgctggcagctggatctcagtgcgctgctggcgagcctgcaggaagaggatggtgcagcaaccaacaagaaaacactg gcagattacgcccgtgccttatccggagaggatgaatgacgcgacaggaagaacttgccgctgcccgtgcggcactgcatgacctgat gacaggtaaacgggtggcaacagtacagaaagacggacgaagggtggagtttacggccacttccgtgtctgacctgaaaaaatatatt gcagagctggaagtgcagaccggcatgacacagcgacgcaggggacctgcaggattttatgtatgaaaacgcccaccattcccaccct tctggggccggacggcatgacatcgctgcgcgaatatgccggttatcacggcggtggcagcggatttggagggcagttgcggtcgtg gaacccaccgagtgaaagtgtggatgcagccctgttgcccaactttacccgtggcaatgcccgcgcagacgatctggtacgcaataac ggctatgccgccaacgccatccagctgcatcaggatcatatcgtcgggtctttttttccggctcagtcatcgcccaagctggcgctatctgg gcatcggggaggaagaagcccgtgccttttcccgcgaggttgaagcggcatggaaagagtttgccgaggatgactgctgctgcattga cgttgagcgaaaacgcacgtttaccatgatgattcgggaaggtgtggccatgcacgcctttaacggtgaactgttcgttcaggccacctg ggataccagttcgtcgcggcttttccggacacagttccggatggtcagcccgaagcgcatcagcaacccgaacaataccggcgacagc cggaactgccgtgccggtgtgcagattaatgacagcggtgcggcgctgggatattacgtcagcgaggacgggtatcctggctggatgc TABLE 9-continued

| Sequence of pSL-LuxABE10 (SEQ ID NO: 3). Sequences encoding luciferase subunits are shown in underline. |
|---|
| cgcagaaatggacatggataccccgtgagttacccggcgggcgcgcctcgttcattcacgtttttgaacccgtggaggacgggcagact |
| cgcggtgcaaatgtgttttacagcgtgatggagcagatgaagatgctcgacacgctgcagaacacgcagctgcagagcgccattgtga |
| aggcgatgtatgccgccaccattgagagtgagctggatacgcagtcagcgatggattttattctgggcgcgaacagtcaggagcagcg |
| ggaaaggctgaccggctggattggtgaaattgccgcgtattacgccgcagcgccggtccggctgggaggcgcaaaagtaccgcacct |
| gatgccgggtgactcactgaacctgcagacggctcaggatacggataacggctactccgtgtttgagcagtcactgctgcggtatatcg |
| ctgccgggctgggtgtctcgtatgagcagctttcccggaattacgcccagatgagctactccacggcacgggccagtgcgaacgagtc |
| gtgggcgtactttatggggcggcgaaaattcgtcgcatcccgtcaggcgagccagatgtttctgtgctggctggaagaggccatcgttcg |
| ccgcgtggtgacgttaccttcaaaagcgcgcttcagttttcaggaagcccgcagtgcctggggaactgcgactggataggctccggtc |
| gtatggccatcgatggtctgaaagaagttcaggaagcggtgatgctgatagaagccggactgagtacctacgagaaagagtgcgcaaa |
| acgcggtgacgactatcaggaaatttttgcccagcaggtccgtgaaacgatggagcgccgtgcagccggtcttaaaccgcccgcctgg |
| gcggctgcagcatttgaatccgggctgcgacaatcaacagaggaggagaagagtgacagcagagctgcgtaatctcccgcatattgcc |
| agcatggcctttaatgagccgctgatgcttgaacccgcctatgcgcgggttttcttttgtgcgcttgcaggccagcttgggatcagcagcct |
| gacggatgcggtgtccggcgacagcctgactgcccaggaggcactcgcgacgctggcattatccggtgatgatgacggaccacgac |
| aggcccgcagttatcaggtcatgaacggcatcgccgtgctgccggtgtccggcacgctggtcagccggacgcgggcgctgcagccgt |
| actcggggatgaccggttacaacggcattatcgcccgtctgcaacaggctgccagcgatccgatggtggacggcattctgctcgatatg |
| gacacgcccggcgggatggtggcggggggcatttgactgcgctgacatcatcgcccgtgtgcgtgacataaaaccggtatgggcgcttg |
| ccaacgacatgaactgcagtgcaggtcagttgcttgccagtgccgcctcccggcgtctggtcacgcagaccgcccggacaggctccat |
| cggcgtcatgatggctcacagtaattacggtgctgcgctggagaaacagggtgtggaaatcacgctgatttacagcggcagccataag |
| gtggatggcaacccctacagccatcttccggatgacgtccgggagacactgcagtcccggatggacgcaacccgccagatgtttgcgc |
| agaaggtgtcggcatataccggcctgtccgtgcaggttgtgctggataccgaggctgcagtgtacagcggtcaggaggccattgatgc |
| cggactggctgatgaacttgttaacagcaccgatgcgatcaccgtcatgcgtgatgcactggatgcacgtaaatcccgtctctcaggagg |
| gcgaatgaccaaagagactcaatcaacaactgtttcagccactgcttcgcaggctgacgttactgacgtggtgccagcgacggagggc |
| gagaacgccagcgcggcgcagccggacgtgaacgcgcagatcaccgcagcggttgcggcagaaaacagccgcattatggggatcc |
| tcaactgtgaggaggctcacggacgcgaagaacaggcacgcgtgctggcagaaacccccggtatgaccgtgaaaacggcccgccg |
| cattctggccgcagcaccacagagtgcacaggcgcgcagtgacactgcgctggatcgtctgatgcagggggcaccggcaccgctgg |
| ctgcaggtaacccggcatctgatgccgttaacgatttgctgaacacaccagtgtaagggatgtttatgacgagcaaagaaacctttaccca |
| ttaccagccgcagggcaacagtgacccggctcataccgcaaccgcgcccctagaccttcatcactaaaggccgcctgtgcggcttttttt |
| acgggatttttttatgtcgatgtacacaaccgcccaactgctggcggcaaatgagcagaaatttaagtttgatccgctgtttctgcgtctctttt |
| tccgtgagagctatcccttcaccacggagaaagtctatctctcacaaattccgggactggtaaacatggcgctgtacgtttcgccgattgtt |
| tccggtgaggttatccgttcccgtggcggctccacctctgaatttacgccgggatatgtcaagccgaagcatgaagtgaatccgcagatg |
| accctgcgtcgcctgccggatgaagatccgcagaatctggcggacccggcttaccgccgccgtcgcatcatcatgcagaacatgcgtg |
| acgaagagctggccattgctcaggtcgaagagatgcaggcagtttctgccgtgcttaagggcaaatacaccatgaccggtgaagccttc |
| gatccggttgaggtggatatgggccgcagtgaggagaataacatcacgcagtccggcggcacggagtggagcaagcgtgacaagtc |
| cacgtatgacccgaccgacgatatcgaagcctacgcgctgaacgccagcggtgtggtgaatatcatcgtgttcgatccgaaaggctgg |
| gcgctgttccgttccttcaaagccgtcaaggagaagctggatacccgtcgtggctctaattccgagctggagacagcggtgaaagacct |
| gggcaaagcggtgtcctataaggggatgtatggcgatgtggccatcgtcgtgtattccggacagtacgtggaaaacggcgtcaaaaag |
| aacttcctgccggacaacacgatggtgctggggaacactcaggcacgcggtctgcgcacctatggctgcattcaggatgcggacgcac |
| agcgcgaaggcattaacgcctctgcccgttacccgaaaaactgggtgaccaccggcgatccggcgcgtgagttcaccatgattcagtc |
| agcaccgctgatgctgctggctgaccctgatgagttcgtgtccgtacaactggcgtaatcatggcccttcggggccattgtttctctgtgga |

TABLE 9-continued

Sequence of pSL-LuxABE10 (SEQ ID NO: 3). Sequences encoding luciferase subunits are shown in underline.

ggagtccatgacgaaagatgaactgattgcccgtctccgctcgctgggtgaacaactgaaccgtgatgtcagcctgacggggacgaaa gaagaactggcgctccgtgtggcagagctgaaagaggagcttgatgacacggatgaaactgccggtcaggacacccctctcagccgg gaaaatgtgctgaccggacatgaaaatgaggtgggatcagcgcagccggataccgtgattctggatacgtctgaactggtcacggtcgt ggcactggtgaagctgcatactgatgcacttcacgccacgcgggatgaacctgtggcatttgtgctgccgggaacggcgtttcgtgtctc tgccggtgtggcagccgaaatgacagagcgcggcctggccagaatgcaataacgggaggcgctgtggctgatttcgataacctgttcg atgctgccattgcccgcgccgatgaaacgatacgcgggtacatgggaacgtcagccaccattacatccggtgagcagtcaggtgcggt gatacgtggtgtttttgatgaccctgaaaatatcagctatgccggacagggcgtgcgcgttgaaggctccagcccgtccctgtttgtccgg actgatgaggtgcggcagctgcggcgtggagacacgctgaccatcggtgaggaaaatttctgggtagatcgggtttcgccggatgatg gcggaagttgtcatctctggcttggacggggcgtaccgcctgccgttaaccgtcgccgctgaaaggggggatgtatggccataaaaggtc ttgagcaggccgttgaaaacctcagccgtatcagcaaaacggcggtgcctggtgccgccgcaatggccattaaccgcgttgcttcatcc gcgatatcgcagtcggcgtcacaggttgcccgtgagacaaaggtacgccggaaactggtaaaggaaagggccaggctgaaaagggc cacggtcaaaaatccgcaggccagaatcaaagttaaccgggggatttgcccgtaatcaagctgggtaatgcgcgggttgtcctttcgc gccgcaggcgtcgtaaaaaggggcagcgttcatccctgaaaggtggcggcagcgtgcttgtggtgggtaaccgtcgtattcccggcgc gtttattcagcaactgaaaaatggccggtggcatgtcatgcagcgtgtggctgggaaaaaccgttaccccattgatgtggtgaaaatccc gatggcggtgccgctgaccacggcgtttaaacaaaatattgagcggatacggcgtgaacgtcttccgaaagagctgggctatgcgctg cagcatcaactgaggatggtaataaagcgatgaaacatactgaactccgtgcagccgtactggatgcactggagaagcatgacaccgg ggcgacgtttttgatggtcgccccgctgtttttgatgaggcggattttccggcagttgccgtttatctcaccggcgctgaatacacgggcg aagagctggacagcgatacctggcaggcggagctgcatatcgaagttttcctgcctgctcaggtgccggattcagagctggatgcgtgg atggagtcccggatttatccggtgatgagcgatatcccggcactgtcagatttgatcaccagtatggtggccagcggctatgactaccgg cgcgacgatgatgcgggcttgtggagttcagccgatctgacttatgtcattacctatgaaatgtgaggacgctatgcctgtaccaaatccta caatgccggtgaaaggtgccgggaccaccctgtgggtttataaggggagcggtgacccttacgcgaatccgctttcagacgttgactgg tcgcgtctggcaaaagttaaagacctgacgcccggcgaactgaccgctgagtcctatgacgacagctatctcgatgatgaagatgcaga ctggactgcgaccgggcaggggcagaaatctgccggagataccagcttcacgctggcgtggatgcccggagagcaggggcagcag gcgctgctggcgtggtttaatgaaggcgatacccgtgcctataaaatccgcttcccgaacggcacggtcgatgtgttccgtggctgggtc agcagtatcggtaaggcggtgacggcgaaggaagtgatcacccgcacggtgaaagtcaccaatgtgggacgtccgtcgatggcaga agatcgcagcacggtaacagcggcaaccggcatgaccgtgacgcctgccagcacctcggtggtgaaagggcagagcaccacgctg accgtggccttccagccggagggcgtaaccgacaagagctttcgtgcggtgtctgcggataaaacaaaagccaccgtgtcggtcagtg gtatgaccatcaccgtgaacggcgttgctgcaggcaaggtcaacattccggttgtatccggtaatggtgagtttgctgcggttgcagaaat taccgtcaccgccagttaatccggagagtcagcgatgttcctgaaaaccgaatcatttgaacataacggtgtgaccgtcacgctttctgaa ctgtcagccctgcagcgcattgagcatctcgccctgatgaaacggcaggcagaacaggcggagtcagacagcaaccggaagtttact gtggaagacgccatcagaaccggcgcgtttctggtggcgatgtccctgtggcataaccatccgcagaagacgcagatgccgtccatga atgaagccgttaaacagattgagcaggaagtgcttaccacctggcccacggaggcaatttctcatgctgaaaacgtggtgtaccggctgt ctggtatgtatgagtttgtggtgaataatgcccctgaacagacagaggacgccgggcccgcagagcctgtttctgcgggaaagtgttcg acggtgagctgagttttgccctgaaactggcgcgtgagatggggcgacccgactggcgtgccatgcttgccgggatgtcatccacgga gtatgccgactggcaccgcttttacagtacccattattttcatgatgttctgctggatatgcacttttccgggctgacgtacaccgtgctcagc ctgtttttcagcgatccggatatgcatccgctggatttcagtctgctgaaccggcgcgaggctgacgaagagcctgaagatgatgtgctg atgcagaaagcggcagggcttgccggaggtgtccgctttggcccggacgggaatgaagttatccccgcttccccggatgtggcggac atgacggaggatgacgtaatgctgatgacagtatcagaagggatcgcaggaggagtccggtatggctgaaccggtaggcgatctggtc TABLE 9-continued

| Sequence of pSL-LuxABE10 (SEQ ID NO: 3). Sequences encoding luciferase subunits are shown in underline. |
|---|
| gttgatttgagtctggatgcggccagatttgacgagcagatggccagagtcaggcgtcatttttctggtacggaaagtgatgcgaaaaaa |
| acagcggcagtcgttgaacagtcgctgagccgacaggcgctggctgcacagaaagcggggatttccgtcgggcagtataaagccgc |
| catgcgtatgctgcctgcacagttcaccgacgtggccacgcagcttgcaggcgggcaaagtccgtggctgatcctgctgcaacagggg |
| gggcaggtgaaggactccttcggcgggatgatccccatgttcagggggcttgccggtgcgatcaccctgccgatggtgggggccacc |
| tcgctggcggtggcgaccggtgcgctggcgtatgcctggtatcagggcaactcaaccctgtccgatttcaacaaaacgctggtcctttcc |
| ggcaatcaggcgggactgacggcagatcgtatgctggtcctgtccagagccgggcaggcggcagggctgacgtttaaccagaccag |
| cgagtcactcagcgcactggttaaggcgggggtaagcggtgaggctcagattgcgtccatcagccagagtgtggcgcgtttctcctctg |
| catccggcgtggaggtggacaaggtcgctgaagccttcgggaagctgaccacagacccgacgtcggggctgacggcgatggctcgc |
| cagttccataacgtgtcggcggagcagattgcgtatgttgctcagttgcagcgttccggcgatgaagccggggcattgcaggcggcga |
| acgaggccgcaacgaaagggtttgatgaccagacccgccgcctgaaagagaacatgggcacgctggagacctgggcagacaggac |
| tgcgcgggcattcaaatccatgtgggatgcggtgctggatattggtcgtcctgataccgcgcaggagatgctgattaaggcagaggctg |
| cgtataagaaagcagacgacatctggaatctgcgcaaggatgattattttgttaacgatgaagcgcgggcgcgttactgggatgatcgtg |
| aaaaggcccgtcttgcgcttgaagccgcccgaaagaaggctgagcagcagactcaacaggacaaaaatgcgcagcagcagagcgat |
| accgaagcgtcacggctgaaatataccgaagaggcgcagaaggcttacgaacggctgcagacgccgctggagaaatataccgcccg |
| tcaggaagaactgaacaaggcactgaaagacgggaaaatcctgcaggcggattacaacacgctgatggcggcggcgaaaaaggatt |
| atgaagcgacgctgaaaaagccgaaacagtccagcgtgaaggtgtctgcgggcgatcgtcaggaagacagtgctcatgctgccctgc |
| tgacgcttcaggcagaactccggacgctggagaagcatgccggagcaaatgagaaaatcagccagcagcgccgggatttgtggaag |
| gcggagagtcagttcgcggtactggaggaggcggcgcaacgtcgccagctgtctgcacaggagaaatccctgctggcgcataaagat |
| gagacgctggagtacaaacgccagctggctgcacttggcgacaaggttacgtatcaggagcgcctgaacgcgctggcgcagcaggc |
| ggataaattcgcacagcagcaacgggcaaaacgggccgccattgatgcgaaaagccgggggctgactgaccggcaggcagaacgg |
| gaagccacggaacagcgcctgaaggaacagtatggcgataatccgctggcgctgaataacgtcatgtcagagcagaaaaagacctgg |
| gcggctgaagaccagcttcgcgggaactggatggcaggcctgaagtccggctggagtgagtgggaagagagcgccacggacagta |
| tgtcgcaggtaaaaagtgcagccacgcagacctttgatggtattgcacagaatatggcggcgatgctgaccggcagtgagcagaactg |
| gcgcagcttcacccgttccgtgctgtccatgatgacagaaattctgcttaagcaggcaatggtggggattgtcgggagtatcggcagcgc |
| cattggcggggctgttggtggcggcgcatccgcgtcaggcggtacagccattcaggccgctgcggcgaaattccattttgcaaccgga |
| ggatttacgggaaccggcggcaaatatgagccagcggggattgttcaccgtggtgagtttgtcttcacgaaggaggcaaccagccgga |
| ttggcgtggggaatctttaccggctgatgcgcggctatgccaccggcggttatgtcggtacaccgggcagcatggcagacagccggtc |
| gcaggcgtccgggacgtttgagcagaataaccatgtggtgattaacaacgacggcacgaacgggcagataggtccggctgctctgaa |
| ggcggtgtatgacatggcccgcaagggtgcccgtgatgaaattcagacacagatgcgtgatggtggcctgttctccggaggtggacga |
| tgaagaccttccgctggaaagtgaaacccggtatggatgtggcttcggtcccttctgtaagaaaggtgcgctttggtgatggctattctcag |
| cgagcgcctgccgggctgaatgccaacctgaaaacgtacagcgtgacgctttctgtcccccgtgaggaggccacggtactggagtcgt |
| ttctggaagagcacgggggctggaaatcctttctgtggacgccgccttatgagtggcggcagataaaggtgacctgcgcaaaatggtcg |
| tcgcgggtcagtatgctgcgtgttgagttcagcgcagagtttgaacaggtggtgaactgatgcaggatatccggcaggaaacactgaat |
| gaatgcacccgtgcggagcagtcggccagcgtggtgctctgggaaatcgacctgacagaggtcggtggagaacgttatttttctgtaat |
| gagcagaacgaaaaaggtgagccggtcacctggcaggggcgacagtatcagccgtatcccattcaggggagcggttttgaactgaat |
| ggcaaaggcaccagtacgcgccccacgctgacggtttctaacctgtacggtatggtcaccgggatggcggaagatatgcagagtctgg |
| tcggcggaacggtggtccggcgtaaggtttacgcccgttttctggatgcggtgaacttcgtcaacggaaacagttacgccgatccggag |
| caggaggtgatcagccgctggcgcattgagcagtgcagcgaactgagcgcggtgagtgcctcctttgtactgtccacgccgacggaaa |
| cggatggcgctgtttttccgggacgtatcatgctggccaacacctgcacctggacctatcgcggtgacgagtgcggttatagcggtccg |

TABLE 9-continued

| Sequence of pSL-LuxABE10 (SEQ ID NO: 3). Sequences encoding luciferase subunits are shown in underline. |
|---|
| gctgtcgcggatgaatatgaccagccaacgtccgatatcacgaaggataaatgcagcaaatgcctgagcggttgtaagttccgcaataa |
| cgtcggcaactttggcggcttcctttccattaacaaactttcgcagtaaatcccatgacacagacagaatcagcgattctggcgcacgccc |
| ggcgatgtgcgccagcggagtcgtgcggcttcgtggtaagcacgccggaggggaaagatatttcccctgcgtgaatatctccggtga |
| gccggaggctatttccgtatgtcgccggaagactggctgcaggcagaaatgcagggtgagattgtggcgctggtccacagccacccc |
| ggtggtctgccctggctgagtgaggccgaccggcggctgcaggtgcagagtgatttgccgtggtggctggtctgccgggggacgattc |
| ataagttccgctgtgtgccgcatctcaccgggcggcgctttgagcacggtgtgacggactgttacacactgttccgggatgcttatcatct |
| ggcggggattgagatgccggactttcatcgtgaggatgactggtggcgtaacggccagaatctctatctggataatctggaggcgacgg |
| ggctgtatcaggtgccgttgtcagcggcacagccgggcgatgtgctgctgtgctgttttggttcatcagtgccgaatcacgccgcaattta |
| ctgcggcgacggcgagctgctgcaccatattcctgaacaactgagcaaacgagagaggtacaccgacaaatggcagcgacgcacac |
| actccctctggcgtcaccgggcatggcgcgcatctgcctttacggggatttacaacgatttggtcgccgcatcgaccttcgtgtgaaaac |
| gggggctgaagccatccgggcactggccacacagctcccggcgtttcgtcagaaactgagcgacggctggtatcaggtacggattgc |
| cgggcgggacgtcagcacgtccgggttaacggcgcagttacatgagactctgcctgatggcgctgtaattcatattgttcccagagtcgc |
| cggggccaagtcaggtggcgtattccagattgtcctgggggctgccgccattgccggatcattctttaccgccggagccacccttgcag |
| catggggggcagccattggggccggtggtatgaccggcatcctgttttctctcggtgccagtatggtgctcggtggtgtggcgcagatg |
| ctggcaccgaaagccagaactccccgtatacagacaacggataacggtaagcagaacacctatttctcctcactggataacatggttgc |
| ccagggcaatgttctgcctgttctgtacggggaaatgcgcgtggggtcacgcgtggtttctcaggagatcagcacggcagacgaaggg |
| gacggtggtcaggttgtggtgattggtcgctgatgcaaaatgttttatgtgaaaccgcctgcgggcggttttgtcatttatggagcgtgagg |
| aatgggtaaaggaagcagtaaggggcataccccgcgcgaagcgaaggacaacctgaagtccacgcagttgctgagtgtgatcgatgc |
| catcagcgaagggccgattgaaggtccggtggatggcttaaaaagcgtgctgctgaacagtacgccggtgctggacactgaggggaa |
| taccaacatatccggtgtcacggtggtgttccgggctggtgagcaggagcagactccgccggagggatttgaatcctccggctccgag |
| acggtgctgggtacggaagtgaaatatgacacgccgatcacccgcaccattacgtctgcaaacatcgaccgtctgcgctttaccttcggt |
| gtacaggcactggtggaaaccacctcaaagggtgacaggaatccgtcggaagtccgcctgctggttcagatacaacgtaacggtggct |
| gggtgacggaaaaagacatcaccattaagggcaaaaccacctcgcagtatctggcctcggtggtgatgggtaacctgccgccgcgcc |
| cgtttaatatccggatgcgcaggatgacgccggacagcaccacagaccagctgcagaacaaaacgctctggtcgtcatacactgaaat |
| catcgatgtgaaacagtgctacccgaacacggcactggtcggcgtgcaggtggactcggagcagttcggcagccagcaggtgagcc |
| gtaattatcatctgcgcgggcgtattctgcaggtgccgtcgaactataacccgcagacgcggcaatacagcggtatctgggacggaacg |
| tttaaaccggcatacagcaacaacatggcctggtgtctgtgggatatgctgacccatccgcgctacggcatggggaaacgtcttggtgc |
| ggcggatgtggataaatgggcgctgtatgtcatcggccagtactgcgaccagtcagtgccggacggctttggcggcacggagccgcg |
| catcacctgtaatgcgtacctgaccacacagcgtaaggcgtgggatgtgctcagcgatttctgctcggcgatgcgctgtatgccggtatg |
| gaacgggcagacgctgacgttcgtgcaggaccgaccgtcggataagacgtggacctataaccgcagtaatgtggtgatgccggatgat |
| ggcgcgccgttccgctacagcttcagcgccctgaaggaccgccataatgccgttgaggtgaactggattgacccgaacaacggctgg |
| gagacggcgacagagcttgttgaagatacgcaggccattgcccgttacggtcgtaatgttacgaagatggatgcctttggctgtaccagc |
| cgggggcaggcacaccgcgccgggctgtggctgattaaaacagaactgctggaaacgcagaccgtggatttcagcgtcggcgcaga |
| agggcttcgccatgtaccgggcgatgttattgaaatctgcgatgatgactatgccggtatcagcaccggtggtcgtgtgctggcggtgaa |
| cagccagacccggacgctgacgctcgaccgtgaaatcacgctgccatcctccggtaccgcgctgataagcctggttgacggaagtgg |
| caatccggtcagcgtggaggttcagtccgtcaccgacggcgtgaaggtaaaagtgagccgtgttcctgacggtgttgctgaatacagcg |
| tatgggagctgaagctgccgacgctgcgccagcgactgttccgctgcgtgagtatccgtgagaacgacgacggcacgtatgccatcac |
| cgccgtgcagcatgtgccggaaaaagaggccatcgtggataacggggcgcactttgacggcgaacagagtggcacggtgaatggtg |

TABLE 9-continued

Sequence of pSL-LuxABE10 (SEQ ID NO: 3). Sequences encoding luciferase subunits are shown in underline.

tcacgccgccagcggtgcagcacctgaccgcagaagtcactgcagacagcggggaatatcaggtgctggcgcgatgggacacacc gaaggtggtgaagggcgtgagtttcctgctccgtctgaccgtaacagcggacgacggcagtgagcggctggtcagcacggcccgga cgacggaaaccacataccgcttcacgcaactggcgctggggaactacaggctgacagtccgggcggtaaatgcgtgggggcagcag ggcgatccggcgtcggtatcgttccggattgccgcaccggcagcaccgtcgaggattgagctgacgccgggctattttcagataaccg ccacgccgcatcttgccgtttatgacccgacggtacagtttgagttctggttctcggaaaagcagattgcggatatcagacaggttgaaac cagcacgcgttatcttggtacggcgctgtactggatagccgccagtatcaatatcaaaccgggccatgattattacttttatatccgcagtgt gaacaccgttggcaaatcggcattcgtggaggccgtcggtcgggcgagcgatgatgcggaaggttacctggatttttttcaaaggcaaga taaccgaatcccatctcggcaaggagctgctggaaaaagtcgagctgacggaggataacgccagcagactggaggagttttcgaaag agtggaaggatgccagtgataagtggaatgccatgtgggctgtcaaaattgagcagaccaaagacggcaaacattatgtcgcgggtatt ggcctcagcatggaggacacggaggaaggcaaactgagccagtttctggttgccgccaatcgtatcgcatttattgacccggcaaacg ggaatgaaacgccgatgtttgtggcgcagggcaaccagatattcatgaacgacgtgttcctgaagcgcctgacggcccccaccattacc agcggcggcaatcctccggccttttccctgacaccggacggaaagctgaccgctaaaaatgcggatatcagtggcagtgtgaatgcga actccgggacgctcagtaatgtgacgatagctgaaaactgtacgataaacggtacgctgagggcggaaaaaatcgtcggggacattgt aaaggcggcgagcgcggcttttccgcgccagcgtgaaagcagtgtggactggccgtcaggtacccgtactgtcaccgtgaccgatga ccatccttttgatcgccagatagtggtgcttccgctgacgtttcgcggaagtaagcgtactgtcagcggcaggacaacgtattcgatgtgtt atctgaaagtactgatgaacggtgcggtgatttatgatggcgcggcgaacgaggcggtacaggtgttctcccgtattgttgacatgccag cgggtcggggaaacgtgatcctgacgttcacgcttacgtccacacggcattcggcagatattccgccgtatacgtttgccagcgatgtgc aggttatggtgattaagaaacaggcgctgggcatcagcgtggtctgagtgtgttacagaggttcgtccgggaacgggcgttttattataa acagtgagaggtgaacgatgcgtaatgtgtgtattgccgttgctgtctttgccgcacttgcggtgacagtcactccggcccgtgcggaag gtggacatggtacgtttacggtgggctattttcaagtgaaaccgggtacattgccgtcgttgtcgggcggggataccggtgtgagtcatct gaaagggattaacgtgaagtaccgttatgagctgacggacagtgtgggggtgatggcttccctggggttcgccgcgtcgaaaaagagc agcacagtgatgaccggggaggatacgtttcactatgagagcctgcgtggacgttatgtgagcgtgatggccggaccggttttacaaat cagtaagcaggtcagtgcgtacctggcacgacaggtttcccgactggaaagcgggcagtgagcgcaacgcaattaatgtgagttagct cactcattaggcaccccaggctttacactttatgcttccggctcgtatgttgtgtggaattgtgagcggataacaatttcacacaggaaaca gctatgaccatgattacgccaagctatttaggtgacactatagaatactcaagctatgcatccaacgcgttgggagctctcccatatggtcg acctgcaggcggccgcgaattcactagtgattatggtaaagcaagatgaagttatcacattgttatcaaatattcgtagtaatcgatgcaag atatattctttgttaggaagttcgcatgacttgagtgaaaatttagtggtcctgcgcaatttttatcaatcggttacgaaagccgctatcgcgat ggataatgatcatctggatattgatgttgatattactgaaccgtcatttgaacatttaactattgcgacagtcaatgaacgccgaatgagaatt gagattgaaaatcaagcaatttctctgtcttaaaatctattgagatattctatcactcaaatagcaatataaggactctctatgaaatttggaaa ctttttgcttacataccaacctccccaatttctcaaacagaggtaatgaaacgtttggttaaattaggtcgcatctctgaggagtgtggttttg ataccgtatggttactggagcatcatttcacggagtttggtttgcttggtaacccttatgtcgctgctgcatatttacttggcgcgactaaaaaa ttgaatgtaggaactgccgctattgttcttcccacagcccatccagtacgccaacttgaagatgtgaatttattggatcaaatgtcaaaagga cgatttcggtttggtatttgccgagggctttacaacaaggactttcgcgtattcggcacagatatgaataacagtcgcgccttagcggaatg ctggtacgggctgataaagaatggcatgacagagggatatatggaagctgataatgaacatatcaagttccataaggtaaaagtaaaccc cgcggcgtatagcagaggtggcgcaccggtttatgtggtggctgaatcagcttcgacgactgagtgggctgctcaatttggcctaccgat gatattaagttggattataaatactaacgaaaagaaagcacaacttgagctttataatgaagtggctcaagaatatgggcacgatattcata atatcgaccattgcttatcatatataacatctgtagatcatgactcaattaaagcgaaagagatttgccggaaatttctggggcattggtatga ttcttatgtgaatgctacgactatttttgatgattcagaccaaacaagaggttatgatttcaataaagggcagtggcgtgactttgtattaaaag gacataaagatactaatcgccgtattgattacagttacgaaatcaatcccgtgggaacgccgcaggaatgtattgacataattcaaaaaga TABLE 9-continued

| Sequence of pSL-LuxABE10 (SEQ ID NO: 3). Sequences encoding luciferase subunits are shown in underline. |
|---|
| cattgatgctacaggaatatcaaatatttgttgtggatttgaagctaatggaacagtagacgaaattattgcttccatgaagctcttccagtct |
| gatgtcatgccatttcttaaagaaaaacaacgttcgctattatattagctaaggagaaagaaatgaaatttggattgttcttccttaacttcatc |
| aattcaacaactgttcaagaacaaagtatagttcgcatgcaggaaataacggagtatgttgataagttgaattttgaacagattttagtgtatg |
| aaaatcattttcagataatggtgttgtcggcgctcctctgactgtttctggttttctgctcggtttaacagagaaaattaaaattggttcattaaa |
| tcacatcattacaactcatcatcctgtcgccatagcggaggaagcttgcttattggatcagttaagtgaagggagatttattttagggtttagt |
| gattgcgaaaaaaaagatgaaatgcatttttttaatcgcccggttgaatatcaacagcaactatttgaagagtgttatgaaatcattaacgatg |
| ctttaacaacaggctattgtaatccagataacgattttttatagcttccctaaaatatctgtaaatccccatgcttatacgccaggcggacctcg |
| gaaatatgtaacagcaaccagtcatcatattgttgagtgggcggccaaaaaaggtattcctctcatctttaagtgggatgattctaatgatgtt |
| agatatgaatatgctgaaagatataaagccgttgcggataaatatgacgttgacctatcagagatagaccatcagttaatgatattagttaac |
| tataacgaagatagtaataaagctaaacaagagacgcgtgcatttattagtgattatgttcttgaaatgcaccctaatgaaaatttcgaaaat |
| aaacttgaagaaataattgcagaaaacgctgtcggaaattatacggagtgtataactgcggctaagttggcaattgaaaagtgtggtgcg |
| aaaagtgtattgctgtcctttgaaccaatgaatgatttgatgagccaaaaaaatgtaatcaatattgttgatgataatattaagaagtaccacat |
| ggaatatacctaatagatttcgagttgcagcgaggcggcaagtgaacgaatccccaggagcatagataactatgtgactggggtgagtg |
| aaagcagccaacaaagcagcagcttgaaagatgaagggtataaaagagtatgacagcagtgctgccatactttctaatattatcttgagg |
| agtaaaacaggtatgacttcatatgttgataaacaagaaattacagcaagctcagaaattgatgatttgatttttcgagcgatccattagtgt |
| ggtcttacgacgagcaggaaaaaatcagaaagaaacttgtgcttgatgcatttcgtaatcattataaacattgtcgagaatatcgtcactact |
| gtcaggcacacaaagtagatgacaatattacggaaattgatgacatacctgtattcccaacatcggtttttaagtttactcgcttattaacttct |
| caggaaaacgagattgaaagttggtttaccagtagcggcacgaatggtttaaaaagtcaggtggcgcgtgacagattaagtattgagag |
| actcttaggctctgtgagttatggcatgaaatatgttggtagttggtttgatcatcaaatagaattagtcaatttgggaccagatagatttaatg |
| ctcataatatttggtttaaatatgttatgagtttggtggaattgttatatcctacgacatttaccgtaacagaagaacgaatagattttgttaaaac |
| attgaatagtcttgaacgaataaaaaatcaagggaaagatctttgtcttattggttcgccatactttatttatttactctgccattatatgaaagat |
| aaaaaaatctcattttctggagataaaagcctttatatcataaccggaggcggctggaaaagttacgaaaaagaatctctgaaacgtgatg |
| atttcaatcatcttttatttgatactttcaatctcagtgatattagtcagatccgagatatatttaatcaagttgaactcaacacttgtttctttgagg |
| atgaaatgcagcgtaaacatgttccgccgtgggtatatgcgcgagcgcttgatcctgaaacgttgaaacctgtacctgatggaacgccgg |
| ggttgatgagttatatggatgcgtcagcaaccagttatccagcatttattgttaccgatgatgtcgggataattagcagagaatatggtaagt |
| atcccggcgtgctcgttgaaattttacgtcgcgtcaatacgaggacgcagaaagggtgtgctttaagcttaaaccaagcatttaatagttga |
| cataatcgaattcccgcggccgccatggcggccgggagcatgcgacgtcgggcccaattcgccctatagtgagtcgtattacaattcac |
| tggccgtcgttttacaacgtcgtgactgggaaaaccctggcgttacccaacttaatcgccttgcagcacatccccctttcgccaggtacgc |
| catggccggagtggctcacagtcggtggtccggcagtacaatggattaccgtaagacggaaatcactcccgggatcctctagagtcga |
| cctgcaggcatgcaagcttggcgtaatcatggtcatagctgtttcctgtgtgaaattgttatccgctcacaattccacacaacatacgagcc |
| ggaagcataaagtgtaaagcctggggtgcctaatgagtgagctaactcacattaattgcgttgcgctcactgcccgctttccagtcggga |
| aacctgtcgtgccagctgcattaatgaatcggccaacgcgcggggagaggcggtttgcgtattgggcgctcttccgcttcctcgctcact |
| gactcgctgcgctcggtcgttcggctgcggcgagcggtatcagctcactcaaaggcggtaatacggttatccacagaatcaggggataa |
| cgcaggaaagaacatgtgagcaaaaggccagcaaaaggccaggaaccgtaaaaaggccgcgttgctggcgtttttccataggctccg |
| cccccctgacgagcatcacaaaaatcgacgctcaagtcagaggtggcgaaacccgacaggactataaagataccaggcgtttccccct |
| ggaagctccctcgtgcgctctcctgttccgaccctgccgcttaccggatacctgtccgcctttctcccttcgggaagcgtggcgctttctca |
| tagctcacgctgtaggtatctcagttcggtgtaggtcgttcgctccaagctgggctgtgtgcacgaaccccccgttcagcccgaccgctg |
| cgccttatccggtaactatcgtcttgagtccaacccggtaagacacgacttatcgccactggcagcagccactggtaacaggattagcag |

TABLE 9-continued

| Sequence of pSL-LuxABE10 (SEQ ID NO: 3). Sequences encoding luciferase subunits are shown in underline. |
|---|
| agcgaggtatgtaggcggtgctacagagttcttgaagtggtggcctaactacggctacactagaaggacagtatttggtatctgcgctctg |
| ctgaagccagttaccttcggaaaaagagttggtagctcttgatccggcaaacaaaccaccgctggtagcggtggtttttttgtttgcaagca |
| gcagattacgcgcagaaaaaaaggatctcaagaagatcctttgatcttttctacggggtctgacgctcagtggaacgaaaactcacgttaa |
| gggattttggtcatgagattatcaaaaaggatcttcacctagatccttttaaattaaaaatgaagttttaaatcaatctaaagtatatatgagtaa |
| acttggtctgacagttaccaatgcttaatcagtgaggcacctatctcagcgatctgtctatttcgttcatccatagttgcctgactccccgtcgt |
| gtagataactacgatacgggagggcttaccatctggccccagtgctgcaatgataccgcgagacccacgctcaccggctccagatttat |
| cagcaataaaccagccagccggaagggccgagcgcagaagtggtcctgcaactttatccgcctccatccagtctattaattgttgccgg |
| gaagctagagtaagtagttcgccagttaatagtttgcgcaacgttgttgccattgctacaggcatcgtggtgtcacgctcgtcgtttggtatg |
| gcttcattcagctccggttcccaacgatcaaggcgagttacatgatcccccatgttgtgcaaaaaagcggttagctccttcggtcctccgat |
| cgttgtcagaagtaagttggccgcagtgttatcactcatggttatggcagcactgcataattctcttactgtcatgccatccgtaagatgctttt |
| ctgtgactggtgagtactcaaccaagtcattctgagaatagtgtatgcggcgaccgagttgctcttgcccggcgtcaatacgggataatac |
| cgcgccacatagcagaactttaaaagtgctcatcattggaaaacgttcttcggggcgaaaactctcaaggatcttaccgctgttgagatcc |
| agttcgatgtaacccactcgtgcacccaactgatcttcagcatcttttactttcaccagcgtttctgggtgagcaaaaacaggaaggcaaaa |
| tgccgcaaaaaagggaataagggcgacacggaaatgttgaatactcatactcttcctttttcaatattattgaagcatttatcagggttattgt |
| ctcatgagcggatacatatttgaatgtatttagaaaaataaacaaataggggttccgcgcacatttccccgaaaagtgccacctgacgtcta |
| agaaaccattattatcatgacattaacctataaaaataggcgtatcacgaggccctttcgtctcgcgcgtttcggtgatgacggtgaaaacc |
| tctgacacatgcagctcccggagacggtcacagcttgtctgtaagcggatgccgggagcagacaagcccgtcagggcgcgtcagcg |
| ggtgttggcgggtgtcggggctggcttaactatgcggcatcagagcagattgtactgagagtgcaccatatgcggtgtgaaataccgca |
| cagatgcgtaaggagaaaataccgcatcaggcgccattcgccattcaggctgcgcaactgttgggaagggcgatcggtgcgggcctct |
| tcgctattacgccagctggcgaaagggggatgtgctgcaaggcgattaagttgggtaacgccagggttttcccagtcacgacgttgtaaa |
| acgacggccagtgaattcgattttaagatacattgatgagtttggacaaaccacaactagaatgcagtgaaaaaaatgctttatttgtgaaat |
| ttgtgatgctattgctttatttgtaaccattataagctgcaataaacaagttaacaacaacaattgcattcattttatgtttcaggttcaggggga |
| ggtgtgggaggttttttaaagcaagtaaaacctctacaaatgtggtatggctgattatgatcagttatctagagtcgcggccgctttacttgta |
| cagctcgtccatgccgagagtgatcccggcggcggtcacgaactccagcaggaccatgtgatcgcgcttctcgttggggtctttgctca |
| gggcggactgggtgctcaggtagtggttgtcgggcagcagcacggggccgtcgccgatgggggtgttctgctggtagtggtcggcga |
| gctgcacgctgccgtcctcgatgttgtggcggatcttgaagttcaccttgatgccgttcttctgcttgtcggccatgatatagacgttgtggct |
| gttgtagttgtactccagcttgtgccccaggatgttgccgtcctccttgaagtcgatgcccttcagctcgatgcggttcaccagggtgtcgc |
| cctcgaacttcacctcggcgcgggtcttgtagttgccgtcgtccttgaagaagatggtgcgctcctggacgtagccttcgggcatggcgg |
| acttgaagaagtcgtgctgcttcatgtggtcggggtagcggctgaagcactgcacgccgtaggtcagggtggtcacgagggtgggcca |
| gggcacgggcagcttgccggtggtgcagatgaacttcagggtcagcttgccgtaggtggcatcgccctcgccctcgccggacacgct |
| gaacttgtggccgtttacgtcgccgtccagctcgaccaggatgggcaccaccccggtgaacagctcctcgcccttgctcaccatggtgg |
| cgaccggtggatcgatcctagcggatctgacggttcactaaaccagctctgcttatatagacctcccaccgtacacgcctaccgcccattt |
| gcgtcaatggggcggagttgttacgacattttggaaagtcccgttgattttggtgccaaaacaaactcccattgacgtcaatggggtggag |
| acttggaaatccccgtgagtcaaaccgctatccacgcccattgatgtactgccaaaaccgcatcaccatggtaatagcgatgactaatac |
| gtagatgtactgccaagtaggaaagtcccataaggtcatgtactgggcataatgccaggcgggccatttaccgtcattgacgtcaatagg |
| gggcgtacttggcatatgatacacttgatgtactgccaagtgggcagtttaccgtaaatactccacccattgacgtcaatggaaagtcccta |
| ttggcgttactatgggaacatacgtcattattgacgtcaatgggcgggggtcgttgggcggtcagccaggcgggccatttaccgtaagtt |
| atgtaacgcggaactccatatatgggctatgaactaatgaccccgtaattgattactattaaatcactagtgaattcgattaaagcgacggc |
| acagctcgcggaaaatatcaaagtcgttgcgcgcctcgaactgcggcggcaccacctgtttcatggcgataatgccacggttggagtgg |

TABLE 9-continued

| Sequence of pSL-LuxABE10 (SEQ ID NO: 3). Sequences encoding luciferase subunits are shown in underline. |
| --- |
| ttgccgtactggtcgagatcgttacgctcaaactgcgtggtcgcaggcagcacgatatcggcaaagcggcaggttgaggtccactggtt |
| atctatggcgataaccgtttccagcttgcgccagccttcaataatgcggttgatctgctgatggcgatggaatgggttagttccggcaaaaa |
| tacacattttcagcggcggcagttttaccgatttaccgttccagttgatcactttccccggttcgaggatcgcatcgataaaacgggcaatc |
| ggaatggtgctgctgtagcctttgtaatcactgttgtcgtgaacaggcggaatcgacgtagagccggagaaaccactcagaataacgcct |
| ttacgccccggcgtgcctgcgccgttatagtgccagccaaaaccaaagccaccacctggcaggccaatttgccccagcatcgccgcca |
| gaaccacaatcatccacgcccactgttcaccgtgctgcatacgctgcacgcaccagccagcaataatttgcgttctgttcgccgccatctg |
| ccgcgccagcccacgaatggtttcggcatcaatgccggtcagtttttcagcccatgcggcatctttcggctgaccgtctttctcacccagc |
| aggtacggcaggaactgctcaaaacccacacagtagttagcgaggaagtttttgtcgtacaggttttcactgtacagcgtatacgccagc |
| gccagttgcagcggcacatcagtttgcgggttaaccgcaatgtgcttcacatgctcgcgccccagatactcatgggtggatgtgacaacc |
| ggatcgatgctgatgacctcaatttcaccggcggtgactttcgcttttagctgcgcgtaatattcataaacatcgtgatccgggcaccacca |
| gttcgcttgctggtttttcagcaaatcagagccccacagcacaatggttttgctgttctgcaataccagcggccaggaggtttgctgttcata |
| cacttccattgagccaaccacgcgcggcaggatcacctgcgcagcaccggtagagtaatctccgcccgtaccaacgctattaccatgca |
| aggcaatagctttcgccagcatccccgaagcgttatggaacatccccgtcgattgccaaccactggcggtcagcaaggcactcggccc |
| gtgagttttctgcacgcgttccagttcttcatagaacatgtcgagggcttcatcccagctcacgcgcacaaaacggttatcaccgcgctgg |
| gaggtatcgctgagatggcgcttacgcagccagtccacgcgtaccatcggataacgaatacgcgccgcgttgtgtacgtgatccggca |
| atccggcaatcattttcgacggatatttatccagttcgaacggttttgccgccacaaagcgaccatccttcaccgtcgcgcggatagcccc |
| ccagtgcgacccggtaagaatgccctctttcgagatgacagcctcagtcgccgcttgcgccgcagtcgcacggcgcggcgttaacaat |
| gacggccccagcatcccggcgacggttaagccgccgagttgtgccagaaaacgccgacgtgatgcctgaaagagatcgttattgttca |
| ttatttttcttccttcttatcgccgtgagccttacctgcggtgtcagacgcattcatttgcagatatttcaacaaagtgcgttcttcacgtttatcg |
| agactggtaaagccaatcatgccgttgagcgtgccgatccaaccgttagcgtcaaagtgggcgatttccggtgcgccgtggcactggtt |
| acaggtgccgttgtacaacgaatccgcataagcccagatcggtttgatatcgttcaccatgtcgcctttcttcatccacgcagtggcctgca |
| acttgctccactcggtattggtgtcggcaacggtggttttctccagcgtttttacctgctgctgcacatcaccacgaatcgaggcaacaaag |
| atgcgtttacctgggaattgggtgagtacacgctgacgtccggcgctttccgtccagccggtaatttcaatttgcagccagtcgccgtcac |
| gtttaaggactttcacttccgaagcaggcagcagagaaccagaggcttctttatcgcctttcgccgcataaattggcttaatatcaatagagt |
| acagcgtgtcaccactgtcattagcactggcgcgcagctcatcgaactgcttacggaagccgctactcatatccggtaactggtgggcaa |
| tacctttatgacagtcgatgcaggattgattatctttcgctgccaccttcatctgacgtgccgcttcaggatgctgcttcgcatgatccatcgc |
| atcgtagttatggcaggagcggcaggttgccgagttgttttctttcattcgcgcccattcacgctcggcaagttccgcgcgtttggcttcga |
| atttttcaggtgtatcaatggagtgagcaataaaggtctggtagatatcattgctcgcttccagtttgcgcttcaccatgcctggaatatccgg |
| cgggatatgacagtcatggcattcagctcgcacgccggaggcgttctggaaatgcaccgactgtttatattcttcatacaccggttgcata |
| ctgtggcaactgacacaaaattcggttgtgctggtgactttgatcccaacgtgtggcaatacaatcagcgcaatgccaatcacaatcccaa |
| ttgcgaccagcgccagtaccgaccaacgagcactgggtcggcgtagcgcgttccagagtttccgcataatagcccctgtaaaattatgg |
| tttagtgaagcgatcttaatgagcaaatatgaacagcggcactggtcaggatgaacggcttacggcagaatatgaacagatatgaacag |
| aatgagtaaaaccctctgatgccacatcacattgttattgttgaagatgagccggttacccaggcgcgattacaatcttacttcactcagga |
| ggggtataccgtttccgttacagcgagcggtgccgggctgcgggaaattatgcagaatcagccggtagatttaattctgctggatatcaa |
| cttacccgatgaaaatggcctgatgttaacccgcgccctgcgagaacgctcaacggtggggattattctggttaccggacgcagcgatc |
| ggattgaccgtattgttgggctggaaatgggcgcagacgattacgtcaccaaaccgctggaactgcgcgaactggtagtacgggtgaa |
| aaatctgctctggcgaatcgacctcgcgcgacaagctcaaccgcacactcaggacaactgctatcgctttgccggttattgcctgaatgtg |
| tcgcgccatacgctggagcgggatggcgagccgattaaactgacccgcgcagagtatgaaatgttggtggcatttgtgacgaatccgg |

TABLE 9-continued

Sequence of pSL-LuxABE10 (SEQ ID NO: 3). Sequences encoding luciferase subunits are shown in underline.

gcgaaattctcagccgtgaacgtctgctacgtatgctttctgcgcgtcgggtggaaaaccctgacctgcgcaccgtcgatgtgttaattcgt cgtttacgtcataaactcagcgcggatttactggtgacgcaacatggtgaaggttatttcttagccgctgatgtgtgctgataaaaatagacc ggacgaaatcccccctggtgacagcgagcggcggatatgttctcggtcggcatttttcggcgtcagaactaaaatcggtgggctgacatta tcagacaccgattgcccctgtaattgcctgatggcctgctcaactgccagttccccctgccagaccatttgatcgctggcagccataatca ctcttccccgcttcagcccgcgatacacctgatgtgaaagataaaacgacaccacggtaagcggcgttttcaggttacgcccttcacccat tgccgcctctgccgcaatggccgttccggcaacgacgtcaatttctgggtggcgttccagcatctcctgcaacaggttacgctggatttca atatcgttatcaccaagcgcaatatcaacaatacgcaccgggcttccggcaatggctgcgcgaaaaccctcgaccatctctttactgccc ccggcattatcgggtccgggcatcaacagcacgttcagtggtttaccgtgcgcccattgcaccaaatatcgcccaggttgatagcccatc tgaaaccagggtacaccaacgcggcttttcacctggggagcatcaatagcatttaccagttcgatcaccggcagacttgctacctgctttt gcagatcgggaaatgaggtcgtgctactaccgagtaaaatggcctctgcgccccactgtttacactggtcgatttgtgcttgctgggtagc caactggctgtagccgcctgcctccagcacttttaaatccacaccatagcggcgagctgcctcctgcataccatagttcaacgataacca gtatgaatctttcaggctgggataaagcgcgcacagtttccatgcgcgtttggctttaagcggcatagaggcttgcaccgtgaaatgctgc gcatcatgccagcgcaacaggttatcagccgaaaatgccggcaacatgaaaagggaaagaagtaaaaatagcagtacgcgcatgata gcctcatcaataataaggctttatgctagatgcattccgctttgcgactcaaccttttttcaccttaagtgcaccgaccgtgaatttaaccctga cccgaagactctggatgggctttgccctgatggcgctgttaaccctgaccagtaccctggtgggatggtacaacctgcgctttatcagcc aggtggaaaaagacaacactcaggcattgattcctaccatgaatatggcgcgccagttgagcgaagccagcgcctgggaacttttcgcc gcgcagaacctgaccagtgccgataacgaaaagatgtggcaggcgcaggggcgaatgctcaccgcacaaagcctgaagattaatgc gttgctgcaagcgttacgggaacaaggttttgataccaccgctattgaacaacaggagcaggagatctcccgttcattacgtcagcaagg ggaactggtggggcggcgtctgcaactacgccagcaacaacggcaactcagtcagcagatagtcgctgccgccgatgagatcgcac gcctggcgcaaggtcaggcgaataatgcgacaacttccgctggagcgacccaggccgggatttacgatttgatcgaacaagatcagcg tcaggctgctgaaagtgcactcgatcggctgattgatatcgatcttgagtatgttaaccagatgaatgaactgcgccttagcgctctgcgg gtgcagcaaatggtgatgaatctggggctggagcagatccagaaaaatgcaccaacgctggaaaagcagctcaataatgcggtgaaa attctgcaacgtcggcaaatacgcattgaagatccgggtgttcgtgcgcaggtcgcaacaacgttaactaccgttagccaatatagcgatt tgctggcgctgtatcagcaggacagtgaaatcagcaatcacctacaaactctcgcacaaaataacatcgcccagttcgcgcagtttagta gcgaagtcagtcagctggtcgactcggtacccggggatccactcgttattctcggacgagtgttcagtaatgaacctctggagagaacca tgtatatgatcgttatctgggttggacttctgcttttaagcccagataactggcctgaatatgttaatgagagaatcggtattcctcatgtgtgg catgttttcgtctttgctcttgcattttcgctagcaattaatgtgcatcgattatcagctattgccagcgccagatataagcgatttaagctaaga aaacgcattaagatgcaaaacgataaagtgcgatcagtaattcaaaaccttacagaagagcaatctatggttttgtgcgcagcccttaatg aaggcaggaagtatgtggttacatcaaaacaattcccatacattagtgagttgattgagcttggtgtgttgaacaaaactttttcccgatgga atggaaagcatatattattccctattgaggatatttactggactgaattagttgccagctatgatccatataatattgagataaagccaaggcc aatatctaagtaactagataagaggaatcgattttcccttaattttctggcgtccactgcatgttatgccgcgttcgccaggcttgctgtaccat gtgcgctgattcttgcgctcaatacgttgcaggttgctttcaatctgtttgtggtattcagccagcactgtaaggtctatcggatttagtgcgct ttctactcgtgatttcggtttgcgattcagcgagagaatagggcggttaactggttttgcgcttaccccaaccaacaggggatttgctgcttt ccattgagcctgtttctctgcgcgacgttcgcggcggcgtgtttgtgcatccatctggattctcctgtcagttagctttggtggtgtgtggcag ttgtagtcctgaacgaaaacccccgcgattggcacattggcagctaatccggaatcgcacttacggccaatgcttcgtttcgtatcacac accccaaagccttctgctttgaatgctgcccttcttcagggcttaattttaagagcgtcaccttcatggtggtcagtgcgtcctgctgatgtg ctcagtatcaccgccagtggtatttatgtcaacaccgccagagataatttatcaccgcagatggttatctgtatgtttttatatgaatttattttt gcaggggggcattgtttggtaggtgagagatctgaattgctatgtttagtgagttgtatctatttatttttcaataaatacaattggttatgtgtttt gggggcgatcgtgaggcaaagaaaacccggcgctgaggccgggttattcttgttctctggtcaaattatatagttggaaaacaaggatgc TABLE 9-continued

| Sequence of pSL-LuxABE10 (SEQ ID NO: 3). Sequences encoding luciferase subunits are shown in underline. |
|---|
| atatatgaatgaacgatgcagaggcaatgccgatggcgatagtgggtatcatgtagccgcttatgctggaaagaagcaataacccgcag |
| aaaaacaaagctccaagctcaacaaaactaagggcatagacaataactaccgatgtcatatacccatactctctaatcttggccagtcgg |
| cgcgttctgcttccgattagaaacgtcaaggcagcaatcaggattgcaatcatggttcctgcatatgatgacaatgtcgccccaagaccat |
| ctctatgagctgaaaaagaaacaccaggaatgtagtggcggaaaaggagatagcaaatgcttacgataacgtaaggaattattactatgt |
| aaacaccaggcatgattctgttccgcataattactcctgataattaatccttaactttgcccacctgccttttaaaacattccagtatatcactttt |
| cattcttgcgtagcaatatgccatctcttcagctatctcagcattggtgaccttgttcagaggcgctgagagatggcctttttctgatagataat |
| gttctgttaaaatatctccggcctcatcttttgcccgcaggctaatgtctgaaaattgaggtgacgggttaaaaataatatccttggcaaccttt |
| tttatatcccttttaaattttggcttaatgactatatccaatgagtcaaaaagctccccttcaatatctgttgcccctaagacctttaatatatcgcc |
| aaatacaggtagcttggcttctaccttcaccgttgttcggccgatgaaatgcatatgcataacatcgtctttggtggttcccctcatcagtggc |
| tctatctgaacgcgctctccactgcttaatgacattcctttcccgattaaaaaatctgtcagatcggatgtggtcggcccgaaaacagttctg |
| gcaaaaccaatggtgtcgccttcaacaaacaaaaaagatgggaatcccaatgattcgtcatctgcgaggctgttcttaatatcttcaactga |
| agctttagagcgatttatcttctgaaccagactcttgtcatttgttttggtaaagagaaaagtttttccatcgattttatgaatatacaaataattg |
| gagccaacctgcaggtgatgattatcagccagcagagaattaaggaaaacagacaggtttattgagcgcttatctttccctttatttttgctg |
| cggtaagtcgcataaaaaccattcttcataattcaatccatttactatgttatgttctgaggggagtgaaaattcccctaattcgatgaagattc |
| ttgctcaattgttatcagctatgcgccgaccagaacaccttgccgatcagccaaacgtctcttcaggccactgactagcgataactttcccc |
| acaacggaacaactctcattgcatgggatcattgggtactgtgggtttagtggttgtaaaaacacctgaccgctatccctgatcagtttcttg |
| aaggtaaactcatcacccccaagtctggctatgcagaaatcacctggctcaacagcctgctcagggtcaacgagaattaacattccgtca |
| ggaaagcttggcttggagcctgttggtgcggtcatggaattaccttcaacctcaagccagaatgcagaatcactggctttttttggttgtgctt |
| acccatctctccgcatcacctttggtaaaggttctaagctcaggtgagaacatccctgcctgaacatgagaaaaaacagggtactcatact |
| cacttctaagtgacggctgcatactaaccgcttcatacatctcgtagatttctctggcgattgaagggctaaattcttcaacgctaactttgag |
| aatttttgcaagcaatgcggcgttataagcatttaatgcattgatgccattaaataaagcaccaacgcctgactgccccatccccatcttgtct |
| gcgacagattcctgggataagccaagttcatttttctttttttcataaattgctttaaggcgacgtgcgtcctcaagctgctcttgtgttaatggtt |
| tctttttttgtgctcatacgttaaatctatcaccgcaagggataaatatctaacaccgtgcgtgttgactattttacctctggcggtgataatggtt |
| gcatgtactaaggaggttgtatggaacaacgcataaccctgaaagattatgcaatgcgctttgggcaaaccaagacagctaaagatctcg |
| gcgtatatcaaagcgcgatcaacaaggccattcatgcaggccgaaagatttttttaactataaacgctgatggaagcgtttatgcggaaga |
| ggtaaagcccttcccgagtaacaaaaaaacaacagcataaataaccccgctcttacacattccagccctgaaaaagggcatcaaattaa |
| accacacctatggtgtatgcatttatttgcatacattcaatcaattgttatctaaggaaatacttacatatggttcgtgcaaacaaacgcaacg |
| aggctctacgaatcgagagtgcgttgcttaacaaaatcgcaatgcttggaactgagaagacagcggaagctgtgggcgttgataagtcg |
| cagatcagcaggtggaagagggactggattccaaagttctcaatgctgcttgctgttcttgaatggggggtcgttgacgacgacatggct |
| cgattggcgcgacaagttgctgcgattctcaccaataaaaaacgcccggcggcaaccgagcgttctgaacaaatccagatggagttctg |
| aggtcattactggatctatcaacaggagtcattatgacaaatacagcaaaaatactcaacttcggcagaggtaactttgccggacaggag |
| cgtaatgtggcagatctcgatgatggttacgccagactatcaaatatgctgcttgaggcttattcgggcgcagatctgaccaagcgacagt |
| ttaaagtgctgcttgccattctgcgtaaaacctatgggtggaataaaccaatggacagaatcaccgattctcaacttagcgagattacaaag |
| ttacctgtcaaacggtgcaatgaagccaagttagaactcgtcagaatgaatattatcaagcagcaaggcggcatgtttggaccaaataaa |
| aacatctcagaatggtgcatccctcaaaacgagggaaaatcccctaaaacgagggataaaacatccctcaaattgggggattgctatcc |
| ctcaaaacagggggacacaaaagacactattacaaaagaaaaaagaaaagattattcgtcagannnnnntggcgaatcctctgacca |
| gccagaaaacgacctttctgtggtgaaaccggatgctgcaattcagagcggcagcaagtgggggacagcagaagacctgaccgccg |
| cagagtggatgtttgacatggtgaagactatcgcaccatcagccagaaaaccgaattttgctgggtgggctaacgatatccgcctgatgc |

TABLE 9-continued

| Sequence of pSL-LuxABE10 (SEQ ID NO: 3). Sequences encoding luciferase subunits are shown in underline. |
|---|
| gtgaacgtgacggacgtaaccaccgcgacatgtgtgtgctgttccgctgggcatgccaggacaacttctggtccggtaacgtgctgagc |
| ccggccaaactccgcgataagtggacccaactcgaaatcaaccgtaacaagcaacaggcaggcgtgacagccagcaaaccaaaact |
| cgacctgacaaacacagactggatttacggggtggatctatgaaaaacatcgccgcacagatggttaactttgaccgtgagcagatgcg |
| tcggatcgccaacaacatgccggaacagtacgacgaaaagccgcaggtacagcaggtagcgcagatcatcaacggtgtgttcagcca |
| gttactggcaactttcccggcgagcctggctaaccgtgaccagaacgaagtgaacgaaatccgtcgccagtgggttctggcttttcggg |
| aaaacgggatcaccacgatggaacaggttaacgcaggaatgcgcgtagcccgtcggcagaatcgaccatttctgccatcacccgggc |
| agtttgttgcatggtgccgggaagaagcatccgttaccgccggactgccaaacgtcagcgagctggttgatatggtttacgagtattgcc |
| ggaagcgaggcctgtatccggatgcggagtcttatccgtggaaatcaaacgcgcactactggctggttaccaacctgtatcagaacatg |
| cgggccaatgcgcttactgatgcggaattacgccgtaaggccgcagatgagcttgtccatatgactgcgagaattaaccgtggtgaggc |
| gatccctgaaccagtaaaacaacttcctgtcatgggcggtagacctctaaatcgtgcacaggctctggcgaagatcgcagaaatcaaag |
| ctaagttcggactgaaaggagcaagtgtatgacgggcaaagaggcaattattcattacctggggacgcataatagcttctgtgcgccgg |
| acgttgccgcgctaacaggcgcaacagtaaccagcataaatcaggccgcggctaaaatggcacgggcaggtcttctggttatcgaagg |
| taaggtctggcgaacggtgtattaccggtttgctaccagggaagaacgggaaggaaagatgagcgatgaacaaactggatacgattgg |
| attcgacaacaaaaaagacctgcttatctcggtgggcgatttggttgatcgtggtgcagagaacgttgaatgcctggaattaatcacattcc |
| cctggttcagagctgtacgtggaaaccatgagcaaatgatgattgatggcttatcagagcgtggaaacgttaatcactggctgcttaatgg |
| cggtggctggttctttaatctcgattacgacaaagaaattctggctaaagctcttgcccataaagcagatgaacttccgttaatcatcgaact |
| ggtgagcaaagataaaaaatatgttatctgccacgccgattatccctttgacgaatacgagtttggaaagccagttgatcatcagcaggta |
| atctggaaccgcgaacgaatcagcaactcacaaaacgggatcgtgaaagaaatcaaaggcgcggacacgttcatctttggtcatacgc |
| cagcagtgaaaccactcaagtttgccaaccaaatgtatatcgataccggcgcagtgttctgcggaaacctaacattgattcaggtacagg |
| gagaaggcgcatgagactcgaaagcgtagctaaatttcattcgccaaaaagcccgatgatgagcgactcaccacgggccacggcttct |
| gactctctttccggtactgatgtgatggctgctatggggatggcgcaatcacaagccggattcggtatggctgcattctgcggtaagcacg |
| aactcagccagaacgacaaacaaaaggctatcaactatctgatgcaatttgcacacaaggtatcggggaaataccgtggtgtggcaaag |
| cttgaaggaaatactaaggcaaaggtactgcaagtgctcgcaacattcgcttatgcggattattgccgtagtgccgcgacgccgggggc |
| aagatgcagagattgccatggtacaggccgtgcggttgatattgccaaaacagagctgtgggggagagttgtcgagaaagagtgcgga |
| agatgcaaaggcgtcggctattcaaggatgccagcaagcgcagcatatcgcgctgtgacgatgctaatcccaaaccttacccaaccca |
| cctggtcacgcactgttaagccgctgtatgacgctctggtggtgcaatgccacaaagaagagtcaatcgcagacaacattttgaatgcgg |
| tcacacgttagcagcatgattgccacggatggcaacatattaacggcatgatattgacttattgaataaaattgggtaaatttgactcaacga |
| tgggttaattcgctcgttgtggtagtgagatgaaaagaggcggcgcttactaccgattccgcctagttggtcacttcgacgtatcgtctgga |
| actccaaccatcgcaggcagagaggtctgcaaaatgcaatcccgaaacagttcgcaggtaatagttagagcctgcataacggtttcggg |
| atttttatatctgcacaacaggtaagagcattgagtcgataatcgtgaagagtcggcgagcctggttagccagtgctctttccgttgtgctg |
| aattaagcgaataccggaagcagaaccggatcaccaaatgcgtacaggcgtcatcgccgcccagcaacagcacaacccaaactgag |
| ccgtagccactgtctgtcctnnnnnnattagtaatagttacgctgcggccttttacacatgaccttcgtgaaagcgggtggcaggaggtc |
| gcgctaacaacctcctgccgttttgcccgtgcatatcggtcacgaacaaatctgattactaaacacagtagcctggatttgttctatcagtaa |
| tcgaccttattcctaattaaatagagcaaatccccttattgggggtaagacatgaagatgccagaaaaacatgacctgttggccgccattct |
| cgcggcaaaggaacaaggcatcggggcaatccttgcgtttgcaatggcgtaccttcgcggcagatataatggcggtgcgtttacaaaaa |
| cagtaatcgacgcaacgatgtgcgccattatcgcctggttcattcgtgaccttctcgacttcgccggactaagtagcaatctcgcttatataa |
| cgagcgtgtttatcggctacatcggtactgactcgattggttcgcttatcaaacgcttcgctgctaaaaaagccggagtagaagatggtag |
| aaatcaataatcaacgtaaggcgttcctcgatatgctggcgtggtcggagggaactgataacggacgtcagaaaaccagaaatcatggt |
| tatgacgtcattgtaggcggagagctatttactgattactccgatcaccctcgcaaacttgtcacgctaaacccaaaactcaaatcaacagg |

TABLE 9-continued

| Sequence of pSL-LuxABE10 (SEQ ID NO: 3). Sequences encoding luciferase subunits are shown in underline. |
|---|
| cgccggacgctaccagcttctttcccgttggtgggatgcctaccgcaagcagcttggcctgaaagacttctctccgaaaagtcaggacg |
| ctgtggcattgcagcagattaaggagcgtggcgctttacctatgattgatcgtggtgatatccgtcaggcaatcgaccgttgcagcaatat |
| ctgggcttcactgccgggcgctggttatggtcagttcgagcataaggctgacagcctgattgcaaaattcaaagaagcgggcggaacg |
| gtcagagagattgatgtatgagcagagtcaccgcgattatctccgctctggttatctgcatcatcgtctgcctgtcatgggctgttaatcatta |
| ccgtgataacgccattacctacaaagcccagcgcgacaaaaatgccagagaactgaagctggcgaacgcggcaattactgacatgca |
| gatgcgtcagcgtgatgttgctgcgctcgatgcaaaatacacgaaggagttagctgatgctaaagctgaaaatgatgctctgcgtgatgat |
| gttgccgctggtcgtcgtcggttgcacatcaaagcagtctgtcagtcagtgcgtgaagccaccaccgcctccggcgtggataatgcagc |
| ctcccccgactggcagacaccgctgaacgggattatttcaccctcagagagaggctgatcactatgcaaaaacaactggaaggaacc |
| cagaagtatattaatgagcagtgcagatagagttgcccatatcgatgggcaactcatgcaattattgtgagcaatacacacgcgcttccag |
| cggagtataaatgcctaaagtaataaaaccgagcaatccatttacgaatgtttgctgggtttctgttttaacaacattttctgcgccgccacaa |
| atttggctgcatcgacagttttcttctgcccaattccagaaacgaagaaatgatgggtgatggtttcctttggtgctactgctgccggtttgtt |
| ttgaacagtaaacgtctgttgagcacatcctgtaataagcagggccagcgcagtagcgagtagcatttttttcatggtgttattcccgatgct |
| ttttgaagttcgcagaatcgtatgtgtagaaaattaaacaaaccctaaacaatgagttgaaatttcatattgttaatatttattaatgtatgtcag |
| gtgcgatgaatcgtcattgtattcccggattaactatgtccacagccctgacggggaacttctctgcgggagtgtccgggaataattaaaa |
| cgatgcacacagggtttagcgcgtacacgtattgcattatgccaacgccccggtgctgacacggaagaaaccggacgttatgatttagc |
| gtggaaagatttgtgtagtgttctgaatgctctcagtaaatagtaatgaattatcaaaggtatagtaatatcttttatgttcatggatatttgtaac |
| ccatcggaaaactcctgctttagcaagattttccctgtattgctgaaatgtgatttctcttgatttcaacctatcataggacgtttctataagatg |
| cgtgtttcttgagaatttaacatttacaacctttttaagtccttttattaacacggtgttatcgttttctaacacgatgtgaatattatctgtggctag |
| atagtaaatataatgtgagacgttgtgacgttttagttcagaataaaacaattcacagtctaaatcttttcgcacttgatcgaatatttctttaaaa |
| atggcaacctgagccattggtaaaaccttccatgtgatacgagggcgcgtagtttgcattatcgtttttatcgtttcaatctggtctgacctcct |
| tgtgttttgttgatgatttatgtcaaatattaggaatgttttcacttaatagtattggttgcgtaacaaagtgcggtcctgctggcattctggagg |
| gaaatacaaccgacagatgtatgtaaggccaacgtgctcaaatcttcatacagaaagatttgaagtaatattttaaccgctagatgaagag |
| caagcgcatggagcgacaaaatgaataaagaacaatctgctgatgatccctccgtggatctgattcgtgtaaaaaatatgcttaatagcac |
| catttctatgagttaccctgatgttgtaattgcatgtatagaacataaggtgtctctggaagcattcagagcaattgaggcagcgttggtgaa |
| gcacgataataatatgaaggattattccctggtggttgactgatcaccataactgctaatcattcaaactatttagtctgtgacagagccaac |
| acgcagtctgtcactgtcaggaaagtggtaaaactgcaactcaattactgcaatgccctcgtaattaagtgaatttacaatatcgtcctgttc |
| ggagggaagaacgcgggatgttcattcttcatcacttttaattgatgtatatgctctcttttctgacgttagtctccgacggcaggcttcaatg |
| acccaggctgagaaattcccggacccttttgctcaagagcgatgttaatttgttcaatcatttggttaggaaagcggatgttgcgggttgtt |
| gttctgcgggttctgttcttcgttgacatgaggttgccccgtattcagtgtcgctgatttgtattgtctgaagttgttttacgttaagttgatgca |
| gatcaattaatacgatacctgcgtcataattgattatttgacgtggtttgatggcctccacgcacgttgtgatatgtagatgataatcattatcactttacg |
| ggtcctttccggtgatccgacaggttacg |

TABLE 10

| Sequence of λ::Tn-I-Sce2-PsapLuxAB-Cm5 (SEQ ID NO: 4). |
|---|
| ctgtctcttatacacatctcaaccctgaagctcttgttggctagtgcgtagtcgttggcaagcttgcatgcctgcagtagggataacagggt |
| aatgtcgacttgcatgcctgcataaatttgaattttataaaaaattatgttataattcgcgcagtacgatggataatgatcatctggatattgatg |
| ttgatattactgaaccgtcatttgaacatttaactattgcgacagtcaatgaacgccgaatgagaattgagattgaaaatcaagcaatttctct |
| gtcttaaaatctattgagatattctatcactcaaatagcaatataaggactctctatgaaatttggaaactttttgcttacataccaacctcccca |

TABLE 10-continued

| Sequence of λ::Tn-I-Sce2-PsapLuxAB-Cm5 (SEQ ID NO: 4). |
|---|
| attttctcaaacagaggtaatgaaacgtttggttaaattaggtcgcatctctgaggagtgtggttttgataccgtatggttactggagcatcatt |
| tcacggagtttggtttgcttggtaacccttatgtcgctgctgcatatttacttggcgcgactaaaaaattgaatgtaggaactgccgctattgtt |
| cttcccacagcccatccagtacgccaacttgaagatgtgaatttattggatcaaatgtcaaaaggacgatttcggtttggtatttgccgagg |
| gctttacaacaaggactttcgcgtattcggcacagatatgaataacagtcgcgccttagcggaatgctggtacgggctgataaagaatgg |
| catgacagagggatatatggaagctgataatgaacatatcaagttccataaggtaaaagtaaaccccgcggcgtatagcagaggtggcg |
| caccggtttatgtggtggctgaatcagcttcgacgactgagtgggctgctcaatttggcctaccgatgatattaagttggattataaatacta |
| acgaaaagaaagcacaacttgagctttataatgaagtggctcaagaatatgggcacgatattcataatatcgaccattgcttatcatatataa |
| catctgtagatcatgactcaattaaagcgaaagagatttgccggaaatttctggggcattggtatgattcttatgtgaatgctacgactattttt |
| gatgattcagaccaaacaagaggttatgatttcaataaagggcagtggcgtgactttgtattaaaaggacataaagatactaatcgccgtat |
| tgattacagttacgaaatcaatcccgtgggaacgccgcaggaatgtattgacataattcaaaaagacattgatgctacaggaatatcaaat |
| atttgttgtggatttgaagctaatggaacagtagacgaaattattgcttccatgaagctcttccagtctgatgtcatgccatttcttaaagaaaa |
| acaacgttcgctattatattagctaaggagaaagaaatgaaatttggattgttcttccttaacttcatcaattcaacaactgttcaagaacaaa |
| gtatagttcgcatgcaggaaataacggagtatgttgataagttgaattttgaacagattttagtgtatgaaaatcatttttcagataatggtgttg |
| tcggcgctcctctgactgtttctggttttctgctcggtttaacagagaaaattaaaattggttcattaaatcacatcattacaactcatcatcctgt |
| cgccatagcggaggaagcttgcttattggatcagttaagtgaagggagatttattttagggtttagtgattgcgaaaaaaaagatgaaatgc |
| attttttaatcgcccggttgaatatcaacagcaactatttgaagagtgttatgaaatcattaacgatgctttaacaacaggctattgtaatcca |
| gataacgattttttatagcttccctaaaatatctgtaaatccccatgcttatacgccaggcggacctcggaaatatgtaacagcaaccagtcat |
| catattgttgagtgggcggccaaaaaaggtattcctctcatctttaagtgggatgattctaatgatgttagatatgaatatgctgaaagatata |
| aagccgttgcggataaatatgacgttgacctatcagagatagaccatcagttaatgatattagttaactataacgaagatagtaataaagct |
| aaacaagagacgcgtgcatttattagtgattatgttcttgaaatgcaccctaatgaaaatttcgaaaataaacttgaagaaataattgcagaa |
| aacgctgtcggaaattatacggagtgtataactgcggctaagttggcaattgaaaagtgtggtgcgaaaagtgtattgctgtcctttgaacc |
| aatgaatgatttgatgagccaaaaaaatgtaatcaatattgttgatgataatattaagaagtaccacatggaatatacctaatagatttcgagtt |
| gcagcgaggcggcaagtgaacgaatccccaggagcatagataactatgtgactggggtgagtgaaagcagccaacaaagcagcagc |
| ttgaaagatgaagggtataaaagagtatgacagcagtgctgccatactttctaatattatcttgaggagtaaaacaggtatgacttcatatgtt |
| gataaacaagaaattacagcaagctcagaaattgatgatttgatttttttcgagcgatccatagatctggagctaaggaagctaaaatggag |
| aaaaaaatcactggatataccaccgttgatatatcccaatggcatcgtaaagaacattttgaggcatttcagtcagttgctcaatgtacctata |
| accagaccgttcagctggatattacggcctttttaaagaccgtaaagaaaaataagcacaagttttatccggcctttattcacattcttgccc |
| gcctgatgaatgctcatccggaattccgtatggcaatgaaagacggtgagctggtgatatgggatagtgttcacccttgttacaccgttttc |
| catgagcaaactgaaacgttttcatcgctctggagtgaataccacgacgatttccggcagtttctacacatatattcgcaagatgtggcgtg |
| ttacggtgaaaacctggcctatttccctaaagggtttattgagaatatgtttttcgtctcagccaatccctgggtgagtttcaccagttttgattt |
| aaacgtggccaatatggacaacttcttcgcccccgttttcaccatgggcaaatattatacgcaaggcgacaaggtgctgatgccgctggc |
| gattcaggttcatcatgccgtctgtgatggcttccatgtcggcagaatgcttaatgaattacaacagtactgcgatgagtggcagggcggg |
| gcgtaatttcaattcattaccctgttatccctacccgagaaaattcatcgatgatggttgagatgtgtataagagacaggttaaatctatcacc |
| gcaagggataaatatctaacaccgtgcgtgttgactattttacctctggcggtgataatggttgcatgtactaaggaggttgtatggaacaa |
| cgcataaccctgaaagattatgcaatgcgctttgggcaaaccaagacagctaaagatctcggcgtatatcaaagcgcgatcaacaaggc |
| cattcatgcaggccgaaagatttttttaactataaacgctgatggaagcgtttatgcggaagaggtaaagcccttcccgagtaacaaaaaa |
| acaacagcataaataaccccgctcttacacattccagccctgaaaaagggcatcaaattaaaccacacctatggtgtatgcatttatttgca |
| tacattcaatcaattgttatctaaggaaatacttacatatggttcgtgcaaacaaacgcaacgaggctctacgaatcgagagtgcgttgctta |
| acaaaatcgcaatgcttggaactgagaagacagcggaagctgtgggcgttgataagtcgcagatcagcaggtggaagagggactgga |

TABLE 10-continued

| Sequence of λ::Tn-I-Sce2-PsapLuxAB-Cm5 (SEQ ID NO: 4). |
| --- |
| ttccaaagttctcaatgctgcttgctgttcttgaatggggggtcgttgacgacgacatggctcgattggcgcgacaagttgctgcgattctc |
| accaataaaaaacgcccggcggcaaccgagcgttctgaacaaatccagatggagttctgaggtcattactggatctatcaacaggagtc |
| attatgacaaatacagcaaaaatactcaacttcggcagaggtaactttgccggacaggagcgtaatgtggcagatctcgatgatggttac |
| gccagactatcaaatatgctgcttgaggcttattcgggcgcagatctgaccaagcgacagtttaaagtgctgcttgccattctgcgtaaaac |
| ctatgggtggaataaaccaatggacagaatcaccgattctcaacttagcgagattacaaagttacctgtcaaacggtgcaatgaagccaa |
| gttagaactcgtcagaatgaatattatcaagcagcaaggcggcatgtttggaccaaataaaaacatctcagaatggtgcatccctcaaaac |
| gagggaaaatcccctaaaacgagggataaaacatccctcaaattgggggattgctatccctcaaaacagggggacacaaaagacacta |
| ttacaaaagaaaaaagaaaagattattcgtcagagaattctggcgaatcctctgaccagccagaaaacgacctttctgtggtgaaaccgg |
| atgctgcaattcagagcggcagcaagtgggggacagcagaagacctgaccgccgcagagtggatgtttgacatggtgaagactatcg |
| caccatcagccagaaaaccgaattttgctgggtgggctaacgatatccgcctgatgcgtgaacgtgacggacgtaaccaccgcgacat |
| gtgtgtgctgttccgctgggcatgccaggacaacttctggtccggtaacgtgctgagcccggccaaactccgcgataagtggacccaac |
| tcgaaatcaaccgtaacaagcaacaggcaggcgtgacagccagcaaaccaaaactcgacctgacaaacacagactggatttacgggg |
| tggatctatgaaaaacatcgccgcacagatggttaactttgaccgtgagcagatgcgtcggatcgccaacaacatgccggaacagtacg |
| acgaaaagccgcaggtacagcaggtagcgcagatcatcaacggtgtgttcagccagttactggcaactttcccggcgagcctggctaa |
| ccgtgaccagaacgaagtgaacgaaatccgtcgccagtgggttctggcttttcgggaaaacgggatcaccacgatggaacaggttaac |
| gcaggaatgcgcgtagcccgtcggcagaatcgaccatttctgccatcacccgggcagtttgttgcatggtgccgggaagaagcatccgt |
| taccgccggactgccaaacgtcagcgagctggttgatatggtttacgagtattgccggaagcgaggcctgtatccggatgcggagtctta |
| tccgtggaaatcaaacgcgcactactggctggttaccaacctgtatcagaacatgcgggccaatgcgcttactgatgcggaattacgccg |
| taaggccgcagatgagcttgtccatatgactgcgagaattaaccgtggtgaggcgatccctgaaccagtaaaacaacttcctgtcatggg |
| cggtagacctctaaatcgtgcacaggctctggcgaagatcgcagaaatcaaagctaagttcggactgaaaggagcaagtgtatgacgg |
| gcaaagaggcaattattcattacctggggacgcataatagcttctgtgcgcccggacgttgccgcgctaacaggcgcaacagtaaccagc |
| ataaatcaggccgcggctaaaatggcacgggcaggtcttctggttatcgaaggtaaggtctggcgaacggtgtattaccggtttgctacc |
| agggaagaacgggaaggaaagatgagcacgaacctggtttttaaggagtgtcgccagagtgccgcgatgaaacgggtattggcggta |
| tatggagttaaaagatgaccatctacattactgagctaataacaggcctgctggtaatcgcaggcctttttatttgggggagagggaagtca |
| tgaaaaaactaacctttgaaattcgatctccagcacatcagcaaaacgctattcacgcagtacagcaaatccttccagacccaaccaaac |
| caatcgtagtaaccattcaggaacgcaaccgcagcttagaccaaaacaggaagctatgggcctgcttaggtgacgtctctcgtcaggttg |
| aatggcatggtcgctggctggatgcagaaagctggaagtgtgtgtttaccgcagcattaaagcagcaggatgttgttcctaaccttgccg |
| ggaatggctttgtggtaataggccagtcaaccagcaggatgcgtgtaggcgaatttgcggagctattagagcttatacaggcattcggta |
| cagagcgtggcgttaagtggtcagacgaagcgagactggctctggagtggaaagcgagatggggagacagggctgcatgataaatgt |
| cgttagtttctccggtggcaggacgtcagcatatttgctctggctaatggagcaaaagcgacgggcaggtaaagacgtgcattacgttttc |
| atggatacaggttgtgaacatccaatgacatatcggtttgtcagggaagttgtgaagttctgggatataccgctcaccgtattgcaggttgat |
| atcaacccggagcttggacagccaaatggttatacggtatgggaaccaaaggatattcagacgcgaatgcctgttctgaagccatttatc |
| gatatggtaaagaaatatggcactccatacgtcggcggcgcgttctgcactgacagattaaaactcgttcccttcaccaaatactgtgatg |
| accatttcgggcgagggaattacaccacgtggattggcatcagagctgatgaaccgaagcggctaaagccaaagcctggaatcagata |
| tcttgctgaactgtcagactttgagaaggaagatatcctcgcatggtggaagcaacaaccattcgatttgcaaataccggaacatctcggt |
| aactgcatattctgcattaaaaaatcaacgcaaaaaatcggacttgcctgcaaagatgaggagggattgcagcgtgtttttaatgaggtcat |
| cacgggatcccatgtgcgtgacggacatcgggaaacgccaaaggagattatgtaccgaggaagaatgtcgctggacggtatcgcgaa |
| aatgtattcagaaaatgattatcaagccctgtatcaggacatggtacgagctaaaagattcgataccggctcttgttctgagtcatgcgaaat |
| atttggagggcagcttgatttcgacttcgggagggaagctgcatgatgcgatgttatcggtgcggtgaatgcaaagaagataaccgcttc |

TABLE 10-continued

| Sequence of λ::Tn-I-Sce2-PsapLuxAB-Cm5 (SEQ ID NO: 4). |
| --- |
| cgaccaaatcaaccttactggaatcgatggtgtctccggtgtgaaagaacaccaacaggggtgttaccactaccgcaggaaaaggagg |
| acgtgtggcgagacagcgacgaagtatcaccgacataatctgcgaaaactgcaaataccttccaacgaaacgcaccagaaataaaccc |
| aagccaatcccaaaagaatctgacgtaaaaaccttcaactacacggctcacctgtgggatatccggtggctaagacgtcgtgcgaggaa |
| aacaaggtgattgaccaaaatcgaagttacgaacaagaaagcgtcgagcgagctttaacgtgcgctaactgcggtcagaagctgcatgt |
| gctggaagttcacgtgtgtgagcactgctgcgcagaactgatgagcgatccgaatagctcgatgcacgaggaagaagatgatggctaa |
| accagcgcgaagacgatgtaaaaacgatgaatgccgggaatggtttcaccctgcattcgctaatcagtggtggtgctctccagagtgtg |
| gaaccaagatagcactcgaacgacgaagtaaagaacgcgaaaaagcggaaaaagcagcagagaagaaacgacgacgagaggag |
| cagaaacagaaagataaacttaagattcgaaaactcgccttaaagccccgcagttactggattaaacaagcccaacaagccgtaaacgc |
| cttcatcagagaaagagaccgcgacttaccatgtatctcgtgcggaacgctcacgtctgctcagtgggatgccggacattaccggacaa |
| ctgctgcggcacctcaactccgatttaatgaacgcaatattcacaagcaatgcgtggtgtgcaaccagcacaaaagcggaaatctcgttc |
| cgtatcgcgtcgaactgattagccgcatcgggcaggaagcagtagacgaaatcgaatcaaaccataaccgccatcgctggactatcga |
| agagtgcaaggcgatcaaggcagagtaccaacagaaactcaaagacctgcgaaatagcagaagtgaggccgcatgacgttctcagta |
| aaaaccattccagacatgctcgttgaagcatacggaaatcagacagaagtagcacgcagactgaaatgtagtcgcggtacggtcagaa |
| aatacgttgatgataaagacgggaaaatgcacgccatcgtcaacgacgttctcatggttcatcgcggatggagtgaaagagatgcgctat |
| tacgaaaaaaattgatggcagcaaataccgaaatatttgggtagttggcgatctgcacggatgctacacgaacctgatgaacaaactggat |
| acgattggattcgacaacaaaaaagacctgcttatctcggtgggcgatttggttgatcgtggtgcagagaacgttgaatgcctggaattaa |
| tcacattcccctggttcagagctgtacgtggaaaccatgagcaaatgatgattgatggcttatcagagcgtggaaacgttaatcactggct |
| gcttaatggcggtggctggttctttaatctcgattacgacaaagaaattctggctaaagctcttgcccataaagcagatgaacttccgttaat |
| catcgaactggtgagcaaagataaaaaatatgttatctgccacgccgattatccctttgacgaatacgagtttggaaagccagttgatcatc |
| agcaggtaatctggaaccgcgaacgaatcagcaactcacaaaacgggatcgtgaaagaaatcaaaggcgcggacacgttcatctttgg |
| tcatacgccagcagtgaaaccactcaagtttgccaaccaaatgtatatcgataccggcgcagtgttctgcggaaacctaacattgattcag |
| gtacagggagaaggcgcatgagactcgaaagcgtagctaaatttcattcgccaaaaagcccgatgatgagcgactcaccacgggcca |
| cggcttctgactctctttccggtactgatgtgatggctgctatggggatggcgcaatcacaagccggattcggtatggctgcattctgcggt |
| aagcacgaactcagccagaacgacaaacaaaaggctatcaactatctgatgcaatttgcacacaaggtatcggggaaataccgtggtgt |
| ggcaaagcttgaaggaaatactaaggcaaaggtactgcaagtgctcgcaacattcgcttatgcggattattgccgtagtgccgcgacgc |
| cgggggcaagatgcagagattgccatggtacaggccgtgcggttgatattgccaaaacagagctgtgggggagagttgtcgagaaag |
| agtgcggaagatgcaaaggcgtcggctattcaaggatgccagcaagcgcagcatatcgcgctgtgacgatgctaatcccaaaccttac |
| ccaacccacctggtcacgcactgttaagccgctgtatgacgctctggtggtgcaatgccacaaagaagagtcaatcgcagacaacatttt |
| gaatgcggtcacacgttagcagcatgattgccacggatggcaacatattaacggcatgatattgacttattgaataaaattgggtaaatttg |
| actcaacgatgggttaattcgctcgttgtggtagtgagatgaaaagaggcggcgcttactaccgattccgcctagttggtcacttcgacgt |
| atcgtctggaactccaaccatcgcaggcagagaggtctgcaaaatgcaatcccgaaacagttcgcaggtaatagttagagcctgcataa |
| cggtttcgggatttttttatatctgcacaacaggtaagagcattgagtcgataatcgtgaagagtcggcgagcctggttagccagtgctctttc |
| cgttgtgctgaattaagcgaataccggaagcagaaccggatcaccaaatgcgtacaggcgtcatcgccgcccagcaacagcacaacc |
| caaactgagccgtagccactgtctgtcctgaattcattagtaatagttacgctgcggccttttacacatgaccttcgtgaaagcgggtggca |
| ggaggtcgcgctaacaacctcctgccgttttgcccgtgcatatcggtcacgaacaaatctgattactaaacacagtagcctggatttgttct |
| atcagtaatcgaccttattcctaattaaatagagcaaatccccttattgggggtaagacatgaagatgccagaaaaacatgacctgttggcc |
| gccattctcgcggcaaaggaacaaggcatcggggcaatccttgcgtttgcaatggcgtaccttcgcggcagatataatggcggtgcgttt |
| acaaaaaacagtaatcgacgcaacgatgtgcgccattatcgcctggttcattcgtgaccttctcgacttcgccggactaagtagcaatctcg |
| cttatataacgagcgtgtttatcggctacatcggtactgactcgattggttcgcttatcaaacgcttcgctgctaaaaaagccggagtagaa |

TABLE 10-continued

| Sequence of λ::Tn-I-Sce2-PsapLuxAB-Cm5 (SEQ ID NO: 4). |
| --- |
| gatggtagaaatcaataatcaacgtaaggcgttcctcgatatgctggcgtggtcggagggaactgataacggacgtcagaaaaccaga |
| aatcatggttatgacgtcattgtaggcggagagctatttactgattactccgatcaccctcgcaaacttgtcacgctaaacccaaaactcaa |
| atcaacaggcgccggacgctaccagcttctttcccgttggtgggatgcctaccgcaagcagcttggcctgaaagacttctctccgaaaag |
| tcaggacgctgtggcattgcagcagattaaggagcgtggcgctttacctatgattgatcgtggtgatatccgtcaggcaatcgaccgttgc |
| agcaatatctgggcttcactgccgggcgctggttatggtcagttcgagcataaggctgacagcctgattgcaaaattcaaagaagcggg |
| cggaacggtcagagagattgatgtatgagcagagtcaccgcgattatctccgctctggttatctgcatcatcgtctgcctgtcatgggctgt |
| taatcattaccgtgataacgccattacctacaaagcccagcgcgacaaaaatgccagagaactgaagctggcgaacgcggcaattactg |
| acatgcagatgcgtcagcgtgatgttgctgcgctcgatgcaaaatacacgaaggagttagctgatgctaaagctgaaaatgatgctctgc |
| gtgatgatgttgccgctggtcgtcgtcggttgcacatcaaagcagtctgtcagtcagtgcgtgaagccaccaccgcctccggcgtggata |
| atgcagcctccccccgactggcagacaccgctgaacgggattatttcaccctcagagagaggctgatcactatgcaaaaacaactgga |
| aggaacccagaagtatattaatgagcagtgcagatagagttgcccatatcgatgggcaactcatgcaattattgtgagcaatacacacgc |
| gcttccagcggagtataaatgcctaaagtaataaaaccgagcaatccatttacgaatgtttgctgggtttctgttttaacaacattttctgcgc |
| cgccacaaattttggctgcatcgacagttttcttctgcccaattccagaaacgaagaaatgatgggtgatggtttcctttggtgctactgctg |
| ccggtttgttttgaacagtaaacgtctgttgagcacatcctgtaataagcagggccagcgcagtagcgagtagcatttttttcatggtgttatt |
| cccgatgctttttgaagttcgcagaatcgtatgtgtagaaaattaaacaaaccctaaacaatgagttgaaatttcatattgttaatatttattaat |
| gtatgtcaggtgcgatgaatcgtcattgtattcccggattaactatgtccacagccctgacggggaacttctctgcgggagtgtccgggaa |
| taattaaaacgatgcacacagggtttagcgcgtacacgtattgcattatgccaacgccccggtgctgacacggaagaaaccggacgttat |
| gatttagcgtggaaagatttgtgtagtgttctgaatgctctcagtaaatagtaatgaattatcaaaggtatagtaatatcttttatgttcatggata |
| tttgtaacccatcggaaaactcctgctttagcaagattttccctgtattgctgaaatgtgatttctcttgatttcaacctatcataggacgtttctat |
| aagatgcgtgtttcttgagaatttaacatttacaaccttttttaagtccttttattaacacggtgttatcgttttctaacacgatgtgaatattatctgt |
| ggctagatagtaaatataatgtgagacgttgtgacgttttagttcagaataaaacaattcacagtctaaatcttttcgcacttgatcgaatatttc |
| tttaaaaatggcaacctgagccattggtaaaaccttccatgtgatacgagggcgcgtagtttgcattatcgtttttatcgtttcaatctggtctg |
| acctccttgtgttttgttgatgatttatgtcaaatattaggaatgttttcacttaatagtattggttgcgtaacaaagtgcggtcctgctggcattct |
| ggagggaaatacaaccgacagatgtatgtaaggccaacgtgctcaaatcttcatacagaaagatttgaagtaatattttaaccgctagatg |
| aagagcaagcgcatggagcgacaaaatgaataaagaacaatctgctgatgatccctccgtggatctgattcgtgtaaaaaatatgcttaat |
| agcaccatttctatgagttaccctgatgttgtaattgcatgtatagaacataaggtgtctctggaagcattcagagcaattgaggcagcgttg |
| gtgaagcacgataataatatgaaggattattccctggtggttgactgatcaccataactgctaatcattcaaactatttagtctgtgacagag |
| ccaacacgcagtctgtcactgtcaggaaagtggtaaaactgcaactcaattactgcaatgccctcgtaattaagtgaatttacaatatcgtc |
| ctgttcggagggaagaacgcgggatgttcattcttcatcacttttaattgatgtatatgctctcttttctgacgttagtctccgacggcaggctt |
| caatgacccaggctgagaaattcccggacccttttgctcaagagcgatgttaatttgttcaatcatttggttaggaaagcggatgttgcgg |
| gttgttgttctgcgggttctgttcttcgttgacatgaggttgccccgtattcagtgtcgctgatttgtattgtctgaagttgtttttacgttaagttg |
| atgcagatcaattaatacgatacctgcgtcataattgattatttgacgtggtttgatggcctccacgcacgttgtgatatgtagatgataatcat |
| tatcactttacgggtcctttccggtgatccgacaggttacggggcggcgacctcgcgggttttcgctatttatgaaaattttccggtttaagg |
| cgtttccgttcttcttcgtcataacttaatgtttttatttaaaataccctctgaaaagaaaggaaacgacaggtgctgaaagcgaggctttttgg |
| cctctgtcgtttcctttctctgtttttgtccgtggaatgaacaatggaagtcaacaaaaagcagctggctgacattttcggtgcgagtatccgt |
| accattcagaactggcaggaacagggaatgcccgttctgcgaggcggtggcaagggtaatgaggtgctttatgactctgccgccgtcat |
| aaaatggtatgccgaaagggatgctgaaattgagaacgaaaagctgcgccgggaggttgaagaactgcggcaggccagcgaggca |
| gatctccagccaggaactattgagtacgaacgccatcgacttacgcgtgcgcaggccgacgcacaggaactgaagaatgccagagac |
| tccgctgaagtggtggaaaccgcattctgtactttcgtgctgtcgcggatcgcaggtgaaattgccagtattctcgacgggctccccctgt |

TABLE 10-continued

| Sequence of λ::Tn-I-Sce2-PsapLuxAB-Cm5 (SEQ ID NO: 4). |
|---|
| cggtgcagcggcgttttccggaactggaaaaccgacatgttgatttcctgaaacgggatatcatcaaagccatgaacaaagcagccgcg |
| ctggatgaactgataccggggttgctgagtgaatatatcgaacagtcaggttaacaggctgcggcattttgtccgcgccgggcttcgctc |
| actgttcaggccggagccacagaccgccgttgaatgggcggatgctaattactatctcccgaaagaatccgcataccaggaagggcgc |
| tgggaaacactgccctttcagcgggccatcatgaatgcgatgggcagcgactacatccgtgaggtgaatgtggtgaagtctgcccgtgt |
| cggttattccaaaatgctgctgggtgtttatgcctactttatagagcataagcagcgcaacacccttatctggttgccgacggatggtgatg |
| ccgagaactttatgaaaacccacgttgagccgactattcgtgatattccgtcgctgctggcgctggccccgtggtatggcaaaaagcacc |
| gggataacacgctcaccatgaagcgtttcactaatgggcgtggcttctggtgcctgggcggtaaagcggcaaaaaactaccgtgaaaa |
| gtcggtggatgtggcgggttatgatgaacttgctgcttttgatgatgatattgaacaggaaggctctccgacgttcctgggtgacaagcgta |
| ttgaaggctcggtctggccaaagtccatccgtggctccacgccaaaagtgagaggcacctgtcagattgagcgtgcagccagtgaatc |
| cccgcattttatgcgttttcatgttgcctgcccgcattgcggggaggagcagtatcttaaatttggcgacaaagagacgccgtttggcctca |
| aatggacgccggatgacccctccagcgtgttttatctctgcgagcataatgcctgcgtcatccgccagcaggagctggactttactgatgc |
| ccgttatatctgcgaaaagaccgggatctggacccgtgatggcattctctggttttcgtcatccggtgaagagattgagccacctgacagt |
| gtgacctttcacatctggacagcgtacagcccgttcaccacctgggtgcagattgtcaaagactggatgaaaacgaaaggggatacgg |
| gaaaacgtaaaaccttcgtaaacaccacgctcggtgagacgtgggaggcgaaaattggcgaacgtccggatgctgaagtgatggcag |
| agcggaaagagcattattcagcgcccgttcctgaccgtgtggcttacctgaccgccggtatcgactcccagctggaccgctacgaaatg |
| cgcgtatggggatgggggccgggtgaggaaagctggctgattgaccggcagattattatgggccgccacgacgatgaacagacgctg |
| ctgcgtgtggatgaggccatcaataaaacctatacccgccggaatggtgcagaaatgtcgatatcccgtatctgctgggatactggcgg |
| gattgacccgaccattgtgtatgaacgctcgaaaaaacatgggctgttccgggtgatccccattaaaggggcatccgtctacggaaagc |
| cggtggccagcatgccacgtaagcgaaacaaaaacggggtttaccttaccgaaatcggtacggataccgcgaaagagcagatttataa |
| ccgcttcacactgacgccggaaggggatgaaccgcttcccggtgccgttcacttcccgaataacccggatatttttgatctgaccgaagc |
| gcagcagctgactgctgaagagcaggtcgaaaaatgggtggatggcaggaaaaaaatactgtgggacagcaaaaagcgacgcaatg |
| aggcactcgactgcttcgtttatgcgctggcggcgctgcgcatcagtatttcccgctggcagctggatctcagtgcgctgctggcgagcc |
| tgcaggaagaggatggtgcagcaaccaacaagaaaacactggcagattacgcccgtgccttatccggagaggatgaatgacgcgaca |
| ggaagaacttgccgctgcccgtgcggcactgcatgacctgatgacaggtaaacgggtggcaacagtacagaaagacggacgaaggg |
| tggagtttacggccacttccgtgtctgacctgaaaaaatatattgcagagctggaagtgcagaccggcatgacacagcgacgcagggg |
| acctgcaggattttatgtatgaaaacgcccaccattcccacccttctggggccggacggcatgacatcgctgcgcgaatatgccggttat |
| cacggcggtggcagcggatttggagggcagttgcggtcgtggaacccaccgagtgaaagtgtggatgcagccctgttgcccaacttta |
| cccgtggcaatgcccgcgcagacgatctggtacgcaataacggctatgccgccaacgccatccagctgcatcaggatcatatcgtcgg |
| gtctttttttccggctcagtcatcgcccaagctggcgctatctgggcatcggggaggaagaagcccgtgccttttcccgcgaggttgaagc |
| ggcatggaaagagtttgccgaggatgactgctgctgcattgacgttgagcgaaaacgcacgtttaccatgatgattcgggaaggtgtgg |
| ccatgcacgcctttaacggtgaactgttcgttcaggccacctgggataccagttcgtcgcggcttttccggacacagttccggatggtcag |
| cccgaagcgcatcagcaacccgaacaataccggcgacagccggaactgccgtgccggtgtgcagattaatgacagcggtgcggcgc |
| tgggatattacgtcagcgaggacgggtatcctggctggatgccgcagaaatggacatggataccccgtgagttacccggcgggcgcg |
| cctcgttcattcacgtttttgaacccgtggaggacgggcagactcgcggtgcaaatgtgttttacagcgtgatggagcagatgaagatgct |
| cgacacgctgcagaacacgcagctgcagagcgccattgtgaaggcgatgtatgccgccaccattgagagtgagctggatacgcagtc |
| agcgatggattttattctgggcgcgaacagtcaggagcagcgggaaaggctgaccggctggattggtgaaattgccgcgtattacgcc |
| gcagcgccggtccggctgggaggcgcaaaagtaccgcacctgatgccgggtgactcactgaacctgcagacggctcaggatacgga |
| taacggctactccgtgtttgagcagtcactgctgcggtatatcgctgccgggctgggtgtctcgtatgagcagctttcccggaattacgcc |
| cagatgagctactccacggcacgggccagtgcgaacgagtcgtgggcgtactttatggggcggcgaaaattcgtcgcatcccgtcagg |

TABLE 10-continued

| Sequence of λ::Tn-I-Sce2-PsapLuxAB-Cm5 (SEQ ID NO: 4). |
| --- |
| cgagccagatgtttctgtgctggctggaagaggccatcgttcgccgcgtggtgacgttaccttcaaaagcgcgcttcagttttcaggaag |
| cccgcagtgcctgggggaactgcgactggataggctccggtcgtatggccatcgatggtctgaaagaagttcaggaagcggtgatgct |
| gatagaagccggactgagtacctacgagaaagagtgcgcaaaacgcggtgacgactatcaggaaatttttgcccagcaggtccgtgaa |
| acgatggagcgccgtgcagccggtcttaaaccgcccgcctgggcggctgcagcatttgaatccgggctgcgacaatcaacagaggag |
| gagaagagtgacagcagagctgcgtaatctcccgcatattgccagcatggcctttaatgagccgctgatgcttgaacccgcctatgcgc |
| gggttttcttttgtgcgcttgcaggccagcttgggatcagcagcctgacggatgcggtgtccggcgacagcctgactgcccaggaggca |
| ctcgcgacgctggcattatccggtgatgatgacggaccacgacaggcccgcagttatcaggtcatgaacggcatcgccgtgctgccgg |
| tgtccggcacgctggtcagccggacgcgggcgctgcagccgtactcggggatgaccggttacaacggcattatcgcccgtctgcaac |
| aggctgccagcgatccgatggtggacggcattctgctcgatatggacacgcccggcgggatggtggcgggggcatttgactgcgctg |
| acatcatcgcccgtgtgcgtgacataaaaccggtatgggcgcttgccaacgacatgaactgcagtgcaggtcagttgcttgccagtgcc |
| gcctcccggcgtctggtcacgcagaccgcccggacaggctccatcggcgtcatgatggctcacagtaattacggtgctgcgctggaga |
| aacagggtgtggaaatcacgctgatttacagcggcagccataaggtggatggcaacccctacagccatcttccggatgacgtccggga |
| gacactgcagtcccggatggacgcaacccgccagatgtttgcgcagaaggtgtcggcatataccggcctgtccgtgcaggttgtgctg |
| gataccgaggctgcagtgtacagcggtcaggaggccattgatgccggactggctgatgaacttgttaacagcaccgatgcgatcaccgt |
| catgcgtgatgcactggatgcacgtaaatcccgtctctcaggagggcgaatgaccaaagagactcaatcaacaactgtttcagccactg |
| cttcgcaggctgacgttactgacgtggtgccagcgacggagggcgagaacgccagcgcggcgcagccggacgtgaacgcgcagat |
| caccgcagcggttgcggcagaaaacagccgcattatggggatcctcaactgtgaggaggctcacggacgcgaagaacaggcacgc |
| gtgctggcagaaacccccggtatgaccgtgaaaacggcccgccgcattctggccgcagcaccacagagtgcacaggcgcgcagtga |
| cactgcgctggatcgtctgatgcagggggcaccggcaccgctggctgcaggtaacccggcatctgatgccgttaacgatttgctgaaca |
| caccagtgtaagggatgtttatgacgagcaaagaaacctttacccattaccagccgcagggcaacagtgacccggctcataccgcaac |
| cgcgcccggcggattgagtgcgaaagcgcctgcaatgaccccgctgatgctggacacctccagccgtaagctggttgcgtgggatgg |
| caccaccgacggtgctgccgttggcattcttgcggttgctgctgaccagaccagcaccacgctgacgttctacaagtccggcacgttcc |
| gttatgaggatgtgctctggccggaggctgccagcgacgagacgaaaaaacggaccgcgtttgccggaacggcaatcagcatcgttta |
| actttacccttcatcactaaaggccgcctgtgcggcttttttacgggatttttttatgtcgatgtacacaaccgcccaactgctggcggcaaa |
| tgagcagaaatttaagtttgatccgctgtttctgcgtctctttttccgtgagagctatcccttcaccacggagaaagtctatctctcacaaattc |
| cgggactggtaaacatggcgctgtacgtttcgccgattgtttccggtgaggttatccgttcccgtggcggctccacctctgaatttacgccg |
| ggatatgtcaagccgaagcatgaagtgaatccgcagatgaccctgcgtcgcctgccggatgaagatccgcagaatctggcggacccg |
| gcttaccgccgccgtcgcatcatcatgcagaacatgcgtgacgaagagctggccattgctcaggtcgaagagatgcaggcagtttctgc |
| cgtgcttaagggcaaatacaccatgaccggtgaagccttcgatccggttgaggtggatatgggccgcagtgaggagaataacatcacg |
| cagtccggcggcacggagtggagcaagcgtgacaagtccacgtatgacccgaccgacgatatcgaagcctacgcgctgaacgccag |
| cggtgtggtgaatatcatcgtgttcgatccgaaaggctgggcgctgttccgttccttcaaagccgtcaaggagaagctggatacccgtcg |
| tggctctaattccgagctggagacagcggtgaaagacctgggcaaagcggtgtcctataaggggatgtatggcgatgtggccatcgtc |
| gtgtattccggacagtacgtggaaaacggcgtcaaaaagaacttcctgccggacaacacgatggtgctggggaacactcaggcacgc |
| ggtctgcgcacctatggctgcattcaggatgcggacgcacagcgcgaaggcattaacgcctctgcccgttacccgaaaaactgggtga |
| ccaccggcgatccggcgcgtgagttcaccatgattcagtcagcaccgctgatgctgctggctgaccctgatgagttcgtgtccgtacaac |
| tggcgtaatcatggcccttcggggccattgtttctctgtggaggagtccatgacgaaagatgaactgattgcccgtctccgctcgctgggt |
| gaacaactgaaccgtgatgtcagcctgacggggacgaaagaagaactggcgctccgtgtggcagagctgaaagaggagcttgatga |
| cacggatgaaactgccggtcaggacacccctctcagccgggaaaatgtgctgaccggacatgaaaatgaggtgggatcagcgcagc |
| cggataccgtgattctggatacgtctgaactggtcacggtcgtggcactggtgaagctgcatactgatgcacttcacgccacgcgggatg |

TABLE 10-continued

| Sequence of λ::Tn-I-Sce2-PsapLuxAB-Cm5 (SEQ ID NO: 4). |
| --- |
| aacctgtggcatttgtgctgccgggaacggcgtttcgtgtctctgccggtgtggcagccgaaatgacagagcgcggcctggccagaat |
| gcaataacgggaggcgctgtggctgatttcgataacctgttcgatgctgccattgcccgcgccgatgaaacgatacgcgggtacatggg |
| aacgtcagccaccattacatccggtgagcagtcaggtgcggtgatacgtggtgtttttgatgaccctgaaaatatcagctatgccggaca |
| gggcgtgcgcgttgaaggctccagcccgtccctgtttgtccggactgatgaggtgcggcagctgcggcgtggagacacgctgaccatc |
| ggtgaggaaaatttctgggtagatcgggtttcgccggatgatggcggaagttgtcatctctggcttggacggggcgtaccgcctgccgtt |
| aaccgtcgccgctgaaaggggggatgtatggccataaaaggtcttgagcaggccgttgaaaacctcagccgtatcagcaaaacggcggt |
| gcctggtgccgccgcaatggccattaaccgcgttgcttcatccgcgatatcgcagtcggcgtcacaggttgcccgtgagacaaaggtac |
| gccggaaactggtaaaggaaagggccaggctgaaaagggccacggtcaaaaatccgcaggccagaatcaaagttaaccgggggga |
| tttgcccgtaatcaagctgggtaatgcgcgggttgtcctttcgcgccgcaggcgtcgtaaaaaggggcagcgttcatccctgaaaggtg |
| gcggcagcgtgcttgtggtgggtaaccgtcgtattcccggcgcgtttattcagcaactgaaaaatggccggtggcatgtcatgcagcgtg |
| tggctgggaaaaaccgttaccccattgatgtggtgaaaatcccgatggcggtgccgctgaccacggcgtttaaacaaaatattgagcgg |
| atacggcgtgaacgtcttccgaaagagctgggctatgcgctgcagcatcaactgaggatggtaataaagcgatgaaacatactgaactc |
| cgtgcagccgtactggatgcactggagaagcatgacaccggggcgacgtttttgatggtcgccccgctgtttttgatgaggcggattttc |
| cggcagttgccgtttatctcaccggcgctgaatacacgggcgaagagctggacagcgatacctggcaggcggagctgcatatcgaagt |
| tttcctgcctgctcaggtgccggattcagagctggatgcgtggatggagtcccggatttatccggtgatgagcgatatcccggcactgtca |
| gatttgatcaccagtatggtggccagcggctatgactaccggcgcgacgatgatgcgggcttgtggagttcagccgatctgacttatgtc |
| attacctatgaaatgtgaggacgctatgcctgtaccaaatcctacaatgccggtgaaaggtgccgggaccaccctgtgggtttataaggg |
| gagcggtgacccttacgcgaatccgctttcagacgttgactggtcgcgtctggcaaaagttaaagacctgacgcccggcgaactgacc |
| gctgagtcctatgacgacagctatctcgatgatgaagatgcagactggactgcgaccgggcaggggcagaaatctgccggagatacc |
| agcttcacgctggcgtggatgcccggagagcaggggcagcaggcgctgctggcgtggtttaatgaaggcgatacccgtgcctataaa |
| atccgcttcccgaacggcacggtcgatgtgttccgtggctgggtcagcagtatcggtaaggcggtgacggcgaaggaagtgatcaccc |
| gcacggtgaaagtcaccaatgtgggacgtccgtcgatggcagaagatcgcagcacggtaacagcggcaaccggcatgaccgtgacg |
| cctgccagcacctcggtggtgaaagggcagagcaccacgctgaccgtggccttccagccggagggcgtaaccgacaagagctttcgt |
| gcggtgtctgcggataaaacaaaagccaccgtgtcggtcagtggtatgaccatcaccgtgaacggcgttgctgcaggcaaggtcaaca |
| ttccggttgtatccggtaatggtgagtttgctgcggttgcagaaattaccgtcaccgccagttaatccggagagtcagcgatgttcctgaaa |
| accgaatcatttgaacataacggtgtgaccgtcacgctttctgaactgtcagccctgcagcgcattgagcatctcgccctgatgaaacggc |
| aggcagaacaggcggagtcagacagcaaccggaagtttactgtggaagacgccatcagaaccggcgcgtttctggtggcgatgtccc |
| tgtggcataaccatccgcagaagacgcagatgccgtccatgaatgaagccgttaaacagattgagcaggaagtgcttaccacctggcc |
| cacggaggcaatttctcatgctgaaaacgtggtgtaccggctgtctggtatgtatgagtttgtggtgaataatgcccctgaacagacagag |
| gacgccgggcccgcagagcctgtttctgcgggaaagtgttcgacggtgagctgagttttgccctgaaactggcgcgtgagatggggcg |
| acccgactggcgtgccatgcttgccgggatgtcatccacggagtatgccgactggcaccgcttttacagtacccattattttcatgatgttct |
| gctggatatgcacttttccgggctgacgtacaccgtgctcagcctgtttttcagcgatccggatatgcatccgctggatttcagtctgctgaa |
| ccggcgcgaggctgacgaagagcctgaagatgatgtgctgatgcagaaagcggcagggcttgccggaggtgtccgctttggcccgg |
| acgggaatgaagttatccccgcttccccggatgtggcggacatgacggaggatgacgtaatgctgatgacagtatcagaagggatcgc |
| aggaggagtccggtatggctgaaccggtaggcgatctggtcgttgatttgagtctggatgcggccagatttgacgagcagatggccaga |
| gtcaggcgtcatttttctggtacggaaagtgatgcgaaaaaaacagcggcagtcgttgaacagtcgctgagccgacaggcgctggctg |
| cacagaaagcggggatttccgtcgggcagtataaagccgccatgcgtatgctgcctgcacagttcaccgacgtggccacgcagcttgc |
| aggcgggcaaagtccgtggctgatcctgctgcaacagggggggcaggtgaaggactccttcggcgggatgatccccatgttcagggg |
| gcttgccggtgcgatcaccctgccgatggtgggggccacctcgctggcggtggcgaccggtgcgctggcgtatgcctggtatcaggg |

TABLE 10-continued

| Sequence of λ::Tn-I-Sce2-PsapLuxAB-Cm5 (SEQ ID NO: 4). |
| --- |
| caactcaaccctgtccgatttcaacaaaacgctggtcctttccggcaatcaggcgggactgacggcagatcgtatgctggtcctgtccag |
| agccgggcaggcggcagggctgacgtttaaccagaccagcgagtcactcagcgcactggttaaggcgggggtaagcggtgaggctc |
| agattgcgtccatcagccagagtgtggcgcgtttctcctctgcatccggcgtggaggtggacaaggtcgctgaagccttcgggaagctg |
| accacagacccgacgtcggggctgacggcgatggctcgccagttccataacgtgtcggcggagcagattgcgtatgttgctcagttgc |
| agcgttccggcgatgaagccggggcattgcaggcggcgaacgaggccgcaacgaaagggtttgatgaccagacccgccgcctgaa |
| agagaacatgggcacgctggagacctgggcagacaggactgcgcgggcattcaaatccatgtgggatgcggtgctggatattggtcgt |
| cctgataccgcgcaggagatgctgattaaggcagaggctgcgtataagaaagcagacgacatctggaatctgcgcaaggatgattatttt |
| gttaacgatgaagcgcgggcgcgttactgggatgatcgtgaaaaggcccgtcttgcgcttgaagccgcccgaaagaaggctgagcag |
| cagactcaacaggacaaaaatgcgcagcagcagagcgataccgaagcgtcacggctgaaatataccgaagaggcgcagaaggctta |
| cgaacggctgcagacgccgctggagaaatataccgcccgtcaggaagaactgaacaaggcactgaaagacgggaaaatcctgcag |
| gcggattacaacacgctgatggcggcggcgaaaaaggattatgaagcgacgctgaaaaagccgaaacagtccagcgtgaaggtgtct |
| gcgggcgatcgtcaggaagacagtgctcatgctgccctgctgacgcttcaggcagaactccggacgctggagaagcatgccggagc |
| aaatgagaaaatcagccagcagcgccgggatttgtggaaggcggagagtcagttcgcggtactggaggaggcggcgcaacgtcgcc |
| agctgtctgcacaggagaaatccctgctggcgcataaagatgagacgctggagtacaaacgccagctggctgcacttggcgacaaggt |
| tacgtatcaggagcgcctgaacgcgctggcgcagcaggcggataaattcgcacagcagcaacgggcaaaacgggccgccattgatg |
| cgaaaagccgggggctgactgaccggcaggcagaacgggaagccacggaacagcgcctgaaggaacagtatggcgataatccgct |
| ggcgctgaataacgtcatgtcagagcagaaaaagacctgggcggctgaagaccagcttcgcgggaactggatggcaggcctgaagt |
| ccggctggagtgagtgggaagagagcgccacggacagtatgtcgcaggtaaaaagtgcagccacgcagacctttgatggtattgcac |
| agaatatggcggcgatgctgaccggcagtgagcagaactggcgcagcttcacccgttccgtgctgtccatgatgacagaaattctgctta |
| agcaggcaatggtggggattgtcgggagtatcggcagcgccattggcggggctgttggtggcggcgcatccgcgtcaggcggtaca |
| gccattcaggccgctgcggcgaaattccattttgcaaccggaggatttacgggaaccggcggcaaatatgagccagcggggattgttca |
| ccgtggtgagtttgtcttcacgaaggaggcaaccagccggattggcgtggggaatctttaccggctgatgcgcggctatgccaccggc |
| ggttatgtcggtacaccgggcagcatggcagacagccggtcgcaggcgtccgggacgtttgagcagaataaccatgtggtgattaaca |
| acgacggcacgaacgggcagataggtccggctgctctgaaggcggtgtatgacatggcccgcaagggtgcccgtgatgaaattcaga |
| cacagatgcgtgatggtggcctgttctccggaggtggacgatgaagaccttccgctggaaagtgaaacccggtatggatgtggcttcgg |
| tcccttctgtaagaaaggtgcgctttggtgatggctattctcagcgagcgcctgccgggctgaatgccaacctgaaaacgtacagcgtga |
| cgctttctgtcccccgtgaggaggccacggtactggagtcgtttctggaagagcacgggggctggaaatcctttctgtggacgccgcctt |
| atgagtggcggcagataaaggtgacctgcgcaaaatggtcgtcgcgggtcagtatgctgcgtgttgagttcagcgcagagtttgaacag |
| gtggtgaactgatgcaggatatccggcaggaaacactgaatgaatgcacccgtgcggagcagtcggccagcgtggtgctctgggaaa |
| tcgacctgacagaggtcggtggagaacgttatttttctgtaatgagcagaacgaaaaaggtgagccggtcacctggcaggggcgaca |
| gtatcagccgtatcccattcaggggagcggttttgaactgaatggcaaaggcaccagtacgcgccccacgctgacggtttctaacctgta |
| cggtatggtcaccgggatggcggaagatatgcagagtctggtcggcggaacggtggtccggcgtaaggtttacgcccgttttctggatg |
| cggtgaacttcgtcaacggaaacagttacgccgatccggagcaggaggtgatcagccgctggcgcattgagcagtgcagcgaactga |
| gcgcggtgagtgcctcctttgtactgtccacgccgacggaaacggatggcgctgtttttccgggacgtatcatgctggccaacacctgca |
| cctggacctatcgcggtgacgagtgcggttatagcggtccggctgtcgcggatgaatatgaccagccaacgtccgatatcacgaaggat |
| aaatgcagcaaatgcctgagcggttgtaagttccgcaataacgtcggcaactttggcggcttcctttccattaacaaactttcgcagtaaat |
| cccatgacacagacagaatcagcgattctggcgcacgcccggcgatgtgcgccagcggagtcgtgcggcttcgtggtaagcacgccg |
| gaggggaaagatatttcccctgcgtgaatatctccggtgagccggaggctatttccgtatgtcgccggaagactggctgcaggcagaa |
| atgcagggtgagattgtggcgctggtccacagccaccccggtggtctgccctggctgagtgaggccgaccggcggctgcaggtgcag |

TABLE 10-continued

| Sequence of λ::Tn-I-Sce2-PsapLuxAB-Cm5 (SEQ ID NO: 4). |
|---|
| agtgatttgccgtggtggctggtctgccgggggacgattcataagttccgctgtgtgccgcatctcaccgggcggcgctttgagcacggt |
| gtgacggactgttacacactgttccgggatgcttatcatctggcggggattgagatgccggactttcatcgtgaggatgactggtggcgta |
| acggccagaatctctatctggataatctggaggcgacggggctgtatcaggtgccgttgtcagcggcacagccgggcgatgtgctgct |
| gtgctgttttggttcatcagtgccgaatcacgccgcaatttactgcggcgacggcgagctgctgcaccatattcctgaacaactgagcaaa |
| cgagagaggtacaccgacaaatggcagcgacgcacacactccctctggcgtcaccgggcatggcgcgcatctgcctttacggggattt |
| acaacgatttggtcgccgcatcgaccttcgtgtgaaaacggggggctgaagccatccgggcactggccacacagctcccggcgtttcgt |
| cagaaactgagcgacggctggtatcaggtacggattgccgggcgggacgtcagcacgtccgggttaacggcgcagttacatgagact |
| ctgcctgatggcgctgtaattcatattgttcccagagtcgccggggccaagtcaggtggcgtattccagattgtcctgggggctgccgcc |
| attgccggatcattctttaccgccggagccacccttgcagcatgggggcagccattggggccggtggtatgaccggcatcctgttttct |
| ctcggtgccagtatggtgctcggtggtgtggcgcagatgctggcaccgaaagccagaactccccgtatacagacaacggataacggta |
| agcagaacacctatttctcctcactggataacatggttgcccagggcaatgttctgcctgttctgtacggggaaatgcgcgtggggtcacg |
| cgtggtttctcaggagatcagcacggcagacgaaggggacggtggtcaggttgtggtgattggtcgctgatgcaaaatgttttatgtgaa |
| accgcctgcgggcggttttgtcatttatggagcgtgaggaatgggtaaaggaagcagtaaggggcataccccgcgcgaagcgaagga |
| caacctgaagtccacgcagttgctgagtgtgatcgatgccatcagcgaagggccgattgaaggtccggtggatggcttaaaaagcgtg |
| ctgctgaacagtacgccggtgctggacactgaggggaataccaacatatccggtgtcacggtggtgttccgggctggtgagcaggagc |
| agactccgccggagggatttgaatcctccggctccgagacggtgctgggtacggaagtgaaatatgacacgccgatcacccgcaccat |
| tacgtctgcaaacatcgaccgtctgcgctttaccttcggtgtacaggcactggtggaaaccacctcaaagggtgacaggaatccgtcgg |
| aagtccgcctgctggttcagatacaacgtaacggtggctgggtgacggaaaaagacatcaccattaagggcaaaaccacctcgcagta |
| tctggcctcggtggtgatgggtaacctgccgccgcgcccgtttaatatccggatgcgcaggatgacgccggacagcaccacagacca |
| gctgcagaacaaaacgctctggtcgtcatacactgaaatcatcgatgtgaaacagtgctacccgaacacggcactggtcggcgtgcag |
| gtggactcggagcagttcggcagccagcaggtgagccgtaattatcatctgcgcgggcgtattctgcaggtgccgtcgaactataaccc |
| gcagacgcggcaatacagcggtatctgggacggaacgtttaaaccggcatacagcaacaacatggcctggtgtctgtgggatatgctg |
| acccatccgcgctacggcatggggaaacgtcttggtgcggcggatgtggataaatgggcgctgtatgtcatcggccagtactgcgacc |
| agtcagtgccggacggctttggcggcacggagccgcgcatcacctgtaatgcgtacctgaccacacagcgtaaggcgtgggatgtgct |
| cagcgatttctgctcggcgatgcgctgtatgccggtatggaacgggcagacgctgacgttcgtgcaggaccgaccgtcggataagacg |
| tggacctataaccgcagtaatgtggtgatgccggatgatggcgcgccgttccgctacagcttcagcgccctgaaggaccgccataatgc |
| cgttgaggtgaactggattgacccgaacaacggctgggagacggcgacagagcttgttgaagatacgcaggccattgcccgttacggt |
| cgtaatgttacgaagatggatgcctttggctgtaccagccgggggcaggcacaccgcgccgggctgtggctgattaaaacagaactgc |
| tggaaacgcagaccgtggatttcagcgtcggcgcagaagggcttcgccatgtaccgggcgatgttattgaaatctgcgatgatgactatg |
| ccggtatcagcaccggtggtcgtgtgctggcggtgaacagccagacccggacgctgacgctcgaccgtgaaatcacgctgccatcctc |
| cggtaccgcgctgataagcctggttgacggaagtggcaatccggtcagcgtggaggttcagtccgtcaccgacggcgtgaaggtaaa |
| agtgagccgtgttcctgacggtgttgctgaatacagcgtatgggagctgaagctgccgacgctgcgccagcgactgttccgctgcgtga |
| gtatccgtgagaacgacgacggcacgtatgccatcaccgccgtgcagcatgtgccggaaaaagaggccatcgtggataacggggcg |
| cactttgacggcgaacagagtggcacggtgaatggtgtcacgccgccagcggtgcagcacctgaccgcagaagtcactgcagacag |
| cggggaatatcaggtgctggcgcgatgggacacaccgaaggtggtgaagggcgtgagtttcctgctccgtctgaccgtaacagcgga |
| cgacggcagtgagcggctggtcagcacggcccggacgacggaaaccacataccgcttcacgcaactggcgctggggaactacagg |
| ctgacagtccgggcggtaaatgcgtgggggcagcagggcgatccggcgtcggtatcgttccggattgccgcaccggcagcaccgtc |
| gaggattgagctgacgccgggctattttcagataaccgccacgccgcatcttgccgtttatgacccgacggtacagtttgagttctggttct |
| cggaaaagcagattgcggatatcagacaggttgaaaccagcacgcgttatcttggtacggcgctgtactggatagccgccagtatcaat |

TABLE 10-continued

| Sequence of λ::Tn-I-Sce2-PsapLuxAB-Cm5 (SEQ ID NO: 4). |
|---|
| atcaaaccgggccatgattattacttttatatccgcagtgtgaacaccgttggcaaatcggcattcgtggaggccgtcggtcgggcgagc |
| gatgatgcggaaggttacctggatttttttcaaaggcaagataaccgaatcccatctcggcaaggagctgctggaaaaagtcgagctgac |
| ggaggataacgccagcagactggaggagttttcgaaagagtggaaggatgccagtgataagtggaatgccatgtgggctgtcaaaatt |
| gagcagaccaaagacggcaaacattatgtcgcgggtattggcctcagcatggaggacacggaggaaggcaaactgagccagtttctg |
| gttgccgccaatcgtatcgcatttattgacccggcaaacgggaatgaaacgccgatgtttgtggcgcagggcaaccagatattcatgaac |
| gacgtgttcctgaagcgcctgacggcccccaccattaccagcggcggcaatcctccggccttttccctgacaccggacggaaagctga |
| ccgctaaaaatgcggatatcagtggcagtgtgaatgcgaactccgggacgctcagtaatgtgacgatagctgaaaactgtacgataaac |
| ggtacgctgagggcggaaaaaatcgtcggggacattgtaaaggcggcgagcgcggcttttccgcgccagcgtgaaagcagtgtgga |
| ctggccgtcaggtacccgtactgtcaccgtgaccgatgaccatccttttgatcgccagatagtggtgcttccgctgacgtttcgcggaagt |
| aagcgtactgtcagcggcaggacaacgtattcgatgtgttatctgaaagtactgatgaacggtgcggtgatttatgatggcgcggcgaac |
| gaggcggtacaggtgttctcccgtattgttgacatgccagcgggtcggggaaacgtgatcctgacgttcacgcttacgtccacacggcat |
| tcggcagatattccgccgtatacgtttgccagcgatgtgcaggttatggtgattaagaaacaggcgctgggcatcagcgtggtctgagtgt |
| gttacagaggttcgtccgggaacgggcgttttattataaaacagtgagaggtgaacgatgcgtaatgtgtgtattgccgttgctgtctttgcc |
| gcacttgcggtgacagtcactccggcccgtgcggaaggtggacatggtacgtttacggtgggctattttcaagtgaaaccgggtacattg |
| ccgtcgttgtcgggcggggataccggtgtgagtcatctgaaagggattaacgtgaagtaccgttatgagctgacggacagtgtgggggt |
| gatggcttccctggggttcgccgcgtcgaaaaagagcagcacagtgatgaccggggaggatacgtttcactatgagagcctgcgtgga |
| cgttatgtgagcgtgatggccggaccggttttacaaatcagtaagcaggtcagtgcgtacgccatggccggagtggctcacagtcggtg |
| gtccggcagtacaatggattaccgtaagacggaaatcactcccgggtatatgaaagagacgaccactgccagggacgaaagtgcaat |
| gcggcatacctcagtggcgtggagtgcaggtatacagattaatccggcagcgtccgtcgttgttgatattgcttatgaaggctccggcagt |
| ggcgactggcgtactgacggattcatcgttggggtcggttataaattctgattagccaggtaacacagtgttatgacagcccgccggaac |
| cggtgggcttttttgtggggtgaatatggcagtaaagatttcaggagtcctgaaagacggcacaggaaaaccggtacagaactgcacca |
| ttcagctgaaagccagacgtaacagcaccacggtggtggtgaacacggtgggctcagagaatccggatgaagccgggcgttacagca |
| tggatgtggagtacggtcagtacagtgtcatcctgcaggttgacggttttccaccatcgcacgccgggaccatcaccgtgtatgaagattc |
| acaaccggggacgctgaatgattttctctgtgccatgacggaggatgatgcccggccggaggtgctgcgtcgtcttgaactgatggtgg |
| aagaggtggcgcgtaacgcgtccgtggtggcacagagtacggcagacgcgaagaaatcagccggcgatgccagtgcatcagctgct |
| caggtcgcggcccttgtgactgatgcaactgactcagcacgcgccgccagcacgtccgccggacaggctgcatcgtcagctcaggaa |
| gcgtcctccggcgcagaagcggcatcagcaaaggccactgaagcggaaaaaagtgccgcagccgcagagtcctcaaaaaacgcgg |
| cggccaccagtgccggtgcggcgaaaacgtcagaaacgaatgctgcagcgtcacaacaatcagccgccacgtctgcctccaccgcg |
| gccacgaaagcgtcagaggccgccacttcagcacgagatgcggtggcctcaaaagaggcagcaaaatcatcagaaacgaacgcatc |
| atcaagtgccggtcgtgcagcttcctcggcaacggcggcagaaaattctgccagggcggcaaaaacgtccgagacgaatgccaggtc |
| atctgaaacagcagcggaacggagcgcctctgccgcggcagacgcaaaaacagcggcggcggggagtgcgtcaacggcatccac |
| gaaggcgacagaggctgcgggaagtgcggtatcagcatcgcagagcaaaagtgcggcagaagcggcggcaatacgtgcaaaaaat |
| tcggcaaaaacgtgcagaaagatatagcttcagctgtcgcgcttgaggatgcggacacaacgagaaaggggatagtgcagctcagcagt |
| gcaaccaacagcacgtctgaaacgcttgctgcaacgccaaaggcggttaaggtggtaatggatgaaacgaacagaaaagcccactgg |
| acagtccggcactgaccggaacgccaacagcaccaaccgcgctcaggggaacaaacaatacccagattgcgaacaccgcttttgtac |
| tggccgcgattgcagatgttatcgacgcgtcacctgacgcactgaatacgctgaatgaactggccgcgagcgctcgggaatgatccagat |
| tttgctaccaccatgactaacgcgcttgcgggtaaacaaccgaagaatgcgacactgacggcgctggcagggctttccacggcgaaaa |
| ataaattaccgtattttgcggaaaatgatgccgccagcctgactgaactgactcaggttggcagggatattctggcaaaaaattccgttgca |
| gatgttcttgaataccttggggccggtgagaattcggcctttccggcaggtgcgccgatcccgtggccatcagatatcgttccgtctggct |

TABLE 10-continued

| Sequence of λ::Tn-I-Sce2-PsapLuxAB-Cm5 (SEQ ID NO: 4). |
| --- |
| acgtcctgatgcaggggcaggcgtttgacaaatcagcctacccaaaacttgctgtcgcgtatccatcgggtgtgcttcctgatatgcgag |
| gctggacaatcaaggggaaacccgccagcggtcgtgctgtattgtctcaggaacaggatggaattaagtcgcacacccacagtgccag |
| tgcatccggtacggatttggggacgaaaaccacatcgtcgtttgattacgggacgaaaacaacaggcagtttcgattacggcaccaaatc |
| gacgaataacacgggggctcatgctcacagtctgagcggttcaacaggggccgcgggtgctcatgcccacacaagtggtttaaggatg |
| aacagttctggctggagtcagtatggaacagcaaccattacaggaagtttatccacagttaaaggaaccagcacacagggtattgcttatt |
| tatcgaaaacggacagtcagggcagccacagtcactcattgtccggtacagccgtgagtgccggtgcacatgcgcatacagttggtatt |
| ggtgcgcaccagcatccggttgttatcggtgctcatgcccattctttcagtattggttcacacggacacaccatcaccgttaacgctgcgg |
| gtaacgcggaaaacaccgtcaaaaacattgcatttaactatattgtgaggcttgcataatggcattcagaatgagtgaacaaccacggac |
| cataaaaatttataatctgctggccggaactaatgaatttattggtgaaggtgacgcatatattccgcctcataccggtctgcctgcaaacag |
| taccgatattgcaccgccagatattccggctggctttgtggctgttttcaacagtgatgaggcatcgtggcatctcgttgaagaccatcggg |
| gtaaaaccgtctatgacgtggcttccggcgacgcgttatttatttctgaactcggtccgttaccggaaaatttacctggttatcgccgggag |
| gggaatatcagaagtggaacggcacagcctgggtgaaggatacggaagcagaaaaactgttccggatccgggaggcggaagaaac |
| aaaaaaaagcctgatgcaggtagccagtgagcatattgcgccgcttcaggatgctgcagatctggaaattgcaacgaaggaagaaacc |
| tcgttgctggaagcctggaagaagtatcgggtgttgctgaaccgtgttgatacatcaactgcacctgatattgagtggcctgctgtccctgt |
| tatggagtaatcgttttgtgatatgccgcagaaacgttgtatgaaataacgttctgcggttagttagtatattgtaaagctgagtattggtttattt |
| ggcgattattatcttcaggagaataatggaagttctatgactcaattgttcatagtgtttacatcaccgccaattgcttttaagactgaacgcat |
| gaaatatggtttttcgtcatgttttgagtctgctgttgatatttctaaagtcggtttttttttcttcgttttctctaactattttccatgaaatacatttttga |
| ttattatttgaatcaattccaattacctgaagtctttcatctataattggcattgtatgtattggtttattggagtagatgcttgcttttctgagccata |
| gctctgatatccaaatgaagccataggcatttgttattttggctctgtcagctgcataacgccaaaaaatatatttatctgcttgatcttcaaatg |
| ttgtattgattaaatcaattggatggaattgtttatcataaaaaattaatgtttgaatgtgataaccgtcctttaaaaaagtcgtttctgcaagctt |
| ggctgtatagtcaactaactcttctgtcgaagtgatatttttaggcttatctaccagttttagacgctctttaatatcttcaggaattattttattgtc |
| atattgtatcatgctaaatgacaatttgcttatggagtaatcttttaattttaaataagttattctcctggcttcatcaaataaagagtcgaatgatg |
| ttggcgaaatcacatcgtcacccattggattgtttatttgtatgccaagagagttacagcagttatacattctgccatagattatagctaaggc |
| atgtaataattcgtaatcttttagcgtattagcgacccatcgtctttctgatttaataatagatgattcagttaaatatgaaggtaatttcttttgtgc |
| aagtctgactaactttttttataccaatgtttaacatactttcatttgtaataaactcaatgtcattttcttcaatgtaagatgaaataagagtagcctt |
| tgcctcgctatacatttctaaatcgccttgtttttctatcgtattgcgagaattttttagcccaagccattaatggatcatttttccatttttcaataac |
| attattgttataccaaatgtcatatcctataatctggtttttgtttttttgaataataaatgttactgttcttgcggtttggaggaattgattcaaattca |
| agcgaaataattcagggtcaaaatatgtatcaatgcagcatttgagcaagtgcgataaatctttaagtcttctttcccatggtttttttagtcataa |
| aactctccatttgataggttgcatgctagatgctgatatattttagaggtgataaaattaactgcttaactgtcaatgtaatacaagttgtttgat |
| ctttgcaatgattcttatcagaaaccatatagtaaattagttacacaggaaatttttaatattattattatcattcattatgtattaaaattagagttgt |
| ggcttggctctgctaacacgttgctcataggagatatggtagagccgcagacacgtcgtatgcaggaacgtgctgcggctggctggtga |
| acttccgatagtgcgggtgttgaatgatttccagttgctaccgattttacatatttttttgcatgagagaatttgtaccacctcccaccgaccatc |
| tatgactgtacgccactgtccctaggactgctatgtgccggagcggacattacaaacgtccttctcggtgcatgccactgttgccaatgac |
| ctgcctaggaattggttagcaagttactaccggattttgtaaaaacagccctcctcatataaaaagtattcgttcacttccgataagcgtcgta |
| attttctatctttcatcatattctagatccctctgaaaaaatcttccgagtttgctaggcactgatacataactcttttccaataattggggaagtc |
| attcaaatctataataggtttcagatttgcttcaataaattctgactgtagctgctgaaacgttgcggttgaactatatttccttataacttttacga |
| aagagtttctttgagtaatcacttcactcaagtgcttccctgcctccaaacgatacctgttagcaatatttaatagcttgaaatgatgaagagct |
| ctgtgtttgtcttcctgcctccagttcgccgggcattcaacataaaaactgatagcacccggagttccggaaacgaaatttgcatatacccca |
| ttgctcacgaaaaaaaatgtccttgtcgatatagggatgaatcgcttggtgtacctcatctactgcgaaaacttgacctttctctcccatattg |

TABLE 10-continued

| Sequence of λ::Tn-I-Sce2-PsapLuxAB-Cm5 (SEQ ID NO: 4). |
| --- |
| cagtcgcggcacgatggaactaaattaataggcatcaccgaaaattcaggataatgtgcaataggaagaaaatgatctatatttttgtctgt |
| cctatatcaccacaaaatggacatttttcacctgatgaaacaagcatgtcatcgtaatatgttctagcgggtttgtttttatctcggagattatttt |
| cataaagcttttctaatttaacctttgtcaggttaccaactactaaggttgtaggctcaagagggtgtgtcctgtcgtaggtaaataactgacc |
| tgtcgagcttaatattctatattgttgttctttctgcaaaaaagtggggaagtgagtaatgaaattatttctaacatttatctgcatcataccttcc |
| gagcatttattaagcatttcgctataagttctcgctggaagaggtagtttttttcattgtactttaccttcatctctgttcattatcatcgcttttaaaa |
| cggttcgaccttctaatcctatctgaccattataatttttttagaatggtttcataagaaagctctgaatcaacggactgcgataataagtggtgg |
| tatccagaatttgtcacttcaagtaaaaacacctcacgagttaaaacacctaagttctcaccgaatgtctcaatatccggacggataatattta |
| ttgcttctcttgaccgtaggactttccacatgcaggattttggaacctcttgcagtactactggggaatgagttgcaattattgctacaccattg |
| cgtgcatcgagtaagtcgcttaatgttcgtaaaaaagcagagagcaaaggtggatgcagatgaacctctggttcatcgaataaaactaat |
| gacttttcgccaacgacatctactaatcttgtgatagtaaataaaacaattgcatgtccagagctcattcgaagcagatatttctggatattgtc |
| ataaaacaatttagtgaatttatcatcgtccacttgaatctgtggttcattacgtcttaactcttcatatttagaaatgaggctgatgagttccata |
| tttgaaaagttttcatcactacttagtttttttgatagcttcaagccagagttgtctttttctatctactctcatacaaccaataaatgctgaaatgaa |
| ttctaagcggagatcgcctagtgattttaaactattgctggcagcattcttgagtccaatataaaagtattgtgtaccttttgctgggtcaggtt |
| gttctttaggaggagtaaaaggatcaaatgcactaaacgaaactgaaacaagcgatcgaaaatatccctttgggattcttgactcgataag |
| tctattattttcagagaaaaaatattcattgttttctgggttggtgattgcaccaatcattccattcaaaattgttgttttaccacacccattccgcc |
| cgataaaagcatgaatgttcgtgctgggcatagaattaaccgtcacctcaaaaggtatagttaaatcactgaatccgggagcactttttctat |
| taaatgaaaagtggaaatctgacaattctggcaaaccatttaacacacgtgcgaactgtccatgaatttctgaaagagttacccctctaagt |
| aatgaggtgttaaggacgctttcattttcaatgtcggctaatcgatttggccatactactaaatcctgaatagctttaagaaggttatgtttaaa |
| accatcgcttaatttgctgagattaacatagtagtcaatgctttcacctaaggaaaaaaacatttcagggagttgactgaatttttttatctattaa |
| tgaataagtgcttacttcttctttttgacctacaaaaccaattttaacatttccgatatcgcattttttcaccatgctcatcaaagacagtaagataa |
| aacattgtaacaaaggaatagtcattccaaccatctgctcgtaggaatgccttatttttttctactgcaggaatatacccgcctctttcaataac |
| actaaactccaacatatagtaacccttaattttattaaaataaccgcaatttatttggcggcaacacaggatctctcttttaagttactctctatta |
| catacgttttccatctaaaaattagtagtattgaacttaacggggcatcgtattgtagttttccatatttagctttctgcttccttttggataaccca |
| ctgttattcatgttgcatggtgcactgtttataccaacgatatagtctattaatgcatatatagtatcgccgaacgattagctcttcaggcttctg |
| aagaagcgtttcaagtactaataagccgatagatagccacggacttcgtagccatttttcataagtgttaacttccgctcctcgctcataaca |
| gacattcactacagttatggcggaaaggtatgcatgctgggtgtggggaagtcgtgaaagaaaagaagtcagctgcgtcgtttgacatca |
| ctgctatcttcttactggttatgcaggtcgtagtgggtggcacacaaagctttgcactggattgcgaggctttgtgcttctctggagtgcgac |
| aggtttgatgacaaaaaattagcgcaagaagacaaaaatcaccttgcgctaatgctctgttacaggtcactaataccatctaagtagttgatt |
| catagtgactgcatatgttgtgttttacagtattatgtagtctgtttttttatgcaaaatctaatttaatatattgatatttatatcattttacgtttctcgtt |
| cagctttttttatactaagttggcattataaaaaagcattgcttatcaatttgttgcaacgaacaggtcactatcagtcaaaataaaatcattattt |
| gatttcaattttgtcccactccctgcctctgtcatcacgatactgtgatgccatggtgtccgacttatgcccgagaagatgttgagcaaactta |
| tcgcttatctgcttctcatagagtcttgcagacaaactgcgcaactcgtgaaaggtaggcggatccccttcgaaggaaagacctgatgcttt |
| tcgtgcgcgcataaaataccttgatactgtgccggatgaaagcggttcgcgacgagtagatgcaattatggtttctccgccaagaatctctt |
| tgcatttatcaagtgtttccttcattgatattccgagagcatcaatatgcaatgctgttgggatggcaatttttacgcctgttttgctttgctcgac |
| ataaagatatccatctacgatatcagaccacttcatttcgcataaatcaccaactcgttgcccggtaacaacagccagttccattgcaagtct |
| gagccaacatggtgatgattctgctgcttgataaattttcaggtattcgtcagccgtaagtcttgatctccttacctctgattttgctgcgcgag |
| tggcagcgacatggtttgttgttatatggccttcagctattgcctctcggaatgcatcgctcagtgttgatctgattaacttggctgacgccgc |
| cttgccctcgtctatgtatccattgagcattgccgcaatttcttttgtggtgatgtcttcaagtggagcatcaggcagacccctccttattgcttt |
| aattttgctcatgtaatttatgagtgtcttctgcttgattcctctgctggccaggatttttttcgtagcgatcaagccatgaatgtaacgtaacgga |

TABLE 10-continued

| Sequence of λ::Tn-I-Sce2-PsapLuxAB-Cm5 (SEQ ID NO: 4). |
|---|
| attatcactgttgattctcgctgtcagaggcttgtgtttgtgtcctgaaaataactcaatgttggcctgtatagcttcagtgattgcgattcgcct |
| gtctctgcctaatccaaactctttacccgtccttgggtccctgtagcagtaatatccattgtttcttatataaaggttaggggtaaatcccggc |
| gctcatgacttcgccttcttcccatttctgatcctcttcaaaaggccacctgttactggtcgatttaagtcaacctttaccgctgattcgtggaa |
| cagatactctcttccatccttaaccggaggtgggaatatcctgcattcccgaacccatcgacgaactgtttcaaggcttcttggacgtcgct |
| ggcgtgcgttccactcctgaagtgtcaagtacatcgcaaagtctccgcaattacacgcaagaaaaaaccgccatcaggcggcttggtgtt |
| ctttcagttcttcaattcgaatattggttacgtctgcatgtgctatctgcgcccatatcatccagtggtcgtagcagtcgttgatgttctccgctt |
| cgataactctgttgaatggctctccattccattctcctgtgactcggaagtgcatttatcatctccataaaacaaaacccgccgtagcgagtt |
| cagataaaataaatccccgcgagtgcgaggattgttatgtaatattgggtttaatcatctatatgttttgtacagagagggcaagtatcgtttc |
| caccgtactcgtgataataattttgcacggtatcagtcatttctcgcacattgcagaatggggatttgtcttcattagacttataaaccttcatg |
| gaatatttgtatgccgactctatatctataccttcatctacataaacaccttcgtgatgtctgcatggagacaagacaccggatctgcacaac |
| attgataacgcccaatctttttgctcagactctaactcattgatactcatttataaactccttgcaatgtatgtcgtttcagctaaacggtatcag |
| caatgtttatgtaaagaaacagtaagataatactcaacccgatgtttgagtacggtcatcatctgacactacagactctggcatcgctgtga |
| agacgacgcgaaattcagcattttcacaagcgttatcttttacaaaaccgatctcactctcctttgatgcgaatgccagcgtcagacatcata |
| tgcagatactcacctgcatcctgaacccattgacctccaaccccgtaatagcgatgcgtaatgatgtcgatagttactaacgggtcttgttc |
| gattaactgccgcagaaactcttccaggtcaccagtgcagtgcttgataacaggagtcttcccaggatggcgaacaacaagaaactggtt |
| tccgtcttcacggacttcgttgctttccagtttagcaatacgcttactcccatccgagataacaccttcgtaatactcacgctgctcgttgagtt |
| ttgattttgctgtttcaagctcaacacgcagtttccctactgttagcgcaatatcctcgttctcctggtcgcggcgtttgatgtattgctggtttct |
| ttcccgttcatccagcagttccagcacaatcgatggtgttaccaattcatggaaaaggtctgcgtcaaatccccagtcgtcatgcattgcct |
| gctctgccgcttcacgcagtgcctgagagttaatttcgctcacttcgaacctctctgtttactgataagttccagatcctcctggcaacttgca |
| caagtccgacaaccctgaacgaccaggcgtcttcgttcatctatcggatcgccacactcacaacaatgagtggcagatatagcctggtg |
| gttcaggcggcgcatttttattgctgtgttgcgctgtaattcttctatttctgatgctgaatcaatgatgtctgccatctttcattaatccctgaact |
| gttggttaatacgcttgagggtgaatgcgaataataaaaaaggagcctgtagctccctgatgattttgcttttcatgttcatcgttccttaaaga |
| cgccgtttaacatgccgattgccaggcttaaatgagtcggtgtgaatcccatcagcgttaccgtttcgcggtgcttcttcagtacgctacgg |
| caaatgtcatcgacgtttttatccggaaactgctgtctggctttttttgatttcagaattagcctgacgggcaatgctgcgaagggcgttttcct |
| gctgaggtgtcattgaacaagtcccatgtcggcaagcataagcacacagaatatgaagcccgctgccagaaaaatgcattccgtggttgt |
| catacctggtttctctcatctgcttctgctttcgccaccatcatttccagcttttgtgaaagggatgcggctaacgtatgaaattcttcgtctgttt |
| ctactggtattggcacaaacctgattccaatttgagcaaggctatgtgccatctcgatactcgttcttaactcaacagaagatgctttgtgcat |
| acagcccctcgtttattatttatctcctcagccagccgctgtgctttcagtggatttcggataacagaaaggccgggaaatacccagcctcg |
| ctttgtaacggagtagacgaaagtgattgcgcctacccggatattatcgtgaggatgcgtcatcgccattgctccccaaatacaaaaccaa |
| tttcagccagtgcctcgtccatttttttcgatgaactccggcacgatctcgtcaaaactcgccatgtacttttcatcccgctcaatcacgacata |
| atgcaggccttcacgcttcatacgcgggtcatagttggcaaagtaccaggcatttttttcgcgtcacccacatgctgtactgcacctgggcc |
| atgtaagctgactttatggcctcgaaaccaccgagccggaacttcatgaaatcccgggaggtaaacgggcatttcagttcaaggccgttg |
| ccgtcactgcataaaccatcgggagagcaggcggtacgcatactttcgtcgcgatagatgatcggggattcagtaacattcacgccgga |
| agtgaattcaaacagggttctggcgtcgttctcgtactgttttccccaggccagtgctttagcgttaacttccggagccacaccggtgcaaa |
| cctcagcaagcagggtgtggaagtaggacattttcatgtcaggccacttctttccggagcggggttttgctatcacgttgtgaacttctgaa |
| gcggtgatgacgccgagccgtaatttgtgccacgcatcatccccctgttcgacagctctcacatcgatcccggtacgctgcaggataatg |
| tccggtgtcatgctgccaccttctgctctgcggctttctgtttcaggaatccaagagcttttactgcttcggcctgtgtcagttctgacgatgc |
| acgaatgtcgcggcgaaatatctgggaacagagcggcaataagtcgtcatcccatgttttatccagggcgatcagcagagtgttaatctc |
| ctgcatggtttcatcgttaaccggagtgatgtcgcgttccggctgacgttctgcagtgtatgcagtattttcgacaatgcgctcggcttcatc |

TABLE 10-continued

| Sequence of λ::Tn-I-Sce2-PsapLuxAB-Cm5 (SEQ ID NO: 4). |
|---|
| cttgtcatagataccagcaaatccgaaggccagacgggcacactgaatcatggctttatgacgtaacatccgtttgggatgcgactgcca |
| cggccccgtgatttctctgccttcgcgagttttgaatggttcgcggcggcattcatccatccattcggtaacgcagatcggatgattacggt |
| ccttgcggtaaatccggcatgtacaggattcattgtcctgctcaaagtccatgccatcaaactgctggttttcattgatgatgcgggaccag |
| ccatcaacgcccaccaccggaacgatgccattctgcttatcaggaaaggcgtaaatttctttcgtccacggattaaggccgtactggttgg |
| caacgatcagtaatgcgatgaactgcgcatcgctggcatcacctttaaatgccgtctggcgaagagtggtgatcagttcctgtgggtcga |
| cagaatccatgccgacacgttcagccagcttcccagccagcgttgcgagtgcagtactcattcgttttatacctctgaatcaatatcaacct |
| ggtggtgagcaatggtttcaaccatgtaccggatgtgttctgccatgcgctcctgaaactcaacatcgtcatcaaacgcacgggtaatgga |
| tttttgctggccccgtggcgttgcaaatgatcgatgcatagcgattcaaacaggtgctggggcaggcctttttccatgtcgtctgccagttc |
| tgcctctttctcttcacgggcgagctgctggtagtgacgcgcccagctctgagcctcaagacgatcctgaatgtaataagcgttcatggct |
| gaactcctgaaatagctgtgaaaatatcgcccgcgaaatgccgggctgattaggaaaacaggaaagggggttagtgaatgcttttgcttg |
| atctcagtttcagtattaatatccatttttataagcgtcgacggcttcacgaaacatcttttcatcgccaataaaagtggcgatagtgaatttag |
| tctggatagccataagtgtttgatccattctttgggactcctggctgattaagtatgtcgataaggcgtttccatccgtcacgtaatttacgggt |
| gattcgttcaagtaaagattcggaagggcagccagcaacaggccaccctgcaatggcatattgcatggtgtgctccttatttatacataac |
| gaaaaacgcctcgagtgaagcgttattggtatgcggtaaaaccgcactcaggcggccttgatagtcatatcatctgaatcaaatattcctg |
| atgtatcgatatcggtaattcttattccttcgctaccatccattggaggccatccttcctgaccatttccatcattccagtcgaactcacacaca |
| acaccatatgcatttaagtcgcttgaaattgctataagcagagcatgttgcgccagcatgattaatacagcatttaatacagagccgtgtttat |
| tgagtcggtattcagagtctgaccagaaattattaatctggtgaagtttttcctctgtcattacgtcatggtcgatttcaatttctattgatgctttc |
| cagtcgtaatcaatgatgtatttttgatgtttgacatctgttcatatcctcacagataaaaaatcgccctcacactggagggcaaagaagatt |
| tccaataatcagaacaagtcggctcctgtttagttacgagcgacattgctccgtgtattcactcgttggaatgaatacacagtgcagtgtttat |
| tctgttatttatgccaaaaataaaggccactatcaggcagctttgttgttctgtttaccaagttctctggcaatcattgccgtcgttcgtattgcc |
| catttatcgacatatttcccatcttccattacaggaaacatttcttcaggcttaaccatgcattccgattgcagcttgcatccattgcatcgcttg |
| aattgtccacaccattgatttttatcaatagtcgtagtcatacggatagtcctggtattgttccatcacatcctgaggatgctcttcgaactcttc |
| aaattcttcttccatatatcaccttaaatagtggattgcggtagtaaagattgtgcctgtcttttaaccacatcaggctcggtggttctcgtgtac |
| ccctacagcgagaaatcggataaactattacaacccctacagtttgatgagtatagaaatggatccactcgttattctcggacgagtgttca |
| gtaatgaacctctggagagaaccatgtatatgatcgttatctgggttggacttctgcttttaagcccagataactggcctgaatatgttaatga |
| gagaatcggtattcctcatgtgtggcatgttttcgtctttgctcttgcattttcgctagcaattaatgtgcatcgattatcagctattgccagcgc |
| cagatataagcgatttaagctaagaaaacgcattaagatgcaaaacgataaagtgcgatcagtaattcaaaaccttacagaagagcaatc |
| tatggttttgtgcgcagcccttaatgaaggcaggaagtatgtggttacatcaaaacaattcccatacattagtgagttgattgagcttggtgt |
| gttgaacaaaactttttcccgatggaatggaaagcatatattattccctattgaggatatttactggactgaattagttgccagctatgatccat |
| ataatattgagataaagccaaggccaatatctaagtaactagataagaggaatcgattttcccttaattttctggcgtccactgcatgttatgc |
| cgcgttcgccaggcttgctgtaccatgtgcgctgattcttgcgctcaatacgttgcaggttgctttcaatctgtttgtggtattcagccagcac |
| tgtaaggtctatcggatttagtgcgctttctactcgtgatttcggtttgcgattcagcgagagaatagggcggttaactggttttgcgcttacc |
| ccaaccaacaggggatttgctgctttccattgagcctgtttctctgcgcgacgttcgcggcggcgtgtttgtgcatccatctggattctcctg |
| tcagttagctttggtggtgtgtggcagttgtagtcctgaacgaaaacccccgcgattggcacattggcagctaatccggaatcgcactta |
| cggccaatgcttcgtttcgtatcacacaccccaaagccttctgctttgaatgctgcccttcttcagggcttaatttttaagagcgtcaccttcat |
| ggtggtcagtgcgtcctgctgatgtgctcagtatcaccgccagtggtatttatgtcaacaccgccagagataatttatcaccgcagatggtt |
| atctgtatgtttttatatgaatttatttttgcagggggcattgtttggtaggtgagagatctgaattgctatgtttagtgagttgtatctatttattt |
| ttcaataaatacaattggttatgtgttttgggggcgatcgtgaggcaaagaaaacccggcgctgaggccgggttattcttgttctctggtca |
| aattatatagttggaaaacaaggatgcatatatgaatgaacgatgcagaggcaatgccgatggcgatagtgggtatcatgtagccgcttat |

TABLE 10-continued

| Sequence of λ::Tn-I-Sce2-PsapLuxAB-Cm5 (SEQ ID NO: 4). |
|---|
| gctggaaagaagcaataacccgcagaaaaacaaagctccaagctcaacaaaactaagggcatagacaataactaccgatgtcatatac |
| ccatactctctaatcttggccagtcggcgcgttctgcttccgattagaaacgtcaaggcagcaatcaggattgcaatcatggttcctgcatat |
| gatgacaatgtcgccccaagaccatctctatgagctgaaaaagaaacaccaggaatgtagtggcggaaaaggagatagcaaatgctta |
| cgataacgtaaggaattattactatgtaaacaccaggcatgattctgttccgcataattactcctgataattaatccttaactttgcccacctgc |
| cttttaaaacattccagtatatcacttttcattcttgcgtagcaatatgccatctcttcagctatctcagcattggtgaccttgttcagaggcgct |
| gagagatggcctttttctgatagataatgttctgttaaaatatctccggcctcatcttttgcccgcaggctaatgtctgaaaattgaggtgacg |
| ggttaaaaataatatccttggcaacctttttatatccctttttaaatttggcttaatgactatatccaatgagtcaaaaagctccccttcaatatct |
| gttgcccctaagacctttaatatatcgccaaatacaggtagcttggcttctaccttcaccgttgttcggccgatgaaatgcatatgcataacat |
| cgtctttggtggttcccctcatcagtggctctatctgaacgcgctctccactgcttaatgacattcctttcccgattaaaaaatctgtcagatcg |
| gatgtggtcggcccgaaaacagttctggcaaaaccaatggtgtcgccttcaacaaacaaaaaagatgggaatcccaatgattcgtcatct |
| gcgaggctgttcttaatatcttcaactgaagctttagagcgatttatcttctgaaccagactcttgtcatttgttttggtaaagagaaaagtttttc |
| catcgattttatgaatatacaaataattggagccaacctgcaggtgatgattatcagccagcagagaattaaggaaaacagacaggtttatt |
| gagcgcttatctttccctttatttttgctgcggtaagtcgcataaaaaccattcttcataattcaatccatttactatgttatgttctgaggggagt |
| gaaaattcccctaattcgatgaagattcttgctcaattgttatcagctatgcgccgaccagaacaccttgccgatcagccaaacgtctcttca |
| ggccactgactagcgataactttccccacaacggaacaactctcattgcatgggatcattgggtactgtgggtttagtggttgtaaaaacac |
| ctgaccgctatccctgatcagtttcttgaaggtaaactcatcacccccaagtctggctatgcagaaatcacctggctcaacagcctgctca |
| gggtcaacgagaattaacattccgtcaggaaagcttggcttggagcctgttggtgcggtcatggaattaccttcaacctcaagccagaat |
| gcagaatcactggctttttggttgtgcttacccatctctccgcatcacctttggtaaaggttctaagctcaggtgagaacatccctgcctgaa |
| catgagaaaaaacagggtactcatactcacttctaagtgacggctgcatactaaccgcttcatacatctcgtagatttctctggcgattgaa |
| gggctaaattcttcaacgctaactttgagaatttttgcaagcaatgcggcgttataagcatttaatgcattgatgccattaaataaagcaccaa |
| cgcctgactgccccatccccatcttgtctgcgacagattcctgggataagccaagttcattttttctttttttcataaattgctttaaggcgacgt |
| gcgtcctcaagctgctcttgtgttaatggtttctttttttgtgctcatacgttaaatct |

Equivalents

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 proteins refers to groups having 1, 2, or 3 proteins. Similarly, a group having 1-5 proteins refers to groups having 1, 2, 3, 4, or 5 proteins, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application was specifically and individually incorporated by reference in its entirety for all purposes.

REFERENCES

Burbulis, I., Yamaguchi, K., Gordon, A., Carlson, R., Brent, R., 2005. Using protein-DNA chimeras to detect and count small numbers of molecules. Nat Methods 2, 31-37.

Chen, B. X., Szabolcs, M. J., Matsushima, A. Y., Erlanger, B. E. F., 1996. A strategy for immunohistochemical signal enhancement by end-product amplification. The journal of histochemistry and cytochemistry: official journal of the Histochemistry Society 44, 819-24.

Chiu, N. H., Christopoulos, T. K., 1999. Two-site expression immunoassay using a firefly luciferase-coding DNA label. Clin Chem 45, 1954-1959.

Christopoulos, T. K., Chiu, N. H., 1995. Expression immunoassay. Antigen quantitation using antibodies labeled with enzyme-coding DNA fragments. Anal Chem 67, 4290-4294.

Guo, Y., Zhou, Y.-F., Zhang, X., Zhang, Z., Qiao, Y., Bi, L.-J., Wen, J., Liang, M., Zhang, J., 2006. Phage display mediated immuno-PCR. Nucleic acids research 34, 4-9.

Hill, P. J., Rees, C. E., Winson, M. K., Stewart, G. S., 1993. The application of lux genes. Biotechnology and applied biochemistry 17 (Pt 1), 3-14.

Hill, P. J., Stewart, G. S., 1994. Use of lux genes in applied biochemistry. Journal of bioluminescence and chemiluminescence 9, 211-5.

Johannsson, A., Stanley, C. J., Self, C. H., 1985. A fast highly sensitive colorimetric enzyme immunoassay system demonstrating benefits of enzyme amplification in clinical chemistry. Clin Chim Acta 148, 119-124.

Kazane, S. A., Sok, D., Cho, E. H., Uson, M. L., Kuhn, P., Schultz, P. G., Smider, V. V, 2012. Site-specific DNA-antibody conjugates for specific and sensitive immuno-PCR. Proc Natl Acad Sci USA 109, 3731-3736.

Lansdorp, P. M., Van der Kwast, T. H., De Boer, M., Zeijlemaker, W. P., 1984. Stepwise amplified immunoperoxidase (PAP) staining I Cellular morphology in relation to membrane markers. J Histochem Cytochem 32, 172-178.

Lind, K., Kubista, M., 2005. Development and evaluation of three real-time immuno-PCR assemblages for quantification of PSA. J Immunol Methods 304, 107-116.

Manukhov, I. V, Rastorguev, S. M., Eroshnikov, G. E., Zarubina, A. P., Zavil'gel'skiĭ, G. B., 2000. [Cloning and expression of the lux-operon of *Photorhabdus luminescens*, strain Zm1: nucleotide sequence of luxAB genes and basic properties of luciferase]. Genetika 36, 322-30.

Meighen, E. A., 1991. Molecular biology of bacterial bioluminescence. Microbiol. Rev 55, 123-142.

Niemeyer, C. M., Adler, M., Wacker, R., 2007. Detecting antigens by quantitative immuno-PCR. Nat Protoc 2, 1918-1930.

Sano, T., Smith, C. L., Cantor, C. R., 1992. Immuno-PCR: very sensitive antigen detection by means of specific antibody-DNA conjugates. Science 258, 120-122.

Scholle, M. D., Kehoe, J. W., Kay, B. K., 2005. Efficient construction of a large collection of phage-displayed combinatorial peptide libraries. Comb Chem High Throughput Screen 8, 545-551.

Schweitzer, B., Wiltshire, S., Lambert, J., O'Malley, S., Kukanskis, K., Zhu, Z., Kingsmore, S. F., Lizardi, P. M., Ward, D. C., 2000. Inaugural article: immunoassays with rolling circle DNA amplification: a versatile platform for ultrasensitive antigen detection. Proc Natl Acad Sci USA 97, 10113-10119.

Smith, G. P., 1985. Filamentous fusion phage: novel expression vectors that display cloned antigens on the virion surface. Science 228, 1315-1317.

Sternberger, L. A., Hardy Jr., P. H., Cuculis, J. J., Meyer, H. G., 1970. The unlabeled antibody enzyme method of immunohistochemistry: preparation and properties of soluble antigen-antibody complex (horseradish peroxidase-antihorseradish peroxidase) and its use in identification of spirochetes. J Histochem Cytochem 18, 315-333.

Stewart, G. S., Williams, P., 1992. lux genes and the applications of bacterial bioluminescence. Journal of general microbiology 138, 1289-300.

Szittner, R., Meighen, E., 1990. Nucleotide sequence, expression, and properties of luciferase coded by lux genes from a terrestrial bacterium. The Journal of biological chemistry 265, 16581-7.

Takeda, S., Tsukiji, S., Nagamune, T., 2004. Site-specific conjugation of oligonucleotides to the C-terminus of recombinant protein by expressed protein ligation. Bioorg Med Chem Lett 14,2407-2410.

Tummuru, M. K., Blaser, M. J., 1992. Characterization of the *Campylobacter fetus* sapA promoter: evidence that the sapA promoter is deleted in spontaneous mutant strains. J Bacteriol 174,5916-5922.

What is claimed is:

1. A method for detecting a target molecule, comprising:

a) contacting an immobilized target molecule with a modified bacteriophage comprising SEQ ID NO: 1, SEQ ID NO:2, SEQ ID NO:3, or SEQ ID NO:4, wherein the bacteriophage specifically binds the target molecule, under conditions that promote binding of the bacteriophage to the target molecule, to produce a target molecule-bacteriophage complex;

b) contacting the target molecule-bacteriophage complex with a bacterial strain susceptible to infection by the bacteriophage;

c) incubating the target molecule-bacteriophage complex with the bacterial strain under conditions that promote the propagation of the bacteriophage in the bacteria and expression of the luciferase, to produce a bacteriophage-infected culture;

d) adding to the bacteriophage-infected culture a substrate for the luciferase; and e) measuring the presence and/or magnitude of fluorescence produced from the action of the luciferase on its substrate.

2. The method of claim 1, wherein the target molecule comprises a first affinity tag and the bacteriophage comprises a second affinity tag, wherein the first and second affinity tags specifically bind to each other.

3. The method of claim 2, wherein the first and second affinity tags are enzymatically or chemically coupled to the target molecule and the bacteriophage, respectively.

4. The method of claim 2, wherein the first affinity tag is streptavidin and the second affinity tag is biotin.

5. The method of claim 1, wherein the bacteriophage is engineered to bind directly to the target molecule using phage display.

6. A method for detecting a target molecule, comprising:

a) contacting an immobilized target molecule with a first affinity ligand that specifically binds the target molecule, under conditions that promote target molecule-affinity ligand binding, to form a target molecule-first affinity ligand complex, and optionally contacting the target molecule-first affinity ligand complex with one or more additional affinity ligands under conditions that promote affinity ligand-affinity ligand binding, to produce a target molecule-first affinity ligand-additional affinity ligand complex, wherein the one or more affinity ligands are added sequentially, and wherein each successive affinity ligand specifically binds to the affinity ligand added immediately previous;

b) contacting the target molecule-first affinity ligand complex or the target molecule-first affinity ligand-additional affinity ligand complex with a modified bacteriophage comprising SEQ ID NO: 1, SEQ ID NO:2, SEQ ID NO:3, or SEQ ID NO:4, wherein the bacteriophage binds to the first affinity ligand, or if one or more additional affinity ligands are used, binds to the ultimate affinity ligand, to form a target molecule-affinity ligand-bacteriophage complex;

c) contacting the target molecule-affinity ligand-bacteriophage complex with a bacterial strain susceptible to infection by the bacteriophage;

d) incubating the target molecule-affinity ligand-bacteriophage complex with the bacterial strain under conditions that promote the propagation of the bacteriophage in the bacteria and expression of the luciferase, to produce a bacteriophage-infected culture;

e) adding to the bacteriophage-infected culture a substrate for the luciferase; and f) measuring the presence and/or magnitude of fluorescence produced from the action of the luciferase on its substrate.

7. The method of claim 6, wherein the first affinity ligand, or if one or more additional affinity ligands are used, the ultimate affinity ligand, comprises a first affinity tag, and the bacteriophage comprises a second affinity tag, wherein the first and second affinity tags specifically bind to each other.

8. The method of claim 6, wherein the first and second affinity tags are enzymatically or chemically coupled to the affinity ligand and the bacteriophage, respectively.

9. The method of claim 6, wherein the first affinity tag is streptavidin and the second affinity tag is biotin.

10. The method of claim 6, wherein the bacteriophage is engineered to bind directly to the affinity ligand using phage display.

* * * * *